(12) United States Patent
Fahey et al.

(10) Patent No.: US 12,151,071 B2
(45) Date of Patent: Nov. 26, 2024

(54) ADJUSTABLE SHUNTS AND ASSOCIATED SYSTEMS AND METHODS

(71) Applicant: Shifamed Holdings, LLC, Campbell, CA (US)

(72) Inventors: Brian Fahey, Menlo Park, CA (US); Scott Robertson, Portland, OR (US); William L Gould, Campbell, CA (US); William Jason Fox, San Mateo, CA (US); Claudio Argento, Felton, CA (US); Anthony Pantages, San Jose, CA (US); Miles Alexander, Fremont, CA (US); Peter Andriola, Castro Valley, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 802 days.

(21) Appl. No.: 17/016,192

(22) Filed: Sep. 9, 2020

(65) Prior Publication Data
US 2021/0085935 A1 Mar. 25, 2021

Related U.S. Application Data

(60) Provisional application No. 62/897,943, filed on Sep. 9, 2019, provisional application No. 62/907,696, filed
(Continued)

(51) Int. Cl.
*A61M 27/00* (2006.01)
*A61M 39/22* (2006.01)

(52) U.S. Cl.
CPC .......... *A61M 27/002* (2013.01); *A61M 39/22* (2013.01); *A61M 2205/0266* (2013.01);
(Continued)

(58) Field of Classification Search
CPC ..... A61F 2/82; A61F 2/06; A61F 2/07; A61B 2017/1139; A61M 27/002
See application file for complete search history.

(56) References Cited

U.S. PATENT DOCUMENTS

| | | | |
|---|---|---|---|
| 3,874,388 | A | 4/1975 | King et al. |
| 4,601,309 | A | 7/1986 | Chang |

(Continued)

FOREIGN PATENT DOCUMENTS

| | | |
|---|---|---|
| AU | 2005211243 | 8/2005 |
| AU | 2010344182 | 8/2012 |

(Continued)

OTHER PUBLICATIONS

International Search Report and Written Opinion received for International Application No. PCT/US22/35764, filed Jun. 30, 2022; Applicant: Shifamed Holdings, LLC; dated Sep. 19, 2022; 10 pages.
(Continued)

*Primary Examiner* — Brian A Dukert
(74) *Attorney, Agent, or Firm* — Perkins Coie LLP

(57) ABSTRACT

The present technology is directed to adjustable interatrial shunting systems that selectively control blood flow between the left atrium and the right atrium of a patient. The adjustable interatrial devices include a shunting element having an outer surface configured to engage native tissue and an inner surface defining a lumen that enables blood to flow from the left atrium to the right atrium when the system is deployed across the septal wall. The systems can include an actuation assembly for selectively adjusting a geometry of the lumen and/or a geometry of a lumen orifice to control the flow of blood through the lumen.

46 Claims, 51 Drawing Sheets

Related U.S. Application Data on Sep. 29, 2019, provisional application No. 63/003,594, filed on Apr. 1, 2020, provisional application No. 62/907,700, filed on Sep. 29, 2019, provisional application No. 62/929,608, filed on Nov. 1, 2019, provisional application No. 62/907,698, filed on Sep. 29, 2019, provisional application No. 62/959,792, filed on Jan. 10, 2020, provisional application No. 62/976,665, filed on Feb. 14, 2020, provisional application No. 63/003,632, filed on Apr. 1, 2020, provisional application No. 62/977,933, filed on Feb. 18, 2020, provisional application No. 62/994,010, filed on Mar. 24, 2020, provisional application No. 63/002,050, filed on Mar. 30, 2020.

(52) U.S. Cl.
CPC ............... *A61M 2205/3653* (2013.01); *A61M 2210/125* (2013.01)

(56) References Cited

U.S. PATENT DOCUMENTS

| | | | |
|---|---|---|---|
| 4,662,355 A | 5/1987 | Pieronne et al. |
| 4,705,507 A | 11/1987 | Boyles |
| 4,836,204 A | 6/1989 | Landymore et al. |
| 4,969,890 A * | 11/1990 | Sugita | A61F 2/95 606/192 |
| 4,979,955 A | 12/1990 | Smith |
| 4,995,857 A | 2/1991 | Arnold |
| 5,186,431 A | 2/1993 | Tamari |
| 5,197,978 A | 3/1993 | Hess |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,556,386 A | 9/1996 | Todd |
| 5,584,803 A | 12/1996 | Stevens et al. |
| 5,597,377 A | 1/1997 | Aldea |
| 5,611,338 A | 3/1997 | Gallup |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,297 A | 4/1998 | Simon |
| 5,795,307 A | 8/1998 | Krueger |
| 5,810,836 A | 9/1998 | Hussein et al. |
| 5,824,071 A | 10/1998 | Nelson et al. |
| 5,916,193 A | 6/1999 | Stevens et al. |
| 5,941,850 A | 8/1999 | Shah et al. |
| 5,944,019 A | 8/1999 | Kundson et al. |
| 5,957,949 A | 9/1999 | Leonhardt et al. |
| 6,024,743 A | 2/2000 | Edwards |
| 6,039,759 A | 3/2000 | Carpentier et al. |
| 6,077,298 A | 6/2000 | Tu et al. |
| 6,120,534 A | 9/2000 | Ruiz |
| 6,126,686 A | 10/2000 | Badylak et al. |
| 6,165,188 A | 12/2000 | Saadat et al. |
| 6,165,209 A | 12/2000 | Patterson et al. |
| 6,210,318 B1 | 4/2001 | Lederman |
| 6,217,541 B1 | 4/2001 | Yu |
| 6,240,322 B1 | 5/2001 | Peterfeso et al. |
| 6,242,762 B1 | 6/2001 | Brown et al. |
| 6,254,564 B1 | 7/2001 | Wilk et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,358,277 B1 | 3/2002 | Duran |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,478,776 B1 | 11/2002 | Rosenman et al. |
| 6,491,705 B2 | 12/2002 | Gifford, III et al. |
| 6,514,285 B1 | 2/2003 | Pinchasik |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,783,499 B2 | 8/2004 | Schwartz |
| 6,909,920 B2 | 6/2005 | Lokhoff et al. |
| 6,911,043 B2 | 6/2005 | Myers et al. |
| 6,926,670 B2 | 8/2005 | Rich et al. |
| 7,001,409 B2 | 2/2006 | Amplatz |
| 7,011,095 B2 | 3/2006 | Wolf et al. |
| 7,056,294 B2 | 6/2006 | Khairkhahan et al. |
| 7,149,587 B2 | 12/2006 | Wardle et al. |
| 7,175,656 B2 | 2/2007 | Khairkhahan |
| 7,270,675 B2 | 9/2007 | Chun et al. |
| 7,294,115 B1 | 11/2007 | Wilk |
| 7,311,690 B2 | 12/2007 | Burnett |
| 7,311,730 B2 | 12/2007 | Gabbay |
| 7,317,951 B2 | 1/2008 | Schneider et al. |
| 7,389,134 B1 | 6/2008 | Karicherla et al. |
| 7,390,310 B2 | 6/2008 | McCusker et al. |
| 7,513,908 B2 | 4/2009 | Lattouf |
| 7,524,329 B2 | 4/2009 | Rucker |
| 7,524,330 B2 | 4/2009 | Berreklouw |
| 7,524,332 B2 | 4/2009 | Osborne et al. |
| 7,608,067 B2 | 10/2009 | Bonni |
| 7,617,001 B2 | 11/2009 | Penner et al. |
| 7,634,318 B2 | 12/2009 | Tran et al. |
| 7,658,747 B2 | 2/2010 | Forde et al. |
| 7,699,059 B2 | 4/2010 | Fonseca et al. |
| 7,736,327 B2 | 6/2010 | Wilk et al. |
| 7,780,725 B2 | 8/2010 | Haug et al. |
| 7,794,473 B2 | 9/2010 | Tessmer et al. |
| 7,806,921 B2 | 10/2010 | Hoffman |
| 7,860,579 B2 | 12/2010 | Goetzinger et al. |
| 7,892,246 B2 | 2/2011 | Akin et al. |
| 7,905,901 B2 | 3/2011 | Corcoran et al. |
| 7,922,764 B2 | 4/2011 | Gordy et al. |
| 7,938,840 B2 | 5/2011 | Golden et al. |
| 7,967,769 B2 | 6/2011 | Faul et al. |
| 7,988,724 B2 | 8/2011 | Salahieh et al. |
| 8,012,198 B2 | 9/2011 | Hill et al. |
| 8,016,877 B2 | 9/2011 | Seguin et al. |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,147,545 B2 | 4/2012 | Avior |
| 8,157,860 B2 | 4/2012 | McNamara et al. |
| 8,172,896 B2 | 5/2012 | McNamara et al. |
| 8,235,916 B2 | 8/2012 | Whiting et al. |
| 8,235,933 B2 | 8/2012 | Keren et al. |
| 8,246,677 B2 | 8/2012 | Ryan |
| 8,252,042 B2 | 8/2012 | McNamara et al. |
| 8,303,511 B2 | 11/2012 | Eigler et al. |
| 8,328,751 B2 | 12/2012 | Keren et al. |
| 8,348,996 B2 | 1/2013 | Tuval et al. |
| 8,398,708 B2 | 3/2013 | Meiri et al. |
| 8,460,366 B2 | 6/2013 | Rowe |
| 8,460,372 B2 | 6/2013 | McNamara et al. |
| 8,597,225 B2 | 12/2013 | Kapadia |

(56) References Cited

U.S. PATENT DOCUMENTS

| | | |
|---|---|---|
| 8,647,381 B2 | 2/2014 | Essinger et al. |
| 8,696,611 B2 | 4/2014 | Nitzan et al. |
| 8,740,962 B2 | 6/2014 | Finch et al. |
| 8,745,845 B2 | 6/2014 | Finch et al. |
| 8,747,458 B2 | 6/2014 | Tuval et al. |
| 8,752,258 B2 | 6/2014 | Finch et al. |
| 8,764,848 B2 | 7/2014 | Callaghan et al. |
| 8,882,697 B2 | 11/2014 | Celermajer et al. |
| 8,951,223 B2 | 2/2015 | McNamara et al. |
| 9,005,155 B2 | 4/2015 | Sugimoto |
| 9,034,034 B2 | 5/2015 | Nitzan et al. |
| 9,138,213 B2 | 9/2015 | Amin et al. |
| 9,204,842 B2 | 12/2015 | Mothilal et al. |
| 9,205,236 B2 | 12/2015 | McNamara et al. |
| 9,232,997 B2 | 1/2016 | Sugimoto et al. |
| 9,277,995 B2 | 3/2016 | Celermajer et al. |
| 9,358,371 B2 | 6/2016 | McNamara et al. |
| 9,456,812 B2 | 10/2016 | Finch et al. |
| 9,610,041 B2 | 4/2017 | Foster et al. |
| 9,629,715 B2 | 4/2017 | Nitzan et al. |
| 9,642,993 B2 | 5/2017 | McNamara et al. |
| 9,649,480 B2 | 5/2017 | Sugimoto et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,775,636 B2 | 10/2017 | Fazio et al. |
| 9,918,856 B2 | 3/2018 | Favier et al. |
| 9,937,036 B2 | 4/2018 | Sugimoto et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,076,403 B1 | 9/2018 | Eigler et al. |
| 10,188,375 B2 | 1/2019 | McNamara et al. |
| 10,207,087 B2 | 2/2019 | Keren |
| 10,251,740 B2 | 4/2019 | Eigler et al. |
| 10,292,690 B2 | 5/2019 | Celermajer et al. |
| 10,350,384 B2 | 7/2019 | Farnan et al. |
| 10,357,357 B2 | 7/2019 | Levi et al. |
| 10,368,981 B2 | 8/2019 | Nitzan et al. |
| 10,376,359 B2 | 8/2019 | Essinger et al. |
| 10,376,680 B2 | 8/2019 | McNamara et al. |
| 10,398,421 B2 | 9/2019 | Celermajer |
| 10,405,903 B1 | 9/2019 | Biesinger et al. |
| 10,413,284 B2 | 9/2019 | McNamara et al. |
| 10,413,286 B2 | 9/2019 | McNamara et al. |
| 10,463,477 B2 | 11/2019 | Forcucci et al. |
| 10,463,490 B2 | 11/2019 | Rottenberg et al. |
| 10,471,251 B1 | 11/2019 | Manicka |
| 10,478,594 B2 | 11/2019 | Yacoby et al. |
| 10,568,751 B2 | 2/2020 | McNamara |
| 10,588,611 B2 | 3/2020 | Magnin et al. |
| 10,610,210 B2 | 4/2020 | Finch et al. |
| 10,624,621 B2 | 4/2020 | Celermajer |
| 10,632,292 B2 | 4/2020 | Forcucci et al. |
| 10,639,459 B2 | 5/2020 | Nitzan et al. |
| 10,667,896 B2 | 6/2020 | Delaney, Jr. et al. |
| 10,675,450 B2 | 6/2020 | Finch |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,932,786 B2 | 3/2021 | McNamara et al. |
| 10,940,296 B2 | 3/2021 | Keren |
| 10,945,716 B2 | 3/2021 | Chen et al. |
| 11,135,410 B2 | 10/2021 | Finch et al. |
| 11,160,961 B2 | 11/2021 | Fahey et al. |
| 11,253,685 B2 | 2/2022 | Fahey et al. |
| 11,622,695 B1 | 4/2023 | Andriola et al. |
| 11,633,194 B2 | 4/2023 | Alexander et al. |
| 11,801,369 B2 | 10/2023 | Fahey et al. |
| 2002/0072656 A1 | 6/2002 | Vantassel et al. |
| 2002/0115991 A1 | 8/2002 | Edwards |
| 2002/0142119 A1 | 10/2002 | Seward et al. |
| 2002/0161427 A1 | 10/2002 | Rabkin et al. |
| 2002/0169371 A1 | 11/2002 | Gilderdale |
| 2002/0169475 A1 | 11/2002 | Gainor et al. |
| 2002/0177891 A1 | 11/2002 | Miles et al. |
| 2003/0125798 A1 | 7/2003 | Martin |
| 2003/0127090 A1 | 7/2003 | Gifford et al. |
| 2003/0163190 A1 | 8/2003 | LaFont et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0143294 A1 | 7/2004 | Corcoran et al. |
| 2004/0147869 A1 | 7/2004 | Wolf et al. |
| 2004/0147939 A1 | 7/2004 | Rabkin et al. |
| 2004/0158143 A1 | 8/2004 | Flaherty et al. |
| 2004/0162514 A1 | 8/2004 | Alferness et al. |
| 2004/0186566 A1 | 9/2004 | Hindrichs et al. |
| 2004/0210190 A1 | 10/2004 | Kohler et al. |
| 2004/0215067 A1 | 10/2004 | Stiger et al. |
| 2004/0215323 A1 | 10/2004 | Stiger |
| 2005/0004641 A1 | 1/2005 | Pappu |
| 2005/0033351 A1 | 2/2005 | Newton |
| 2005/0060030 A1 | 3/2005 | Lashinski et al. |
| 2005/0101946 A1 | 5/2005 | Govari et al. |
| 2005/0148925 A1 | 7/2005 | Rottenberg et al. |
| 2005/0159789 A1 | 7/2005 | Brockway et al. |
| 2005/0165344 A1 | 7/2005 | Dobak, III |
| 2005/0192627 A1 | 9/2005 | Whisenant et al. |
| 2005/0204811 A1 | 9/2005 | Neff |
| 2005/0251212 A1 | 11/2005 | Kieval et al. |
| 2005/0288722 A1 | 12/2005 | Eigler et al. |
| 2006/0009810 A1 | 1/2006 | Mann et al. |
| 2006/0025857 A1 | 2/2006 | Bergheim et al. |
| 2006/0047205 A1 | 3/2006 | Ludomirsky et al. |
| 2006/0064135 A1 | 3/2006 | Brockway |
| 2006/0111660 A1 | 5/2006 | Wolf et al. |
| 2006/0116625 A1 | 6/2006 | Renati et al. |
| 2006/0200030 A1 | 9/2006 | White et al. |
| 2007/0010837 A1 | 1/2007 | Tanaka |
| 2007/0010852 A1 | 1/2007 | Blaeser et al. |
| 2007/0043435 A1 | 2/2007 | Seguin et al. |
| 2007/0088220 A1 | 4/2007 | Stahmann |
| 2007/0088223 A1 | 4/2007 | Mann et al. |
| 2007/0112344 A1 | 5/2007 | Keilman |
| 2007/0118039 A1 | 5/2007 | Bodecker et al. |
| 2007/0150019 A1 | 6/2007 | Youker et al. |
| 2007/0213813 A1 | 9/2007 | Von Segesser et al. |
| 2007/0282157 A1 | 12/2007 | Rottenberg et al. |
| 2008/0097276 A1 | 4/2008 | Bertrand et al. |
| 2008/0108904 A1 | 5/2008 | Heil |
| 2008/0119891 A1 | 5/2008 | Miles et al. |
| 2008/0127689 A1 | 6/2008 | McCusker et al. |
| 2008/0171941 A1 | 7/2008 | Huelskamp et al. |
| 2008/0208083 A1 | 8/2008 | Lin et al. |
| 2008/0208286 A1 | 8/2008 | Kieval et al. |
| 2009/0025459 A1 | 1/2009 | Zhang et al. |
| 2009/0036975 A1 | 2/2009 | Ward et al. |
| 2009/0243956 A1 | 10/2009 | Keilman et al. |
| 2009/0270742 A1 | 10/2009 | Wolinsky et al. |
| 2009/0276040 A1 | 11/2009 | Rowe et al. |
| 2009/0281557 A1* | 11/2009 | Sander ............... A61B 17/3468 606/151 |
| 2010/0063375 A1 | 3/2010 | Kassab et al. |
| 2010/0076366 A1 | 3/2010 | Henderson, Sr. et al. |
| 2010/0076517 A1 | 3/2010 | Imran |
| 2010/0106028 A1 | 4/2010 | Penner et al. |
| 2010/0160906 A1 | 6/2010 | Jarrard |
| 2010/0168672 A1 | 7/2010 | Carr |
| 2010/0179449 A1 | 7/2010 | Chow et al. |
| 2010/0241241 A1 | 9/2010 | McKnight et al. |
| 2010/0249560 A1 | 9/2010 | Levinson et al. |
| 2010/0275592 A1 | 11/2010 | Topliss et al. |
| 2010/0298930 A1 | 11/2010 | Orlov |
| 2011/0054515 A1 | 3/2011 | Bridgeman et al. |
| 2011/0082377 A1 | 4/2011 | Ah |
| 2011/0218480 A1 | 9/2011 | Rottenberg et al. |
| 2011/0218481 A1 | 9/2011 | Rottenberg et al. |
| 2011/0257723 A1 | 10/2011 | McNamara |

(56) References Cited

U.S. PATENT DOCUMENTS

| | | |
|---|---|---|
| 2011/0264194 A1 | 10/2011 | Griswold |
| 2011/0282217 A1 | 11/2011 | Nashet |
| 2011/0295183 A1 | 12/2011 | Finch et al. |
| 2012/0053686 A1 | 3/2012 | McNamara et al. |
| 2012/0059431 A1 | 3/2012 | Williams et al. |
| 2012/0229272 A1 | 9/2012 | Jacob et al. |
| 2012/0265296 A1 | 10/2012 | McNamara et al. |
| 2012/0283773 A1 | 11/2012 | Van Tassel et al. |
| 2012/0290062 A1 | 11/2012 | McNamara et al. |
| 2013/0085350 A1 | 4/2013 | Schugt et al. |
| 2013/0123569 A1 | 5/2013 | Gross |
| 2013/0144379 A1 | 6/2013 | Najafi et al. |
| 2013/0178783 A1 | 7/2013 | McNamara et al. |
| 2013/0178784 A1 | 7/2013 | McNamara et al. |
| 2013/0190799 A1 | 7/2013 | Clark |
| 2013/0192611 A1 | 8/2013 | Taepke, II et al. |
| 2013/0197423 A1 | 8/2013 | Keren et al. |
| 2013/0211221 A1 | 8/2013 | Sunnarborg et al. |
| 2013/0253343 A1 | 9/2013 | Waldhauser et al. |
| 2013/0261531 A1 | 10/2013 | Gallagher et al. |
| 2013/0293025 A1 | 11/2013 | Xu et al. |
| 2014/0012342 A1 | 1/2014 | Penner et al. |
| 2014/0046427 A1 | 2/2014 | Michalak |
| 2014/0121750 A1 | 5/2014 | Hadley et al. |
| 2014/0128795 A1 | 5/2014 | Karen et al. |
| 2014/0128796 A1 | 5/2014 | Keren et al. |
| 2014/0163449 A1 | 6/2014 | Rottenberg et al. |
| 2014/0213915 A1 | 7/2014 | Doan et al. |
| 2014/0213959 A1 | 7/2014 | Nitzan et al. |
| 2014/0222040 A1 | 8/2014 | Park et al. |
| 2014/0222144 A1 | 8/2014 | Eberhardt et al. |
| 2014/0249616 A1* | 9/2014 | Strauss ............ A61F 2/89 623/1.11 |
| 2014/0277054 A1 | 9/2014 | McNamara et al. |
| 2015/0034217 A1 | 2/2015 | Vad |
| 2015/0039084 A1 | 2/2015 | Levi et al. |
| 2015/0084585 A1 | 3/2015 | Moran |
| 2015/0119796 A1 | 4/2015 | Finch |
| 2015/0148731 A1 | 5/2015 | McNamara et al. |
| 2015/0157268 A1 | 6/2015 | Winshtein et al. |
| 2015/0208929 A1 | 7/2015 | Rowland et al. |
| 2015/0223707 A1 | 8/2015 | Ludoph |
| 2015/0230843 A1 | 8/2015 | Palmer et al. |
| 2015/0231387 A1 | 8/2015 | Harding et al. |
| 2015/0287544 A1 | 10/2015 | Irazoqui et al. |
| 2016/0022423 A1 | 1/2016 | Mcnamara et al. |
| 2016/0089079 A1 | 3/2016 | Stein |
| 2016/0151179 A1 | 6/2016 | Favier et al. |
| 2016/0158561 A1 | 6/2016 | Reddy |
| 2016/0220357 A1 | 8/2016 | Anand et al. |
| 2016/0235999 A1 | 8/2016 | Nuta et al. |
| 2016/0302808 A1 | 10/2016 | Loganathan et al. |
| 2017/0014067 A1 | 1/2017 | Peppou et al. |
| 2017/0105635 A1 | 4/2017 | Cho et al. |
| 2017/0113026 A1 | 4/2017 | Finch |
| 2017/0312078 A1 | 11/2017 | Krivoruchko |
| 2017/0340460 A1 | 11/2017 | Rosen et al. |
| 2018/0014828 A1 | 1/2018 | Fonte et al. |
| 2018/0117341 A1 | 5/2018 | Kane et al. |
| 2018/0168463 A1 | 6/2018 | Morris et al. |
| 2018/0250014 A1 | 9/2018 | Melanson et al. |
| 2018/0256865 A1 | 9/2018 | Finch et al. |
| 2018/0262037 A1 | 9/2018 | Meskeus |
| 2018/0296375 A1 | 10/2018 | Van Langenhove |
| 2018/0310839 A1 | 11/2018 | McCaffrey et al. |
| 2019/0000327 A1 | 1/2019 | Doan et al. |
| 2019/0014993 A1 | 1/2019 | Kaiser |
| 2019/0015103 A1 | 1/2019 | Sharma |
| 2019/0021861 A1 | 1/2019 | Finch |
| 2019/0150758 A1 | 5/2019 | Bailey et al. |
| 2019/0167197 A1 | 6/2019 | Abuuassar et al. |
| 2019/0175883 A1 | 6/2019 | Wessler et al. |
| 2019/0192864 A1 | 6/2019 | Koop et al. |
| 2019/0254814 A1 | 8/2019 | Nitzan et al. |
| 2019/0262118 A1 | 8/2019 | Elgler et al. |
| 2019/0269392 A1 | 9/2019 | Celermajer et al. |
| 2019/0274855 A1 | 9/2019 | Pate et al. |
| 2019/0298556 A1 | 10/2019 | Bohn et al. |
| 2019/0307459 A1 | 10/2019 | Celermajer et al. |
| 2019/0328513 A1 | 10/2019 | Levi et al. |
| 2019/0336135 A1 | 11/2019 | Inouye et al. |
| 2019/0336163 A1 | 11/2019 | McNamara et al. |
| 2019/0350519 A1 | 11/2019 | Bailey et al. |
| 2020/0008870 A1 | 1/2020 | Gruba et al. |
| 2020/0060825 A1 | 2/2020 | Rottenberg et al. |
| 2020/0078196 A1 | 3/2020 | Rosen et al. |
| 2020/0078558 A1 | 3/2020 | Yacoby et al. |
| 2020/0085600 A1 | 3/2020 | Schwartz et al. |
| 2020/0188143 A1 | 6/2020 | McNamara |
| 2020/0196867 A1 | 6/2020 | Andersen et al. |
| 2020/0196876 A1 | 6/2020 | Minor et al. |
| 2020/0197178 A1 | 6/2020 | Vecchio |
| 2020/0229977 A1 | 7/2020 | Mixter et al. |
| 2020/0229981 A1 | 7/2020 | Mixter et al. |
| 2020/0229982 A1 | 7/2020 | Mixter et al. |
| 2020/0245991 A1 | 8/2020 | Celermajer |
| 2020/0253615 A1 | 8/2020 | Melanson et al. |
| 2020/0260991 A1 | 8/2020 | Rowlaud et al. |
| 2020/0261705 A1 | 8/2020 | Nitzan et al. |
| 2020/0268515 A1 | 8/2020 | Vettukattil et al. |
| 2020/0281611 A1 | 9/2020 | Kelly et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0030273 A1 | 2/2021 | Huang et al. |
| 2021/0038230 A1 | 2/2021 | Larsen et al. |
| 2021/0052378 A1 | 2/2021 | Nitzan et al. |
| 2021/0059527 A1 | 3/2021 | Najafi |
| 2021/0085935 A1 | 3/2021 | Fahey et al. |
| 2021/0100513 A1 | 4/2021 | Sahmauyar et al. |
| 2021/0100665 A1 | 4/2021 | Nae et al. |
| 2021/0121179 A1 | 4/2021 | Ben-david et al. |
| 2021/0145331 A1 | 5/2021 | Simpson et al. |
| 2021/0153776 A1 | 5/2021 | Minar et al. |
| 2021/0177508 A1 | 6/2021 | Kellerman |
| 2021/0205590 A1 | 7/2021 | Fahey et al. |
| 2021/0212638 A1 | 7/2021 | Golda et al. |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0290214 A1 | 9/2021 | Cole et al. |
| 2021/0290356 A1* | 9/2021 | Brinkmann ............ A61F 2/07 |
| 2021/0298763 A1 | 9/2021 | Stahmann et al. |
| 2021/0299425 A1 | 9/2021 | Kume et al. |
| 2021/0299430 A1 | 9/2021 | Ratz et al. |
| 2021/0361238 A1 | 11/2021 | Bak-Boychuk et al. |
| 2021/0361257 A1 | 11/2021 | Eimer et al. |
| 2021/0370032 A1 | 12/2021 | Fahey et al. |
| 2021/0401418 A1 | 12/2021 | Dang et al. |
| 2022/0008014 A1 | 1/2022 | Rowe et al. |
| 2022/0039670 A1 | 2/2022 | Berrada et al. |
| 2022/0039671 A1 | 2/2022 | Fahey |
| 2022/0117555 A1 | 4/2022 | Zarbatauy et al. |
| 2022/0118228 A1 | 4/2022 | Fahey et al. |
| 2022/0142652 A1 | 5/2022 | Alexander et al. |
| 2022/0143368 A1 | 5/2022 | Pulugurtha et al. |
| 2022/0151618 A1 | 5/2022 | Eigler et al. |
| 2022/0167861 A1 | 6/2022 | Stahmann |
| 2022/0184355 A1 | 6/2022 | Fahey et al. |
| 2022/0192677 A1 | 6/2022 | Wedul et al. |
| 2022/0218355 A1 | 7/2022 | Wedul et al. |
| 2022/0226000 A1 | 7/2022 | Alexander et al. |
| 2022/0226623 A1 | 7/2022 | Fahey et al. |
| 2022/0240856 A1 | 8/2022 | Stahmann et al. |
| 2022/0265280 A1 | 8/2022 | Chamorro et al. |
| 2022/0313426 A1 | 10/2022 | Gifford, III et al. |
| 2023/0056924 A1 | 2/2023 | Fox et al. |
| 2023/0084193 A1 | 3/2023 | Fahey et al. |
| 2023/0118243 A1 | 4/2023 | Fox et al. |
| 2023/0129883 A1 | 4/2023 | Andriola et al. |
| 2023/0165672 A1 | 6/2023 | Fahey et al. |
| 2023/0191094 A1 | 6/2023 | Fahey et al. |
| 2023/0201545 A1 | 6/2023 | Alexander et al. |
| 2023/0201546 A1 | 6/2023 | Fahey et al. |

(56) References Cited

U.S. PATENT DOCUMENTS

| | | |
|---|---|---|
| 2023/0240852 A1 | 8/2023 | Fahey et al. |
| 2024/0165381 A1 | 5/2024 | Fahey et al. |
| 2024/0225661 A9 | 7/2024 | Alexander et al. |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 106456308 | 2/2017 |
| CN | 109646063 A | 4/2019 |
| CN | 110536657 | 12/2019 |
| EP | 1547549 | 6/2005 |
| EP | 1112044 | 1/2007 |
| EP | 2097012 | 9/2009 |
| EP | 2528646 | 12/2012 |
| EP | 2642954 | 10/2013 |
| EP | 2967867 | 1/2016 |
| EP | 3087953 | 11/2016 |
| EP | 3291773 | 3/2018 |
| EP | 3300672 | 4/2018 |
| EP | 3329860 | 6/2018 |
| EP | 3579907 | 12/2019 |
| EP | 3589238 | 1/2020 |
| EP | 3624701 | 3/2020 |
| EP | 2999412 | 5/2020 |
| EP | 3705154 | 9/2020 |
| EP | 3716877 | 10/2020 |
| EP | 3740163 | 11/2020 |
| EP | 3766431 | 1/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2005177491 | 7/2005 |
| JP | 2007527742 | 10/2007 |
| JP | 2008504878 | 2/2008 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2017508581 | 3/2017 |
| JP | 2020509812 | 4/2020 |
| KR | 20010046155 | 6/2001 |
| WO | WO99029227 | 6/1999 |
| WO | WO2003028522 | 4/2003 |
| WO | WO2005074367 | 8/2005 |
| WO | WO2006012038 | 2/2006 |
| WO | WO2006089236 | 8/2006 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014091222 | 6/2014 |
| WO | WO2014150106 | 9/2014 |
| WO | WO2014188279 | 11/2014 |
| WO | WO2015135955 | 9/2015 |
| WO | WO2016014821 | 1/2016 |
| WO | WO2016038115 | 3/2016 |
| WO | WO2016178171 | 11/2016 |
| WO | WO2017151566 | 9/2017 |
| WO | WO2018024868 | 2/2018 |
| WO | WO2018132549 | 7/2018 |
| WO | WO2018158747 | 9/2018 |
| WO | WO2019186101 | 2/2019 |
| WO | WO 2019142152 | 7/2019 |
| WO | WO2019175401 | 9/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020023514 | 1/2020 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020132678 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO202104653 | 3/2021 |
| WO | WO2021050589 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021072315 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021126699 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150765 | 7/2021 |
| WO | WO2021158559 | 8/2021 |
| WO | WO2021159001 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021216964 | 10/2021 |

(56) References Cited

FOREIGN PATENT DOCUMENTS

| WO | WO2021217055 | 10/2021 |
|---|---|---|
| WO | WO2021217059 | 10/2021 |
| WO | WO2021224736 | 11/2021 |
| WO | WO2022046921 | 3/2022 |
| WO | WO2022076601 | 4/2022 |
| WO | WO2022081980 | 4/2022 |
| WO | WO2022103973 | 5/2022 |
| WO | WO2022192280 | 9/2022 |
| WO | WO2022266465 | 12/2022 |
| WO | WO2022266503 | 12/2022 |
| WO | WO2022272131 | 12/2022 |
| WO | WO2023278725 | 1/2023 |
| WO | WO2024137843 | 6/2024 |

OTHER PUBLICATIONS

International Search Report and Written Opinion received for International Application No. PCT/US22/34027, filed Jun. 17, 2022; Applicant: Shifamed Holdings, LLC; dated Oct. 25, 2022; 8 pages.
International Search Report and Written Opinion received for International Application No. PCT/US22/34995, filed Jun. 24, 2022; Applicant: Shifamed Holdings, LLC; dated Nov. 18, 2022; 17 pages.
Perk et al., "Catheter-based left atrial appendage occlusion procedure: role of echocardiography," published on behalf of the European Society of Cardiology, Sep. 8, 2011, 7 pages.
Collado et al., "Left Atrial Appendage Occlusion for Stroke Prevention in Nonvalvular Atrial Fibrillation," Journal of the American Heart Association, Jun. 2021, 18 pages.
Jodi Perkins, "Corvia Medical and physiQ Partner in Global Phase 3 Heart Failure Clinical Trial to Leverage Novel Digital Endpoints," Press Release, 2019 Copyright, Medical Alley Association, 3 pages.
Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.
International Search Report and Written Opinion received for International Application No. PCT/US19/69106 filed Dec. 31, 2019; Applicant: Shifamed Holdings, LLC; dated Mar. 23, 2020; 10 pages.
International Search Report and Written Opinion received for International Application No. PCT/US20/49996 filed Sep. 9, 2020; Applicant: Shifamed Holdings, LLC; dated Feb. 17, 2021; 16 pages.
International Search Report and Written Opinion received for International Application No. PCT/US20/063360 filed Dec. 4, 2020; Applicant: Shifamed Holdings, LLC; dated Apr. 5, 2021; 13 pages.
International Search Report and Written Opinion received for International Application No. PCT/US20/64529 filed Dec. 11, 2020; Applicant: Shifamed Holdings, LLC; dated Apr. 8, 2021; 12 pages.
International Search Report and Written Opinion received for International Application No. PCT/US19/68354, filed Dec. 23, 2019; Applicant: Shifamed Holdings, LLC; dated Mar. 17, 2020; 11 pages.
International Search Report and Written Opinion received for International Application No. PCT/US21/16932, filed Feb. 5, 2021; Applicant: Shifamed Holdings, LLC; dated Jun. 3, 2021; 11 pages.
International Search Report and Written Opinion received for International Application No. PCT/US21/14433, filed Jan. 21, 2021; Applicant: Shifamed Holdings, LLC; dated May 14, 2021; 16 pages.
International Search Report and Written Opinion received for International Application No. PCT/US21/14428, filed Jan. 21, 2021; Applicant: Shifamed Holdings, LLC; dated Jun. 8, 2021; 17 pages.
Ando et al., "Left ventricular decompression through a patent foramen ovale in a patient with hypertrophic cardiomyopathy: a case report," Cardiovascular Ultrasound volume, Article No. 2 (2004).
Braunwald, Heart Disease, Chapter 6, 2015, p. 186.
Bridges et al., "The Society of Thoracic Surgeons practice guideline series: transmyocardial laser revascularization," The Annals of Thoracic Surgery, vol. 77, Issue 4, Apr. 2004, pp. 1494-1502.
Bristow et al., "Improvement in cardiac myocyte function by biological effects of medical therapy: A new concept in the treatment of heart failure," European Heart Journal, vol. 16, Issue suppl. F, Jul. 1995, pp. 20-31.
Case et al., "Relief of High Left-Atrial Pressure in Left-Ventricular Failure," Lancet, Oct. 17, 1964, pp. 841-842.
Coats et al., "Controlled trial of physical training in chronic heart failure. Exercise performance, hemodynamics, ventilation, and autonomic function," Circulation, 1992;85:2119-2131.
Davies et al., "Reduced contraction and altered frequency response of isolated ventricular myocytes from patients with heart failure," Circulation, (1995), 92:2540-2549, Circulation, (1995), 92:2540-2549.
Ennezat et al., "An unusual case of low-flow, low gradient severe aortic stenosis: Left-to- right shunt due to atrial septal defect," Cardiology, (2009), 113(2):146-148.
Ewert et al., "Masked Left Ventricular Restriction in Elderly Patients with Atrial Septal Defects: A Contraindication for Closure," Catheterization and Cardiovascular Interventions, 52: 177-180, 2001.
Ewert et al., "Acute left heart failure after interventional occlusion of an atrial septal defect," Z. Kardiol., Catheterization and Cardiovascular Interventions, Z. Kardiol., (May 2001), 90(5):362-366.
Geiran et al., "Changes in cardiac dynamics by opening an interventricular shunt in dogs," J. Surg. Res., (Jan. 1990), 48(1):6-12.
Gelernter-Yaniv et al., "Transcatheter closure of left-to-right interatrial shunts to resolve hypoxemia," Congenit. Heart Dis., (Jan. 2008), 31(1):47-53.
Gewillig et al., "Creation with a stent of an unrestrictive lasting atrial communication," Cardio. Young, (2002), 12(4):404-407.
Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).
Kramer et al., "Controlled study of captopril in chronic heart failure: A rest and exercise hemodynamic study," Circulation, (1983), 67(4):807-816.
Lai et al., "Bidirectional shunt through a residual atrial septal defect after percutaneous transvenous mitral commissurotomy," Cardiology, (1993), 83(3):205-207.
Lemmer et al., "Surgical implications of atrial septal defect complicating aortic balloon valvuloplasty," Ann. thorac. Surg., (Aug. 1989), 48(2):295-297.
Park et al., "Blade atrial septostomy: collaborative study," Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).
Salehian et al., "Improvements in Cardiac Form and Function After Transcatheter Closure of Secundum Atrial Septal Defects," Journal of the American College of Cardiology, 45(4):499-504 (2005).
Schmitto et al., "Chronic heart failure induced by multiple sequential coronary microembolization in sheep," The International Journal of Artificial Organs, 31(4):348-353 (2008).
Schubert et al., "Left ventricular conditioning in the elderly patient to prevent congestive heart failure after transcatheter closure of the atrial septal defect," Catheter Cardiovasc. Interv., (2005), 64(3):333-337.
Stormer et al., "Comparative study of in vitro flow characteristics between a human aortic valve and a designed aortic and six corresponding types of prosthetic heart valves," European Surgical Research, (1976), 8(2):117-131.
Stumper et al., "Modified technique of stent fenestration of the atrial septum, Heart," (2003), 89:1227-1230.
Trainor et al., "Comparative Pathology of an Implantable Left Atrial Pressure Sensor," ASAIO Journal, Clinical Cardiovascular/Cardiopulmonary Bypass, 59(5):486-92 (2013).
Zhou et al., "Unidirectional valve patch for repair of cardiac septal defects with pulmonary hypertension," Annals of Thoracic Surgeons, 60: 1245-1249, 1995.

(56) References Cited

OTHER PUBLICATIONS

International Search Report and Written Opinion received for International Application No. PCT/US20/12059, filed Jan. 2, 2020; Applicant: Shifamed Holdings, LLC; dated Jun. 5, 2020; 12 pages.
International Search Report and Written Opinion received for International Application No. PCT/US20/25509, filed Mar. 27, 2020; Applicant: Shifamed Holdings, LLC; dated Jun. 25, 2020; 9 pages.
International Search Report and Written Opinion received for International Application No. PCT/US20/26738, filed Apr. 3, 2020; Applicant: Shifamed Holdings, LLC; dated Jun. 30, 2020; 8 pages.
International Search Report and Written Opinion received for International Application No. PCT/US21/28931, filed Apr. 23, 2021; Applicant: Shifamed Holdings, LLC; dated Sep. 24, 2021; 20 pages.
International Search Report and Written Opinion received for International Application No. PCT/US21/27747, filed Apr. 16, 2021; Applicant: Shifamed Holdings, LLC; dated Oct. 1, 2021; 16 pages.
International Search Report and Written Opinion received for International Application No. PCT/US21/55191, filed Oct. 15, 2021; Applicant: Shifamed Holdings, LLC; dated Mar. 1, 2022; 12 pages.
Anomet Products "Conductive Nitinol Wire" Aug. 15, 2020, Retrieved from website <URL: https://helpx.adobe.com/acrobat/using/allow-or-block-links-internet.html?mv=product&mv2=acrobat>, 4 pages.
International Search Report and Written Opinion received for International Application No. PCT/US21/58996, filed Nov. 11, 2021; Applicant: Shifamed Holdings, LLC; dated Feb. 7, 2022; 18 pages.
International Search Report and Written Opinion received for International Application No. PCT/US22/19374, filed Mar. 8, 2022; Applicant: Shifamed Holdings, LLC; dated Jun. 24, 2022; 11 pages.
International Search Report and Written Opinion received for International Application No. PCT/US21/53836, filed Oct. 6, 2021; Applicant: Shifamed Holdings, LLC; dated Jan. 25, 2022; 20 pages.
International Search Report and Written Opinion received for International Application No. PCT/US21/47573, filed Aug. 25, 2021; Applicant: Shifamed Holdings, LLC; dated Feb. 3, 2022; 15 pages.
Kocaturk, O. et al., "Whole shaft visibility and mechanical performance for active MR catheters using copper-nitinol braided polymer tubes," Journal of Cardiovascular Magnetic Resonance. Aug. 12, 2009, vol. 11, No. 29, p. 9, col. 1, ln 5-6.
Hossain, M. et al. "In situ preparation of graphene-ZnO composites for enhanced graphite exfoliation and graphene-nylon-6 composite films," Journal of Applied Polymer Science, Dec. 5, 2016, vol. 134, No. 27, p. 8, ln 15-16.
http://www.collinsdictionary.com/dictionary/english/actuator, actuator definition and meaning, Accessed Oct. 18, 2023, 3 pages.
https://www.ahdictionary.com/word/search.html?q=actuator, American Heritage Dictionary Entry: actuator, Accessed Oct. 18, 2023, 1 page.
https://www.dictionary.com/browse/Actuator, Actuator definition & Meaning, Dictionary.com Accessed Oct. 18, 2023, 1 page.
Extended European Search Report received for Application No. 20896031.0, Applicant: Shifamed Holdings, LLC; Date of Mailing: Dec. 7, 2023; 11 pages.
Huang et al., "Shape Memory Materials," Science Direct, Materials Today, vol. 13, Sep. 1, 2010, 15 pages.
Retrieved from the Internet: URL:https://www.sciencedirect.com/science.article/pii/S1369702110701280#bib1, retrieved on Jan. 22, 2024, 1 page.
Extended European Search Report received for Application No. 20896031.0, Applicant: Shifamed Holdings, LLC; Date of Mailing: Apr. 3, 2024; 6 pages.
English translation of Japanese Office Action received for JP 2022-515509, Applicant: Shefamed Holdings, Inc., mailed on May 30, 2024, 8 pages,
Extended European Search Report received for Application No. 20896031.0, Applicant: Shifamed Holdings, LLC; Date of Mailing: Jul. 4, 2024; 11 pages.

* cited by examiner $C_A > C_C > C_B$

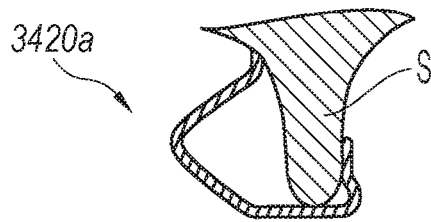
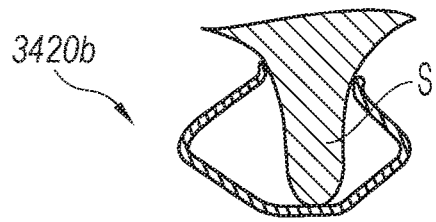
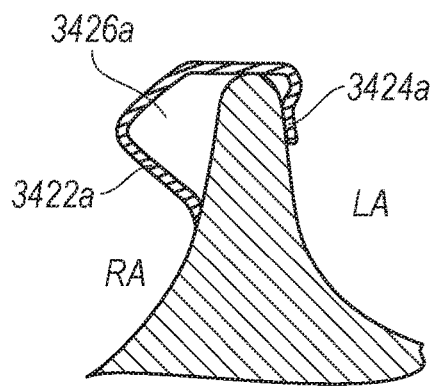
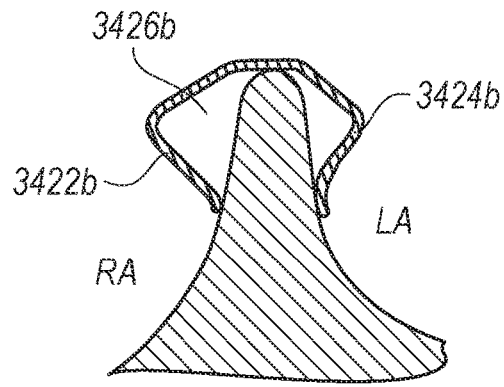
Fig. 34A
Fig. 34B
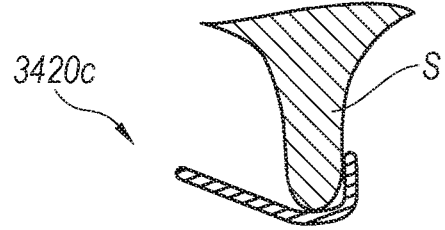
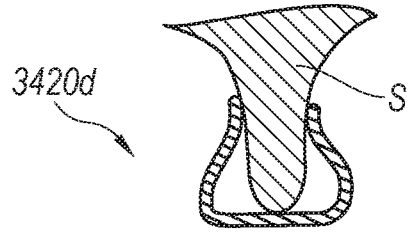
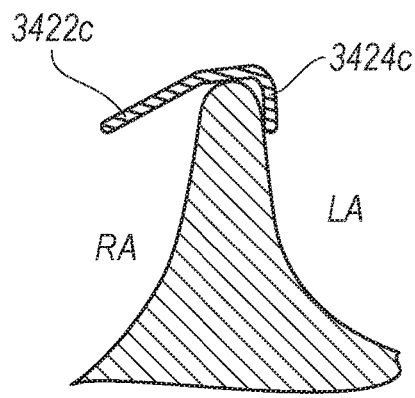
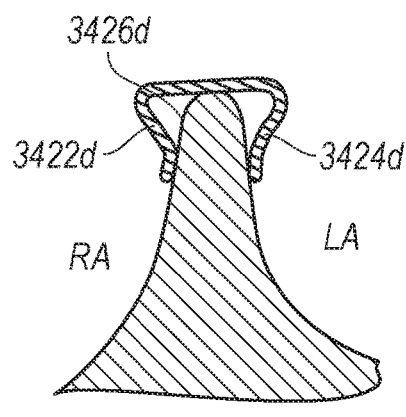
Fig. 34C
Fig. 34D

ADJUSTABLE SHUNTS AND ASSOCIATED SYSTEMS AND METHODS

CROSS-REFERENCE TO RELATED APPLICATION(S)

This application claims the benefit of the following applications:
(a) U.S. Provisional Patent App. No. 62/897,943, filed Sep. 9, 2019;
(b) U.S. Provisional Patent App. No. 62/907,696, filed Sep. 29, 2019;
(c) U.S. Provisional Patent App. No. 62/907,700, filed Sep. 29, 2019;
(d) U.S. Provisional Patent App. No. 62/907,698, filed Sep. 29, 2019;
(e) U.S. Provisional Patent App. No. 62/929,608, filed Nov. 1, 2019;
(f) U.S. Provisional Patent App. No. 62/959,792, filed Jan. 10, 2020;
(g) U.S. Provisional Patent App. No. 62/976,665, filed Feb. 14, 2020;
(h) U.S. Provisional Patent App. No. 62/977,933, filed Feb. 18, 2020;
(i) U.S. Provisional Patent App. No. 62/994,010, filed Mar. 24, 2020;
(j) U.S. Provisional Patent App. No. 63/002,050, filed Mar. 30, 2020;
(k) U.S. Provisional Patent App. No. 63/003,594, filed Apr. 1, 2020; and
(l) U.S. Provisional Patent App. No. 63/003,632, filed Apr. 1, 2020.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology generally relates to implantable medical devices and, in particular, to implantable interatrial systems and associated methods for selectively controlling blood flow between the right atrium and the left atrium of a heart.

BACKGROUND

Heart failure is a medical condition associated with the inability of the heart to effectively pump blood to the body. Heart failure affects millions of people worldwide, and may arise from multiple root causes, but is generally associated with myocardial stiffening, myocardial shape remodeling, and/or abnormal cardiovascular dynamics. Chronic heart failure is a progressive disease that worsens considerably over time. Initially, the body's autonomic nervous system adapts to heart failure by altering the sympathetic and parasympathetic balance. While these adaptations are helpful in the short-term, over a longer period of time they may serve to make the disease worse.

Heart failure (HF) is a medical term that includes both heart failure with reduced ejection fraction (HFrEF) and heart failure with preserved ejection fraction (HFpEF). The prognosis with both HFpEF and HFrEF is poor; one-year mortality is 26% and 22%, respectively, according to one epidemiology study. In spite of the high prevalence of HFpEF, there remain limited options for HFpEF patients. Pharmacological therapies have been shown to impact mortality in HFrEF patients, but there are no similarly-effective evidence-based pharmacotherapies for treating HFpEF patients. Current practice is to manage and support patients while their health continues to decline.

A common symptom among heart failure patients is elevated left atrial pressure. In the past, clinicians have treated patients with elevated left atrial pressure by creating a shunt between the left and right atria using a blade or balloon septostomy. The shunt decompresses the left atrium (LA) by relieving pressure to the right atrium (RA) and systemic veins. Over time, however, the shunt typically will close or reduce in size. More recently, percutaneous interatrial shunt devices have been developed which have been shown to effectively reduce left atrial pressure. However, these percutaneous devices often have an annular passage with a fixed diameter which fails to account for a patient's changing physiology and condition. For this reason, existing percutaneous shunt devices may have a diminishing clinical effect after a period of time. Many existing percutaneous shunt devices typically are also only available in a single size that may work well for one patient but not another. Also, sometimes the amount of shunting created during the initial procedure is later determined to be less than optimal months later. Accordingly, there is a need for improved devices, systems, and methods for treating heart failure patients, particularly those with elevated left atrial pressure.

BRIEF DESCRIPTION OF THE DRAWINGS

FIGS. 34A-34D are schematic illustrations of various anchoring scaffolds for use with adjustable interatrial shunting systems configured in accordance with select embodiments of the present technology.

DETAILED DESCRIPTION

Figure 1:
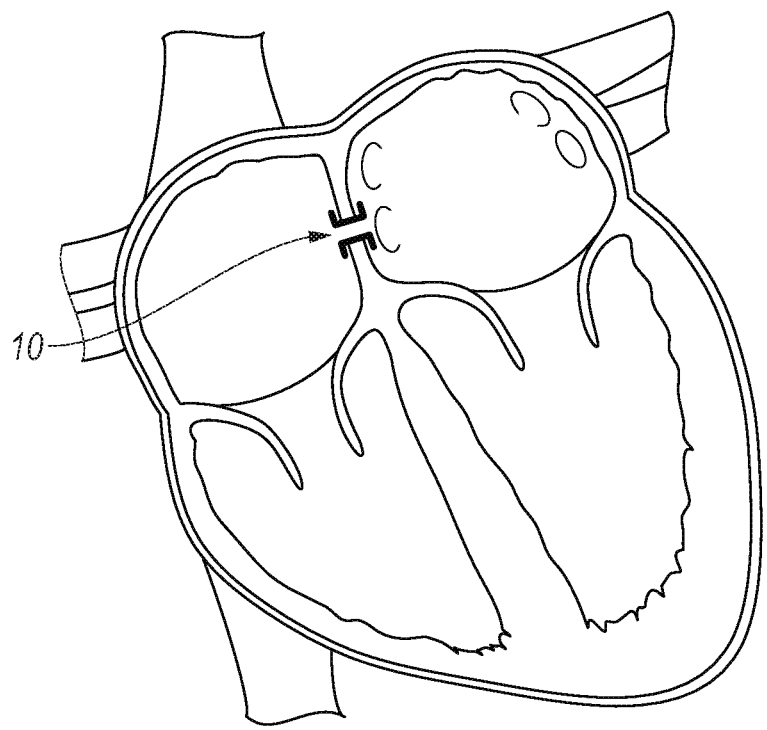
FIG. 1 is a schematic illustration of an interatrial device implanted in a heart and configured in accordance with an embodiment of the present technology.

The present technology is directed to adjustable interatrial shunting systems that selectively control blood flow between the LA and the RA of a patient. For example, in many of the embodiments disclosed herein, the adjustable interatrial devices include a shunting element having an outer surface configured to engage native tissue and an inner surface defining a lumen that enables blood to flow from the LA to the RA when the device is deployed across the septal wall. In many embodiments, the systems include an actuation assembly that can adjust a geometry of the lumen and/or a geometry of a lumen orifice to control the flow of blood through the lumen. In many of the embodiments described herein, the actuation assembly includes one or more actuation elements composed of a shape-memory material and configured to undergo a material phase transformation when heated above a transition temperature that is greater than body temperature.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims but are not described in detail with respect to FIGS. 1-35B. In various respects, the terminology used to describe shape memory behavior may adopt the conventions described in ASTM F2005 (Standard Terminology for Nickel-Titanium Shape Memory Alloys).

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "about" and "approximately" are used herein to mean the stated value plus or minus 10%.

As used herein, in various embodiments, the terms "interatrial device," "interatrial shunt device," "IAD," "IASD," "interatrial shunt," and "shunt" are used interchangeably and, in at least one configuration, refer to a shunting element that provides a blood flow between a first region (e.g., a LA of a heart) and a second region (e.g., a RA or coronary sinus of the heart) of a patient. Although described in terms of a shunt between the atria, namely the LA and the RA, one will appreciate that the technology may be applied equally to other medical devices. For example, the shunt may be positioned between other chambers and passages of the heart or other parts of the cardiovascular system. For example, any of the shunts described herein, including those referred to as "interatrial," may be nevertheless used and/or modified to shunt between the LA and the coronary sinus, or between the right pulmonary vein and the superior vena cava. Moreover, while the disclosure herein primarily describes shunting blood from the LA to the RA, the present technology can be readily adapted to shunt blood from the RA to the LA to treat certain conditions, such as pulmonary hypertension. For example, mirror images of embodiments, or in some cases identical embodiments, used to shunt blood from the LA to the RA can be used to shunt blood from the RA to the LA in certain patients. In another example, the shunt may be used to facilitate flow between an organ and organ, organ and vessel, etc. The shunt may also be used for fluids other than blood. The technologies described herein may be used for an ophthalmology shunt to flow aqueous or fluids to treat gastrointestinal disorders. The technologies described herein may also be used for controlled delivery of other fluids such as saline, drugs, or pharmacological agents.

As used herein, the term "geometry" can include the size and/or the shape of an element. Accordingly, when the present disclosure describes a change in geometry, it can refer to a change in the size of an element (e.g., moving from a smaller circle to a larger circle), a change in the shape of an element (e.g., moving from a circle to an oval), and/or a change in the shape and size of an element (e.g., moving from a smaller circle to a larger oval). In various embodiments, "geometry" refers to the relative arrangements and/or positions of elements in the respective system.

As used herein, the term "manufactured geometry" can refer a preferred geometric configuration of a shape memory component. For example, the shape memory component generally assumes the manufactured geometry in the absence of mechanical stresses or other deformations. The manufactured geometry can include an "as cut" geometry, a heat set geometry, a shape set geometry, or the like.

The headings provided herein are for convenience only and do not interpret the scope or meaning of the claimed present technology.

A. Interatrial Shunts for Treatment of Heart Failure

Heart failure can be classified into one of at least two categories based upon the ejection fraction a patient experiences: (1) HFpEF, historically referred to as diastolic heart failure or (2) HFrEF, historically referred to as systolic heart failure. One definition of HFrEF is a left ventricular ejection fraction lower than 35%-40%. Though related, the underlying pathophysiology and the treatment regimens for each heart failure classification may vary considerably. For example, while there are established pharmaceutical therapies that can help treat the symptoms of HFrEF, and at times slow or reverse the progression of the disease, there are limited available pharmaceutical therapies for HFpEF with only questionable efficacy.

In heart failure patients, abnormal function in the left ventricle (LV) leads to pressure build-up in the LA. This leads directly to higher pressures in the pulmonary venous system, which feeds the LA. Elevated pulmonary venous pressures push fluid out of capillaries and into the lungs. This fluid build-up leads to pulmonary congestion and many of the symptoms of heart failure, including shortness of breath and signs of exertion with even mild physical activity. Risk factors for HF include renal dysfunction, hypertension, hyperlipidemia, diabetes, smoking, obesity, old age, and obstructive sleep apnea. HF patients can have increased stiffness of the LV which causes a decrease in left ventricular relaxation during diastole resulting in increased pressure and inadequate filling of the ventricle. HF patients may also have an increased risk for atrial fibrillation and pulmonary hypertension, and typically have other comorbidities that can complicate treatment options.

Interatrial shunts have recently been proposed as a way to reduce elevated left atrial pressure, and this emerging class of cardiovascular therapeutic interventions has been demonstrated to have significant clinical promise. FIG. 1, for example, shows the conventional placement of a shunt in the septal wall between the LA and RA. Most conventional interatrial shunts (e.g., shunt 10) involve creating a hole or inserting an implant with a lumen into the atrial septal wall, thereby creating a fluid communication pathway between the LA and the RA. As such, elevated left atrial pressure may be partially relieved by unloading the LA into the RA. In early clinical trials, this approach has been shown to improve symptoms of heart failure.

One challenge with many conventional interatrial shunts is determining the most appropriate size and shape of the shunt lumen. A lumen that is too small may not adequately unload the LA and relieve symptoms; a lumen that is too large may overload the RA and right-heart more generally, creating new problems for the patient. Moreover, the relationship between pressure reduction and clinical outcomes and the degree of pressure reduction required for optimized outcomes is still not fully understood, in part because the pathophysiology for HFpEF (and to a lesser extent, HFrEF) is not completely understood. As such, clinicians are forced to take a best guess at selecting the appropriately sized shunt (based on limited clinical evidence) and generally cannot adjust the sizing over time. Worse, clinicians must select the size of the shunt based on general factors (e.g., the size of the patient's anatomical structures, the patient's hemodynamic measurements taken at one snapshot in time, etc.) and/or the design of available devices rather than the individual patient's health and anticipated response. With traditional devices, the clinician does not have the ability to adjust or titrate the therapy once the device is implanted, for example, in response to changing patient conditions such as progression of disease. By contrast, interatrial shunting systems configured in accordance with embodiments of the present technology allow a clinician to select the size—perioperatively or post-implant—based on the patient.

B. Shape Memory Actuation Assemblies

As provided above, the present technology is generally directed to interatrial shunting systems. Such systems include a shunting element implantable into a patient at or adjacent to a septal wall. In some embodiments, the shunting element includes a frame configured to interface with the septal wall, and a membrane coupled to the frame and defining a lumen. The shunting element (e.g., the lumen) can fluidly connect the LA and the RA of the patient to facilitate blood flow therebetween. In some embodiments, the shunting element includes and/or is operably coupled to an actuation assembly that is invasively and/or non-invasively adjustable to selectively control blood flow between the LA and the RA. In some embodiments, the systems can further include energy receiving components, energy storage components, and/or one or more sensors, among other things.

In some embodiments, an interatrial shunting system includes an actuation assembly having one or more actuation elements. As described in detail below, the actuation elements are configured to change a geometry or other characteristic of a lumen extending through the shunting element to alter the flow of fluid through the lumen. For example, in some embodiments the actuation elements can selectively change a size and/or shape of the lumen to alter the flow of fluid through the lumen. In particular, the actuation elements can be configured to selectively increase a diameter of the lumen (or a portion of the lumen) and/or selectively decrease a diameter of the lumen (or a portion of the lumen) in response to an input. Throughout the present disclosure, reference to adjusting a diameter (e.g., increasing a diameter, decreasing a diameter, etc.) can refer to adjusting a hydraulic or equivalent diameter of the lumen, adjusting a diameter at a particular location of the lumen, and/or adjusting a diameter along a length (e.g., a full length) of the lumen. In other embodiments, the actuation elements are configured to otherwise affect a shape or geometry of the lumen. In some embodiments, the actuation elements are configured to adjust a geometry (e.g., a cross-sectional area, a diameter, a dimension) of an orifice or aperture of the lumen (e.g., an inflow orifice or an outflow orifice positioned within or adjacent the LA or the RA, respectively). For example, the actuation elements can be configured to selectively increase a cross-sectional area of the outflow orifice in the RA and/or selectively decrease a cross-sectional area of an outflow orifice in the RA in response to an input. In some embodiments, the actuation elements can selectively change a geometry of both a lumen and a lumen orifice.

The actuation elements can therefore be coupled to the shunting element and/or can be included within the shunting element to drive the geometry change in the lumen and/or orifice. In some embodiments the actuation elements are part of the shunting element and at least partially define the lumen. For example, the actuation elements can be disposed within or otherwise coupled to a membrane that at least partially defines a lumen of the shunting element. In other embodiments, the actuation elements are spaced apart from but are operably coupled to the shunting element.

In some embodiments, at least a portion of the actuation elements can comprise a shape memory element. The shape memory portion can include a shape memory metal or alloy such as nitinol, a shape memory polymer, a pH-based shape memory material, or any other suitable material configured to move or otherwise adjust in response to an input. For example, the actuation elements can include one or more nitinol elements that are configured to change shape in response to applied heat that raises the nitinol elements' temperature above the material's transformation temperature. In such embodiments, the actuation elements can be selectively actuated by applying energy to heat the nitinol element(s). In some embodiments, the shape memory materials may extend around at least a portion of the lumen. In some embodiments, the shape memory materials may extend around at least a portion of a lumen orifice. In some embodiments, the shape memory materials may be separate from but operably coupled to the lumen and/or the lumen orifice.

Movement of an actuation element can be generated through externally-applied input and/or the use of a shape memory effect (e.g., as driven by a change in temperature). The shape memory effect enables deformations that have altered an element from its original or preferred shape-set geometric configuration (also referred to herein as "manufactured geometry" or "heat set geometry") to be largely or entirely reversed during operation of the actuation elements. For example, sufficient heating can reverse deformations by producing a change in material state (e.g., phase change) in the actuator material, inducing a temporary elevated internal stress that promotes a shape change toward the original shape-set geometric configuration. For a shape memory alloy, the change in state can be from a martensitic phase (alternatively, R-phase) at the lower temperature to an austenitic phase (alternatively, R-phase) at the higher temperature. For a shape memory polymer, the change in state can be via a glass transition temperature or a melting temperature. The change in material state can recover deformation(s) of the material—for example, deformation with respect to its manufactured geometry—without any externally applied stress to the actuator element. That is, a deformation that is present in the material at a first temperature (e.g., body temperature) can be recovered and/or altered by raising the material to a second (e.g., higher) temperature. Upon cooling (and re-changing state, e.g., back to a martensitic phase), the actuator element may approximately retain its manufactured geometry. However, with the material in this relatively cooler-temperature condition it may require a lower force or stress to thermoelastically deform the material, and any subsequently applied external stress can cause the actuator element to once again deform away from the manufactured geometry.

The shape memory alloy actuation elements can be processed such that a transition temperature at which the change in state occurs (e.g., the austenite start temperature, the austenite final temperature, etc.) is above a threshold temperature (e.g., body temperature). For example, the transition temperature can be set to be about 40 deg. C., about 45 deg. C., about 50 deg. C., about 55 deg. C., about 60 deg. C., or another higher or lower temperature. In some embodiments, the actuator material is heated from body temperature to a temperature above the austenite start temperature (or alternatively above the R-phase start temperature) such that an upper plateau stress (e.g., "UPS_body temperature") of the material in a first state (e.g., thermoelastic martensitic phase, or thermoelastic R-phase at body temperature) is lower than an upper plateau stress (e.g., "UPS_actuated temperature") of the material in a heated state (e.g., superelastic state), which achieves partial or full free recovery. For example, the actuator material can be heated such that UPS_actuated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase at body temperature") is lower than a lower plateau stress (e.g., "LPS") of the material in a heated state (e.g., superelastic state), which achieves partial or full free recovery. For example, the actuator material can be constructed such that LPS_activated temperature>UPS_body temperature. In some embodiments, the actuator material is heated from body temperature to a temperature above the austenite start temperature (or alternatively above the R-phase start temperature) such that an upper plateau stress of the material in a first state (e.g., thermoelastic martensite or thermoelastic R-phase) is higher than a lower plateau stress of the material in a heated state, which achieves partial free recovery. For example, the actuator material can be constructed such that LPS_activated temperature<UPS_body temperature.

In some embodiments, the actuation assembly is formed by a coupling of at least two actuation elements (e.g., that have differing manufactured geometries) to form a composite actuation element (which can also be referred to as the "actuation assembly"). In some embodiments, at least one of the elements comprising the composite actuation element is a shape memory element. In some embodiments, both the elements comprising the composite actuation element are shape memory elements. In some embodiments, the coupling is performed with at least one actuation element in a thermoelastically deformable (e.g., thermoelastic martensitic or thermoelastic R-phase) state at the implantation temperature. In some embodiments, the coupling is performed with at least one actuation element(s) in a superelastic state. In some embodiments the flow control element comprises an expandable element or a contractile element whose deformation may be achieved via the application of a force (e.g., balloon expansion) at a lower temperature (e.g., body temperature) and/or via the application of a heat (e.g., electrical resistive heating) at a higher temperature (e.g., at a temperature at or above the austenite start or R-phase start temperature). In some embodiments, a shape memory component is constructed in a manner comprising a geometry (e.g., a cross-sectional area, a diameter, a length, a radius of curvature, or a circumference). In some embodiments, at least two actuation elements have geometric configurations (e.g., diameters) $D_{A0}$ and $D_{B0}$, where $D_{A0} > D_{B0}$. In some embodiments, the actuation assembly is formed of at least two actuation elements that have been constructed in substantially the same geometric configuration (e.g., $D_{A0} = D_{B0}$). The flow control element can be assembled such that, prior to or upon introduction into the patient (i.e., implantation), at least one of two or more coupled actuation elements are deformed with respect to their original geometric configuration (e.g., such that $D_{A1} \neq D_{A0}$, and/or $D_{B1} \neq D_{B0}$). In some embodiments, at least two coupled actuation elements can be deformed prior to or upon implantation such that a geometry (e.g. a diameter) of the first actuation element is smaller (e.g., compressed) with respect to its original configuration (e.g., $D_{A1} < D_{A0}$), and that a geometry (e.g., a diameter) of the second actuation element is larger (e.g., expanded) with respect to its original configuration (e.g., $D_{B1} > D_{B0}$). Thermoelastic deformation of the actuation elements to a desired configuration can occur with the shape memory components in a first (e.g., martensitic) material state. At a given temperature, the coupled and deformed actuation elements can (e.g., at equilibrium) form a composite geometry (e.g., cross-sectional area) that has a dimension that differs from either of the shape set configurations of the first and second actuation elements. For example, the composite geometry (e.g., diameter, $D_{C0}$) of the flow control element can be between the shape set configurations of the first and second actuation elements (e.g., $D_{A0} > D_{C0} > D_{B0}$).

The actuation assembly can be formed such that, in operation (e.g., during actuation of an actuation element), its composite geometry and/or dimension is altered (e.g., such that $D_{C1} \neq D_{C0}$). The flow control element can cause a change in an overall dimension of a fluid path (e.g., lumen). For example, the overall dimension can comprise an overall cross-sectional area, a diameter, a length, a circumference, or another attribute. In an embodiment, the first and second actuation elements that are coupled to form a composite element are arranged such that a movement of the first actuation element (e.g., via thermoelastic martensitic transformation to achieve free recovery) is accompanied by (e.g., causes) a complementary full or partial movement of the second actuation element—e.g., by inducing thermoelastic recoverable deformation of a relatively malleable second actuation element while it is at least partially in a thermoelastic martensitic (or thermoelastic R-phase) material state. (For brevity herein, in various embodiments the term "relatively malleable" is used to describe a material state where a component requires a lower force or stress to deform it when compared to another component, or when compared to the same component in a different material state). The movement(s) can comprise a compression (e.g., contraction) or an expansion (e.g., opening) of the composite element. The movement can comprise a deflection or a deformation, which may be fully- or partially-recoverable. The complementary movement of the second actuation element can comprise movement that is (a) along a same axis, (b) about a same axis, or (c) along a same dimension (e.g., radially) as the primary movement of the first actuation element, or another movement. In some embodiments, actuation of the first actuation element from a compressed geometry toward a larger shape set configuration geometry expands the composite geometry via the coupling of the first actuation element with the second actuation element. In some embodiments, this expansion places the composite geometry at a size that is larger than its equilibrium, but smaller than that of the original configuration of the first actuation element (e.g., $D_{A0} > D_{C1} > D_{C0}$). In some embodiments, actuation of the second actuation element from an expanded geometry toward a smaller original configuration geometry contracts (e.g., compresses) the composite geometry, via the coupling of the second actuation element with the first actuation element. In some embodiments, this compression places the composite geometry at a size that is smaller than its equilibrium, but larger than that of the original configuration of the second actuation element (e.g., $D_{C0} > D_{C1} > D_{B0}$).

In a method of operation of an embodiment of the present technology, selective heating of the first actuation element of the flow control element causes it to actuate toward its original geometric configuration (e.g., from $D_{A1}$ toward $D_{A0}$). Actuation can be caused by raising a temperature of the first actuation element at least to a threshold transition temperature. The transition temperature can be a phase transition temperature (e.g., R-phase start temperature, austenite start temperature, R-phase finish temperature, or austenite finish temperature). Raising temperatures to or beyond the transition temperature can induce a change of the material from a first phase (e.g., martensite or R-phase) to a second phase (e.g., R-phase or austenitic). During actuation of the first actuation element, the second actuation element is generally not heated (e.g., remains at or near body temperature), and therefore remains in a first (e.g., martensitic or R-phase) material state. As such, the second actuation element may be relatively malleable in this material state, thereby allowing the elevated forces from partial or complete free recovery of the first actuation element to drive a change in shape and/or geometry of the coupled second element (e.g., a compressive or contracting movement). Due to the relatively malleable nature of the second actuation element in this material state, it may largely retain this induced shape and/or geometry change without substantial recovery (e.g., generally only linear elastic recovery).

Following the completion of a heating period of the first actuation element, the first actuation element cools and transforms to the lower-temperature phase (e.g., martensite or R-phase), in which it is relatively malleable. To reverse the induced change in the configuration of the composite flow control element (e.g., its geometry), the second actuation element can be heated to or beyond its transition temperature to induce a phase change (e.g., to R-phase or austenite) and, consequently, partial or full free recovery in geometry towards its original geometric configuration (e.g., from $D_{B1}$ toward $D_{B0}$). As the first actuation element is not selectively heated and relatively malleable during this time, the return of the second actuation element to its original geometric configuration causes the composite geometry of the flow control element to change (e.g., to reduce in size). In some embodiments, the geometry of flow control element can be repeatably toggled (e.g., between expanded and contracted) by repeating the foregoing operations. The heating of an actuation element can be accomplished via application of incident energy (e.g., via a laser, resistive heating, or inductive coupling). The source of the incident energy may be either internal (e.g., delivered via a catheter) or external to the patient (e.g., non-invasively delivered RF energy).

In some embodiments, the first actuation element can be thermally insulated and/or electrically isolated from the second actuation element. Further, in some embodiments, the first and second actuation elements can be thermally insulated and/or electrically isolated from tissue and blood adjacent the implant site.

Accordingly, the present technology provides actuation assemblies having two or more shape memory material actuation elements that are manufactured into different geometric configurations and coupled together. In additional embodiments, the geometric configurations may be similar, with two or more actuation elements working in an antagonistic or complementary fashion to manipulate a geometric feature of an actuation assembly. In some embodiments, the actuation elements may be manufactured with similar chemical composition and/or thermo-mechanical post-treatments, i.e., they may have similar phase transition temperature profiles. In further embodiments, an actuation assembly may contain two or more actuation elements that have been manufactured with differing chemical composition and/or thermo-mechanical post-treatments such that they do not share identical phase transition temperature profiles. In operation of such an embodiment, energy may be applied to an entire composite actuation assembly (e.g., comprised of two or more individual actuation elements) and not all individual actuation elements may similarly deform toward their original geometric configurations. For example, a first actuation element may have a first transformation temperature profile, and a second actuation element may have a second, higher transformation temperature profile. Heating the composite actuation assembly to a temperature above the first, but below the second, transformation temperature (e.g. R-phase start, austenite start, R-phase finish, or austenite finish temperature) will induce a more substantial thermoelastic recovery in the first actuation element than the second actuation element. This will create a first geometric alteration of an actuation assembly. Heating the composite actuation assembly to a temperature above both the first and second transformation temperatures (e.g., R-phase start, austenite start, R-phase finish, or austenite finish temperature) may induce a meaningful thermoelastic recovery and actuation in both actuation elements. This will create a second geometric alteration of an actuation assembly which may differ from the first geometric alteration.

In embodiments, the geometric changes of an actuation assembly may be toggled between a number of states in response to the actuation of one or more actuation elements. In embodiments, reversal of a geometry change (e.g., making a lumen larger after it had previously been made smaller) is accomplished by utilizing multiple shape memory actuation elements that are coupled to work in an antagonistic manner. In embodiments, other mechanisms (e.g., springs, ratchets, elastic materials such as silicone, etc.) may be additionally or alternatively be utilized in conjunction with actuation elements to provide complementary or counter forces to those actuation elements, thereby affecting a geometry change of an actuation assembly.

In embodiments, the actuation assembly may be thermoelastically expanded to a cross-sectional geometry that is larger than the largest actuation element in the composite structure. For example, one actuation element may have an initial diameter, $D_{A0}$, and another actuation element may have an initial diameter, $D_{B0}$, such that $D_{A0} > D_{B0}$. In such a composite system, the actuation of either actuation element drives the composite actuation assembly to a diameter within the range $D_{B0}$-$D_{A0}$ (inclusive). If, for example, a physician expands (e.g., via the use of a balloon) the actuation assembly to a diameter greater than $D_{A0}$ to enable the crossing of a tool (e.g., during deployment of a transcatheter mitral valve), the lumen of the actuation assembly may later be thermoelastically recovered by actuating either actuation element (e.g., by the application of heat) to drive the recovery of the diameter of the actuation assembly to the original range $D_{B0}$-$D_{A0}$. In various embodiments, the actuation assembly is expanded to a diameter greater than $D_{A0}$ to enable the crossing of a catheter, for example a diagnostic catheter or for a therapeutic. In embodiments, plastic deformation of either (or both) actuation elements may result from the expansion to a lumen greater than $D_{A0}$. Consequently, the achievable actuatable lumen range may shift to $D_{B1}$-$D_{A1}$ where $D_{B1} > D_{B0}$ and $D_{A1} > D_{A0}$ accounting for the permanent plastic deformation.

C. Shunting Assemblies with Adjustable Flow Lumens

The present technology provides interatrial shunting assemblies with adjustable flow lumens. For example, FIGS. 2A-2F illustrate an adjustable interatrial shunting system 200 ("system 200") configured in accordance with select embodiments of the present technology. As one skilled in the art will appreciate, FIGS. 2A-2F are provided merely to demonstrate the adjustable nature of the shunting systems described herein. Additional details of the various components of the present technology are described in greater detail with reference to specific embodiments in FIGS. 3A-35B.

Figure 2A:
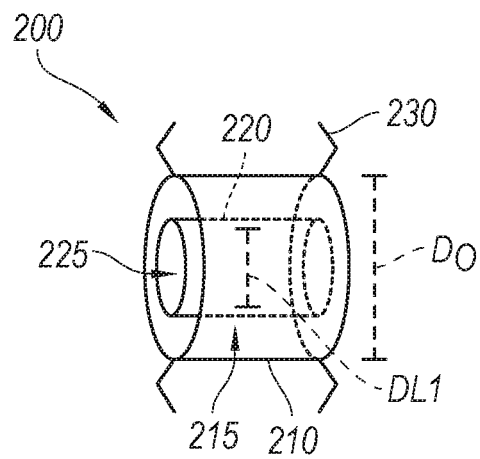
FIGS. 2A-2F are a series of schematic illustrations depicting an adjustable interatrial shunting assembly configured in accordance with select embodiments of the present technology.
Figure 2B:
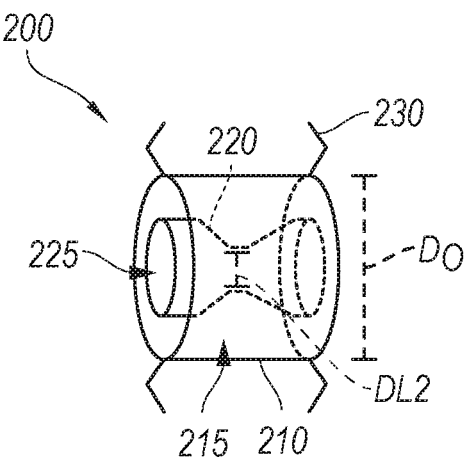
Figure 2C:
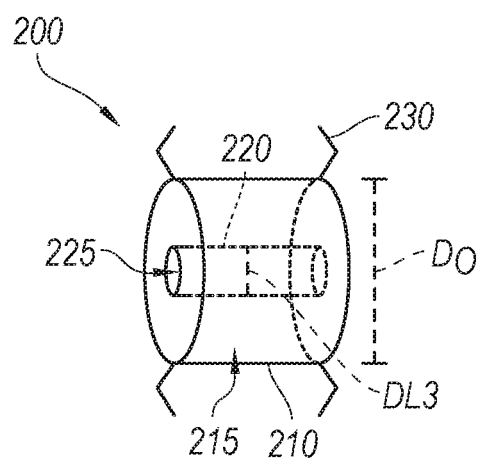

Referring first to FIG. 2A, the system 200 includes a frame 210 and anchors 230 extending from the frame 210. The system 200 further includes a shunting element 215 composed of a membrane 220 defining a lumen 225 extending therethrough. As discussed below, the lumen 225 is configured to fluidly connect the LA and the RA to shunt blood therebetween when the shunt system 200 is implanted across a septal wall S within a heart of a patient. The lumen 225 is shown in FIG. 2A in a first configuration in which it has a first diameter $D_{L1}$. As illustrated, the lumen 225 can have a generally constant diameter along its entire length or substantially its entire length in the first configuration.

The geometry of the lumen 225 can be adjusted to change the flow of blood therethrough. In some embodiments, the diameter at a particular location of the lumen 225 is adjusted. For example, referring to FIG. 2B, the diameter of the lumen 225 is decreased in a central portion of the lumen 225 relative to the first configuration shown in FIG. 2A to assume an hourglass-shaped configuration. The diameter of the lumen at the narrowest portion of the hourglass is $D_{L2}$, which is generally less than the first diameter $D_{L1}$.

In other embodiments, the diameter of the lumen 225 is adjusted along its entire length. For example, referring to FIG. 2C, the diameter of the lumen 225 is decreased along its entire axial length relative to the first configuration shown in FIG. 2A, thereby maintaining a generally cylindrical shape but having a second configuration with a smaller diameter than the first configuration. The diameter of the lumen 225, which is generally constant along its length, is $D_{L3}$, which is generally less than the first diameter $D_{L1}$ and can be the same as or different than the diameter $D_{L2}$. The geometry of the lumen 225 can be adjusted in other manners as well. For example, in other embodiments, the diameter of the lumen 225 remains generally the same, but the diameter of one or more lumen orifices is decreased.

Figure 2D:
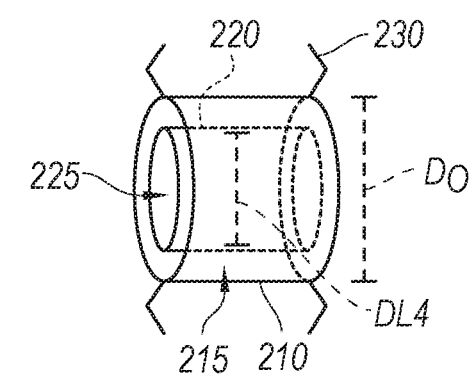

In some embodiments, the geometry of the lumen 225 can be adjusted to increase the flow of blood therethrough. For example, the diameter of the lumen 225 can be increased. As shown in FIG. 2D, the diameter of the lumen 225 has been increased to a diameter $D_{L4}$, which is greater than the first diameter $D_{L1}$. Although FIG. 2D illustrates the lumen 225 has having a generally constant diameter along its entire axial length, the lumen 225 may alternatively have an inverted hourglass shape (e.g., the diameter of the lumen 225 at a central portion is greater than a diameter of the lumen orifices).

Figure 2E:
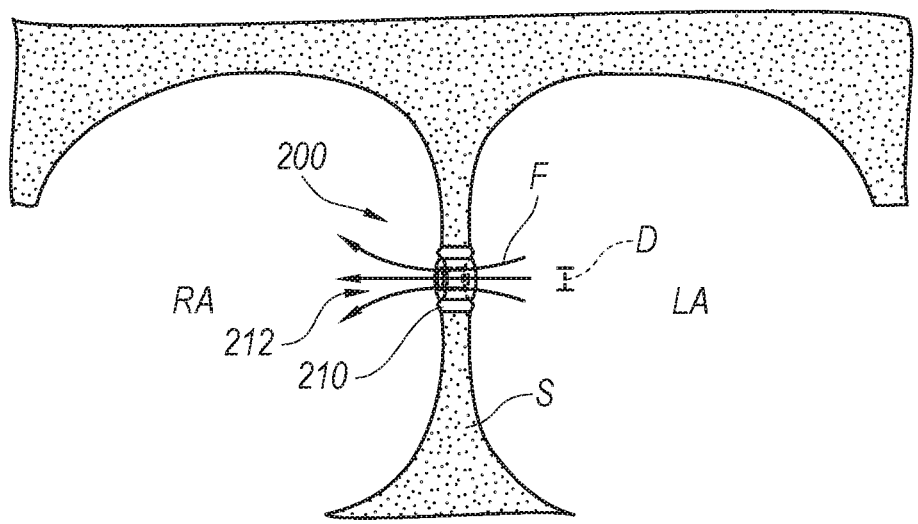
Figure 2F:
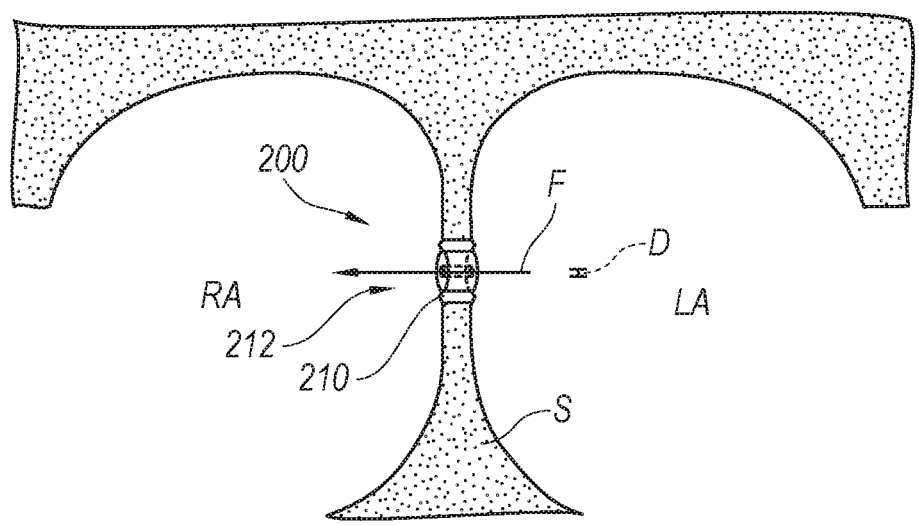

As shown in FIG. 2E, when the system 200 is implanted across a septal wall S in the first configuration (e.g., the configuration shown in FIG. 2A), the lumen 225 enables a first amount (e.g., rate, volume, etc.) of blood to flow between the LA and the RA. FIG. 2F illustrates the system 200 implanted across the septal wall S in the second configuration (i.e., the configuration shown in FIG. 2C). Relative to the first configuration (i.e., the configuration shown in FIG. 2A), the second configuration provides reduced blood flow between the LA and the RA. As one skilled in the art can appreciate, in some embodiments the system 200 can assume the hour-glass configuration (i.e., the configuration shown in FIG. 2B) to reduce blood flow. Likewise, the system 200 can assume the configuration shown in FIG. 2D to increase the flow of blood between the LA and the RA.

The present technology thus provides adjustable interatrial shunting systems that can adjust a geometry of a flow lumen and/or lumen orifice to change the flow of blood therethrough. In particular, FIGS. 3A-23C illustrate adjustments to the lumen geometry, and FIGS. 24-32 illustrate adjustments to orifice geometry. The systems can be adjusted using a variety of actuation mechanisms, which will be described in greater detail below.

i. Stent-Like Actuation Assemblies

Figure 3A:
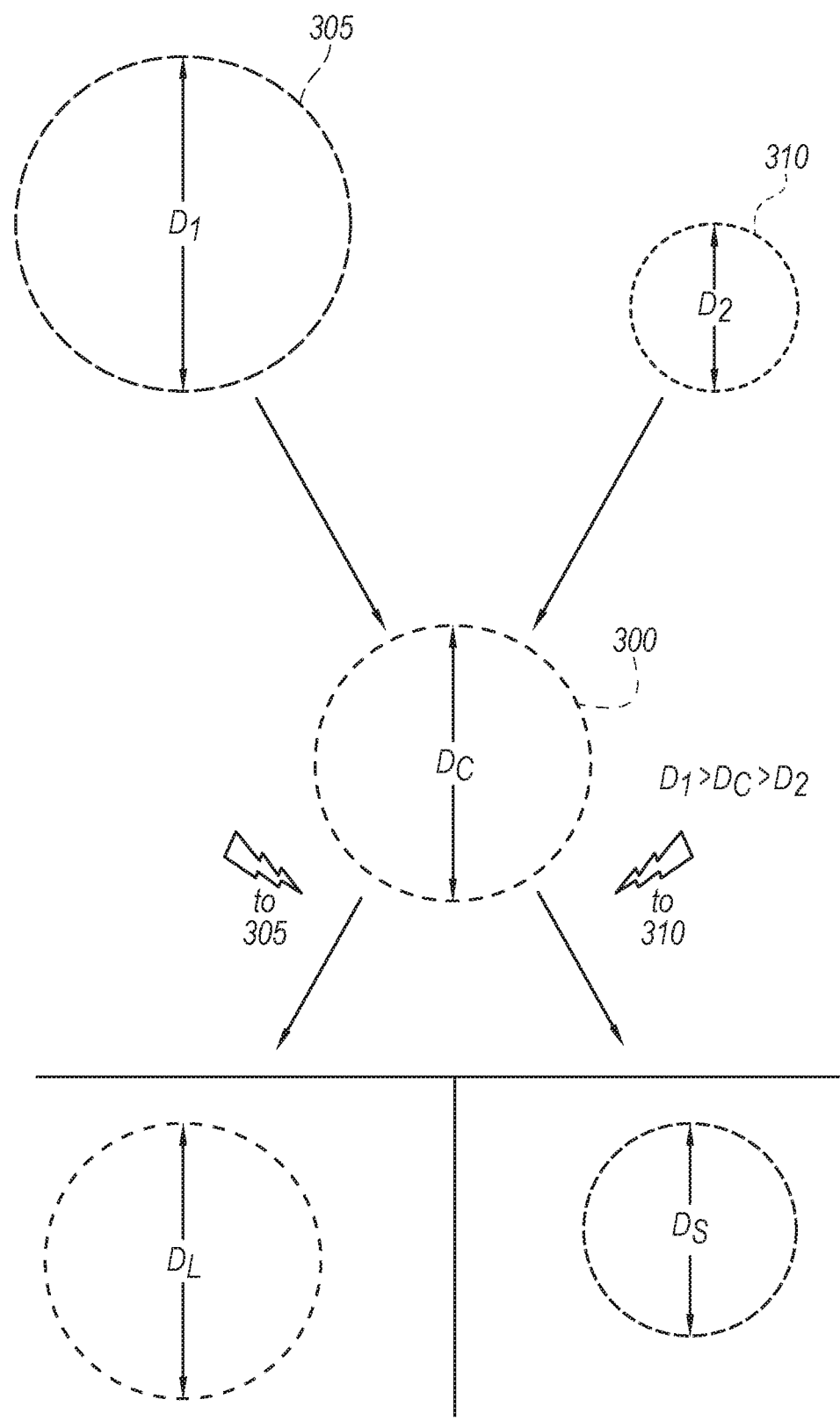
FIGS. 3A and 3B are a schematic illustrations of coupled actuation element members that form a part of an interatrial shunting assembly configured in accordance with select embodiments of the present technology.

FIG. 3A is a schematic illustration of coupled actuation elements (a first actuation element 305 and a second actuation element 310) that form part of an interatrial shunting device configured in accordance with an embodiment of the present technology. The first actuation element 305 can have a different original geometric configuration (e.g., $D_1$) than that of the second actuation element 310 ($D_2$). As provided above, $D_1$ can refer to a hydraulic or equivalent diameter of the first actuation element 305, a diameter of the first actuation element 305 at a specific location (e.g., an orifice of the lumen, a centerpoint of the lumen, etc.), a diameter of the first actuation element 305 along a portion of its length, and/or another dimension. Likewise, $D_2$ can refer to a hydraulic or equivalent diameter of the second actuation element 310, a diameter of the second actuation element 310 at a specific location, a diameter of the second actuation element 310 along a portion of its length, and/or another dimension. The first and second actuation elements 305, 310 may be coupled together to form an actuation assembly 300. Direct coupling of the at least two actuation elements can be accomplished via sutures, adhesives/glue, crimps/rivets, an interference fit, welds/solder, or other techniques known to those skilled in the art. Indirect coupling of at least two actuation elements can be accomplish via direct coupling of each actuation element to a common intermediate element. Following assembly, the actuation assembly 300 can, at a first temperature (e.g., room temperature, body temperature, etc.) have a geometry that is at an equilibrium state between the original geometric configurations of the individual actuation elements (e.g., $D_1 > D_C > D_2$). Actuation of the first actuation element 305 causes the flow control element to assume a geometry ($D_L$) that approaches the original geometric configuration of the first actuation element. For example, actuation of the first actuation element causes the geometry of the flow control element to increase (e.g., $D_L > D_C$). Actuation of the second actuation element 310 causes the flow control element to assume a second geometry ($D_S$) that approaches the original geometric configuration of the second actuation element ($D_2$). For example, actuation of the second actuation element causes the geometry of the flow control element to decrease (e.g., $D_S < D_C$).

In some embodiments, at least one actuation element comprises an insulative element. For example, an actuation element can be coated with electrically- and/or thermally-insulative material. In some embodiments, the insulative element is flexible. The insulative element can comprise a polyimide (e.g., Kapton®), a synthetic polymer (e.g., polytetrafluoroethylene (PTFE) or expanded polytetrafluoroethylene (ePTFE)), thin ceramic coating (e.g., $TiO_x$), or a urethane (e.g., ChronoFlex®), or another suitable material known to those skilled in the art. Polymeric insulative elements can have a dimension (e.g., coating thickness) that is, for example, about 50 microns, about 75 microns, about 100 microns, about 150 microns, about 300 microns, or about 1 millimeter. Ceramic insulative elements can have dimensions (e.g., layer thickness) that is, for example, about 5 nm, about 10 nm, about 100 nm, about 200 nm, about 300 nm, about 400 nm, or about 500 nm. The insulative element can have a dimension that is greater than, less than, or between any of the aforementioned dimensions.

Figure 3B:
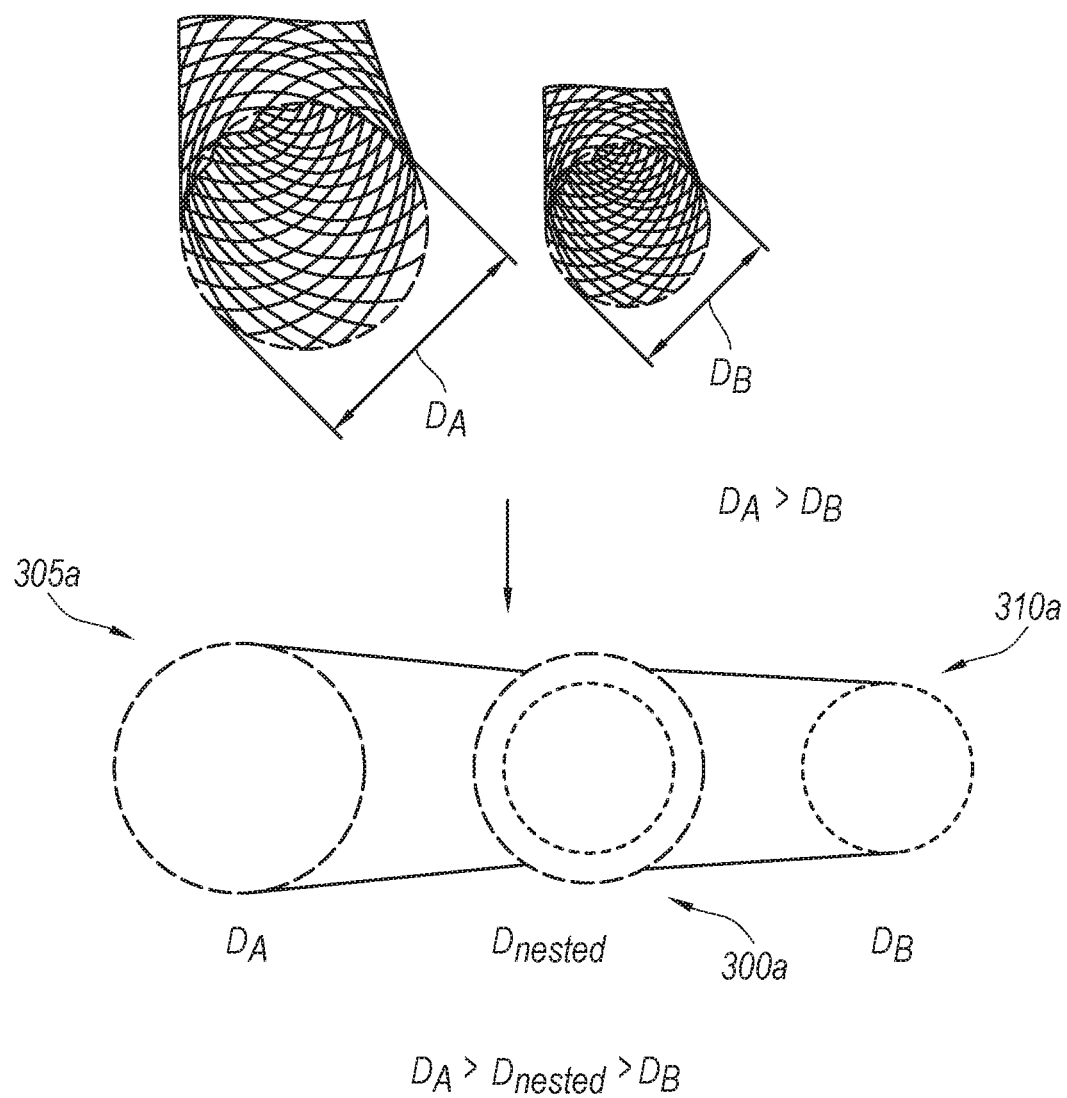

FIG. 3B is a schematic illustration of coupled actuation (elements that form a part of an interatrial shunting device configured in accordance with an embodiment of the present technology. In the example of FIG. 3B, the actuation elements are coupled by nesting one inside of the other (e.g., nesting the element with the larger original geometric configuration within the element with the smaller original geometric configuration). In some embodiments, first and second actuators comprise elongate members (e.g., stents, scaffolds, etc.). A geometry (e.g., cross-sectional area) of the elongate members can be constructed to have different sized configurations. For example, a first member can be manufactured to have a larger cross-sectional diameter ($D_A$) than the cross-sectional diameter of a second member ($D_B$). To form an adjustable composite element (e.g., a flow control element or a portion thereof), a larger member 305a can be deformed and positioned (e.g., compressed) within a smaller member 310a. The coupling of the first and second members can form a nested arrangement 300a. In some embodiments, a nested arrangement comprises a coaxial or concentric arrangement of a plurality of stents. The geometry of the flow control element can have an equilibrium geometry (e.g., $D_{nested}$, such that $D_A > D_{nested} > D_B$). When the larger member 305a is actuated (e.g., heated) to induce a thermoelastic recovery intended to return it toward its original geometric configuration ($D_A$), the composite actuation assembly 300a increases in size, for example to a diameter larger than $D_{nested}$ and less than or equal to $D_A$. Likewise, when the smaller member 310a is actuated (e.g., heated) to induce thermoelastic recovery to return it toward its original geometric configuration ($D_B$), the composite flow control element 300a decreases in size, for example to a diameter smaller than $D_{nested}$ and greater than or equal to $D_B$. In some embodiments, improvement in a granularity of geometry modification is achieved by a coupling more than two actuation elements into a composite structure (e.g., a plurality of stents nested within one another). Actuating any one (or any combination) of the elements (e.g., stents) will drive the composite structure to a different pre-determined geometric configuration. In an embodiment, the actuation elements can be assembled in progression (e.g., largest original geometric configuration to smallest) from the inside to the outside of the composite structure. For example, the assembly can be such that the smallest original geometric configuration is the outermost actuation member in the composite structure. When the outermost element (e.g., the element with the smallest shape set geometry) is actuated, it applies a force to the composite structure that decreases it to its minimum geometric configuration. This may be accomplished since the non-actuated (e.g., unheated) elements may be in a relatively malleable state and as such experience a complementary movement as a result of the elevated forces applied by the actuated element. When an intermediate element is actuated, the composite structure achieves an intermediate geometric configuration, with the non-actuated (i.e., slave) elements being driven by the actuated element to move in a complementary matter to the actuated element. When an innermost element is actuated, the composite structure may achieve a maximum geometric configuration, with the non-actuated (i.e., slave) elements being driven by the actuated element to move in a complementary matter to the actuated element. In some embodiments, at least two actuation elements are actuated substantially simultaneously. In some embodiments, simultaneous actuation of at least two actuation elements produces further granularity and/or precision in flow control element movement with respect to actuation of a single actuation element.

Figures 4A, 4B:
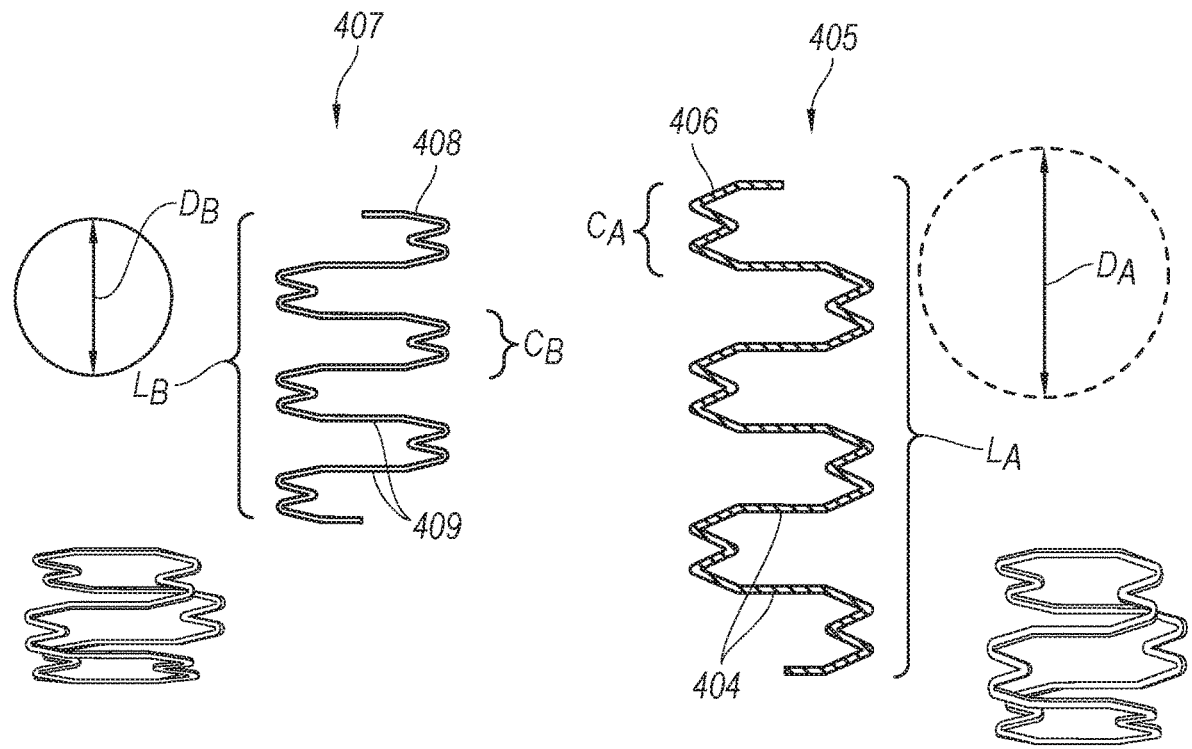
FIGS. 4A-4C are schematic illustrations of an interatrial shunting system having nested actuation elements and configured in accordance with select embodiment of the present technology.
Figure 4C:
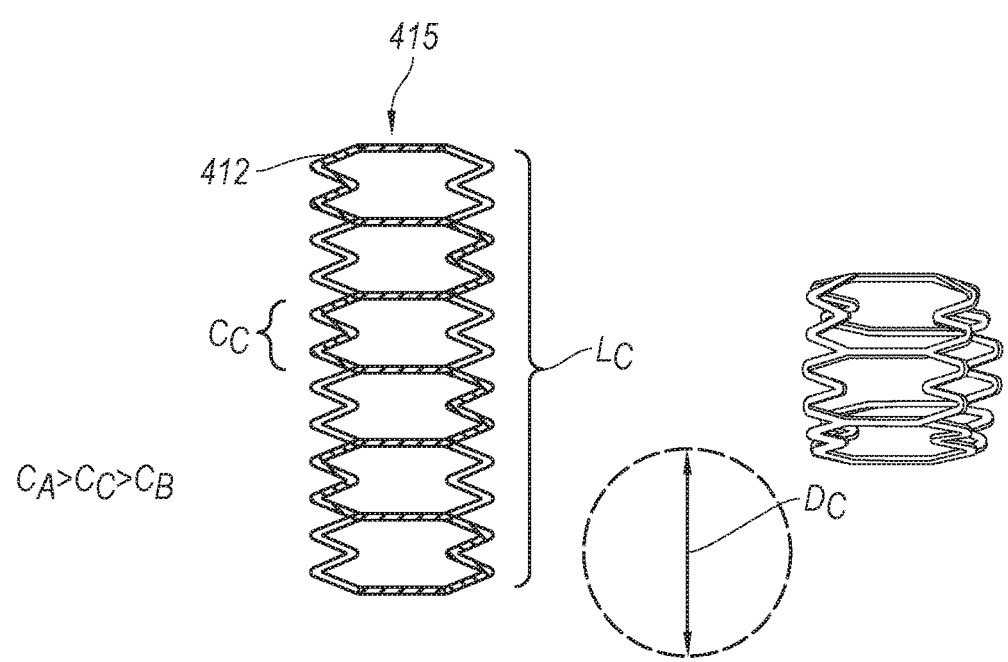

FIGS. 4A-4C are schematic illustrations of coupled actuation element portions that form a part of an interatrial shunting device configured in accordance with an embodiment of the present technology. The individual actuation elements can be comprised of a shape memory material and be manufactured to have similar overall shapes, patterns, and/or dimensions. Referring FIGS. 4A-4C together, the actuation elements (e.g., stents) can be formed by wire forming, laser cutting, or another suitable process. A first actuation element 405 can be manufactured to a first (original) geometric configuration, and may comprise a series of repeating cells 406 having a first cell size $C_A$ and a total (e.g., cumulative) unwrapped length $L_A$ (e.g., circumference when constructed in a cylindrical shape). When wrapped about a central axis, first actuation element 405 can have a geometric configuration with a first cross-sectional diameter $D_A$. A second actuation element 407 can be manufactured to a second geometric configuration, and may comprise a series of repeating cells 408 having a second cell size $C_B$ and a total (e.g., cumulative) unwrapped length $L_B$ (e.g., circumference when constructed in a cylindrical shape). When wrapped about a central axis, second actuation element 407 has a geometric configuration with a second cross-sectional diameter $D_B$. In some embodiments, the first and second actuation elements may be constructed to different geometric configurations, for example $C_A > C_B$, $L_A > L_B$, $D_A > D_B$, etc. In embodiments, the first and second actuation elements 405, 407 have similar patterns to facilitate direct coupling, or features to promote indirect coupling through one or more intermediate members.

The first and second actuation elements 405, 407 can comprise segments (404 and 409) that are configured to enable coupling to another actuation element or to another component of a device. In some embodiments, the portions for coupling comprise longitudinal struts. In embodiments, the segments for coupling can be maintained at a substantially fixed dimension (e.g., length) prior to and following construction of the actuation elements. In embodiments, two or more actuation elements may be coupled together by suture, adhesives/glue, rivets/crimps, welds, an enclosing sleeve, or via other methods. In some embodiments, at least one of the coupling portions (e.g., 404 or 409) comprises an insulative element. In some embodiments, the insulative element provides electrical isolation and/or thermal isolation between coupled actuation elements. As best seen in FIG. 4C, coupling two or more actuation elements can create a composite element 415 that, at a given temperature (e.g., room temperature), has an equilibrium geometric configuration that features at least one series of repeating cells 412 having a composite cell size $C_C$ and has a total (e.g. cumulative) unwrapped length $L_C$. When wrapped about a central axis, the composite actuation element 415 has a geometric configuration with a composite cross-sectional diameter $D_C$. In embodiments, this wrapped composite actuation element may serve as a flow control element that forms part of an interatrial shunting device configured in accordance with an embodiment of the present technology. In embodiments that feature one relatively larger actuation element and one relatively smaller actuation element, the geometry of the composite element may be characterized by sizes that fall between the values of the individual elements (i.e., $C_A > C_C > C_B$; $D_A > D_C > D_B$; $L_A > L_C > L_B$).

One or more elements of the composite flow control element may be actuated to impart a geometry change of the composite structure. For example, actuation of the larger element may cause an increase and/or expansion of a geometric characteristic of the composite element such that it attains a new cross-sectional diameter $D_{N1}$, where $D_{N1} > D_C$. Conversely, actuation of the smaller element may cause a decrease/contraction of a geometric characteristic of the composite element such that it attains a new cross-sectional diameter $D_{N2}$, where $D_{N2} < D_C$.

Figure 5A:
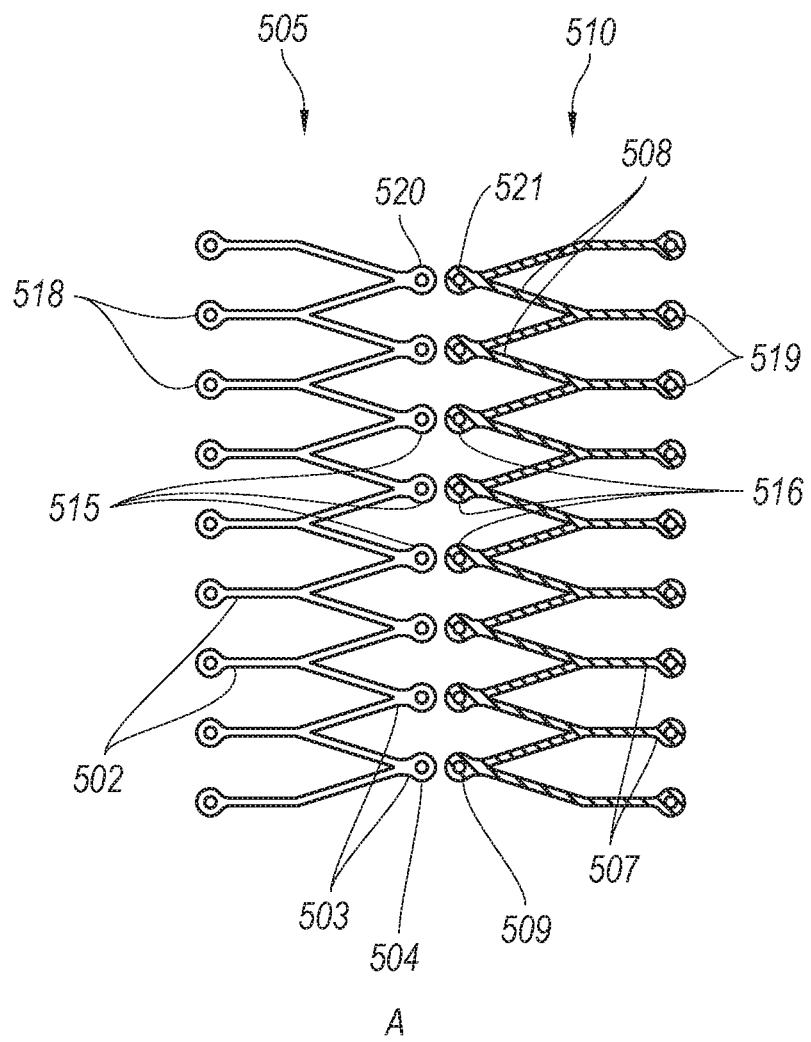
FIGS. 5A and 5B are schematic illustrations of coupled actuation elements for use with an adjustable interatrial shunting system and configured in accordance with select embodiments of the present technology.

FIG. 5A is a flat pattern illustration of interlocking actuation elements that may be coupled to form a part of an interatrial shunting device configured in accordance with embodiments of the present technology. In particular, FIG. 5A illustrates a first actuation element 505 and a second actuation element 510. In some embodiments, the first actuation element 505 and/or the second actuation element 510 are stents or stent-like structures that are coupled to form an actuation assembly. In embodiments, the first actuation element 505 and/or the second actuation element 510 are comprised of a shape memory material. The actuation assembly can be actuated to move through two or more geometric configurations in order to alter the characteristics of fluid flow through the shunting device. The first actuation element 505 contains both arm elements 502 and zig elements 503, with arm elements 502 terminating in eyelet openings 518 and the zig elements 503 terminating in eyelet openings 515. Similarly, the second actuation element 510 contains both arm elements 507 and zig elements 508, with arm elements 507 terminating in eyelet openings 519 and the zig elements 508 terminating in eyelet openings 516. The patterns and/or shape of the first and second actuation elements 505, 510 may be similar. The shape and/or geometries of the first and second actuation elements 505, 510 may be constructed to different configurations during a pre-processing step, as elaborated upon below. Prior to coupling of the first and second actuation elements 505, 510, the first and second actuation elements 505, 510 may be manipulated into shapes and/or geometries that differ from their original geometric configurations (e.g., by flattening shape-memory alloy structures while the structures are at a temperature where the material is at least partially in a martensitic or R-phase, and therefore relatively malleable). In embodiments, the first and second actuation elements 505, 510 may be coupled along the backbone corresponding to the peaks of the zig elements 503 and 508 (e.g., by using sutures or another connection means to secure the series of eyelets 515 and 516 together). Accordingly, unlike the first and second actuation elements 405, 407 described above with respect to FIGS. 4A-4C, the first and second actuation elements 505, 510 are coupled in series or "end-to-end", in which a first end portion of the first actuation element 505 is coupled to a second end portion of the second actuation element 510, and in which the first actuation element 505 is not nested within (e.g., does not generally overlap with) the second actuation element 510. This operation represents an initial coupling operation that is a step in the process of using the first and second actuation elements 505, 510 to create an actuation assembly that is part of an interatrial shunting device.

To create an actuation assembly from the first and second actuation elements 505, 510, additional coupling steps may be implemented. For example, during a secondary coupling step, the flattened configuration of the stent structure (i.e., as shown in FIG. 5A) may be wrapped around a central axis and attached to itself, creating a structure defining a lumen or passageway. For example, the region defined by eyelet openings 504 and 509 (which are already coupled/joined) will be subsequently coupled to the region defined by eyelet openings 520 and 521 (which are also already coupled/joined). Following this operation, the composite element may take on a rounded profile (e.g., a cylindrical profile).

Figure 5B:
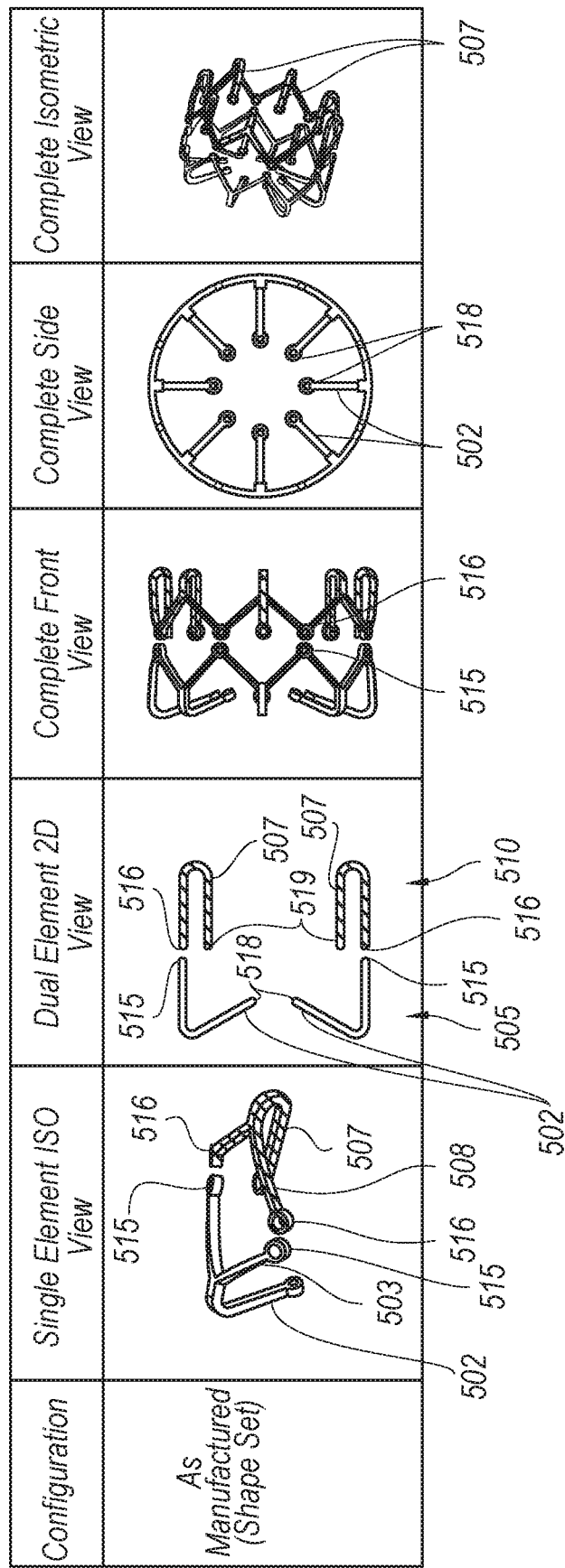

FIG. 5B provides additional schematic illustrations of the first and second actuation elements 505, 510 before they are coupled together to form an actuation assembly, thus illustrating their manufactured geometry (e.g., their preferred geometry). In particular, FIG. 5B illustrates an isometric single element-pair view, a 2D dual element-pair view, a front view, a side view, and an isometric view of the first and second actuation elements 505, 510. As mentioned above, the first and second actuation elements 505, 510 may be constructed (e.g., shape or manufactured) into different configurations prior to coupling. The illustrated geometric configuration involves arm elements 502 and 507 bending off-axis from zig elements 503 and 508 (i.e., in the direction "out of the page" when viewing FIG. 5A). In some embodiments, the angle of off-axis bend may differ for the arm elements 502 relative to the angle of off-axis bend for the arm elements 507 of the second actuation element 510. For example, referring to the 2D dual element-pair view, the arm elements 502 and 507 are bent off-axis, with arm 502 of the first actuation element 505 bent at a relatively larger (e.g., more open) angle and the arm 507 of the second actuation element 610 bent at a relatively smaller/tighter (e.g., more closed) angle. As a result, the eyelet opening 518 of the first actuation element 505 are relatively close together (defining a smaller diameter), while the eyelet openings 519 of the second actuation element 510 are relatively further apart (defining a larger dimeter).

In some embodiments, a third coupling operation may be undertaken to form the composite actuation assembly that includes both the first and second actuation elements 505, 510. In some embodiments, this operation involves using a flexible connection (e.g., an elastic polymer, a stretchable/flexible material, etc.) to couple the bent arms 502 and 507 of the first and second actuation elements 505, 510. For example, a flexible suture material can be utilized to connect the eyelet opening 518 on the first actuation element 505 with its assembled partner eyelet opening 519 on the second actuation element 510. Upon completion of this third coupling operation, the bend angle of arms 502 and 507 may each change and reach an equilibrium angular position. As with other coupling operations described herein, in embodiments the coupling may be performed in a way that maintains and/or establishes electrical and/or thermal isolation between the first and second actuation elements 505, 510. Following or prior to this third coupling operation, a membrane material (not shown) may be interfaced with the composite structure so as to provide an enclosed channel (e.g., an enclosed lumen) through which fluid may pass through the flow control element.

In an example method of use, following the third coupling operation described above, the composite actuation assembly comprised of the first and second actuation elements 505, 510 (e.g., which can also be referred to as "a flow control element") can be (with or without integration into an interatrial shunting system) compressed into a delivery system (e.g., a catheter delivery system) and delivered to a body of a patient. In embodiments, once the composite actuation assembly is positioned in the desired location, it may be deployed and manually expanded to a neutral position (e.g., expanded using a catheter balloon expansion). In embodiments, the composite actuation assembly is in a material state (e.g., at least partially in a martensitic phase) where it is relatively malleable such that it is deformable from a delivery configuration to a neutral configuration. In embodiments, the composite actuation assembly is manufactured such that both at a first temperature (e.g., a room temperature) and at a second temperature higher than the first temperature (e.g., a body temperature), at least a portion of the composite actuation assembly remains in a material phase where it is relatively malleable and deformable (e.g., a nitinol alloy remains at least partially in a martensitic or R-phase).

Figure 6:
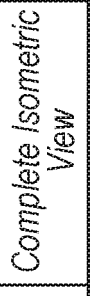
FIG. 6 is a series of schematic illustrates depicting operation of the shunting system shown in FIGS. 5A and 5B.

FIG. 6 provides schematic illustrations of various configurations of the composite actuation assembly formed by coupling the first and second actuation elements 505, 510 shown in FIGS. 5A and 5B. FIG. 6 also schematically illustrates an example mode of operation that may be used to actuate the actuation assembly. Shown in FIG. 6 are isometric single element-pair views, 2D dual element-pair views, complete structure front views, complete structure side views, and complete structure isometric views. In FIG. 6, the first row in the table shows the actuation assembly in a neutral configuration (e.g., after a balloon expansion or other manipulation), the second row shows the actuation assembly in an expanded configuration that creates a relatively smaller lumen for fluid flow, and the third row in the table shows the actuation assembly in a retracted configuration that creates a relatively larger lumen for fluid flow. For clarity, the first and second actuation elements 505, 510 are not shown as being physically coupled (e.g., there are no sutures, welds, flexible connections, etc. in the illustrations, and actuation elements are shown slightly-spaced apart), but the configuration of the first and second actuation elements 505, 510 in each illustration is representative of the mechanical behavior of the coupled actuation assembly.

As illustrated in FIG. 6, the lumen of the actuation assembly may vary in shape along its elongated axis (i.e., the axis of blood flow direction, horizontal in FIG. 6 in the "dual element 2D view" and the "complete front view"). In the configuration in which the cross-sectional short-axis diameter of the lumen is relatively the largest (FIG. 6, third row), the lumen is substantially-cylindrical along its elongated axis (best visualized in the "dual element 2D view" and the "complete side view"). In configurations where portions of the cross-sectional short-axis diameter of the lumen is relatively smaller, the lumen may take on different shapes (e.g., hourglass shape, funnel shape) along the long-axis (as shown in FIG. 6, first and second rows).

The functionality of the example embodiment shown in FIGS. 5A-6 may be similar to other embodiments of actuation assemblies described herein. In a first state, for example, the actuation assembly may be configured as shown in FIG. 6, first row, such that its smallest short-axis cross-sectional diameter is $D_1$. In order to alter the configuration of the actuation assembly into a geometric configuration that allows for a relatively lower volume of flow through a lumen, the first actuation element 505 may be actuated by applying energy to the element (e.g., by heating it beyond a phase transition temperature) in a manner that forces the arms 502 to move towards their relatively more open geometric shape-set configuration. As these arms are coupled via a flexible connection to arms 507 of the second actuation element 510, and because the second actuation element 510 is not substantially heated and remains in a relatively malleable material state, the arms 507 are manipulated into a position corresponding to the position of the arms 502, as shown in FIG. 6, second row. This actuation will change the geometry of the lumen of the actuation assembly and move the smallest short-axis cross-sectional diameter to a value of $D_2$, where $D_2 < D_1$ (as shown in FIG. 6, second row). Similarly, in order to alter the configuration of the actuation assembly into a geometric configuration that allows for a relatively higher volume of flow through a lumen, the second actuation element 510 may be actuated by applying energy to the element (e.g., by heating it beyond a phase transition temperature) in a manner that forces the arms 507 to move towards their relatively more closed geometric shape-set configuration. As these arms 507 are coupled via a flexible connection to the arms 502 of the first actuation element 505, and because the first actuation element 505 is not substantially heated and will be in a relatively malleable material state, the arms 502 are manipulated into a position corresponding to the position of the arms 507, as shown in FIG. 6, third row. This actuation will change the geometry of the lumen of the actuation assembly, and move the smallest short-axis cross-sectional diameter to a value of $D_3$, where $D_3 > D_1$ (as shown in FIG. 6, third row).

In additional embodiments similar to those shown in FIGS. 5A-6, the coupling geometry/configuration between individual actuation element structures 505 and 510 may vary. For example, actuation elements may couple in a manner such that one element substantially sits atop another element (e.g., rather than being connected in series). Alternatively or additionally, one element may be nested within the bends of another element (e.g., within the nook created by the bend of arm 502 relative to zig elements 503). Any number of actuation element structures may be coupled together for use. In some embodiments, the utilization of a higher number of actuation elements is useful because it enables a greater degree of precision and/or granularity in altering the geometry of a actuation assembly.

Figure 7:
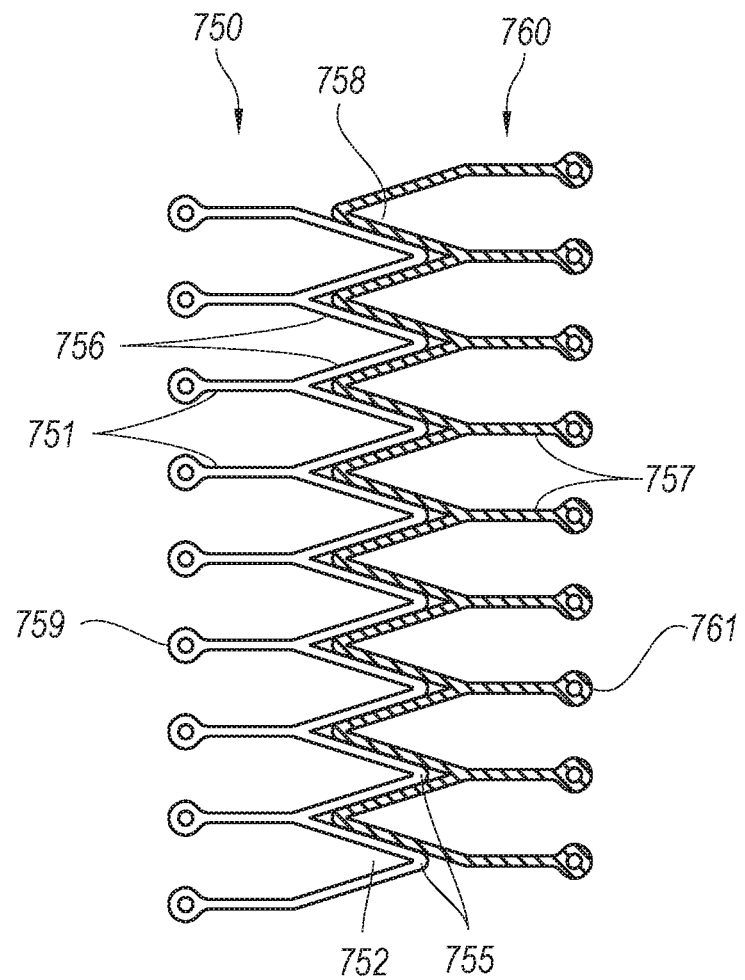
FIG. 7 is a schematic illustration of a coupled actuation elements for use with an adjustable interatrial shunting system and configured in accordance with select embodiments of the present technology.

FIG. 7 is a schematic illustration of coupled actuation elements configured in accordance with another embodiment of the present technology. The structure of FIG. 7 includes a first actuation element 750 and a second actuation element 760 (e.g., stent-like structures). The first and second actuation elements 750, 760 each have arm elements 751 and 757, respectively, and zig elements 752 and 758, respectively. The arm elements 751 and 757 terminate in eyelet openings 759 and 769. The zig elements are comprised of both "peaks" 755 and "valleys" 756. As in the example embodiment depicted in FIG. 5A, the individual stent structures may be, during manufacturing and assembly, constructed into different geometric configurations and then manipulated away from those original geometries prior to coupling. The first and second actuation elements 750, 760 can be coupled together to form a composite actuation assembly structure by nesting the peaks 755 of the first actuation element 750 near to the valleys 756 of the second actuation element 760. The composite structure can be affixed using sutures, adhesives/glue, crimps/rivets, welds, material covering sleeves, or other connection techniques known to those skilled in the art. This operation represents an initial coupling operation that is a step in the process of using the first and second actuation elements 750, 760 to create an actuation assembly that is part of an interatrial shunting device. The composite structure can be formed into a generally cylindrical actuation assembly that has a neutral configuration at body temperature, then manipulated through a variety of configurations by selectively heating the first actuation element 750 or the second actuation element 760 above their respective transition temperatures, as described in detail above with respect to FIG. 6.

ii. Actuation Assemblies Having Elongated Actuation Elements

In addition to the stent-like actuation elements described with respect to FIGS. 3A-7, the present technology also includes actuation assemblies having other types of actuation elements. For example, the present technology includes adjustable shunts having elongated actuation elements (e.g., wires, cables, spindles, struts, etc.). In some embodiments, the elongated actuation elements are composed of a shape memory material that can be thermally manipulated to adjust a geometry of the adjustable shunt to change the flow of fluid therethrough.

Figure 8A:
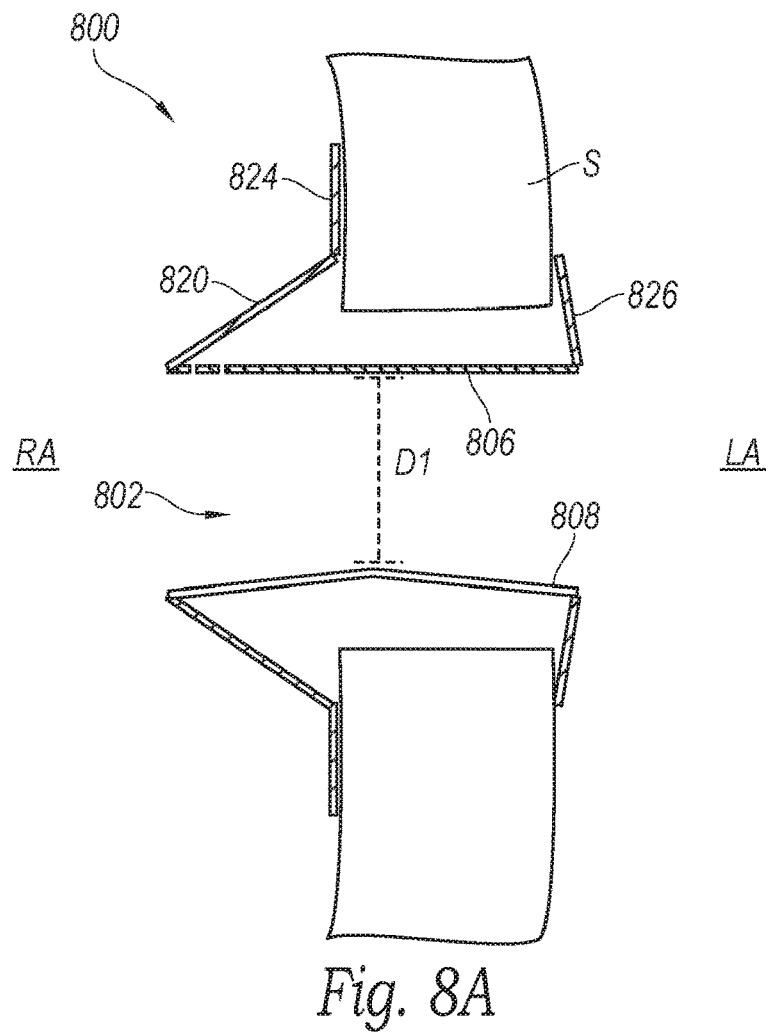
FIGS. 8A-8F are schematic illustrations of an adjustable interatrial shunting system having elongated actuation elements and configured in accordance with select embodiments of the present technology.

For example, FIGS. 8A-8F illustrate aspects of an adjustable interatrial system 800 ("system 800") having a plurality of spindle-like shape memory actuation elements and configured in accordance with select embodiments of the present technology. Referring first to FIG. 8A, which is a cross-sectional view of the system 800 implanted across a septal wall S in a first configuration, the system 800 includes a frame 820 deployable across the septal wall S. The frame 820 can include a first end portion positionable in the RA and a second end portion positionable in the LA. The frame 820 can include RA anchor elements 824 and/or LA anchor elements 826 that secure the frame 820 to the septal wall S. The frame 820 can comprise a superelastic material such as nitinol or another suitable material (e.g., an alloy derivative of nitinol, cobalt chromium, stainless steel, etc.). In embodiments in which the frame 820 is composed of nitinol, the nitinol has a transition temperature less than body temperature such that the nitinol is in an austenitic material state when implanted, and thus the frame 820 is resistant to geometric changes, even if heated. Certain aspects of the frame 820 are omitted from FIG. 8A for clarity. For example, in some embodiments, the frame 820 can have an outer layer for engaging the septal wall S and an inner layer or membrane defining a lumen 802 (e.g., similar to the outer layer and inner layers described below with respect to FIGS. 14-16D). In some embodiments, the frame 820 has a stent-like scaffolding structure. When secured to the septal wall S, the system 800 fluidly connects the LA and the RA to enable blood flow therebetween via a lumen 802.

The system 800 includes a plurality of first actuation elements 806 (only one is shown in FIG. 8A) and a plurality of second actuation elements 808 (only one is shown in FIG. 8A) extending between the RA side and the LA side of the system 800. The first actuation elements 806 and the second actuation elements 808 can be disposed within a membrane (not shown) defining the lumen 802. The first and second actuation elements 806, 808 can be wire-like spindles that extend generally linearly and parallel to a central longitudinal axis of the lumen 802. In some embodiments, the system 800 includes the same number of first actuation elements 806 (e.g., three first actuation elements 806) and second actuation elements 808 (e.g., three second actuation elements 808). In other embodiments, however, the number of first actuation elements 806 may differ from the number of second actuation elements 808. The first actuation elements 806 and the second actuation elements 808 can each have opposing end portions that are secured to the frame 820 via welding, soldering, riveting, gluing, suturing, or the like. For example, the first actuation elements 806 and the second actuation elements 808 can be secured to and extending between the first end portion and the second end portion of the frame.

Figure 8B:
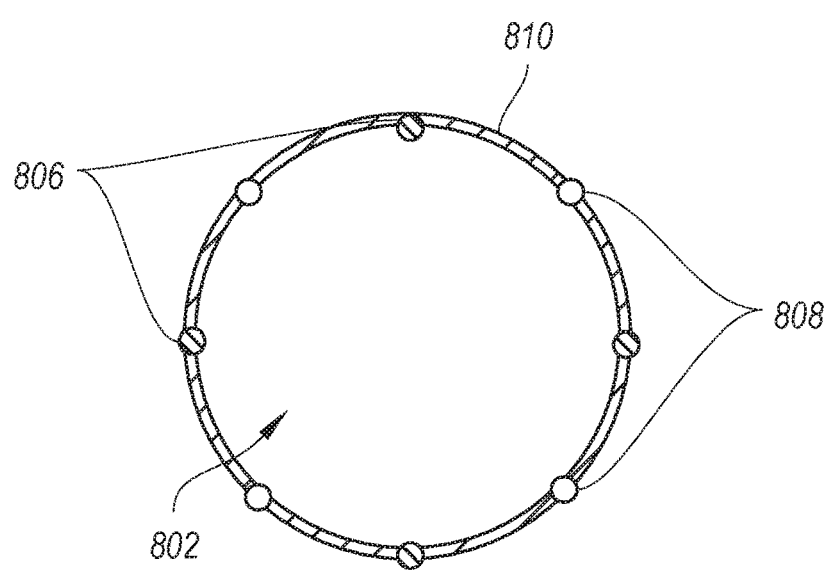

Referring now to FIG. 8B, which is a cross-sectional view of the lumen 802 taken transverse to its axial length, the first and second actuation elements 806, 808 can be arranged around the lumen 802 such that they alternate between first actuation elements 806 and second actuation elements 808. In some embodiments, the first and second actuation elements 806, 808 can be encased in a biocompatible material and/or membrane 810 (e.g., ePTFE), which can at least partially define the outer perimeter of the lumen 802. The membrane 810 can be at least partially flexible to accommodate movement of the first and second actuation elements 806, 808 as they transition between deformed shapes and manufactured shapes, as described below.

The first actuation elements 806 and the second actuation elements 808 can be composed of a shape memory material, such as a shape memory alloy (e.g., nitinol). Accordingly, the first and second actuation elements 806, 808 can be transitionable between a first material state (e.g., a martensitic state, a R-phase, etc.) and a second state (e.g., a shape memory state, an austenitic state, etc.). In the first state, the first actuation elements 806 and the second actuation elements 808 may be deformable (e.g., plastic, malleable, compressible, expandable, etc.). In the second state, the first and second actuation elements 806, 808 may have a preference toward a specific manufactured geometry (e.g., shape, length, and/or or dimension). The first and second actuation elements 806, 808 can be transitioned between the first state and the second state by applying energy to the spindles to heat the spindles above a transition temperature.

In some embodiments, the transition temperature for both the first actuation elements 806 and the second actuation elements 808 is above an average body temperature. Accordingly, both the first actuation elements 806 and the second actuation elements 808 are manufactured such that they are in the deformable first material state when the system 800 is implanted in the body.

If the actuation elements (e.g., the first actuation elements 806) are deformed while in the first material state, heating the actuation elements (e.g., the first actuation elements 806) above their transition temperature causes the actuation element to transition to the second material state and therefore transition from the deformed shape toward its manufactured geometry. Heat can be applied to the actuation elements via RF heating, resistive heating, or the like. In some embodiments, the first actuation elements 806 can be selectively heated independently of the second actuation elements 808, and the second actuation elements 808 can be selectively heated independently of the first actuation elements 806 (e.g., the first and second actuation elements are thermally and/or electrically isolated). For example, in some embodiments, the first actuation elements 806 are on a first electrical circuit for selectively and resistively heating the first actuation elements 806 and the second actuation elements 808 are on a second electrical circuit for selectively and resistively heating the second actuation elements 808. As described in detail below, selectively heating the first actuation elements 806 reduces a diameter of the lumen 802 and selectively heating the second actuation elements 808 increases a diameter of the lumen 802.

To drive actuation of the system 800, the first actuation elements 806 and the second actuation elements 808 generally are manufactured to have different manufactured geometries. Referring now to FIG. 8E, in some embodiments the first actuation elements 806 can have a generally linear manufactured geometry having a length X. Accordingly, when heated above their transition temperature, the first actuation elements 806 will move toward or assume the shape shown in solid line in FIG. 8E with the length X, regardless of their shape prior to heating. However, while in the deformable first (e.g., martensitic) state and/or during attachment to the frame 820, the first actuation elements 806 can be stretched by a distance D (shown in dashed line) to have a second length greater than X (e.g., a length equal to X+D). As noted above, subsequent heating of the first actuation elements 806 above their transition temperature will cause the first actuation elements to contract to move toward or assume the manufactured geometry having the length X. The second actuation elements 808 can also have a manufactured geometry, which in some embodiments can have a length that is generally equal to or greater than the distance X+D. When in the first (e.g., martensitic) state, the second actuation elements 808 can be deformable. However, as described below, the second actuation elements 808 can be manufactured to move toward or assume the manufactured geometry shown in FIG. 8E when heated above their transition temperature. When attached to the frame 820, the second actuation elements 808 can be in their manufactured geometry or another partially deformed shape.

Referring again to FIGS. 8A and 8B, the system 800 is shown in first configuration in which the lumen 802 has a first diameter $D_1$ at its pinch portion (e.g., the narrowest portion of the generally hourglass shaped lumen). In this configuration, at least the first actuation elements 806 are in the first (e.g., martensitic) state and deformed (e.g., stretched) relative to their manufactured shape. In the illustrated configuration, the lumen 802 has a generally circular cross-sectional area, although other configurations are possible without deviating from the scope of the present technology.

Figure 8C:
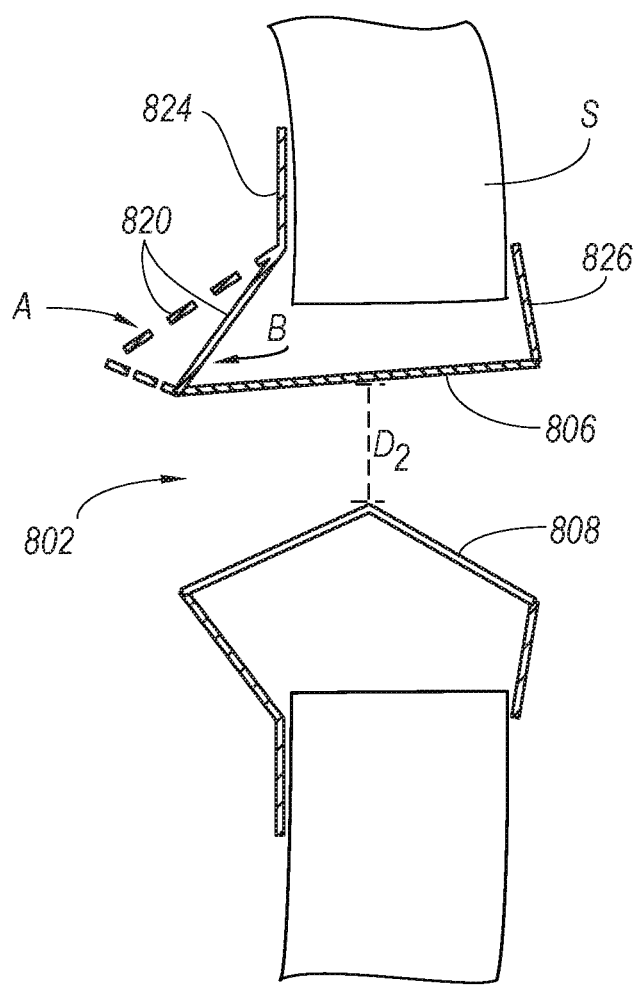
Figure 8D:
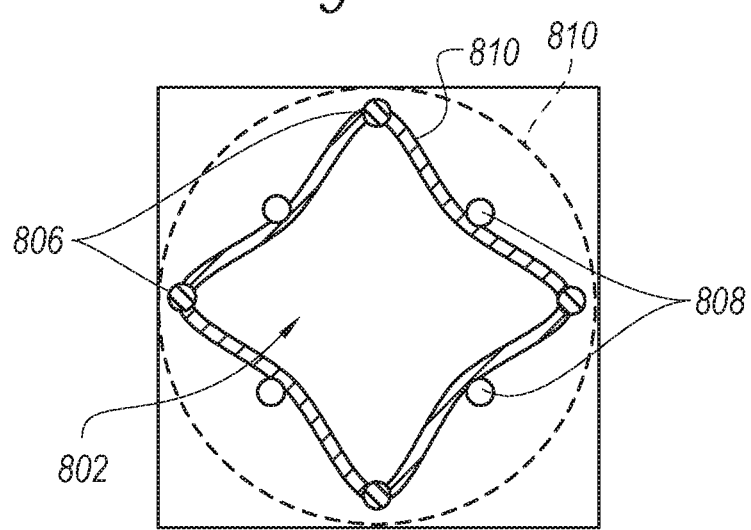
Figure 8E:
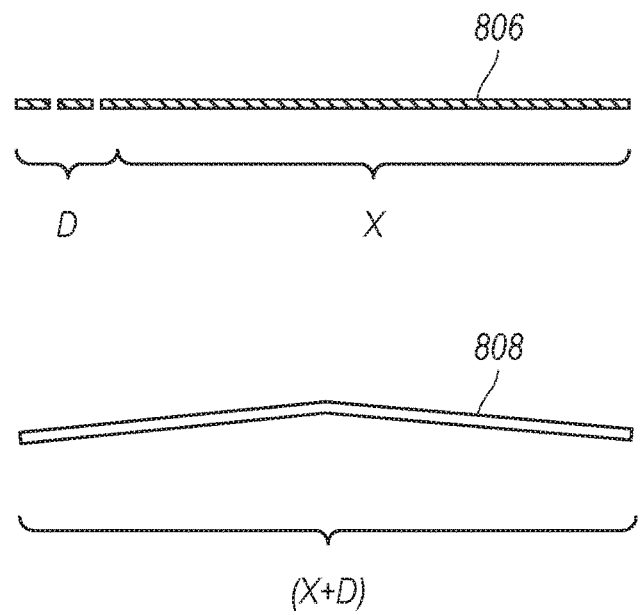

FIGS. 8C and 8D illustrate the system 800 in a second configuration different than the first configuration. FIG. 8C, for example, is a cross-sectional view of the system 800 implanted across a septal wall S in the second configuration, and FIG. 8D is a cross-sectional view of the lumen 802 taken transverse to its axial length. In particular, in the second configuration the system 800 has been actuated relative to the first configuration shown in FIG. 8A to transition the first actuation elements 806 from the first (e.g., martensitic) material state to the second (e.g., austenitic) material state. Because the first actuation elements 806 were stretched (e.g., lengthened) relative to their manufactured geometry while in the first state, heating the first actuation elements 806 above the transition temperature causes the first actuation elements 806 to reduce in length and move toward their manufactured geometry (e.g., having length X, as shown in FIG. 8E). As the first actuation elements 806 reduce in length toward their manufactured geometry, they pull a portion of the frame 820 (shown in dashed line) inward from a first position A to a second position B. This causes the second actuation elements 808, which are not heated above their transition temperature and therefore still in the deformable first (e.g., martensitic) state, to hinge or otherwise bend inwards toward a center longitudinal axis of the lumen 802. This causes a decrease in the diameter of the lumen 802 at the pinch point to a second diameter $D_2$ that is less than the first diameter $D_1$. When implanted in a human heart, decreasing the diameter of the lumen 802 (e.g., by transitioning from the first configuration to the second configuration) is expected to reduce the flow of blood from the LA to the RA.

The system 800 can be returned to the first configuration shown in FIGS. 8A and 8B by heating the second actuation elements 808 above their transition temperature once the first actuation elements 806 have returned to the deformable first state (e.g., by allowing the first actuation elements 806 to cool below the transition temperature). Heating the second actuation elements 808 above their transition temperature causes the second actuation elements 808 to move toward their manufactured geometry (FIG. 8A) which in turn pushes the frame 804 from the second position B to the first position A, deforms (e.g., stretches) the first actuation elements 806, and increases the diameter of the lumen 802. Accordingly, the system 800 can be selectively transitioned between a variety of configurations/geometries by selectively actuating either the first actuation elements 806 or the second actuation elements 808. After actuation, the system 800 can be configured to substantially retain the given configuration until further actuation of the opposing actuation elements. In some embodiments, additional sizes and/or geometries of the lumen 802 can be achieved by selectively heating a subset of the first actuation elements 806 and/or the second actuation elements 808. In some embodiments, the system 800 can include additional actuation elements (e.g., third actuation elements) that have different manufactured geometries than either of the first or second actuation elements, and thus can drive the lumen to additional configurations when actuated.

Figure 8F:
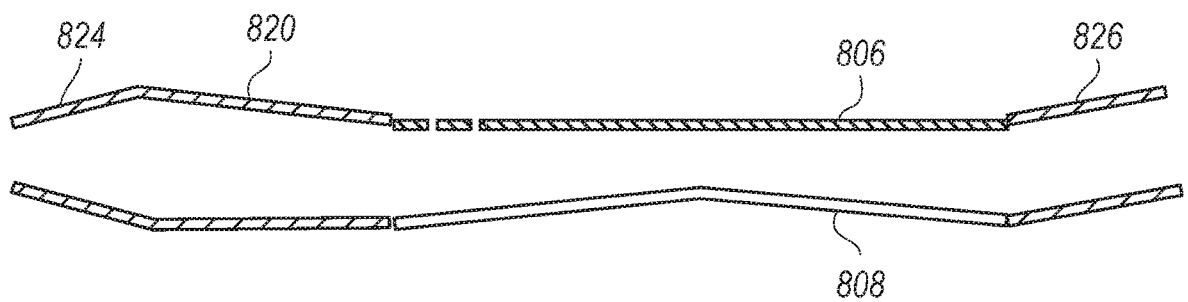

FIG. 8F illustrates a delivery configuration of the system 800. In the delivery configuration, the frame 820, including the RA anchor element 824 and the LA anchor element 826, can be folded, flattened, or otherwise crimped to reduce the overall profile of the system 800. In the delivery configuration, the first actuation elements 806 and the second actuation elements 808 can retain their respective lengths that they will assume when the device is deployed in the first configuration. For example, the first actuation elements 806 can have their deformed (e.g., stretched) geometry having a length equal to X+D (FIG. 8E), and the second actuation elements 808 can have their manufactured geometry with a length also equal to X+D (FIG. 8E). In other embodiments, the first actuation elements 806 and/or the second actuation elements 808 may occupy other shapes or configurations while in the delivery configuration. The crimped system 800 can be inserted into a catheter (not shown) for transvascular delivery to the heart and deployment across the septal wall. Upon deployment of the system 800 from the catheter, the superelastic properties of the frame 820 can cause the system 800 to expand. For example, upon deployment of the system 800, the system 800 may assume the first configuration illustrated with reference to FIGS. 8A and 8B.

Figure 9:
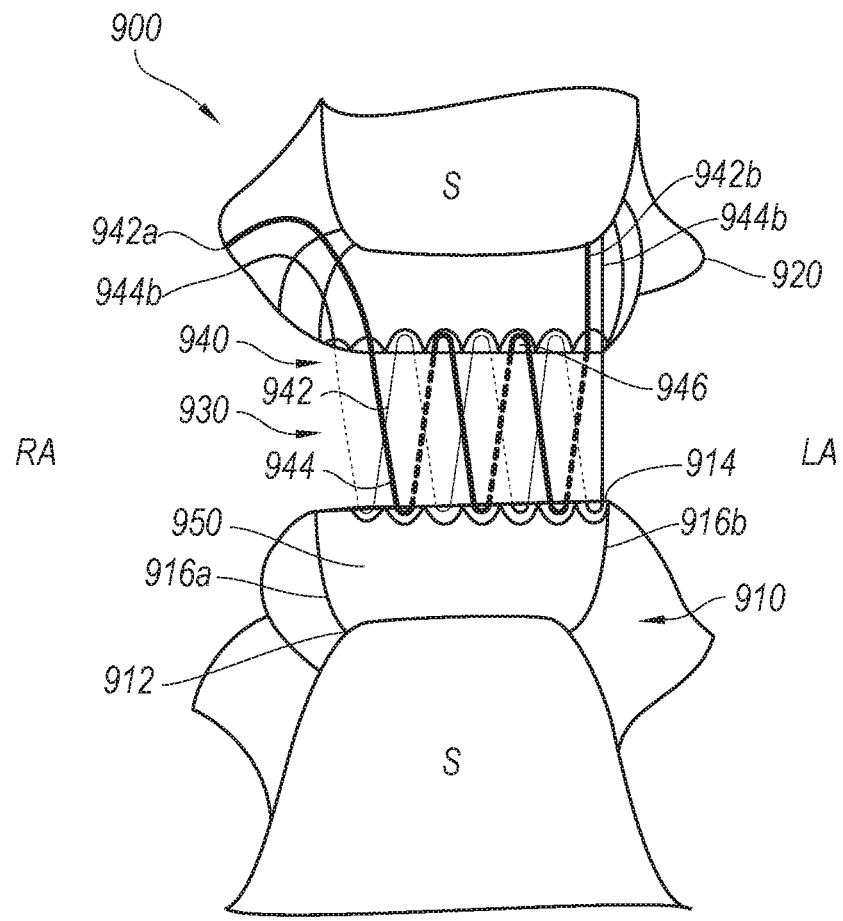
FIG. 9 is a schematic illustration of an adjustable interatrial shunting system having helically shaped actuation elements and configured in accordance with select embodiments of the present technology.

FIG. 9 is a cross-sectional, partially schematic illustration of an adjustable interatrial shunting system 900 ("system 900") having helically wrapped elongated actuation elements and configured in accordance with select embodiments of the present technology. The system 900 includes a shunting element 910, anchoring elements 920, an adjustable inner lumen 930, and an actuation assembly 940. The shunting element 910 is configured to extend between an LA and an RA of the heart when implanted across the septal wall S. The shunting element 910 can have a generally toroidal shape such that it includes an outer surface 912, an inner surface 914, a proximal surface 916a, and a distal surface 916b. The outer surface 912 (which can also be referred to as a "frame") can engage native heart tissue when implanted in a heart. For example, in the illustrated embodiment, the system 900 is shown implanted in a human heart with the outer surface 912 engaging a septal wall S. The inner surface 914 can include a membrane that at least partially defines the adjustable lumen 930. As illustrated, the lumen 930 fluidly connects the LA and the RA when system 900 is implanted in a heart. The proximal surface 916a is configured to reside within the RA and the distal surface 916b is configured to reside within the LA. One or more portions of the shunting element 910 can be composed of or coated with a biocompatible and/or anti-thrombogenic material (e.g., ePTFE). In some embodiments, one or more portions of the shunting element 910 (e.g., the membrane forming the inner surface 914) is composed of an at least partially flexible or malleable material.

In some embodiments, the outer surface 912, the inner surface 914, the proximal surface 916a, and the distal surface 916b of the shunting element 910 define a generally toroidal shaped chamber 950. The chamber 950 can be fluidly isolated from the interior of the lumen 930. The chamber 950 can also be fluidly isolated from the environment surrounding the system 900 via the material encasing the shunting element 910. Accordingly, in some embodiments, the system 900 is configured to prevent blood from flowing into the chamber 950. In some embodiments, the chamber 950 can contain a compressible and/or displaceable liquid, gas, and/or gel. Accordingly, as the diameter of the lumen 930 is adjusted (as described below), the liquid or gas can be compressed, expanded, and/or displaced. In other embodiments, the shunting element 910 is substantially solid throughout its cross-section such that there is no chamber 950. In such embodiments, the shunting element 910 comprises an at least partially compressible and expandable material to conform to changes in the diameter of the lumen 930. The anchoring elements 920 are configured to secure the system 900 in a desired position within the heart. For example, as illustrated, the anchoring elements 920 can secure the system 900 to native heart tissue such as a septal wall S. In some embodiments, the anchoring elements 920 can include right atrium anchors and/or left atrium anchors. The anchoring elements 920 can extend from and/or be integral with one or more aspects of the shunting element 910.

The actuation assembly 940 is configured to selectively adjust a diameter of the lumen 930 to control the flow of blood therethrough. In the illustrated embodiment, the actuation assembly 940 comprises a first actuation element 942 and a second actuation element 944. The first actuation element 942 and the second actuation element 944 wrap around the lumen 930 defined by the inner surface 914. For example, the first actuation element 942 and the second actuation element 944 have a generally helical configuration, with the lumen 930 disposed within the center of the helix. The first actuation element 942 and the second actuation element 944 can be embedded within a membrane defining the lumen and/or otherwise coupled to the inner surface 914 to drive radially movement of the inner surface 914. For example, in some embodiments, the inner surface 914 has a thickness, and the first actuation element 942 and the second actuation element 944 are embedded within the thickness of the inner surface 914. In some embodiments, the system 900 includes one or more fluidly, thermally, and/or electrically isolated channels 946 extending around the inner lumen 930 in a generally helical orientation. The first actuation element 942 and the second actuation element 944 can be housed within the channels 946. The channels 946 can be positioned within the chamber 950, can be embedded within a thickness of the of inner surface 914, and/or can be positioned within the lumen 930 itself. In some embodiments, the system 900 can include a first channel for housing the first actuation element 942 and a second channel for housing the second actuation element 944. In other embodiments, a single channel houses both the first actuation element 942 and the second actuation element 944. The one or more channels 946 are sized and shaped to protect the actuation elements from the environment external to the system 900, and may also electrically and/or thermally isolate the first actuation element 942 from the second actuation element 944.

The first actuation element 942 includes a proximal end region 942a secured to the system 900 and a distal end region 942b secured to the system 900. Likewise, the second actuation element 944 includes a proximal end region 944a secured to the system 900 and a distal end region 944b secured to the system 900. The illustrated embodiment depicts the proximal end regions 942a, 944a secured to a portion of the anchoring element 920 and the distal end regions 942b, 944b, secured to the shunting element 910. However, one skilled in the art will appreciate that the first actuation element 942 and the second actuation element 944 can be secured to any number of structures of system 900 without deviating from the scope of the present technology.

The first actuation element 942 and the second actuation element 944 can be composed of any material suitable to dynamically adjust a diameter of the lumen 330. For example, in some embodiments, the first actuation element 942 and the second actuation element 944 can be composed of a shape-memory material, such as a shape memory alloy (e.g., nitinol). Accordingly, the first and second actuation elements 806, 808 can be transitionable between a first material state (e.g., a martensitic state, a R-phase, etc.) and a second material state (e.g., a shape memory state, an austenitic state, etc.). In the first state, the first actuation elements 806 and the second actuation elements 808 may be deformable (e.g., plastic, malleable, compressible, expandable, etc.). In the second state, the first and second actuation elements 806, 808 may have a preference toward a specific manufactured geometry (e.g., shape, length, and/or or dimension). The first and second actuation elements 942, 944 can be transitioned between the first state and the second state by applying energy to the first and/or second actuation elements 942, 944 to heat (e.g., resistively heat) the first and/or second actuation elements 942, 944 above a transition temperature. In some embodiments, the transition temperature for both the first actuation element 942 and the second actuation element 944 is above an average body temperature. Accordingly, both the first actuation element 942 and the second actuation element 944 are manufactured such that they are in the deformable first state when the system 900 is implanted in the body until they are heated (e.g., actuated).

At least one of the first actuation element 942 and the second actuation element 944 can be at least partially deformed relative to its manufactured geometry when implanted. For example, if the first actuation element 942 is deformed relative to its manufactured geometry, actuating the first actuation element 942 (e.g., by heating it above its transition temperature) causes the first actuation element 942 to move toward its manufactured geometry, which can tighten the first actuation element 942 and cause the lumen 930 to decrease in diameter. If the second actuation element 944 is deformed relative to its manufactured geometry, actuating the second actuation element 944 (e.g., by heating it above its transition temperature) can loosen the second actuation element 944 and cause the lumen 930 to increase in diameter.

Figure 10A:
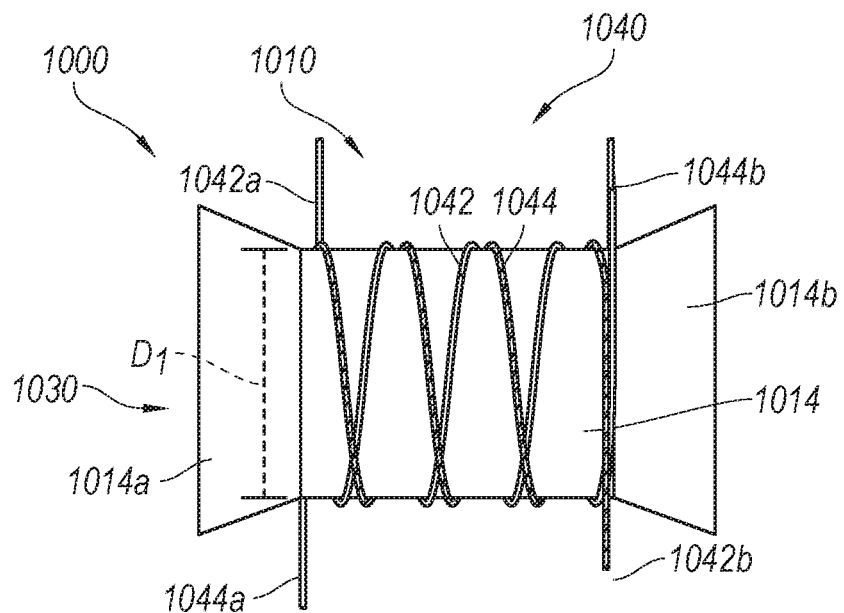
FIGS. 10A and 10B are schematic illustrations of another adjustable interatrial shunting system having helically shaped actuation elements and configured in accordance with select embodiments of the present technology.
Figure 10B:
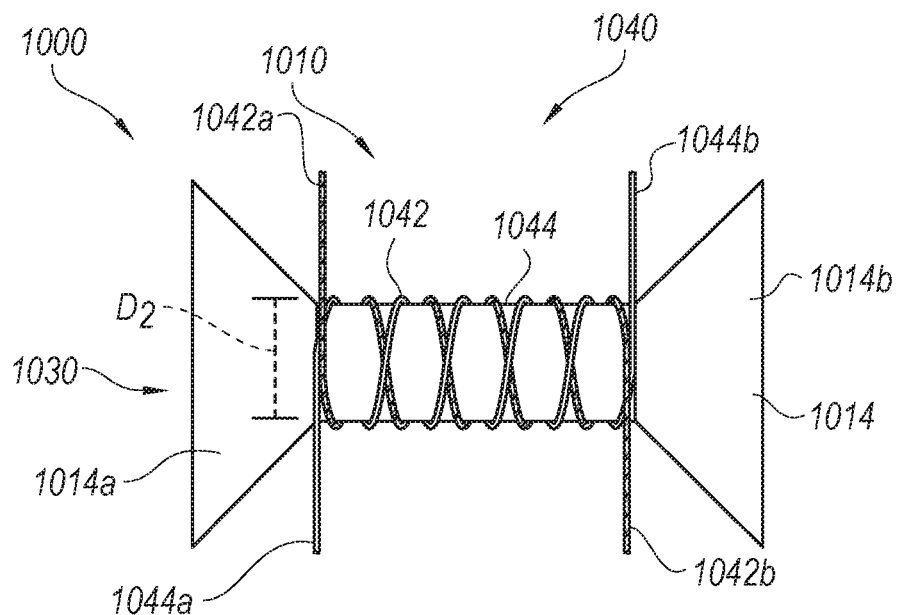

FIGS. 10A and 10B illustrate aspects of an adjustable interatrial system 1000 ("system 1000") configured in accordance with select embodiments of the present technology. The system 1000 is generally similar to the system 900 described in detail above with reference to FIG. 9. For example, the system 1000 can include a shunting element 1010 having an outer surface (not shown) and an inner surface 1014, anchoring elements (not shown), an adjustable lumen 1030, and an actuation assembly 1040. The inner surface 1014 can include a flared proximal end portion 1014a configured to reside within the RA of a heart, and a flared distal end portion 1014b configured to reside within a LA of the heart.

Referring to FIG. 10A, the actuation assembly 1040 includes a first actuation element 1042 and a second actuation element 1044. As with the system 900, the first actuation element 1042 and the second actuation element 1044 can be generally helical coils that wrap around the lumen 1030 defined by the inner surface 1014 (e.g., embedded within a membrane defining the inner surface 1014). For example, the first actuation element 1042 and the second actuation element 1044 have generally spiral-shaped configurations, with the lumen 1030 disposed within the center of the spiral. In the illustrated embodiment, the first actuation element 1042 and the second actuation element 1044 are disposed around the inner surface 1014, although other embodiments, such as those described above with respect to system 900, are suitable. The first actuation element 1042 has a proximal end segment 1042a and a distal end segment 1042b extending from the portion of the first actuation element 1042 wrapped around the lumen 1030. The second actuation element 1044 has a proximal end 1044a and a distal end 1044b extending from the portion of the second actuation element 1044 wrapped around the lumen 1030. The proximal end segments 1042a, 1044a and the distal end segments 1042b, 1044b can be secured to various structures of the system 1000 (not shown).

In some embodiments, the first and second actuation elements 1042, 1044 can be composed of a shape memory material and operate in a manner substantially similar to that described above with respect to the system 900. In other embodiments, the system 1000 can include an additional actuator (e.g., a motor, such as an electromagnetic motor, a mechanical motor, a MEMS motors, a piezoelectric based motor, or the like; not shown) configured to selectively adjust the first actuation element 1042 and the second actuation element 1044. For example, the actuator can adjust the first actuation element 1042 by pulling the proximal end segment 1042a and/or the distal end segment 1042b of the first actuation element 1042, thereby tightening the first actuation element 1042 around the inner surface 1014. Tightening the first actuation element 1042 around the inner surface causes the diameter of the lumen 1030 to decrease. For example, referring to FIG. 10A, the first actuation element 1042 has a first configuration in which the adjustable lumen 1030 has a first diameter $D_1$. To reduce the diameter of the lumen 1030, the actuator selectively tightens the first actuation element 1042, narrowing the diameter of the spiral formed by the first actuation element 1042 and squeezing the inner surface 1014. As a result, the lumen 1030 is transitioned to a second configuration having a second diameter $D_1$ that is less than the first diameter $D_2$, as illustrated in FIG. 10B. Because the first actuation element 1042 extends from the proximal end portion 1014a to the distal end portion 1014b of the inner surface 1014, the lumen 1030 is narrowed along a substantial length of the system 1000. The first actuation element 1042 can be configured to retain its shape following actuation, thereby retaining the second diameter $D_2$ until the actuator drives the system 1000 into a third configuration (not shown).

Actuating the second actuation element 1044 can have the opposite effect of actuation of the first actuation element 1042. For example, actuating the second actuation element 1044 via the actuator and/or via its shape memory properties can increase the diameter of the lumen 1030. More specifically, actuating the second actuation element 1044 causes the second actuation element 1044 to loosen around the inner surface, allowing the inner surface 1014 to expand radially outward. This increases the diameter of the lumen 1030. The second actuation element 1044 can be configured to retain its shape following actuation, thereby retaining the desired diameter until the actuator is further activated. Accordingly, the first actuation element 1042 can be actuated to decrease the diameter of the lumen 1030 and the second actuation element 1044 can be actuated to increase the diameter of the lumen 1030. By having opposite effects, a user can selectively adjust either the first actuation element 1042 or the second actuation element 1044 to achieve a desired lumen diameter.

In some embodiments, the first actuation element 1042 can be individually tightened and/or loosened via the actuator and/or the shape memory effect, and the second actuation element 1044 can be individually tightened and/or loosened via the actuator and/or the shape memory effect. In such embodiments, a single actuation element (e.g., the first actuation element 1042) can be sufficient to both increase and decrease the diameter of the lumen 1030. Additional actuation elements can still be included, however, to further increase the control and operability of the system 1000. Accordingly, some embodiments of the system 1000 include one, two, three, four, five, six, seven, and/or eight or more actuation elements.

Figure 11:
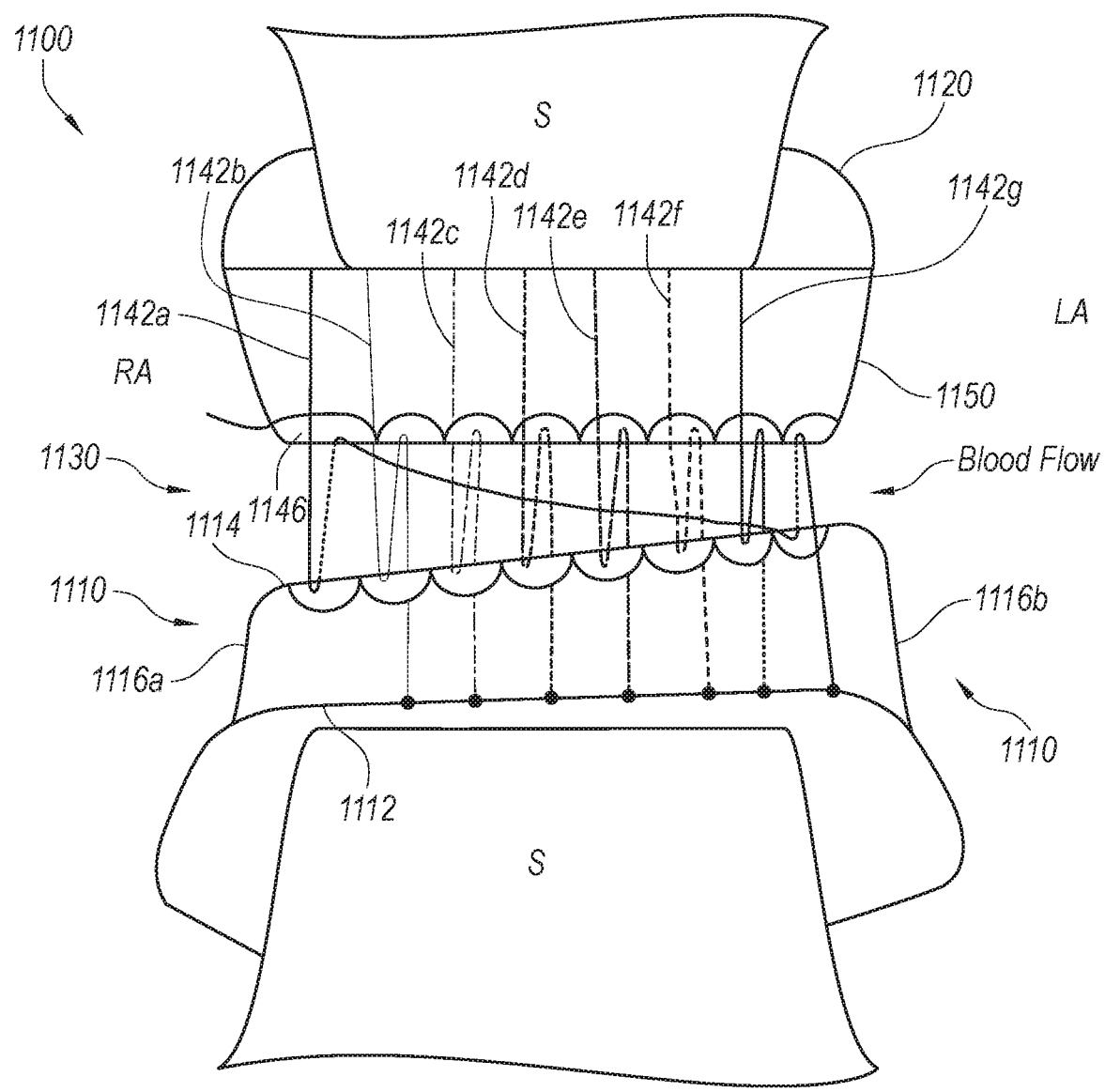
FIG. 11 is a schematic illustration of an adjustable interatrial shunting system having a plurality of discrete actuation elements and configured in accordance with select embodiments of the present technology.

FIG. 11 is a cross-sectional, partially schematic illustration of an additional embodiment of an adjustable interatrial system 1100 ("system 1100") configured in accordance with select embodiments of the present technology. The system 1100 can include certain features generally similar to the systems 900 and 1000 described with respect to FIGS. 9-10B. For example, the system 1100 can include a shunting element 1110 having an outer surface 1112, and inner surface 1114, a proximal (e.g., RA) surface 1116a, and a distal (e.g., LA) surface 1116b. The outer surface 1112 (which can also be referred to as a "frame") can engage native heart tissue (e.g., a septal wall S) when the system 1100 is implanted in a patient. The inner surface 1114 can include a membrane that at least partially defines a lumen 1130 configured to fluidly connect a LA and a RA of a heart. The shunting element 1110 can have a generally toroidal shape. The shunting element 1110 can be hollow to define a chamber 1150. The system 1100 can also have anchoring elements 1120 configured to secure the system 1100 in position by engaging with native heart tissue (e.g., septal wall S).

The system 1100 can include a plurality of actuation elements 1142. For example, the system can include a first actuation element 1142a, a second actuation element 1142b, a third actuation element 1142c, a fourth actuation element 1142d, a fifth actuation element 1142e, a sixth actuation element 1142f, and a seventh actuation element 1142g. Other embodiments can include additional or fewer actuation elements 1142. The actuation elements 1142 wrap around the lumen 1130 (e.g., within the membrane defining the inner surface 1114) and are secured to the shunting element 1110. In some embodiments, individual actuation elements (e.g., the first actuation element 1142a) wrap around the lumen a single time. In other embodiments, individual actuation elements (e.g., first actuation element 1142a) wrap around the lumen more than once. For example, each individual actuation element could be wrapped around both the LA side and the RA side of lumen 1130 such that the diameter of the lumen 1130 is adjusted along a substantial length of the lumen 1130. As described above with respect to FIG. 9, the actuation elements 1142 can be housed within one or more channels 1146.

Each of the actuation elements 1142a-g can be individually actuated. More specifically, each of the actuation elements 1142a-g can be individually actuated to transition from a passive configuration to an active configuration. When an individual actuation element (e.g., actuation element 1142a) is in the passive configuration, it does not dictate the diameter of the lumen 1130. When the individual actuation element (e.g., actuation element 1142a) is actuated and transitions to the active configuration, it adjusts the diameter of the lumen 1130 to a corresponding predetermined diameter. Accordingly, each of the actuation elements 1142a-g can be configured to selectively adjust the diameter of the lumen 1130 to a specific predetermined diameter. For example, actuating actuation element 1142a can adjust the diameter of lumen 1130 to about 12 mm, actuating actuation element 1142b can adjust the diameter of lumen 1130 to about 5 mm, actuating actuation element 1142c can adjust the diameter of lumen 1130 to about 6 mm, actuating actuation element 1142d can adjust the diameter of lumen 1130 to about 7 mm, actuating actuation element 1145e can adjust the diameter of lumen 1130 to about 8 mm, actuating actuation element 1145f can adjust the diameter of lumen 1130 to about 9 mm, and actuating actuation element 1145g can adjust the diameter of lumen 1130 to about 10 mm. Accordingly, specific actuation elements can be targeted to adjust the lumen 1130 to a desired diameter. Following actuation, individual actuation elements can be configured to remain in their active configuration, thereby retaining the corresponding lumen diameter until another individual actuation element is actuated.

In some embodiments, the actuation elements 1142 can be composed of shape-memory material, such as a shape memory alloy (e.g., nitinol). Accordingly, the actuation elements 1142 can be transitionable between a first material state (e.g., a martensitic state, a R-phase, etc.) and a second material state (e.g., a shape memory state, an austenitic state, etc.). In the first state, the actuation elements 1142 may be deformable (e.g., plastic, malleable, compressible, expandable, etc.). In the second state, the actuation elements 1142 may have a preference toward a specific manufactured geometry (e.g., shape, length, and/or or dimension). The actuation elements 1142 can be transitioned between the first state and the second state by applying energy to the actuation elements 1142 to heat (e.g., resistively heat) the actuation elements 1142 above a transition temperature. In some embodiments, the first material state corresponds to the passive configuration described previously and the second material state corresponds to the active configuration described previously. Therefore, in some embodiments the diameter of the lumen 1130 can be adjusted by heating an individual actuation element corresponding to a desired lumen diameter above its transition temperature, thereby transitioning the actuation element from the passive configuration to the active configuration.

Figure 12A:
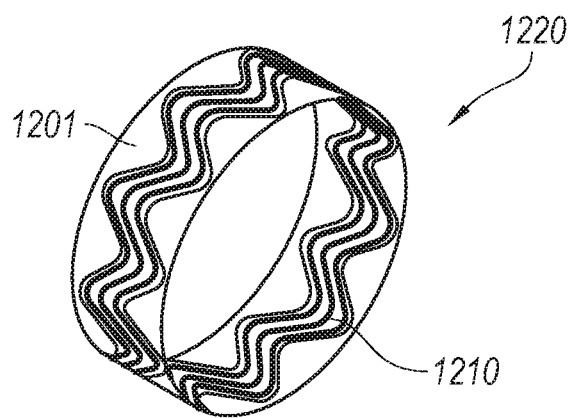
FIGS. 12A and 12B are schematic illustrations of serially coupled actuation elements that form a part of an interatrial shunting system configured in accordance with select embodiments of the present technology.
Figure 12B:
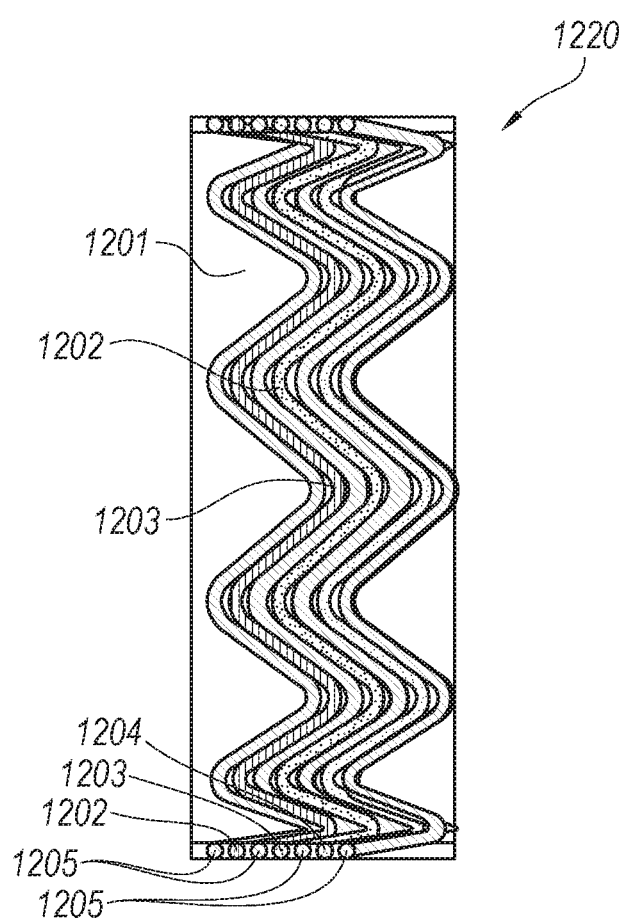

FIGS. 12A and 12B illustrate an actuation assembly 1220 that includes generally circular actuation elements and is configured in accordance with select embodiments of the present technology. More specifically, FIG. 12A is an isometric view of the actuation assembly 1220, and FIG. 12B is cross-sectional front view (with the blood flow axis being horizontal in this view) of the actuation assembly 1220. In some embodiments, the actuation assembly 1220 includes plurality of actuation elements 1202-1204 disposed within a sleeve or membrane 1201. In some embodiments, the membrane 1201 can be insulative, for example thermally- and/or electrically insulative. In embodiments at least a portion of the membrane 1201 is composed of a compliant material (e.g. PTFE, ePTFE, silicone, urethane, nylon, etc.) and/or a non-compliant material (e.g., annealed stainless steel, cobalt chromium). The actuation elements 1202-1204 can be composed of a shape memory material (e.g., nitinol wires or tubes). Each shape memory actuation element may be shape set to have a different geometric configuration. For example, a first actuation element 1202 can be constructed to have a generally sinusoidal flattened pattern and, when wrapped about a central axis, undertake a generally circular geometric configuration with a first diameter $D_1$. A second actuation element 1203 may be constructed to have a similar sinusoidal flattened pattern and, when wrapped about a central axis, undertake a second circular geometric configuration with a second diameter $D_2$. A third actuation element 1204 may be constructed to have a similar sinusoidal flattened pattern and, when wrapped about a central axis, undertake a third circular geometric configuration with a third diameter $D_3$. Any number of additional actuation elements may be included in a similar manner. In further embodiments, the individual actuation elements may have dissimilar shapes, sizes, and/or geometric configurations.

In some embodiments, the actuation elements 1202-1204 are coupled mechanically. In some embodiments, the actuation elements 1202-1204 are thermoelastically manipulated (e.g., deformed) at least partially away from their original geometric configurations (e.g., manufactured geometries) prior to being coupled mechanically. In some embodiments, the actuation elements 1202-1204 are coupled in a manner such that they are nested serially (e.g., with the peaks and valleys of the sinusoid patterns aligning). The actuation elements 1202-1204 may be coupled using sutures, adhesives/glue, rivets/crimps, welds, etc., and/or may be coupled in part using the mechanical constraints/forces applied by the membrane 1201. In some embodiments, the actuation assembly 1220 may include insulative elements 1205 which may have a similar shape, pattern, and/or geometric configuration as one or more of the actuation elements 1202-1204. In some embodiments, the insulative elements 1205 are serially nested between the actuation elements 1202-1204. Additionally or alternatively, the insulative elements 1205 can be located at the ends of the composite element stack (i.e., at the front and back ends of the stack of serially nested elements, as shown in FIGS. 12A and 12B). The insulative elements 1205 may provide electrical and/or thermal insulation, or other types of insulation. The insulative elements 1205 may be comprised of materials such as low-density polymers, PTFE, ePTFE, polyurethanes, silicones, silica, graphene, cellulose, ceramic, or other materials. In some embodiments, the insulative elements 1205 are configured as coatings over one or more actuation elements 1202-1204 and not as discrete components. Once the elements 1202-1205 are coupled, the composite nested structure 1210 may take on an equilibrium composite geometry, for example a cylinder with a composite diameter $D_C$.

To adjust a geometric property (e.g., the shape, diameter, etc.) of the actuation assembly 1220, energy is applied to one or more of the actuation elements 1202-1204 to raise the temperature of the element(s) above the phase transition temperature of the material (e.g., above the R-phase start, austenitic start, R-phase finish, or austenitic finish temperature). The actuated element(s) will undergo a thermoelastic recovery resulting in a shape and/or size change towards its original geometric configuration (e.g., its manufactured geometry). The remaining elements in the composite structure (to which no direct energy and, therefore, no substantial heat, is applied) will remain relatively malleable, and therefore deform in a manner complementary to the movement to the actuated element(s) (e.g., in response to force applied by the coupled actuated elements). By selectively applying energy to various actuation elements 1202-1204 or to various combinations of actuation elements, the actuation assembly 1220 may change geometric configuration (e.g., change shape, expand in cross-sectional area, decrease in cross-sectional area) in a manner that would impact the flow of a fluid therethrough. In embodiments, the actuation assembly 1220 may serve as the lumen for an interatrial shunting system. In other embodiments, the actuation assembly 1220 may integrate with or interface with a lumen of an interatrial shunting system (e.g., the membrane 1201 can be placed around a membrane of the shunting system that defines the shunt lumen.

In some embodiments, the plurality of actuator elements can comprise 1, 2, 3, 4, 5, 6, 7, 8, 9, 10, or more discrete actuation elements. In some embodiments, the possible granularity of a geometry change of the actuation assembly 1220 can be increased by having an increased number of actuation elements. In some embodiments, geometry changes of the actuation assembly 1220 may be achieved via a partial transition of a selected actuation element from an initial state to a second state that is between the initial state and the original geometric configuration of the element. For example, pulses of energy may be delivered to heat the selected actuation element to a temperature that is between the austenite start temperature and the austenite finish temperature of the material (or alternatively between the R-phase start temperature and R-phase finish temperature). Alternatively or additionally, pulses of energy may be delivered to heat only a portion of the actuation element, leaving the rest of the actuation element at a temperature that does not induce a thermoelastic recovery. This may be accomplished, for example, by heating one or more attachments to an element (e.g., heating an element locally) instead of heating the element directly (e.g., global heating of an element).

Figure 13A:
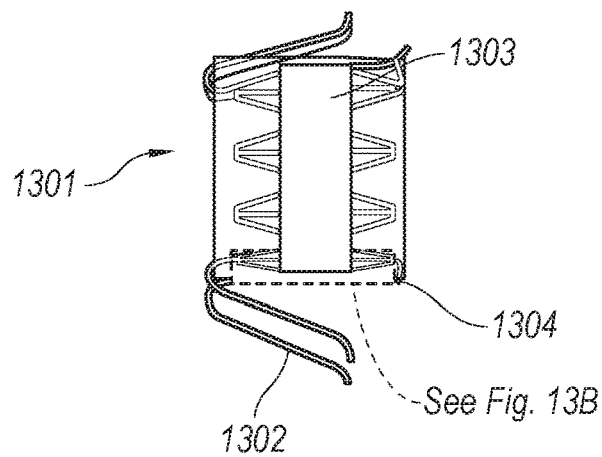
FIGS. 13A-13D illustrate various embodiments of an actuation elements positioned within an interatrial shunting system configured in accordance with an embodiment of the present technology.

FIGS. 13A-13D illustrate various actuation assemblies integrated into an interatrial shunting system configured in accordance with select embodiments of the present technology. FIG. 13A, for example, illustrates a cross-sectional side view of an interatrial shunt assembly 1300. The shunt assembly 1300 includes a lumen 1301 through which a fluid (e.g., blood) may flow. Some embodiments of the shunt assembly 1300 also include anchoring elements 1302 and 1304. Embodiments may also include a flow control element or actuation assembly 1303 that operates to control the flow of fluid through the lumen 1301. In some embodiments, the anchoring elements 1302 and 1304 are comprised of a superelastic material, such as nitinol manufactured to have an austenitic start and/or austenitic finish temperature that is similar to or lower than body temperature. Additional components, for example sensors, energy storage components, electrical components, and data transmission components, may also be included in the shunt assembly 1300, but are not shown in FIGS. 13A-13D for clarity.

Figure 13B:
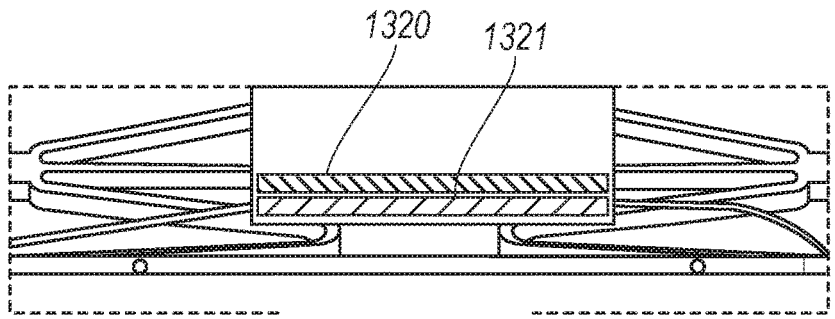
Figure 13C:
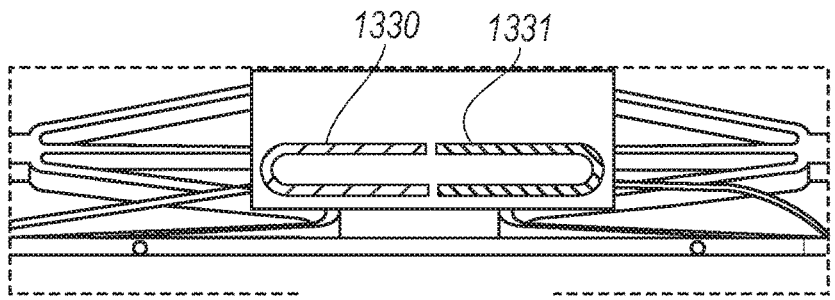
Figure 13D:
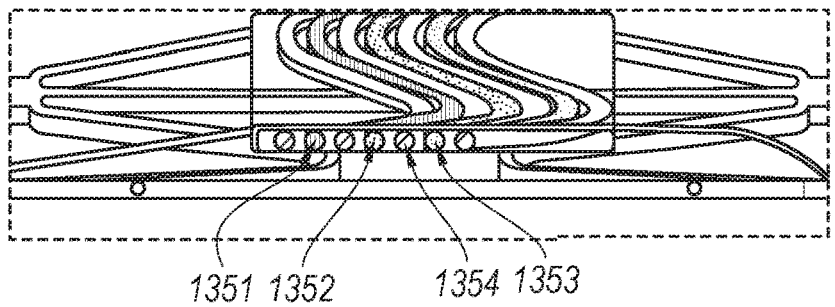

FIGS. 13B-13D are enlarged, cross-sectional views of various example embodiments of actuation assemblies 1303 integrated into the shunt assembly 1300. In embodiments, the actuation assembly can comprise at least two coupled actuation elements (e.g., two shape memory actuation elements). For example, in the example illustrated in FIG. 13B, the actuation assembly comprises concentrically nested actuation elements 1320 and 1321 (e.g., nested stents) in a manner similar to the embodiment shown in FIG. 4A-4C. In a second example illustrated in FIG. 13C, the actuation assembly comprises interlocking actuation elements 1330 and 1331 in a manner similar to the embodiments shown in FIGS. 5A-7. In a third example illustrated in FIG. 13D, the actuation assembly comprises elongated wire-like actuation elements (e.g., rings) 1351-1354 in a manner similar to the embodiment shown in FIGS. 12A-12B. In some embodiments, the actuation assembly 1303 is integrated with (e.g., covered with, encased inside, surrounding, otherwise attached-to, etc.) a material or membrane layer so as to create a lumen through which blood may flow. In embodiments, the membrane layer material is comprised of ePTFE, nylon, urethane, or another suitable material known to those skilled in the art. In some embodiments, the actuation assembly 1303, with or without an integrated material layer, serves as the lumen for the shunting assembly 1300. In other embodiments, the actuation assembly 1303 does not itself constitute the lumen, but directly or indirectly interfaces with and influences the geometry of the lumen of the shunting assembly 1300.

The present technology also provides interatrial shunting systems having actuation elements that do not directly interface with the shunt lumen. For example, unlike the embodiments described with respect to FIGS. 3-13D in which the actuation assemblies define the shunt lumen, are integrated into the lumen, and/or otherwise act directly upon the lumen, the present technology further provides embodiments in which the actuation element is spaced apart from the lumen and therefore does not directly manipulate the lumen.

FIGS. 14A-15C, for example, illustrate an adjustable interatrial shunting system 1400 ("system 1400") configured in accordance with select embodiments of the present technology. The system 1400 includes a shunting element 1401 (e.g., a generally tubular element) having a first end flow aperture 1402 and a second end flow aperture 1404. The shunting element includes a lumen 1405 extending between the first end flow aperture 1402 and the second end flow aperture 1404. When positioned across the septal wall (e.g., as shown in FIG. 14B), the first end flow aperture 1402 can be in fluid communication with a RA and the second end flow aperture 1404 can be in fluid communication with a LA. Accordingly, the lumen 1405 can fluidly connect the LA and the RA.

The shunting element 1401 can include a frame 1410 having an outer surface configured to engage native tissue, such as the septal wall S. In some embodiments, the frame 1410 can define a chamber 1414 that can encase a gel, fluid, foam, gas, or other substance that is compressible and/or displaceable. For example, in some embodiments, the substance can compress and/or expand in response to shape changes of the lumen 1405, described in greater detail below. In other embodiments, the substance can be displaced and/or return to its original location in response to shape changes of the lumen 1405. The shunting element 1401 further includes RA anchors 1424 and LA anchors 1426 configured to secure the device to the septal wall when implanted in a patient.

The shunting element 1401 can further include a membrane 1406 at least partially defining the lumen 1405. The membrane 1406 can define a portion of the chamber 1414, or can be coupled to a portion of the frame 1410 defining the chamber 1414. The membrane 1406 can be composed of any semi-flexible and biocompatible material, such as PTFE, ePTFE, silicone, nylon, polyethylene terephthalate (PET), polyether block amide (pebax), polyurethane, blends or combinations of these materials, or other suitable materials. In some embodiments, a plurality of spindles 1408 are disposed within or otherwise coupled to the membrane 1406. The spindles 1408 can extend at least partially between the first end flow aperture 1402 and the second end flow aperture 1404 and define a shape of the lumen 1405. In some embodiments, and as described in more detail below, the spindles 1408 can be bendable and configured to adjust a diameter of the lumen 1405, thereby controlling the amount of blood flowing through the lumen 1405. In some embodiments, the spindles 1408 are nitinol spindles and can be encased in a thin polymer, such as ePTFE. In some embodiments, the spindles 1408 are hollow and thin to facilitate bending.

The system 1400 can further include a first end element 1416 adjacent the first end flow aperture 1402 and a second end element 1418 adjacent the second end flow aperture 1404. The first end element 1416 can be generally circular or oval-shaped to avoid blocking blood flow through the lumen 1405. The spindles 1408 can extend between and be connected to the first end element 1416 and the second end element 1418. The system 1400 can further include an anchoring element 1420 positioned adjacent the first end element 1416. As one skilled in the art will appreciate from the disclosure herein, the anchoring element 1420 can be positioned adjacent the second end element 1418 and operate in a substantially similar manner. Accordingly, while the below description describes the system 1400 with the anchoring element 1420 positioned adjacent the first end element 1416, the present technology also includes "mirror image" embodiments in which the anchoring element 1420 is positioned adjacent the second end element 1418.

In the illustrated embodiment, the anchoring element 1420 and the second end element 1418 can be secured to a portion of the system 1400 fixedly secured to the septal wall (e.g., the outer surface 1412) and/or can be directly secured to the septal wall. Securing the anchoring element 1420 and the second end element 1418 to the system 1400 or the septal wall prevents the anchoring element 1420 and the second end element 1418 from moving during adjustment of the lumen diameter, as described below. The anchoring element 1420 can be coupled to the first end element 1416 via one or more actuation elements 1422. The actuation elements 1422 can be springs, coils, or other elements configured to adjust a distance between the anchoring element 1420 and the first end element 1416.

The first end element 1416 is moveable with respect to the anchor element 1420. For example, the first end element 1416 can move toward the anchoring element 1420, thereby bending the spindles 1408 inward (e.g., toward a central longitudinal axis of the lumen 1405) and decreasing an inner diameter of the lumen (e.g., moving from the configuration depicted in FIGS. 14A-14C to the configuration depicted in FIGS. 15A-15C). In some embodiments, for example, the spindles 1408 can bend inward until they contact each other, thereby closing the lumen 1405 and generally blocking any flow through the lumen 1405. In other embodiments, however, the spindles 1408 do not bend inward enough to fully close the lumen 1405, and thus the lumen remains partially open at all times. The first end element 1416 can also move away from the anchoring element 1420, thereby straightening and/or bending the spindles 1408 outward (e.g., away from a central longitudinal axis of the lumen 1405), which increases an inner diameter of the lumen 1405 (e.g., moving from the configuration depicted in FIGS. 15A-15C to the configuration depicted in FIGS. 14A-14C). As one skilled in the art will appreciate from the disclosure herein, the spindles 1408 can bend to any number of positions to define any number of central inner diameters, and not just those explicitly illustrated in FIGS. 14A-15C. In some embodiments, a length of the lumen 1405 and or the shunting element 1401 can also change as the inner diameter of the lumen 1405 changes. For example, as the central inner diameter of the lumen 1405 decreases, the length of the lumen 1405 can also decrease. Likewise, as the central inner diameter of the lumen 1405 increases, the length of the lumen 1405 can also increase. However, even in embodiments where a length of the shunting element 1401 changes, the outer diameter of the shunting element 1401 remains generally constant.

Various embodiments of the system 1400 provide different mechanisms to adjust the distance between the anchoring element 1420 and the first end element 1416. For example, in some embodiments, the actuation elements 1422 can be composed of shape-memory material, such as a shape memory alloy (e.g., nitinol). Accordingly, the actuation elements 1422 can be transitionable between a first material state (e.g., a martensitic state, a R-phase, etc.) and a second material state (e.g., a shape memory state, an austenitic state, etc.). In the first state, the actuation elements 1422 may be deformable (e.g., plastic, malleable, compressible, expandable, etc.). In the second state, the actuation elements 1422 may have a preference toward a specific manufactured geometry (e.g., shape, length, and/or or dimension). The actuation elements 1422 can be transitioned between the first state and the second state by applying energy to the actuation elements 1422 to heat (e.g., resistively heat) the actuation elements 1422 above a transition temperature.

Figure 14A:
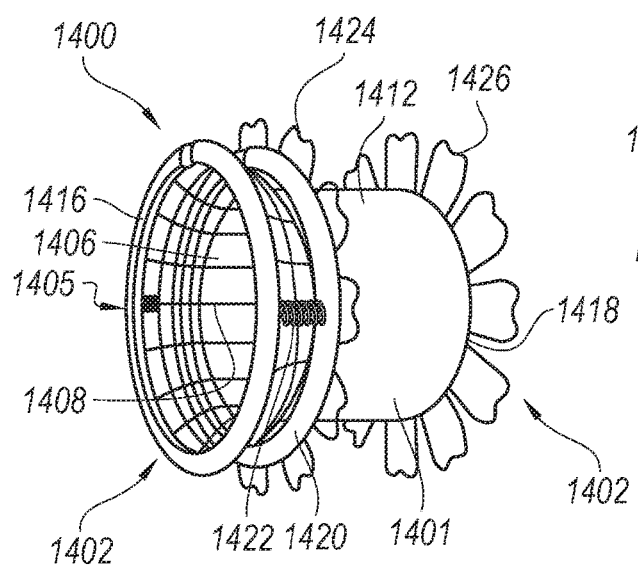
FIGS. 14A-14C illustrate an adjustable interatrial shunting system in a first configuration and configured in accordance with select embodiments of the present technology.
Figure 14B:
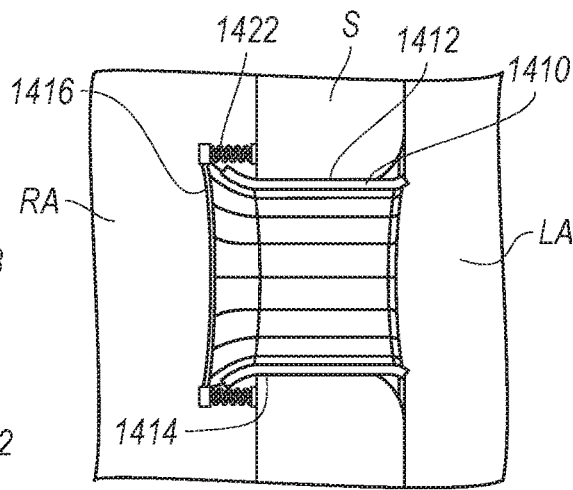
Figure 14C:
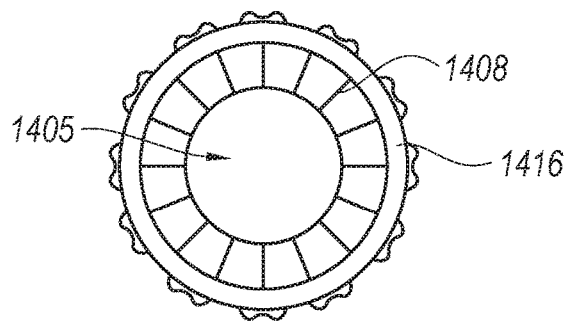
Figure 15A:
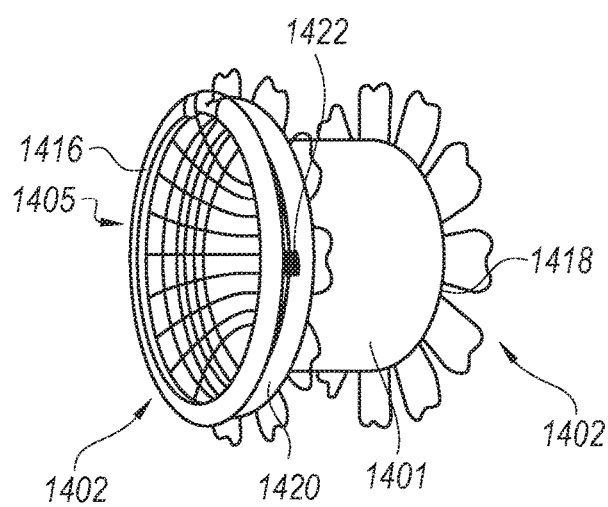
FIGS. 15A-15C illustrate the adjustable interatrial shunting system shown in FIGS. 14A-14C in a second configuration different than the first configuration.
Figure 15B:
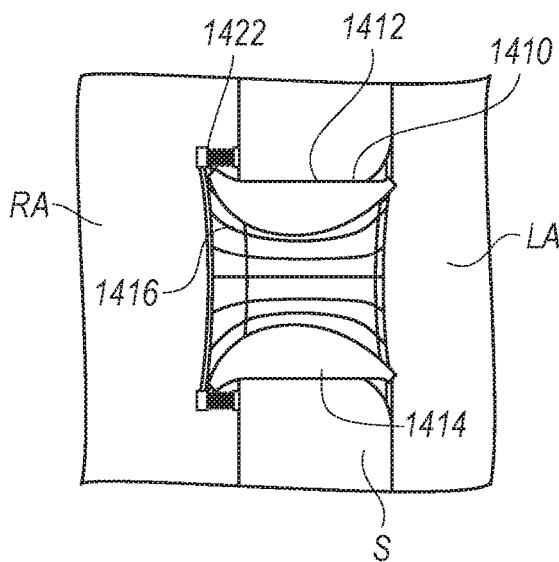
Figure 15C:
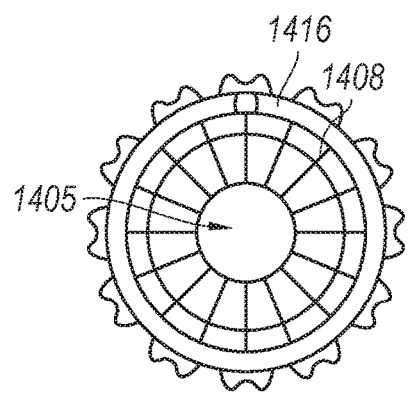

The actuation elements 1422 can be used to drive movement of the first end element 1416 toward or away from the anchor element 1420, thereby adjusting a diameter of the lumen 1405. For example, as shown in FIGS. 14A-14C, the actuation elements can have a first neutral configuration in which they are lengthened relative to their manufactured geometry. Heating the actuation elements 1422 above their transition temperature therefore causes the actuation element to compress toward its manufactured geometry. This pulls the first end element 1416 toward the anchor element 1420, which, as previously described, bends the spindles 1408 toward a central longitudinal axis of the lumen 1405 and decreases a diameter of the lumen (e.g., at the "pinch point" of the hourglass shape). For example, FIGS. 15A-15C illustrates the system 1400 in a second configuration after the actuation elements 1422 have been actuated to decrease the flow through the lumen 1405.

In some embodiments, the actuation elements 1422 may operate without relying on shape memory characteristics. For example, in other embodiments, the actuation elements 1422 are springs having a first tension (e.g., spring constant). The first tension can be adjusted to a second tension to dictate how tightly the first end element 1416 is pulled toward the anchoring element 1420. For example, as the tension in the spring decreases, the distance between the anchoring element 1420 and the first end element 1416 increases, thereby increasing the inner diameter of the lumen 1405. As the tension in the spring increases, the distance between the anchoring element 1420 and the first end element 1416 decreases, thereby decreasing the inner diameter of the lumen 1405. In some embodiments, the spring tension can be adjusted via a magnet external to the patient. In other embodiments, the spring tension can be mechanically adjusted using an adjustment tool delivered via a catheter.

In another embodiment, the actuation elements 1422 are coils. Applying energy to the coils can adjust a length of the coils. For example, applying radiofrequency ("RF") energy can selectively adjust the length of the coil, thereby (a) adjusting a distance between the anchoring element 1420 and the first end element 1416 and (b) adjusting the inner dimeter of the lumen 1405. In some embodiments, the RF energy can be applied externally from the patient to minimize the invasiveness of the adjustment procedure. In some embodiments, the RF energy is delivered at a low frequency to reduce signal attenuation and/or to reduce tissue heating. Low frequency signals include signals having frequencies between about 20 kHz and 300 kHz. However, one skilled in the art will appreciate that other frequencies, such as those less than 20 kHz or greater than 300 kHz, may be used in certain embodiments of the present technology. In some embodiments, the received RF energy may comprise about 10-30 watts. Due to scattering attenuation, however, the device may receive less power than transmitted. Accordingly, the device can be configured to operate with less power than transmitted, such as one watt.

In another embodiment, the system 1400 can include a mechanical adjustment element (e.g., a screw located on the first end element 1416 or the anchoring element 1420). In such embodiments, the system 1400 can be adjusted using an adjustment tool delivered to the system 1400 via a catheter. In another embodiment, the system 1400 can be adjusted using a balloon or other expandable element. For example, a balloon can be delivered into the lumen via a catheter. Inflating the balloon can apply a force that causes the spindles 1408 to bend outward away from the central longitudinal axis of the lumen 1405, thereby increasing the inner diameter of the lumen 1405. The spindles 1408 can comprise a relatively malleable material such that, following deflation and removal of the balloon, the lumen 1405 maintains the set inner diameter.

FIGS. 16A-16D illustrate an embodiment of an adjustable interatrial system 1600 configured in accordance with select embodiments of the present technology. The system 1600 includes a frame 1610 and a membrane 1606 positioned within the frame 1610. The frame 1610 can be composed of a superelastic material (e.g., nitinol having a phase transformation temperature lower than body temperature). The membrane 1606 can be any semi-flexible and biocompatible material that forms a lumen 1605. A plurality of spindles 1608 can be embedded within or otherwise coupled to the membrane 1606 to provide structural integrity to the lumen 1605. The lumen 1605 extends between a first end flow aperture 1602 and a second end flow aperture 1604. Accordingly, when positioned across a septal wall of a heart, the first end flow aperture 1602 can be in fluid communication with a RA and the second end flow aperture 1604 can be in fluid communication with a LA such that the lumen 1605 fluidly connects the LA and the RA. The system 1600 can also include RA anchors 1624 and LA anchors 1625 (e.g., extending form the frame 1610) that secure system 1600 in place when implanted.

The system includes an actuation assembly 1620 extending from the frame 1610. The actuation assembly can include one or more rails 1628 and one or more actuation elements 1622. The membrane 1606 can be slidably coupled to the one or more rails 1628 1724 such that the first end flow aperture 1602 can move along the rails in a direction parallel to the longitudinal axis of the lumen 1605. The one or more actuation elements 1622 can be composed of shape-memory material, such as a shape memory alloy (e.g., nitinol). Accordingly, the actuation elements 1622 can be transitionable between a first material state (e.g., a martensitic state, a R-phase, etc.) and a second material state (e.g., a shape memory state, an austenitic state, etc.). In the first state, the actuation elements 1622 may be deformable (e.g., plastic, malleable, compressible, expandable, etc.). In the second state, the actuation elements 1622 may have a preference toward a specific manufactured geometry (e.g., shape, length, and/or or dimension). The actuation elements 1622 can be transitioned between the first state and the second state by applying energy to the actuation elements 1622 to heat (e.g., resistively heat) the actuation elements 1622 above a transition temperature.

Figure 16A:
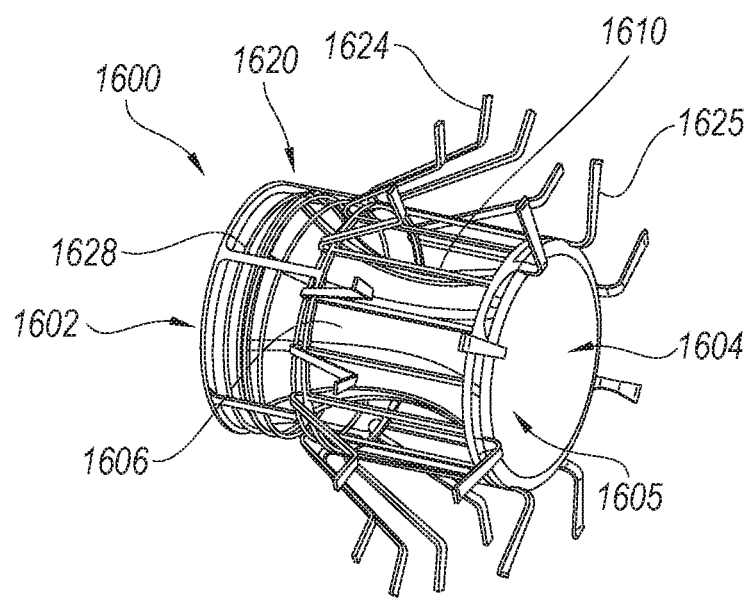
FIGS. 16A-16D illustrate another adjustable interatrial shunting system configured in accordance with select embodiments of the present technology.
Figure 16B:
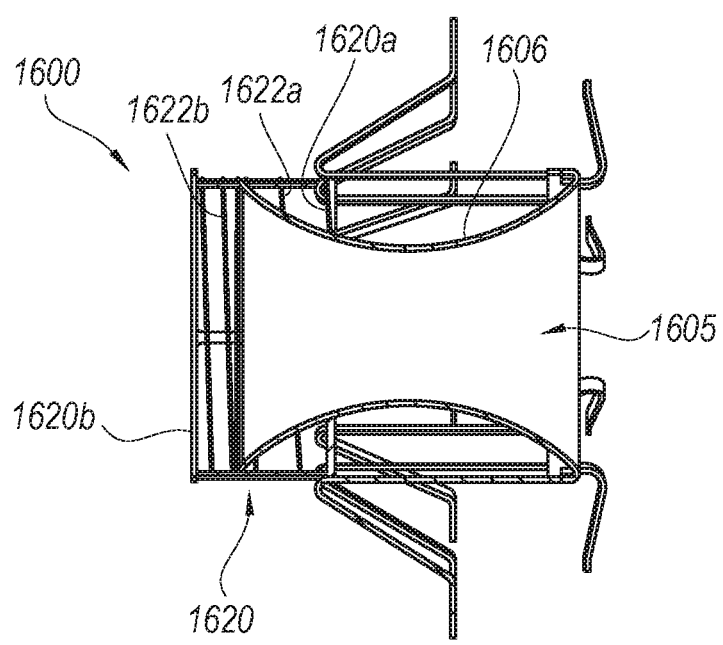
Figure 16C:
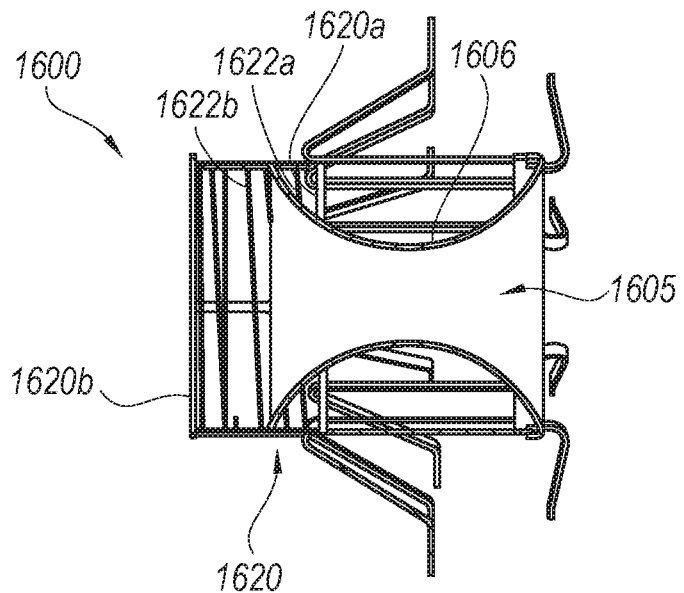
Figure 16D:
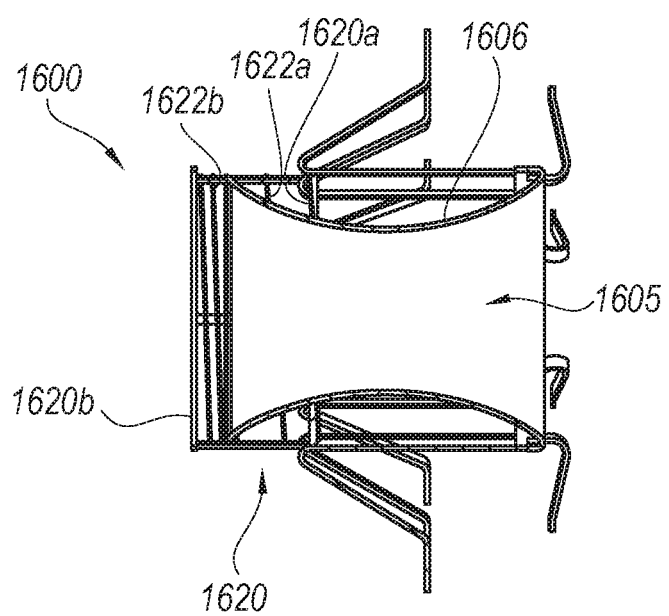

In the illustrated embodiment, the actuation assembly 1620 includes a first actuation element 1622a and a second actuation element 1622b. The first actuation element 1622a extends from a proximal end 1620a of the actuation assembly 1620 and is coupled to a portion of the lumen 1605 at or adjacent the first end flow aperture 1602. The second actuation element 1622b extends from a distal end 1620b of the actuation assembly 1620 and is coupled to a portion of the lumen 1605 at or adjacent the first end flow aperture 1602. At least one of the first actuation element 1622a and the second actuation element 1622b is deformed relative to its manufactured geometry. For example, FIG. 16B illustrates both the first actuation element 1622a and the second actuation element 1622b deformed (e.g., lengthened) relative to their manufactured geometries. Heating the first actuation element 1622a above its transition temperature causes the first actuation element 1622a to transition from the first material state to the second material state and move toward its more compressed manufactured geometry, shown in FIG. 16C. This pulls the first inflow aperture 1602 toward the proximal end 1620a of the actuation assembly 1620, which decreases a length of the lumen 1605 and causes the spindles 1608 (and thus the membrane 1606) to bend inwardly toward a central longitudinal axis of the lumen 1605, thereby decreasing a dimeter of the lumen 1605. Conversely, heating the second actuation element 1622b above its transition temperature causes the second actuation element 1622b to transition from the first material state to the second material state and move toward its more compressed manufactured geometry, shown in FIG. 16D. This pulls the first inflow aperture 1602 toward the distal end 1620b of the actuation assembly 1620, which increases a length of the lumen 1605 and causes the spindles 1608 (and thus the membrane 1606) to bend outwardly away from the central longitudinal axis of the lumen 1605, thereby increasing a diameter of the lumen 1605. Therefore, the first and second actuation elements 1622a, 1622b can be selectively heated to increase or decrease the diameter of the lumen 1605 and adjust the flow of fluid therethrough.

Figure 17A:
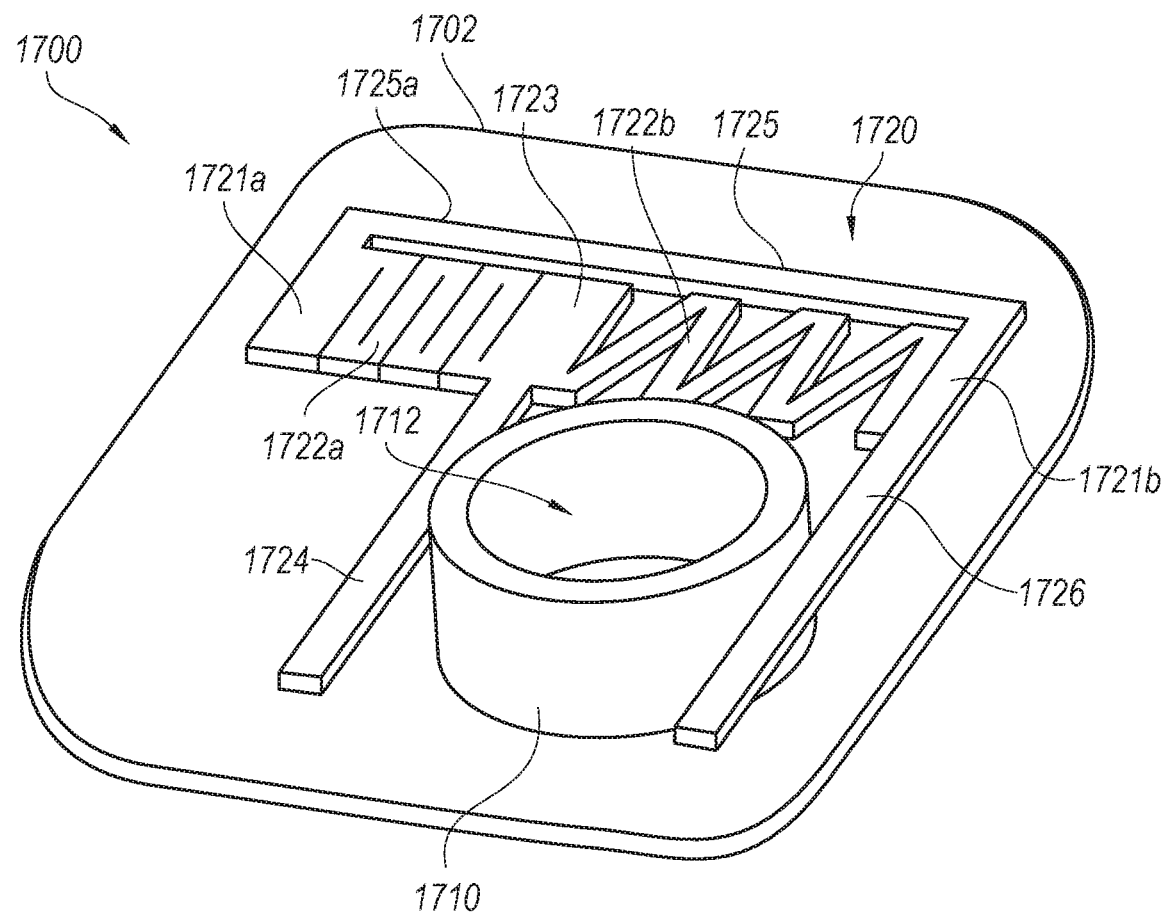
FIGS. 17A-17C illustrate another adjustable interatrial shunting system configured in accordance with select embodiments of the present technology.

FIG. 17A is an isometric partial cut away view of an adjustable interatrial shunting system 1700 ("system 1700") configured in accordance with embodiments of the present technology. The system 1700 includes a plate 1702, a shunting element 1710, and an actuation assembly 1720. The shunting element 1710 and the actuation assembly 1720 can be coupled to the plate 1702. When the system 1700 is implanted in a patient, the plate 1702 can be secured to a septal wall or other anatomical structure to secure the system 1700 in a desired position. The plate 1702 can have any number of shapes and sizes that permit the system 1700 to be delivered across and secured to the septal wall. For example, the plate 1702 may be smaller than illustrated such that it matches the general size profile of the shunting element 1710 and/or the actuation assembly 1720. In some embodiments, some and/or all of the actuation assembly 1720 can be spaced apart from the plate 1702 by a spacing element (not shown). For example, the actuation assembly 1720 can be spaced apart from the plate 1702 by about 1 mm or more. In such embodiments, the plate 1702 may be secured to the septal wall such that the actuation assembly 1720 extends at least partially into a heart chamber (e.g., the RA). In other embodiments, the plate 1702 can be omitted and the shunting element 1710 and/or the actuation assembly 1720 can be secured to the septal wall either directly or with other suitable anchoring mechanisms.

Figure 17B:
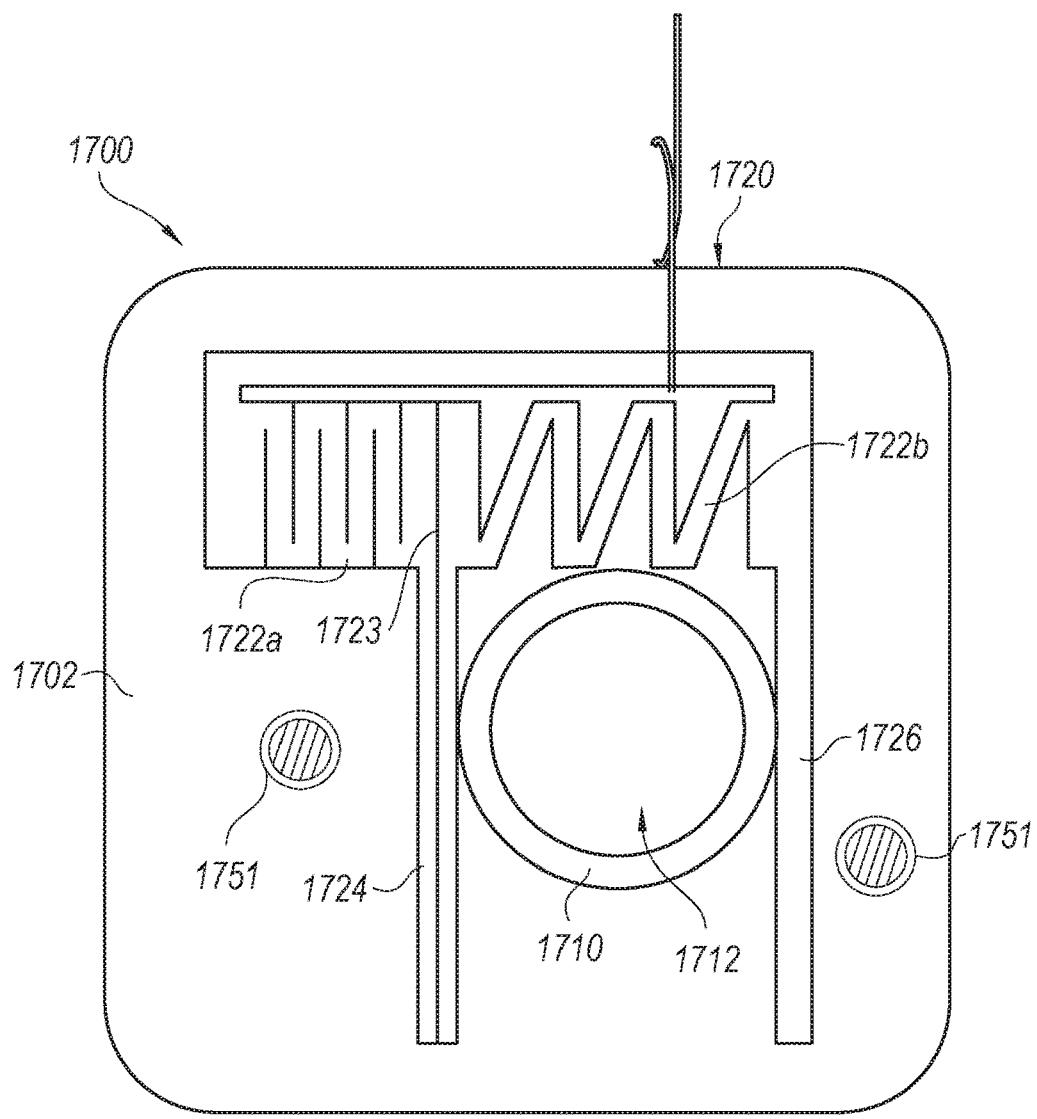
Figure 17C:
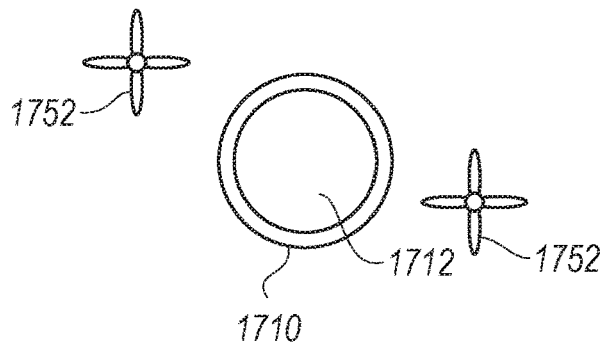

The plate 1702 is configured to reside on a first side (e.g., a RA side) of the septal wall. In some embodiments, the system 1700 may have (e.g., additional) anchors configured to secure the system 1700 to the septal wall. For example, FIGS. 17B and 17C illustrate an embodiment of the system 1700 having an optional anchoring mechanism. FIG. 17B is a view of the system 1700 from the RA and FIG. 17C is a view of the system 1700 from the LA. As illustrated in FIG. 17B, the plate 1702 can optionally include anchor ports 1751. The anchor ports 1751 can be configured to receive and secure (e.g., flared) anchors 1752 (FIG. 17C). As illustrated in FIG. 17C, the flared anchors 1752 can engage the septal wall such that the system 1700 is anchored in place by the plate 1702 on the RA side of the septal wall and the flared anchors 1752 on the LA side of the septal wall. When implanted across a septal wall, the actuation assembly 1720 can be positioned on a RA side or a LA side of the septal wall. In some embodiments, the system 1700 can be collapsed into a delivery catheter having an outer diameter of about 30 Fr or less, or about 20 Fr or less, to facilitate delivery of the system 1700 to the heart.

Returning to FIG. 17A, the shunting element 1710 has a lumen 1712 extending therethrough. In the illustrated embodiment, the shunting element 1710 has a generally tubular or cylindrical shape that defines the lumen 1712. In other embodiments, however, the shunting element 1710 can have other suitable shapes. The shunting element 1710 can comprise an at least partially deformable and/or flexible material. As described in greater detail below, this enables the shunting element 1710 to change shape and/or size. When the system 1700 is implanted adjacent a septal wall, the shunting element 1710 fluidly connects the LA of the patient and the RA of the patient via the lumen 1712.

The actuation assembly 1720 includes a rim 1725 having a spine portion 1725a with a first anchor element 1721a and a second anchor element 1721b extending from and generally perpendicular to opposing end portions of the spine portion 1725a. The second anchor element 1721b can extend generally towards the shunting element 1710 to define a shunting element anchor 1726. In some embodiments, a portion of the shunting element anchor 1726 may engage an exterior surface portion of the shunting element 1710. Some or all of the rim 1725 can be secured to the plate 1702 and/or the septal wall. Accordingly, the rim 1725 is configured to remain static as the actuation assembly 1720 is actuated to adjust the size and/or shape of the lumen 1712, as described in greater detail below.

The actuation assembly 1720 further includes a moveable element 1723, a first actuation element 1722a extending between the first anchor element 1721a and the moveable element 1723, and a second actuation element 1722b extending between the second anchor element 1721b and the moveable element 1723. In the illustrated embodiment, the first actuation element 1722a is in a compressed state and the second actuation element 1722b is in a partially expanded state. However, as will be described in greater detail below with respect to FIGS. 18A-18C, the first actuation element 1722a and second actuation element 1722b can be expanded and compressed to change the configuration of the actuation assembly 1720. The moveable element 1723 is generally between the first actuation element 1722a and the second actuation element 1722b. A moveable arm 1724 extends from the moveable element 1723 and can be generally parallel to the shunting element anchor 1726. The moveable arm 1724 extends generally adjacent to the shunting element 1710 but on a side generally opposite the shunting element anchor 1726. Accordingly, the shunting element 1710 is positioned generally between the moveable arm 1724 and the shunting element anchor 1726. The moveable arm 1724 can engage the shunting element 1710 to change a size and/or shape of the lumen 1712, as described in detail below.

In the illustrated embodiment, the actuation assembly 1720 has a relatively flat profile. For example, the actuation assembly 1720 may extend less than about 10 mm (e.g., less than about 5 mm or less than about 2 mm) outwardly from the plate 1702 and/or the septal wall (when implanted). Accordingly, the actuation assembly 1720 may extend less than about 10 mm (e.g., less than about 5 mm or less than about 2 mm) into a heart chamber (e.g., a RA) when implanted in a patient. Without wishing to be bound by theory, the relatively flat profile of the actuation assembly 1720 is expected to reduce a risk of thromboembolic events. Further, in some embodiments the actuation assembly 1720 can also be positioned within a bladder or other membrane (not shown) to fluidly isolate the actuation assembly 1720 from the surrounding environment.

Various aspects of the actuation assembly 1720 can comprise shape-memory material(s) and/or superelastic material(s) configured to at least partially transition from a martensitic phase to an austenitic phase upon application of energy. For example, at least the first actuation element 1722a and the second actuation element 1722b can be composed of a shape memory alloy such as nitinol. The first actuation element 1722a and the second actuation element 1722b can therefore change shape (e.g., expand and/or compress in length, width, etc.) in response to exposure to energy, such as light and/or electrical current, that creates a temperature increase in the material above the transition temperature. In such embodiments, the actuation assembly 1720 can be selectively actuated by applying energy directly or indirectly to the first actuation element 1722a and/or the second actuation element 1722b. In some embodiments, energy can be applied to individual bend regions (e.g., bend regions 1832a-d—FIG. 18B) of the spring elements. Targeting individual bend regions 1832a-d is expected to provide more control over the adjustment of the system 1700 by enabling a user to selectively titrate the therapy, as described in further detail below. In some embodiments, other aspects of the actuation assembly 1720 can also comprise nitinol or other suitable shape memory material(s) and/or superelastic material(s). For example, the rim 1725 can be composed of nitinol but configured to exhibit superelastic properties at body temperature. Accordingly, in some embodiments, the actuation assembly 1720 can be laser cut from a single sheet of nitinol or other suitable material.

Figure 18A:
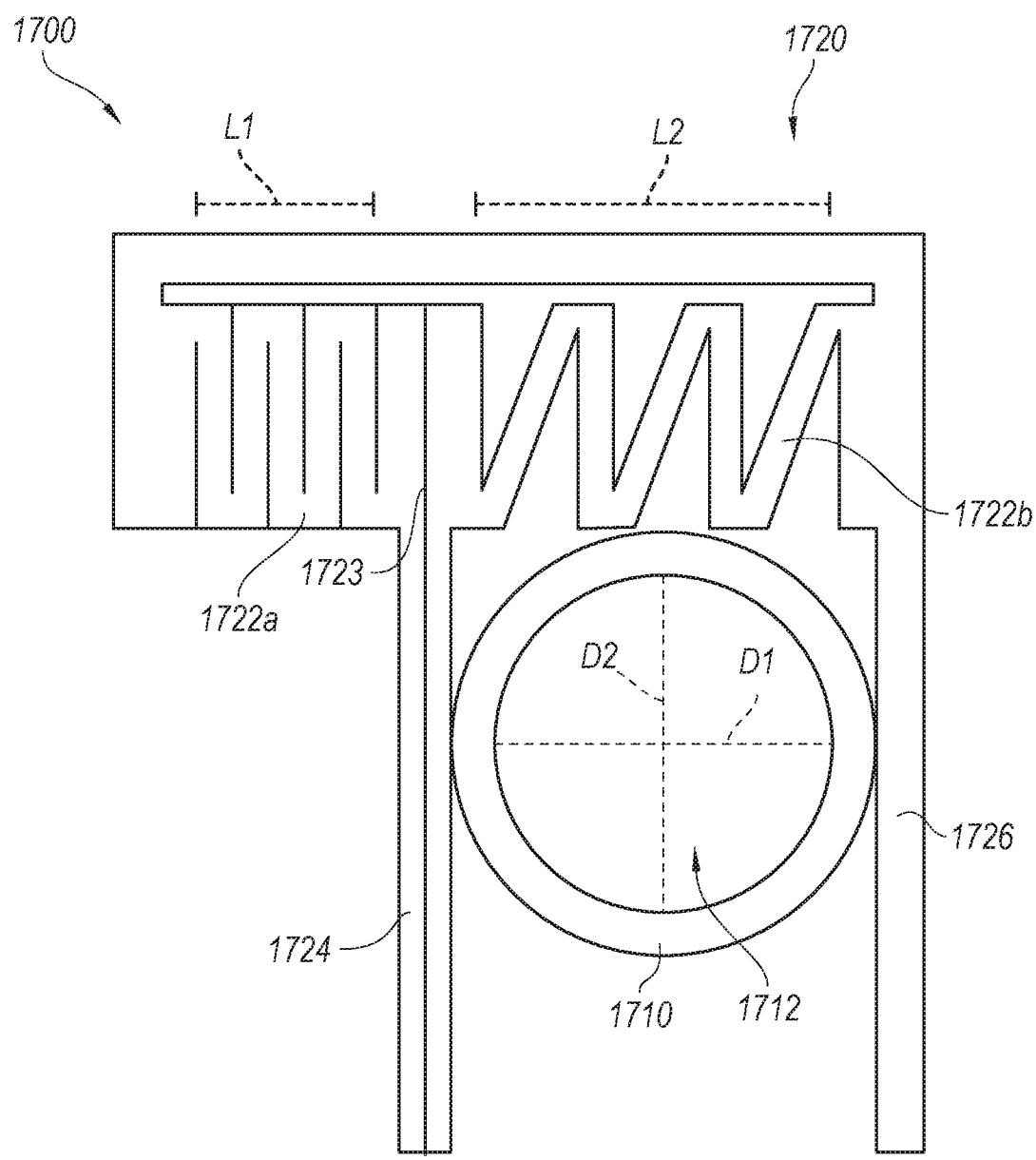
FIGS. 18A-18C illustrate operation of the adjustable interatrial shunting system shown in FIGS. 17A-17C.

FIG. 18A is a top plan view of the system 1700 in the configuration (i.e., a first configuration) depicted in FIG. 17A. In the illustrated state, the first actuation element 1722a is generally compressed and the second actuation element 1722b is at least partially expanded. Accordingly, the first actuation element 1722a has a length $L_1$ and the second actuation element 1722b has a length $L_2$ greater than the length $L_1$. As will be described in greater detail below with respect to FIGS. 18B and 18C, the lengths $L_1$ and $L_2$ can be changed by selectively expanding or compressing the first actuation element 1722a and/or the second actuation element 1722b. When the second actuation element 1722b is at least partially expanded, as in the illustrated configuration of FIG. 18A, the moveable arm 1724 does not compress the lumen 1712, and the lumen 1712 has a generally circular cross-sectional shape. For example, the lumen 1712 has a first diameter $D_1$ (e.g., a generally horizontal diameter) that is approximately equal to a second diameter $D_2$ (e.g., a generally vertical diameter).

Figure 18B:
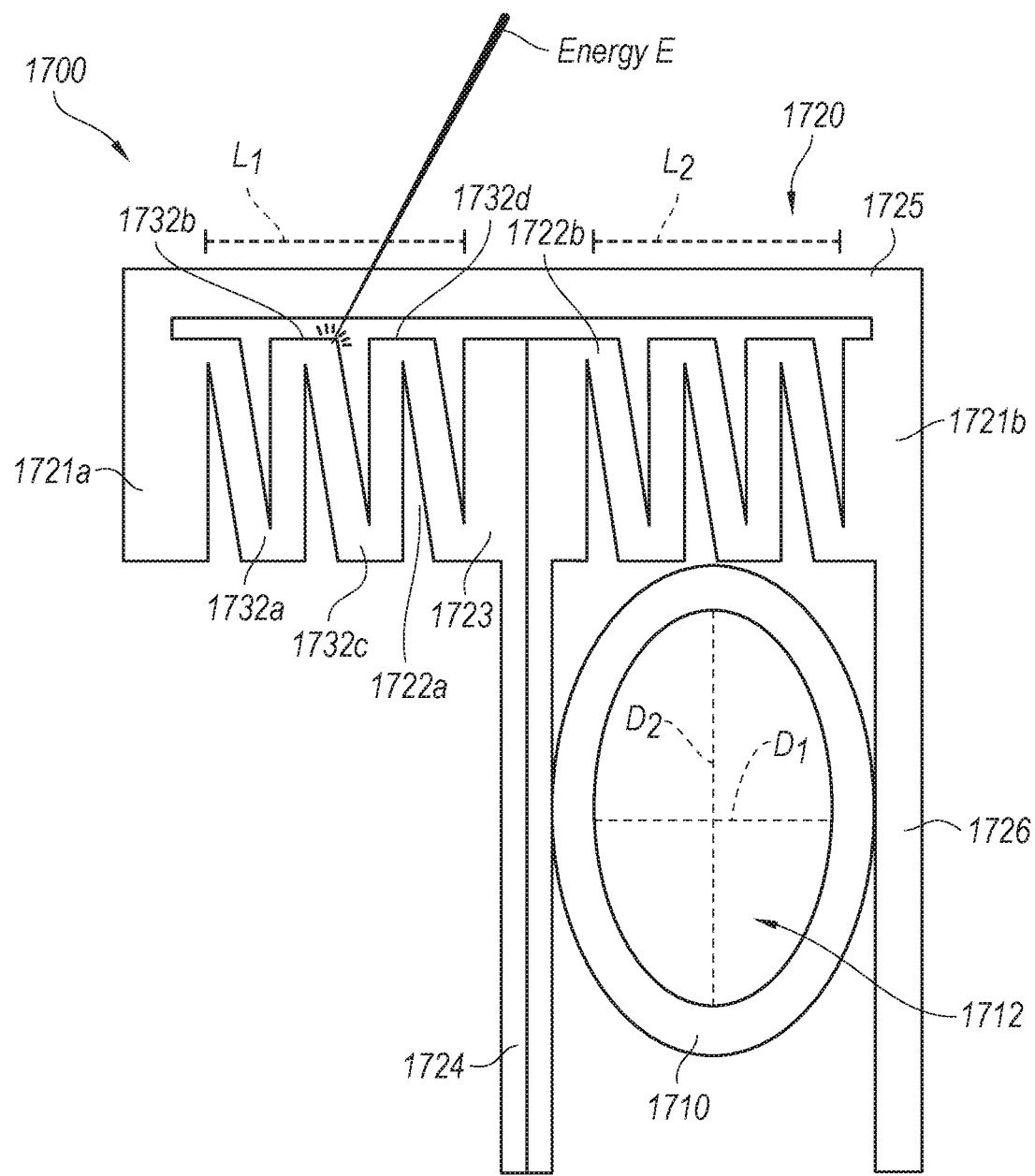

FIG. 18B is a top plan view of the system 1700 in a second configuration following at least partial actuation of the actuation assembly 1720. In particular, the first actuation element 1722a is expanding from a compressed state to a partially expanded state in response to application of energy E. In the illustrated embodiment, the energy E is being applied to a second bend region 232b of the first actuation element 1722a. If heated above its transition temperature, this causes the first actuation element 1722a to transition from a first material state (e.g., martensitic) to a second material state (e.g., austenitic) at least at the second bend region 232b. Accordingly, in some embodiments the individual bend regions can be individually actuated. In other embodiments, more than one individual bend region is actuated and/or expands in response to the application of energy E.

Because the first anchor element 1721a and the second anchor element 1721b are fixedly secured to one another via the spine portion 1725a (e.g., they do not move as the actuation elements move), the first actuation element 1722a pushes the moveable element 1723 towards the second anchor element 1721b as the first actuation element 1722a expands. As a result, the second actuation element 1722b, which remains in a relatively malleable material state, is forced from the partially expanded state towards a compressed state. Therefore, in the illustrated configuration of FIG. 18B, the length $L_1$ of the first actuation element 1722a is approximately equal to the length $L_2$ of the second actuation element 1722b. As the moveable element 1723 is pushed towards the second anchor element 1721b, the moveable arm 1724 also moves towards the shunting element anchor 1726 and engages the shunting element 1710. Because the shunting element anchor 1726 is also fixedly secured (e.g., it does not move as the spring elements move), the lumen 1712 is at least partially deformed (e.g., compressed, squeezed, pinched, etc.) between the moveable arm 1724 and the shunting element anchor 1726. Accordingly, at least one of a size or shape profile of the lumen 1712 changes. In the illustrated embodiment, the lumen 1712 is compressed into a generally oval shape, such that the first diameter $D_1$ is less than the second diameter $D_2$. Without wishing to be bound by theory, changing the shape and/or size of the lumen provides a titratable therapy/amount of shunting that can be specifically adjusted to a patient's needs. In some embodiments, the interaction of moveable arm 1724 and the shunting element 1710 deforms the lumen 1712 along the entirety of or a large portion of the element's working length (e.g., its length in the direction perpendicular to anchor 1726). In some variations, the interaction of moveable arm 1724 and the shunting element 1710 deforms the lumen 1712 locally in a region confined to the vicinity of where the arm and element interface.

Figure 18C:
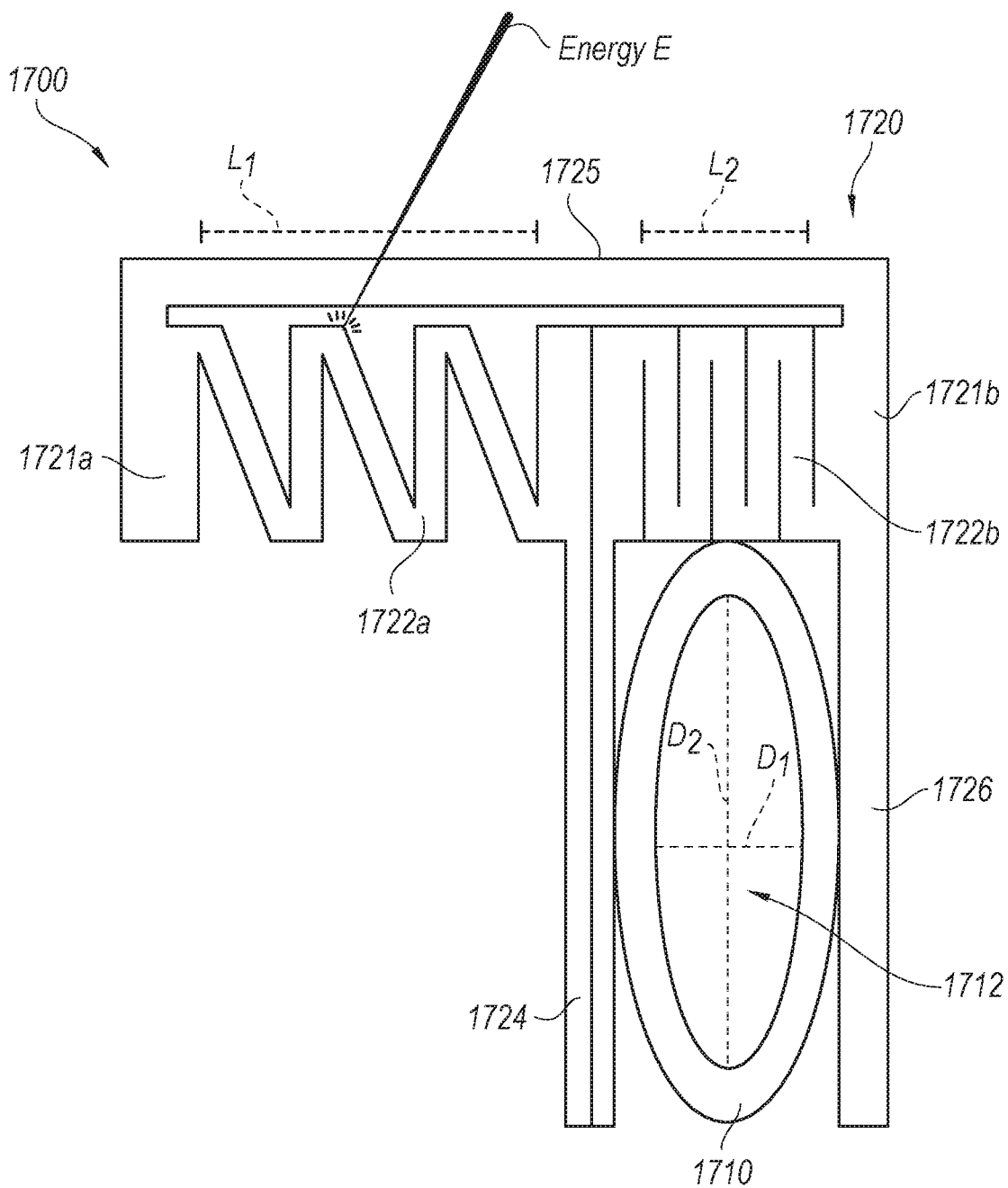

FIG. 18C is a top plan view of the system 1700 in a third configuration following further actuation of the actuation assembly 1720. As the energy E is continually delivered to the first actuation element 1722a (either for longer periods of time, or in additional locations), the first actuation element 1722a continues to expand until the second actuation element 1722b is in a generally compressed state (e.g., the length $L_1$ is greater than the length $L_2$). This causes the moveable element 1723 and the moveable arm 1724 to move further toward the second anchor element 1721b and the shunting element anchor 1726, respectively, further changing the shape and/or size of the lumen 1712. For example, the shunting element 1710 is further pinched such that the first diameter $D_1$ continues to decrease and the second diameter $D_2$ continues to increase, relative to the configurations shown in FIGS. 18A and 18B. When the desired shape and/or size of the lumen 1712 is achieved, the energy source can be turned off. Because the system 1700 can be at least partially composed of shape memory materials, the first actuation element 1722a and/or the second actuation element 1722b can be configured to retain their shape upon cessation of energy input. For example, the system 1700 can retain the configuration illustrated in FIG. 18C until further energy is applied to the first actuation element 1722a and/or the second actuation element 1722b. Accordingly, once a desired lumen shape and/or size is achieved, the lumen 1712 is configured to retain the selected shape and/or size until further application of energy.

In some embodiments, the system 1700 may have a locking mechanism (not shown) to further anchor the actuation assembly 1720 and/or the system 1700 in the desired lumen shape and/or size. In some embodiments, the locking mechanism can be engaged and/or disengaged using (i) the same energy source that is used to adjust the actuation assembly 1720, (ii) the same energy source operating at a different parameter value (e.g., frequency, temperature, etc.), and/or (iii) a different energy source. In some embodiments, the locking mechanism can automatically engage and lock the shunting element 1710 in a given configuration when the actuation assembly 1720 is not being adjusted. In such embodiments, actuation of the actuation assembly 1720 can generate sufficient forces to overcome the locking mechanism.

Altering the shape of the lumen 1712 of the shunting element 1710 may have several benefits, including titrating the rate, velocity, and/or other features of blood flow to more optimally suit a patient's needs. For example, as the shape of a lumen moves from a largely circular cross-section (e.g. as in FIG. 18A) to a largely ovular cross-section (e.g. as in FIG. 18C), the circumference of the lumen 1712 can remain constant while the cross-sectional area is reduced, thereby reducing the flow through the lumen 1712. Although described above with reference to three specific configurations, the system 1700 can be transitioned between any number of configurations using the actuation assembly 1720. In addition, the titratability of system 1700 is reversible: to return the system 1700 to the configuration shown in FIG. 18A, energy can be applied to the second actuation element 1722b, which heats the second actuation element 1722b above its transition temperature, causing it to expand and push the moveable element 1723 and moveable arm 1724 towards the first anchor element 1721a and away from the shunting element 1710. Accordingly, the size and shape of the lumen 312 can be selectively and reversibly manipulated using the actuation assembly 1720.

The lengths $L_1$ and $L_2$ of the first actuation element 1722a and the second actuation element 1722b, respectively, can be the same or different when the first actuation element 1722a and the second actuation element 1722b are in comparable states. For example, the length $L_1$ of the first actuation element 1722a when it is in the compressed state (FIG. 18A) can be generally equal to the length $L_2$ of the second actuation element 1722b when it is in a compressed state (FIG. 18C). In other embodiments, the length $L_1$ of the first actuation element 1722a when it is in the compressed state is not equal to the length $L_2$ of the second actuation element 1722b when it is in a compressed state. Accordingly, as one skilled in the art will appreciate from the disclosure herein, the system 1700 can be manufactured with a variety of dimensions and configurations without deviating from the scope of the present disclosure.

In some embodiments, the actuation assembly 1720 can be biased before implanting the system 1700 into the patient. For example, the actuation assembly 1720 can be biased toward the configuration shown in FIG. 18A or the configuration shown in FIG. 18C, depending on the anticipated needs of the patient. However, if the biased position of the system 1700 is undesirable, the actuation assembly 1720 can be actuated (e.g., either before or after implantation) to achieve the desired shape and/or size of the lumen 1712. In some embodiments when adjusting the system 1700 after implantation, the energy E can be applied from an energy source (e.g., an ultrasound or electromagnetic energy source) positioned external to the body of the patient. Accordingly, the energy can be "non-invasive." In some embodiments, the energy E can be applied from an energy source positioned adjacent the shunt, such as an energy source (e.g., a laser) delivered via a catheter. In some embodiments, the shunts can include one or more energy storage components storing energy at or adjacent the system 1700 and configured to selectively release the energy and apply it to the actuation assembly 1720.

Figure 19A:
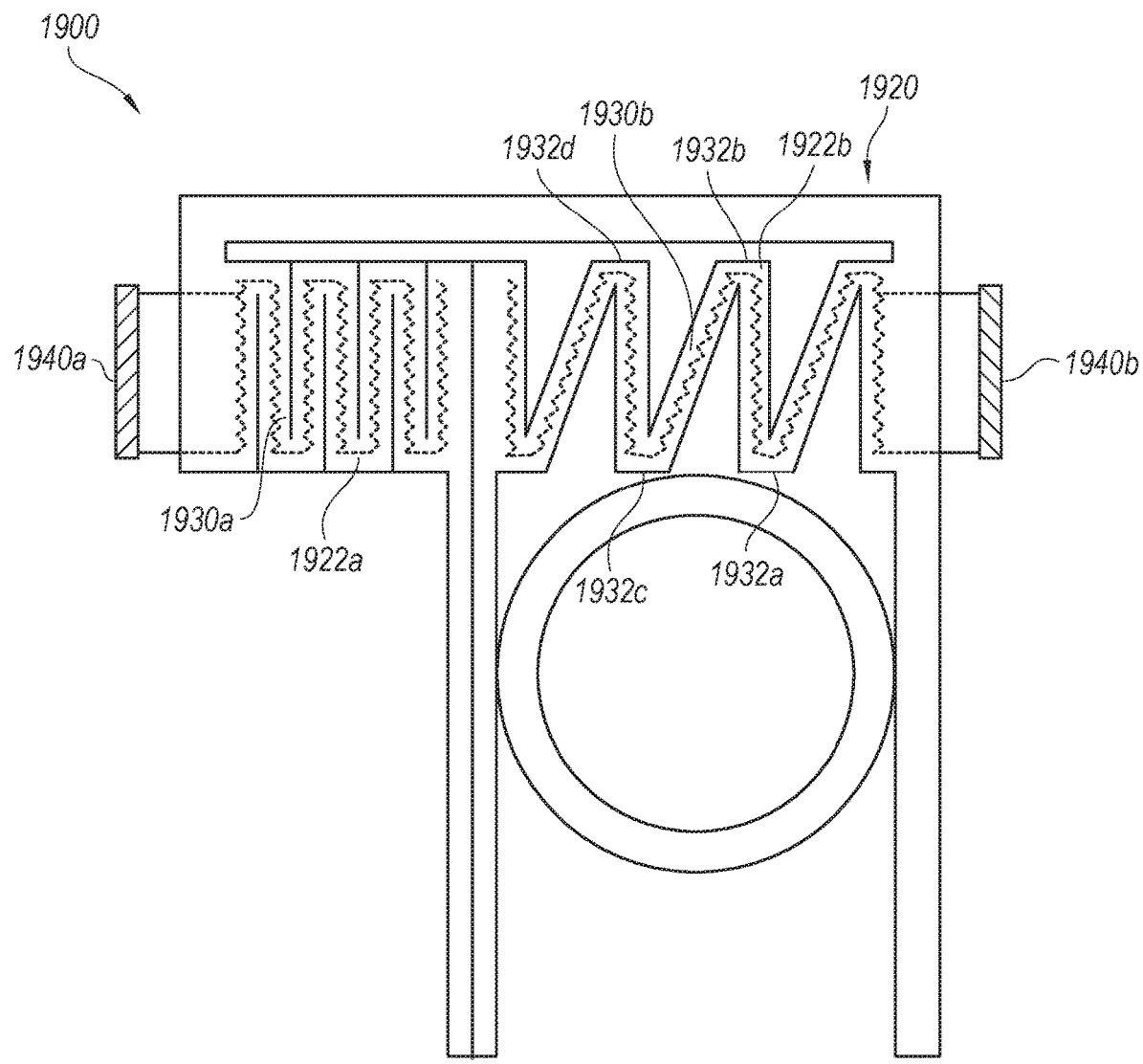
FIGS. 19A-19D illustrates another adjustable interatrial shunting system configured in accordance with select embodiments of the present technology.

FIG. 19A is a top plan view of an adjustable interatrial shunting system 1900 ("system 1900) configured in accordance with embodiments of the present technology. Certain aspects of the system 1900 can be generally similar to the system 1700. For example, the system 1900 includes an actuation assembly 1920. Similar to the actuation assembly 1720 described previously, the actuation assembly 1920 includes a first actuation element 1922a and a second actuation element 1922b. The actuation assembly 1920 differs from the actuation assembly 1720, however, in that the actuation assembly 1920 includes a first resistor or control wire 1930a extending along at least a portion of the first actuation element 1922a and a second resistor or control wire 1930b extending along at least a portion of the second actuation element 1922b. The first control wire 1930a and the second control wire 1930b can be embedded within the first actuation element 1922a and the second actuation element 1922b, respectively, or can be positioned on a surface of the first actuation element 1922a and the second actuation element 1922b, respectively. The control wires 1930a-b can be configured to deliver energy to the actuation elements 1922, thereby heating the actuation elements 1922 above their transition temperatures and inducing a phase change (e.g., transitioning from a martensitic material phase to an austenitic material phase). In some instances, using the control wires 1930a-b to deliver energy to the actuation elements 1922 may provide more evenly distributed heating along the corresponding actuation elements 1922.

The first control wire 1930a and the second control wire 1930b can be selectively actuated to provide energy (e.g., heat) to the first actuation element 1922a or the second actuation element 1922b. For example, the system 1900 can include a first actuator 1940a configured to energize the first control wire 1920a and a second actuator 1940b configured to energize the second control wire 1920b. The first actuator 1940a and the second actuator 1940b can be electronic circuitry or other suitable mechanism(s) that can selectively produce current or other energy. In some embodiments, the first actuator 1940a and the second actuator 1940b can include coils that produce a current in response to magnetic energy. To adjust the shape or size of the lumen 1912, the first actuator 1940a can deliver energy to the first actuation element 1922a via the first control wire 1930a, causing the first actuation element 1922a to expand, as described in detail above with respect to FIGS. 17A-18C. Likewise, the second actuator 1940b can deliver energy to the second actuation element 1922b via the second control wire 1930b, causing the second actuation element 1922b to expand.

In some embodiments, each actuation element may include a plurality of independently activatable control wires 1930. Each of the plurality of independently activatable control wires 1930 can be configured to deliver energy to a specific bend region in a corresponding spring element. For example, a first control wire may deliver energy to a first bend region 1932a in the second actuation element 1922b, a second control wire may deliver energy to a second bend region 1932b in the second actuation element 1922b, a third control wire may deliver energy to a third bend region 1932c in the second actuation element 1922b, and a fourth control wire may deliver energy to a fourth bend region 1932d in the second actuation element 1922b. Similarly, a plurality of independently activatable control wires can be configured to deliver energy to individual bend regions in the first actuation element 1922a. Having individual control wires for the individual bend regions enables a user to selectively actuate discrete portions of the actuation elements, which is expected to provide greater precision in control over actuation of the system 1900.

Figure 19B:
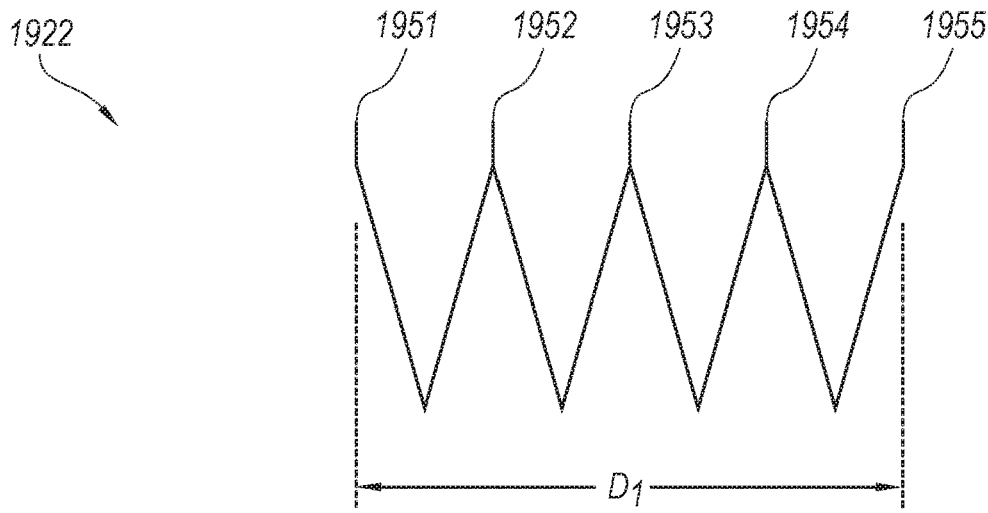
Figure 19C:
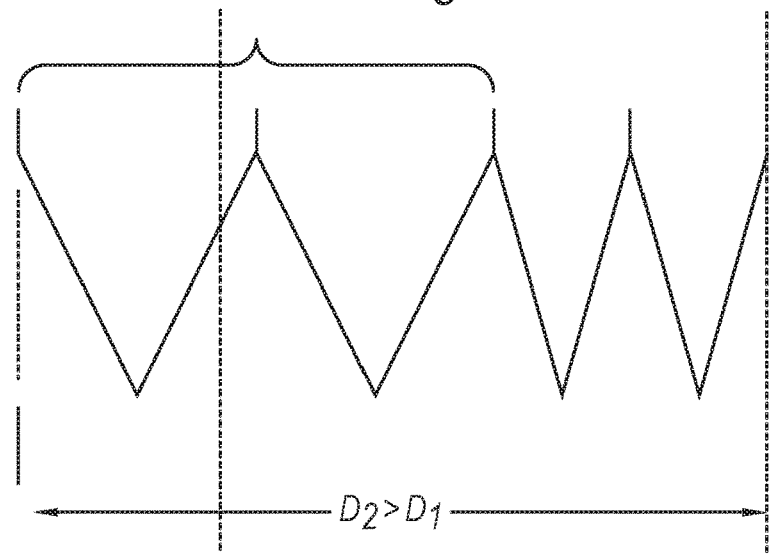
Figure 19D:
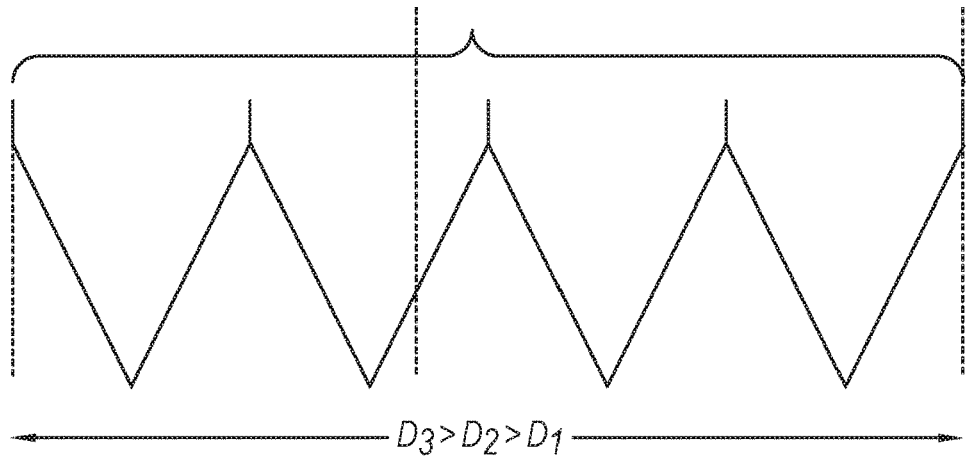

FIGS. 19B-19D show schematic illustrations of an implementation of the actuation element 1922 (which can be either the first actuation element 1922a or the second actuation element 1922b). As previously described, the actuation element 1922 may be composed of a shape memory material that is constructed in a geometric configuration represented in FIG. 19D, a triangular-wave shape member with a projected total element length $D_3$. At a given temperature (e.g., room temperature), actuation element 1922 may be relatively malleable (e.g., at least partially in a martensitic material state) and can be compressed along an axis such that the triangular-wave pattern is characterized by sharper (more acute) angles and the projected total element length changes to $D_1$, where $D_1<D_3$, as illustrated in FIG. 19B. In embodiments, actuation element 1922 includes a plurality of energy exchange points (e.g., electrical connection interface points) 1951-1955 that allow for selective actuation of the element 1922. In an example operation, an electrical energy source, such as the first or second actuator 1940a,b in FIG. 19A, is configured to deliver current through a circuit pathway defined by connection points 1951 and 1953. Accordingly, resistive heating may preferentially occur over the portion of the actuation element 1922 bounded by connection points 1951 and 1953. If heating is sufficient to drive the material to a phase transition temperature (e.g., to or above the R-phase start temperature, austenite start temperature, R-phase finish temperature, or austenitic finish temperature), this portion of the actuation element may expand towards its shape set geometric configuration. The resulting element geometry is shown in FIG. 19B, where the total element length has grown to $D_2$, where $D_1<D_2<D_3$. To return the actuation element 1922 to (or approximately to) its original geometric configuration (projected length of $D_3$), electrical energy may be applied across a circuit between connection points 1951 and 1955. Alternatively, energy may be applied to the entirety of the element 1922 (either simultaneously across the entire element, or incrementally across portions of the element sequentially) to return it to an approximate length $D_3$. Alternatively, energy may be applied across only those elements which had not yet released their thermoelastic energy (e.g., electrically connecting a circuit between connection points 1953 and 1955). As shown, adding localized energy deposition zones may increase the granularity with which a geometry change may be induced in an actuation element. In variation embodiments, a second actuation element (e.g., the opposing actuation element) that has a relatively compressed shape-set geometric configuration may be coupled to actuation element 1922, which allows for the composite element to be toggled back and forth between relatively elongated and relatively compressed geometric configurations, as previously described. Although described with reference to system 1900, one skilled in the art will appreciate that the description related to restively heating the shape memory actuation element can apply to any of the embodiments described herein.

Figure 20A:
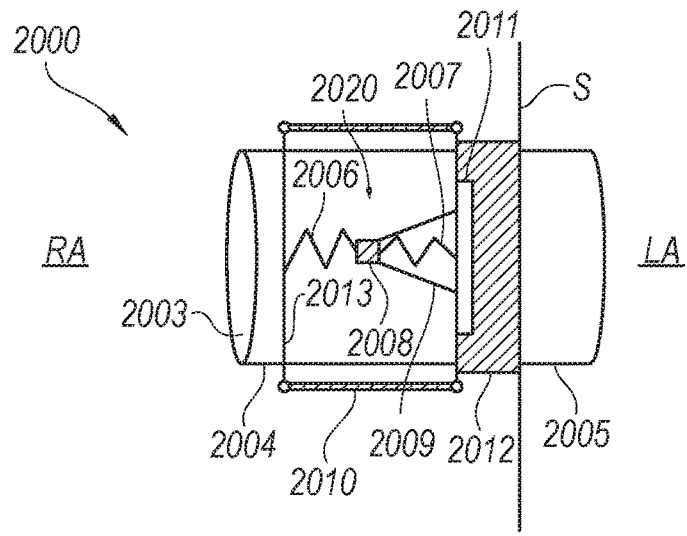
FIGS. 20A-20C illustrate another adjustable interatrial shunting system configured in accordance with select embodiments of the present technology.
Figure 20B:
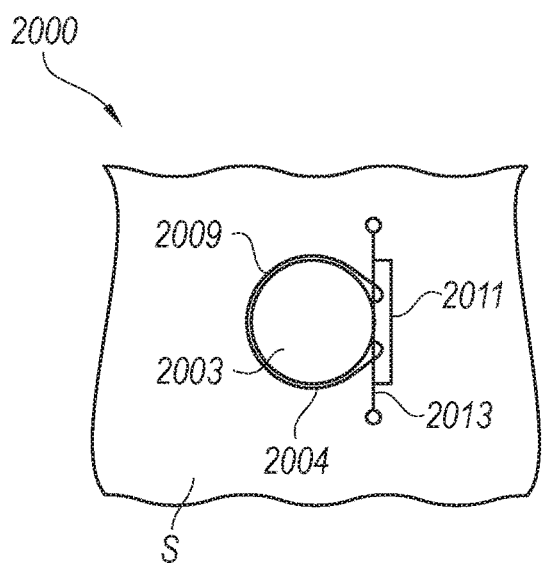
Figure 20C:
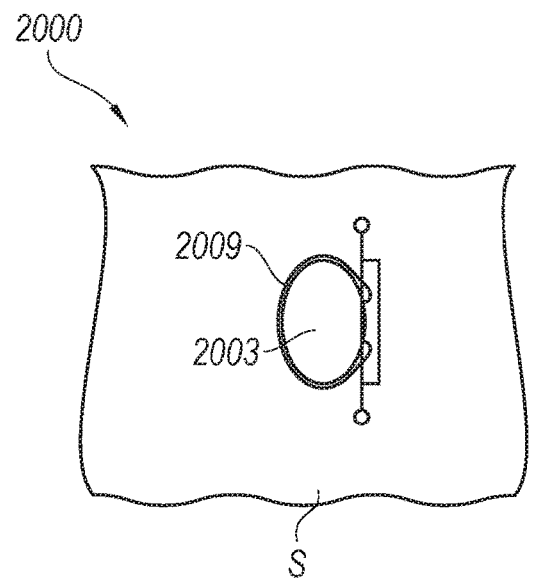

FIG. 20A-20C illustrate another adjustable interatrial shunting system 2000 ("system 2000") configured in accordance with select embodiments of the present technology. Referring to FIG. 20A, the system 2000 includes a first shunting element 2004 with a lumen 2003 on a first (e.g., RA) side of the septal wall S and a second shunting element 2005 on a second (e.g., LA) side of the septal wall S. In some embodiments, the first shunting element 2004 and the second shunting element 2005 may be a continuous structure that traverses the septal wall S. In other embodiments, the first shunting element 2004 and the second shunting element 2005 may be separate components of the system 2000 that are nevertheless fluidly connected. The system 2000 also includes an actuation assembly 2020 that is oriented generally parallel to the first shunting element 2004. In some embodiments, the actuation assembly 2020 can be at least partially spaced apart from the septal wall (e.g., by spacing plate 2012).

The actuation assembly 2020 can include a first shape memory component 2006, a second shape memory component 2007, a shuttle component 2008 residing between the shape memory components 2006, 2007, and a restriction band 2009 connected to the shuttle component 2008. As best seen in FIGS. 20B and 20C, the restriction band 2009 may at least partially wrap around the first shunting element 2004. The shape memory components 2006, 2007 and shuttle component 2008 may interface with (either via a direct connection or via additional intermediate connectors) a stabilization component 2013 that is generally parallel to a vertical diameter axis of the lumen 2003. The top and bottom ends of the stabilization component 2013 can include connecting arms 2010 that interface with the proximal side of the spacing plate 2012. In some embodiments, a distal side of the spacing plate 2012 is configured to interface with the septal wall S. The spacing plate 2012 can include an access notch 2011 that allows the restriction band 2009 to rotate approximately 90 degrees from the plane containing the shuttle component 2008 and shape memory components 2006, 2007 and encircle the first shunting element 2004.

The first shape memory component 2006 and second shape memory component 2007 can function generally similarly to the actuation elements described above with respect to FIGS. 16A-19. Accordingly, the first shape memory component 2006 may be activated with energy to transition the first shape memory component from a relatively contracted martensitic state to a relatively expanded austenitic state. Likewise, the second shape memory component 2007 may be activated with energy to transition the second shape memory component from a relatively contracted martensitic state to a relatively expanded austenitic state. Heating the first shape memory component 2006 pushes the shuttle component 2008 generally toward the spacing plate 2012, and heating the second shape memory component 2007 pushes the shuttle component 2008 generally away from the spacing plate 2012. Moving the shuttle component 2008 adjusts a force on the restriction band 2009, which can affect the size of the shunt. FIG. 20B, for example, is a front view of the system 2000 in a first relatively high flow state. FIG. 20C is a front view of the system 2000 in a second relatively low flow state. The system 2000 can transition between the configurations shown in FIGS. 20B and 20C, among other configurations, following actuation of the actuation assembly 2020 to increase the force on the restriction band 2009.

Figure 21A:
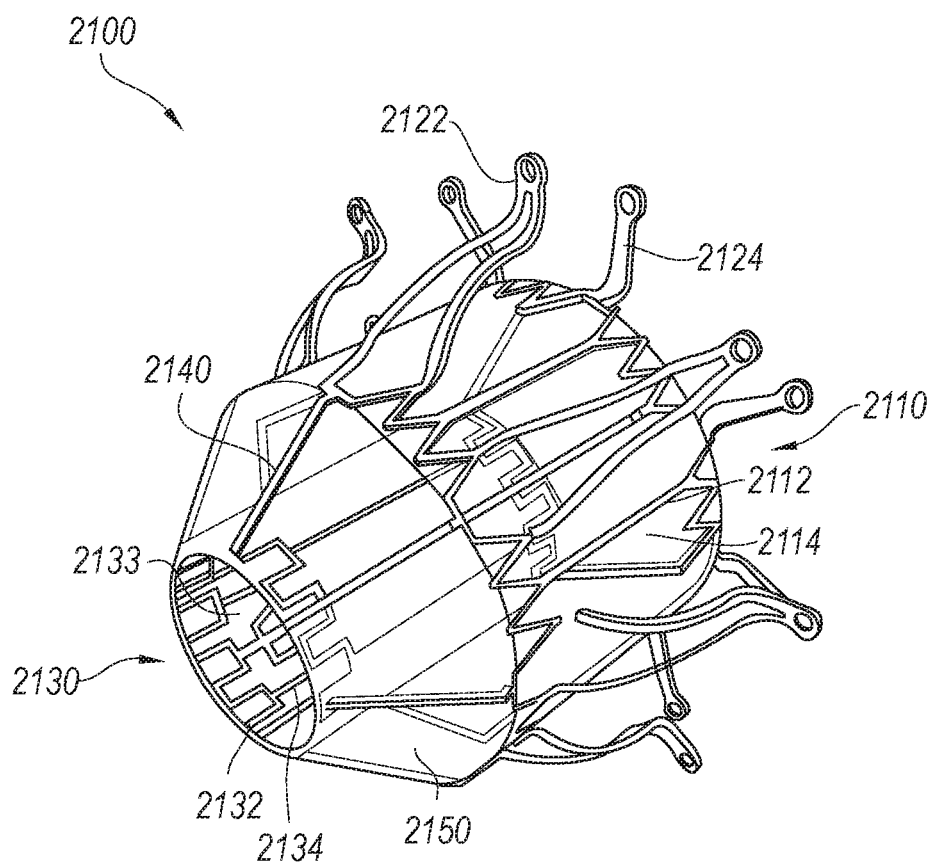
FIGS. 21A-21D illustrate an adjustable interatrial shunting system with a mechanical adjustment mechanism and configured in accordance with select embodiments of the present technology.

FIG. 21A illustrates an adjustable interatrial shunting system 2100 ("system 2100") configured in accordance with select embodiments of the present technology. The system 2100 includes an outer frame 2110 and an adjustable inner lumen 2130. The frame 2110 includes a plurality of arms 2112 defining a scaffolding for the system 2100. The frame can further include a plurality of right atrium anchors 2122 and a plurality of left atrium anchors 2124, which in some embodiments can extend from the plurality of arms 2112.

The right atrium anchors 2122 and left atrium anchors 2124 are configured to engage native heart tissue when the system 2100 is implanted in a heart to secures the system 2100 in place. The frame 2110 can be encased in an outer membrane 2114 suitable to engage native heart tissue. For example, the outer membrane 2114 can be a biocompatible and/or anti-thrombogenic material, such as ePTFE. In some embodiments, the outer membrane 2114 is an elastomeric material that is at least partially stretchable and/or flexible.

The adjustable inner lumen 2130 includes a proximal end portion 2132 positionable within the RA of a human heart. The adjustable inner lumen 2130 extends the longitudinal length of the system 2100 to a distal end portion (not shown). The distal end portion of the lumen 2130 is configured to reside within the LA of the heart when the system 2100 is implanted. Accordingly, the lumen 2130 fluidly connects the LA and the RA of the heart when implanted. The lumen 2130 is defined by a plurality of struts 2134 extending along the axial length of the lumen 2130. The plurality of struts 2134 are generally parallel to a center axis of the lumen 2130. The struts 2134 can comprise a shape-memory material and/or a superelastic material such as nitinol, malleable materials such as annealed or non-annealed stainless steel, cobalt chromium, or other suitable materials. The struts 2134 can be connected to the frame 2110 (e.g., the arms 2112) via one or more connecting struts 2140. The connecting struts 2140 can also comprise a shape-memory material and/or a superelastic material such as nitinol, malleable materials such as annealed or non-annealed stainless steel, cobalt chromium, or other suitable materials. As described below with reference to FIGS. 21B-21D, the one or more connecting struts 2140 can be actuated to alter a position of the struts 2134 and change a diameter of the lumen 2130.

The lumen 2130 is further defined by an inner membrane 2133. In some embodiments, the inner membrane 2133 forms a sheath around the struts 2134 (e.g., the struts 2134 can be embedded within the inner membrane 2133). In other embodiments, the struts 2134 can be positioned adjacent to but not encased within the inner membrane 2133. For example, the struts 2134 can be internal to the inner membrane 2133 (e.g., within the lumen 2130) or external to the inner membrane 2133 (e.g., outside the lumen 2130). When the struts 2134 are not encased within the inner membrane 2133, the struts 2134 can be otherwise connected to the inner membrane 2133, although in other embodiments the struts 2134 are not connected to the inner membrane 2133. Regardless of the relative positioning of the struts 2134 and the inner membrane 2133, the inner membrane 2133 can form a single and/or continuous membrane with the outer membrane 2114 of the frame 2110 (in such embodiments, the outer membrane 2114 and the inner membrane 2133 can be collectively referred to as a single or unitary membrane). The volume of space between the outer membrane 2114 and the inner membrane 2133 can form a generally toroidal shaped chamber 2150, as described in greater detail below. The inner membrane 2133 can comprise the same material as the outer membrane 2114 of the frame 2110. For example, the inner membrane 2133 can be a biocompatible and/or anti-thrombogenic material such as ePTFE and/or an elastomeric material that is at least partially stretchable and/or flexible. For example, in one embodiment, the inner membrane 2133 is ePTFE and forms a sheath around the struts 2134. In some embodiments, the inner membrane 2133 and the outer membrane 2114 can comprise different materials. In some embodiments, the system 2100 has two, three, four, five, six, seven, eight, nine, ten, eleven, and/or twelve struts 2134. As described in greater detail with respect to FIGS. 21B-21D, the struts 2134 can be malleable and/or contain one or more hinges, enabling the struts to dynamically change shape (e.g., expand, fold, or otherwise bend) to change the diameter of the inner lumen 2130.

As described above, the volume between the outer membrane 2114 of the frame 2110 and the inner membrane 2133 of the adjustable inner lumen 2130 defines a generally toroidal shaped chamber 2150. The chamber 2150 can be fluidly isolated from the interior of the lumen 2130 via the inner membrane 2133. The chamber 2150 can also be fluidly isolated from the environment surrounding the system 2100 via the outer membrane 2114. Accordingly, in some embodiments, the system 2100 is configured to prevent blood from flowing into the chamber 2150. In some embodiments, the chamber 2150 can contain a compressible and/or displaceable liquid, gas, and/or gel. Accordingly, as the diameter of the lumen 2130 is adjusted, the liquid or gas can either be compressed, expanded, and/or displaced. The chamber 2150 can also house one or more electronic components (e.g., battery, supercapacitor, etc.). In such embodiments, the electronic components can be electrically isolated from other system components.

Figures 21B, 21C:
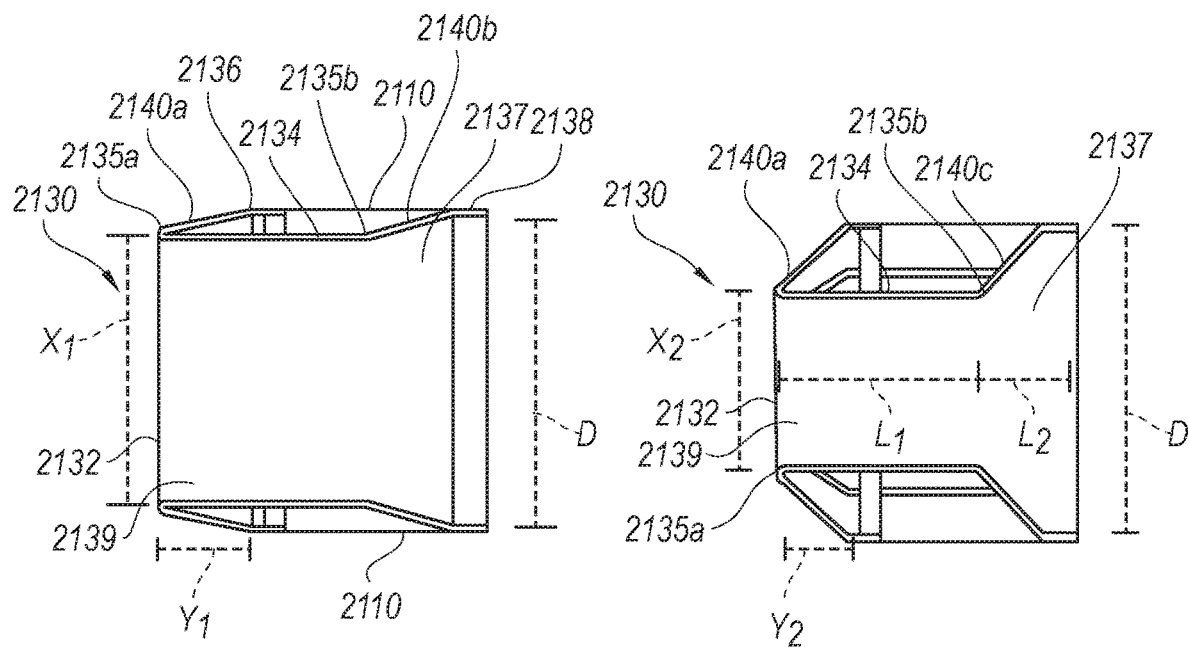
Figure 21D:
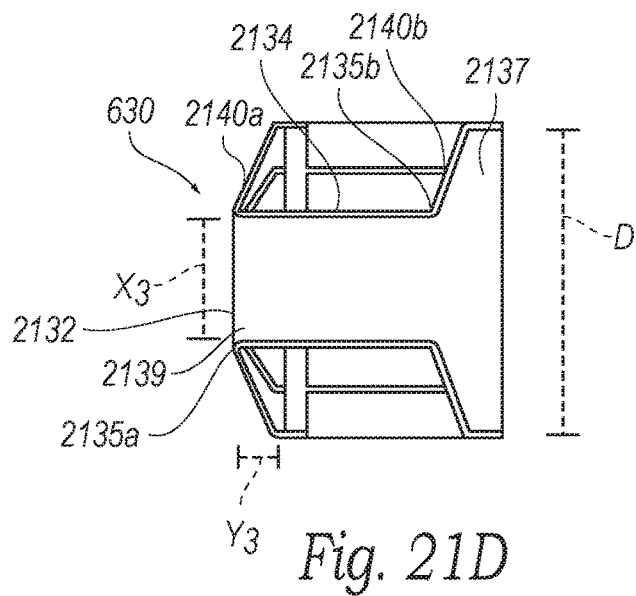
Figure 22A:
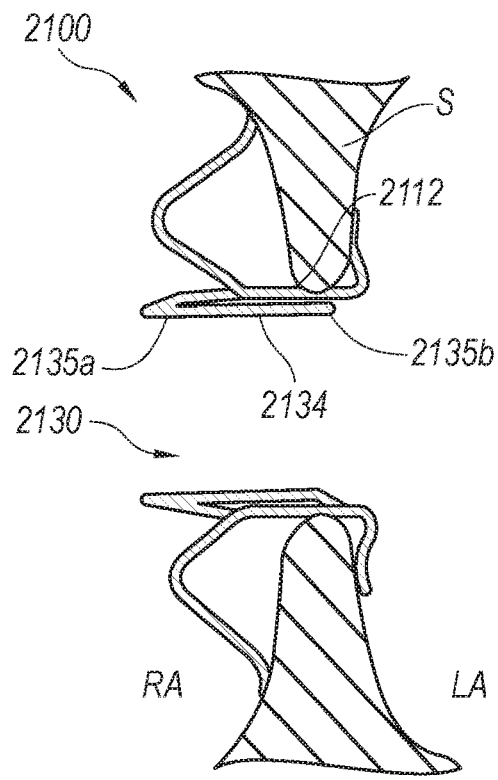
FIGS. 22A-22C illustrate the adjustable interatrial shunting system of FIGS. 21A-21D implanted across a septal wall.
Figure 22B:
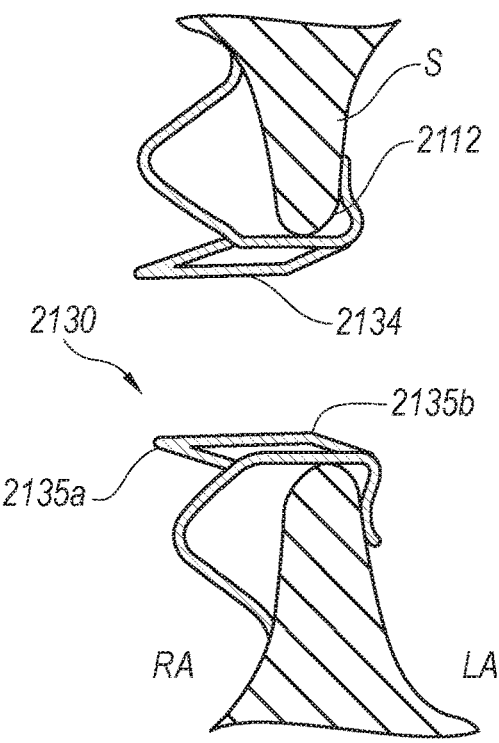
Figure 22C:
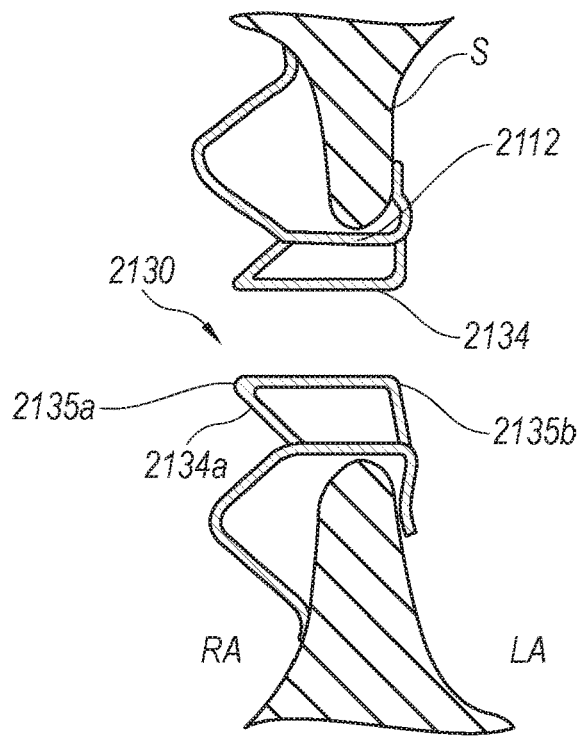

FIGS. 21B-21D schematically illustrate the adjustable inner lumen 2130 of the system 2100. FIGS. 22A-22C are schematic illustrations of the stages of operation shown in FIGS. 21B-21D, but further show the system 2100 implanted across a septal wall S. Referring to FIG. 21B, the struts 2134 are connected to the frame 2110 (e.g., the arms 2112, shown in FIG. 21A) via a first connecting strut 2140a at a proximal end (e.g., right atrium) portion and via a second connecting strut 2140b at a distal end (e.g., LA) portion (collectively referred to as "connecting struts 2140"). As described above, the struts 2134 at least partially define the shape of the lumen 2130. The first connecting strut 2140a can connect the struts 2134 to the frame 2110 at a proximal connection 2136 on the RA side of the system 2100. The second connecting strut 2140b can connect the struts 2134 to the frame 2110 at a distal connection 2138 on the LA side of the system 2100. The transition between the first connecting strut 2140a and the strut 2134 can include a hinge or other bendable aspect 2135a (referred to hereinafter as "hinge 2135a"). Likewise, the transition between the strut 2134 and the second connecting strut 2140b can also include a hinge or bendable aspect 2135b (referred to hereinafter as "hinge 2135b"). As will be described below, the hinges 2135 enable the strut 2134 to bend and/or fold relative to the first and second connecting struts 2140, thereby dynamically adjusting the diameter of the lumen 2130.

Referring to FIG. 21B, the system 2100 is shown in a first configuration in which the lumen 2130 has a first inner diameter $X_1$. The frame 2110 has a diameter D, and the proximal connection 2136 and the hinge 2135a are separated by a distance $Y_1$. To reduce the inner diameter of the lumen 2130, the proximal end portion 2132 of the inner lumen 2130 moves distally (e.g., towards the LA), causing the struts 2134 to bend at hinges 2135a, 2135b. More specifically, in the illustrated embodiment, the angle defined by the first connecting strut 2140a and the strut 2134 at hinge 2135a is increased, while the angle defined by the second connecting strut 2140b and the strut 2134 at hinge 2135b is decreased. Accordingly, in various embodiments, the struts 2134 have a fixed length but are moveable through a range of positions by the connecting struts 2140 to change the diameter of lumen 2130. In such embodiments, the lumen 2130 defined by the struts 2134 remains a constant length (e.g., length $L_1$ remains substantially the same), even when the diameter of the lumen 2130 is changing.

FIG. 21C illustrates a second configuration of system 2100 in which the inner lumen 2130 has a second inner diameter $X_2$ that is less than the first inner diameter $X_1$. The proximal end portion 2132 and the hinge 2135a are separated by a distance $Y_2$ that is less than the distance $Y_1$. The diameter D of the frame 2110 does not substantially change. FIG. 21C illustrates a third configuration of system 2100 in which the inner lumen 2130 has a third inner diameter $X_3$ that is less than the second inner diameter $X_2$. The proximal end portion 2132 and the hinge 2135a are separated by a distance $Y_3$ that is less than the distance $Y_2$. The diameter D of the frame 2110 does not change. As discussed above, the struts 2134 and/or the connecting struts 2140 can comprise a shape memory material. Accordingly, once the struts 2134 and connecting struts 2140 have been transitioned to a desired position, the struts can retain their configuration and the lumen retains a constant diameter until an active input is received (e.g. via an actuation mechanism, as discussed below).

In various embodiments, system 2100 is configured to adjust from a first configuration to a second configuration. In the first configuration, the lumen 2130 has a first substantially constant diameter. In the second configuration, the lumen 2130 has a second substantially constant diameter different than the first substantially constant diameter. The lumen may have a substantially constant diameter along all or substantially all of its entire length. In other embodiments, however, the lumen may have a substantially constant diameter along only a major portion of its length. For example, the lumen diameter may be substantially constant along the portion which extends through the septal wall. In another example, the lumen has a substantially constant diameter along its entire length, and has additional features adjacent to the lumen on one or both ends, such as a flare, funnel, taper, or the like. For example, as will be described in greater detail below, system 2100 shows the lumen 2130 having a funnel shaped inflow component 2137 configured for fluid communication with a left atrium of a heart (not shown) and a cylindrical shaped outflow portion 2139 configured for fluid communication with the right atrium of a heart (not shown).

Although FIGS. 21B-21D (and FIGS. 22A-22C) only illustrate three lumen diameters, one skilled in the art will appreciate that the struts 2134 can be actuated through a plurality of configurations (not shown), resulting in a plurality of discrete lumen diameters. For example, the lumen can take any diameter between a fully open configuration and a fully closed configuration. Moreover, in addition to decreasing the diameter of the lumen 2130 as illustrated, the struts 2134 can be selectively actuated via the connecting struts 2140 to increase the diameter of the lumen 2130. To increase the diameter of the inner lumen 2130, the proximal end portion 2132 of the inner lumen 2130 moves proximally (e.g., further into the RA), such that the angle defined by the first connecting strut 2140a and the strut 2134 at hinge 2135a is decreased, and the angle defined by the strut 2134 and the second connecting strut 2140b at hinge 2135b is increased. Accordingly, system 2100 enables the diameter of the lumen 2130 to by selectively adjusted to control the flow of blood through the lumen 2130. The specific diameter for the lumen 2130 can be selected based off the patient's needs.

The system 2100 can be adjusted between the configurations shown in FIGS. 21B-21D once implanted in a heart. FIG. 22A, for example, illustrates the system 2100 implanted across a septal wall S and in a first configuration (e.g., the configuration shown in FIG. 21A above). To decrease the blood flow through the lumen 2130, the struts 2134 can be directed radially inward by bending at the hinges 2135a, 2135b, as described in detail above, to assume a second configuration shown in FIG. 22B (e.g., which corresponds to the configuration shown in FIG. 21C), and/or a third configuration shown in FIG. 22C (e.g., which corresponds to the configuration shown in FIG. 21D).

Figure 23A:
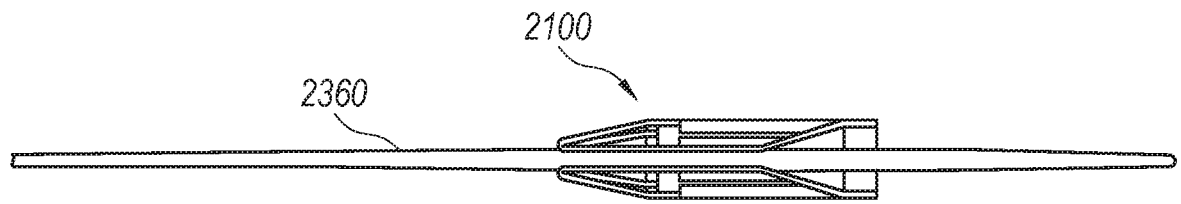
FIGS. 23A-23C illustrate an operation for invasively deploying the adjustable interatrial shunting system of FIGS. 21A-21D.
Figure 23B:
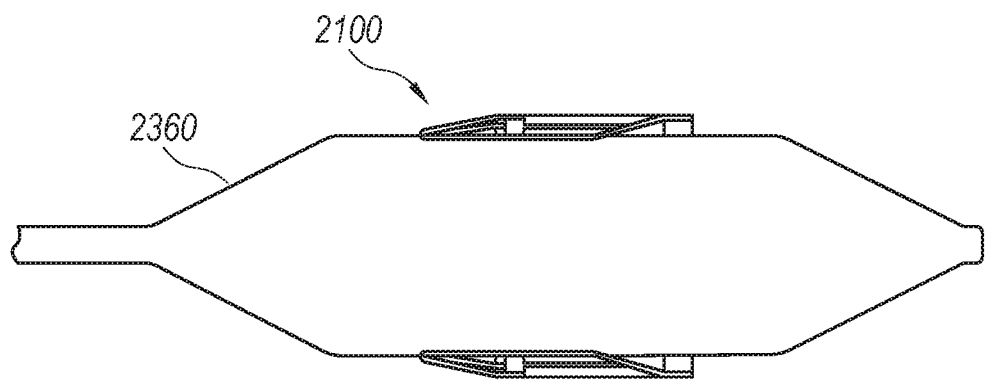
Figure 23C:
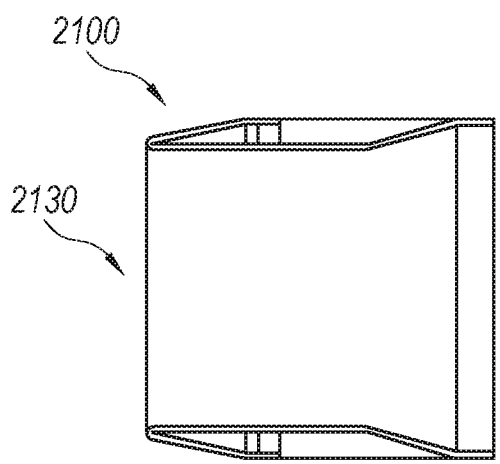

In some embodiments, the system 2100 can be adjusted using an inflatable balloon intravascularly delivered proximate the system 2100. For example, a balloon (not shown) can be delivered via a catheter and positioned within the lumen 2130. Inflating the balloon can push the struts 2134 radially outward, enlarging the lumen (e.g., transitioning from the configuration shown in FIG. 22C to the configuration shown in FIG. 22A). The balloon can also be used to reduce the diameter of the lumen 2130 by pushing the proximal end portion 2132, such as at hinge 2135a, distally. For example, FIGS. 23A-23C illustrate deployment of the system 2100. The system 2100 can have a low-profile delivery configuration, shown in FIG. 23A. The low-profile delivery configuration facilitates transcatheter delivery of the system 2100. Following delivery of the system 2100 to the desired positioning (e.g., across a septal wall), an expandable element such as balloon 2360 can be inserted into the inner lumen 2330 of the system 2100 while the system 2100 is still in the low-profile delivery configuration. The balloon can then be inflated. As shown in FIG. 23B, inflating the balloon expands the system 2100 into a deployed configuration. The balloon can then be deflated and removed. As shown in FIG. 23C, the system 2100 remains in the deployed position. Once deployed, the system 2100 can be selectively actuated to adjust the diameter of the inner lumen. In other embodiments, the system 2100 can be biased toward its deployed configuration such that, upon deployment from a delivery catheter or sheath, the system 2100 automatically expands radially outward into the deployed configuration and does not require mechanical expansion via a balloon 2360.

In some embodiments, the system 2100 can be adjusted using an actuation assembly implanted with the device (not shown). In some embodiments, the actuation assembly is included on the system 2100 and can actively adjust the inner lumen diameter by actuating one or more of the connecting struts 2140, which in turn cause the struts 2134 to change position. In some embodiments, for example, the actuation assembly, when actuated, pulls the proximal end portion 2132 distally, causing the struts 2134 to bend as described above with respect to FIGS. 21B-21D. The actuation assembly can also be configured to directly bend the struts 2134 to alter the diameter of the lumen 2130. In some embodiments, the actuation assembly can be a motor. In addition, other materials that can convert energy to linear motion can be used (e.g., nitinol). In some embodiments, a nitinol element is coupled to a pall or other mechanical element moveable via actuation of the nitinol element.

In addition to the diameter of the lumen, the shape of the lumen can also promote flow through system 2100. For example, referring back to FIGS. 21B-21D, the second connecting struts 2140c can define a funnel shaped inflow component 2137 configured for fluid communication with a LA of a heart (not shown), and the lumen 2130 can include a cylindrical shaped outflow portion 2139 configured for fluid communication with the RA of a heart (not shown). As illustrated in FIG. 21C, the cylindrical shaped outflow portion 2139 can have a length $L_1$ and the adjacent funnel shaped inflow component 2137 can have a length $L_2$. The diameter of the lumen 2130 in the cylindrical shaped outflow portion 2139 along the length $L_1$ is substantially constant. The substantially constant diameter of the lumen 2130 along the length $L_1$ is less than the variable diameter of the funnel shaped inflow component 2137 along the length $L_2$. Although length $L_1$ is shown as greater than length $L_2$ in the illustrated embodiment, other embodiments have a length $L_2$ greater than length $L_1$. In some embodiments, length $L_1$ extends along a major portion of the length of the lumen 2130, and length $L_2$ extends along a minor portion of the length of the lumen 2130. In other embodiments, the struts 2134 defining the cylindrical shaped outflow portion 2139 extend between a distal inflow aperture and a proximal outflow aperture and there is no funnel shaped inflow component 2137. The cylindrical shaped outflow portion 2139 can also have other non-circular cross-sectional shapes that have substantially constant inner dimensions along length $L_1$. For example, the cross-sectional shape of the outflow portion having length $L_1$ can be oval, triangular, rectangular, pentagonal, etc.

When the system 2100 is implanted in a heart, blood flows into the lumen 2130 at the funnel shaped inflow component 2137 (e.g., through the distal inflow aperture), through the cylindrical shaped outflow portion 2139, and into the RA. In the exemplary embodiment, the combination of the funnel shaped inflow component 2137 and the cylindrical shaped outflow portion 2139 are expected to provide the system 2100 with a number of beneficial flow characteristics. For example, the funnel shaped inflow component 2137 can increase blood flow into the lumen 2130 from the LA. The relatively larger distal inflow aperture allows for the gathering of a larger blood volume. Blood then flows from the relatively larger diameter funnel shaped inflow component 2137 to the relatively smaller diameter cylindrical shaped outflow portion 2139. Based on the Venturi effect (Bernoulli's principle in mathematical terms), pressure decreases downstream and the flow velocity increases as the blood flows from the funnel shaped inflow component 2137 into the relatively smaller diameter cylindrical shaped outflow portion 2139. In the exemplary embodiment, the outflow portion 2139 has a cylindrical shape with a substantially constant diameter along length $L_1$. The cylindrical shaped outflow portion 2139 maintains flow therethrough. By contrast, a funnel-shaped outflow would act as a diffuser. Based on Bernoulli's Principle, an increasing diameter on the outflow would decrease flow velocity. The exemplary cylindrical-shaped outflow reduces swirl effects and turbulence from the inflow while also minimizing pressure increases. Combined, these effects are expected to enhance blood flow between the LA and the RA. Additionally, as illustrated in FIGS. 21B-21D, the device retains the funnel shaped inflow component 2137 and the cylindrical shaped outflow portion 2139 as it transitions between configurations.

One will appreciate from the description herein that other lumen shapes are possible and within the scope of the present technology. In some embodiments, for example, the lumen does not have the funnel shaped inlet component but rather retains a substantially constant diameter along substantially the entire length of the lumen. For example, the lumen can be substantially cylindrical with a substantially constant diameter extending between the distal end portion and the proximal end portion. In other embodiments, the lumen is tapered and has a variable diameter extending between the distal end portion and the proximal end portion. For example, the lumen can have a relatively larger inflow aperture at the distal end portion and relatively smaller outflow aperture at the proximal end portion, with the lumen constantly tapering inward between the inflow aperture and the outflow aperture to form a funnel shape. In yet other embodiments, the lumen can have a generally hourglass shape having a central pinch point. As discussed above, altering the shape of the lumen can affect the rate of the blood flow through the lumen. Accordingly, the shape of the lumen provides an additional mechanism for facilitating increased control over the flow of blood between the LA and the RA through shunts configured in accordance with the present technology.

One will further appreciate from the disclosure herein that other flow control mechanisms can be used with the shunting systems described herein. For example, in some embodiments, the shunting systems can include a gate-like valve that can move between a first position blocking or at least partially blocking a flow lumen and a second position unblocking or at least partially unblocking the flow lumen. In such embodiments, the gate-like valve can be coupled to one or more shape memory elements that can be manipulated using energy, such as energy stored in an energy storage component or energy applied directly to the shape memory element via an energy source positioned external to the patient. As another example, the shunting systems can include one or more shape memory coils wrapped around a portion of the shunting element defining the flow lumen. The shape memory coils can be selectively wound or unwound to restrict (e.g., cinch) or relax (e.g., uncinch) a portion of the flow lumen. In yet other embodiments, the shunting element can include a flexible bladder filled with a fluid or gas. The flexible bladder can be generally toroidal shaped such that it defines a flow lumen therethrough. The fluid or gas can be directed into or out of the bladder to decrease or increase the size of the lumen. In yet other embodiments, the shunting element may incorporate at least partially passive concepts that can adjust a size or shape of the flow lumen based on the pressure differential between two heart chambers. Accordingly, the systems described herein are not limited to the flow control mechanisms and/or shunting devices expressly described herein. Other suitable shunting devices can be utilized and are within the scope of the present technology.

D. Shunting Assemblies with Adjustable Inflow and/or Outflow Orifices

Figure 24:
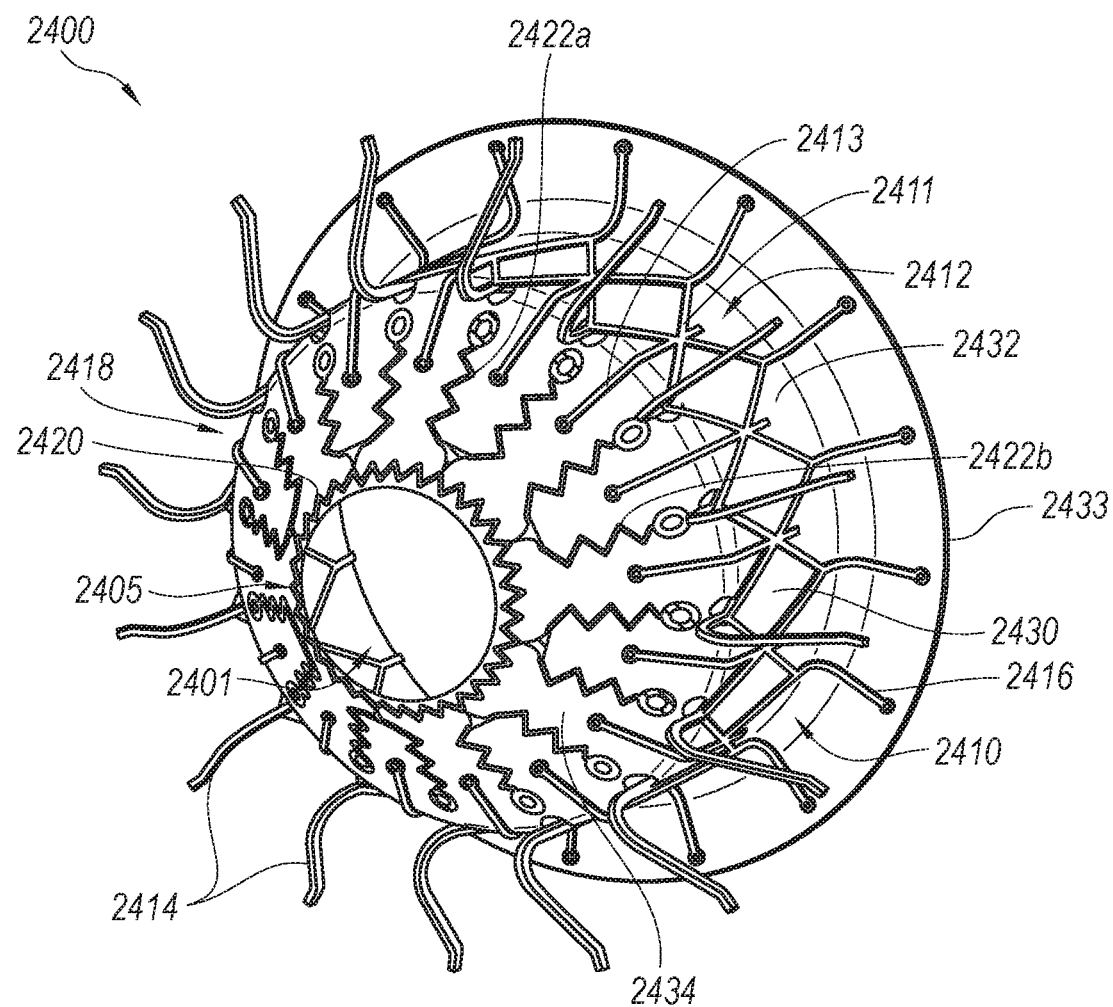
FIG. 24 is a partially isometric view of an adjustable interatrial shunting system having radially arranged actuation elements and configured in accordance with select embodiments of the present technology.

FIG. 24 illustrates an interatrial shunting system/device 2400 ("device 2400") configured in accordance with select embodiments of the present technology. The device 2400 includes a shunting element 2410 having a lumen 2401 extending therethrough. When the device 2400 is implanted across a septal wall (not shown), the lumen 2401 is configured to fluidly connect a LA and a RA to facilitate the flow of blood therebetween. The shunting element 2410 can include a frame 2412 or other outer scaffolding (e.g., stent-like structure). The frame 2412 can extend circumferentially around a diameter of the shunting element 2410. In some embodiments, the frame 2412 is composed of a material configured to be relatively flexible (e.g., nitinol in a material state where it exhibits superelastic properties) at and above body temperature. The frame 2412 can include a central portion comprising a plurality of first struts 2411 arranged in a diamond shape, although other suitable strut shapes and configurations can be used. The frame 2412 can further include a plurality of second struts 2413 extending from the first struts 2411 and angled radially inward towards an orifice 2405 (e.g., an RA or outflow orifice) of the lumen 2401, described in detail below. In the illustrated embodiment, the orifice 2405 is generally circular, although other embodiments can have other shapes, such as elliptical, square, rectangular, polygonal, curvilinear, and the like.

The frame 2412 can further include a plurality of first anchor elements 2414 extending from a first end portion of the frame 2412 and a plurality of second anchor elements 2416 extending from a second end portion of the frame 2412 that is generally opposite the first end portion. In the illustrated embodiment, the plurality of first anchor elements 2414 and the plurality of second anchor elements 2416 extend around the full circumference of the frame 2412, although other embodiments can have different suitable configurations. For example, in other embodiments, the anchor elements 2414 and/or 2416 may be a single element (e.g., a coil-shaped element). The first anchor elements 2414 and the second anchor elements 2416 can engage native tissue to secure the device 2400 in a desired position. For example, the first anchor elements 2414 and the second anchor elements 2416 can secure the device 2400 to a septal wall such that the lumen 2401 fluidly connects the LA and the RA. In such embodiments, the first anchor elements 2414 can be positionable within the RA and configured to engage the RA side of the septal wall, and the second anchor elements 2416 can be positionable in the LA and configured to engage the LA side of the septal wall. A portion of the septal wall can be received between the first anchor elements 2414 and the second anchor elements 2416. In other embodiments, the orientation of the device can be reversed such that the first anchor elements 2414 are positionable in the LA and the second anchor elements 2416 are positionable in the RA. In some embodiments, the first anchor elements 2414 and/or the second anchor elements 2416 are integral with the frame 2412. In other embodiments, the first anchor elements 2414 and/or the second anchor elements 2416 are secured to the frame 2412 using techniques known in the art (e.g., welding, gluing, suturing, etc.).

The shunting element 2410 can include a membrane 2430 coupled to (e.g., affixed, attached, or otherwise connected) to the frame 2412. In some embodiments, the membrane 2430 is flexible and can be made of a material that is impermeable to or otherwise resists blood flow therethrough. In some embodiments, for example, the membrane 2430 can be made of a thin, elastic material such as a polymer. For example, the membrane 2430 can be made of polytetrafluoroethylene (PTFE), ePTFE (ePTFE), silicone, nylon, polyethylene terephthalate (PET), polyether block amide (pebax), polyurethane, blends or combinations of these materials, or other suitable materials. The membrane 2430 can cover and/or enclose at least a portion of the shunting element 2410, such as the interior or exterior surface of the shunting element 2410 between a first end portion positionable in the LA and a second end portion positionable in the RA. The membrane 2430 can extend circumferentially around the frame 2412 to at least partially surround and enclose the lumen 2401, thereby defining (at least in part) a flow path for blood when implanted across the septal wall.

In some embodiments, the membrane 2430 includes a first membrane portion 2432 coupled to a second membrane portion 2434. The first membrane portion 2432 can be operably coupled to and/or extend around a central portion of the frame 2412 (e.g., the portion having the first struts 2411). In some embodiments, the first membrane portion 2432 can also include a flange portion 2433 that is operably coupled to and/or extending around the second anchor elements 2416. The second membrane portion 2434 can be operably coupled to and/or extend around the plurality of second struts 2413 angled radially inward towards the orifice 2405. The second membrane portion 2434 can be at least partially conical or funnel shaped and extend past the second struts 2413 so that at least a portion of the second membrane portion 2434 is positioned over and partially covers the lumen 2401, thereby defining an orifice 2405. The first membrane portion 2432 can be secured to the second membrane portion 2434 via suturing or other suitable techniques. In other embodiments, the membrane 2430 is a unitary membrane comprising both the first membrane portion 2432 and the second membrane portion 2434.

The device 2400 can further include an actuation assembly 2418 configured to change a geometry (e.g., a size and/or shape) of the orifice 2405. The actuation assembly 2418 can include a flow control element 2420, a plurality of first actuation elements 2422a, and a plurality of second actuation elements 2422b. As will be described in greater detail below, the first actuation elements 2422a and/or the second actuation elements 2422b can be selectively actuated to change a geometry of the flow control element 2420. In turn, this adjusts (e.g., stretches and/or compresses) the second membrane portion 2434 surrounding and defining the orifice 2405. As previously described, blood can flow between the LA and the RA via the lumen 2401 when the device 2400 is implanted across a septal wall. Accordingly, changing a geometry of the orifice 2405 is expected to change the relative flow resistance and/or the amount of blood flowing between the LA and the RA.

The flow control element 2420 of device 2400 generally extends around an outer circumference of the orifice 2405 and at least partially defines the geometry of the orifice 2405. For example, the flow control element 2420 can be an annular (e.g., ring-like) structure coupled to the second membrane portion 2434. In embodiments in which the orifice 2405 has other shapes (e.g., square), the flow control element 2420 can have a generally similar shape (e.g., square) such that the flow control element 2420 extends around an outer perimeter of the orifice 2405. The flow control element 2420 can be flexible such that it can expand and contract to change a geometry (e.g., a diameter) of the orifice 2405. For example, when the flow control element 2420 moves in a first manner (e.g., expands), the diameter of the orifice 2405 increases, thereby decreasing the flow resistance through the lumen 2401. When the flow control element 2420 moves in a second manner opposing the first manner (e.g., contracts), the diameter of the orifice 2405 decreases, thereby increasing the flow resistance through the lumen.

The shape of the flow control element 2420 can be at least partially controlled via a plurality of first actuation elements 2422a and a plurality of second actuation elements 2422b. As described in detail with respect to FIGS. 25A-25D, the plurality of first actuation elements 2422a and the plurality of second actuation elements 2422b can be coupled to the flow control element 2420 at a first end portion and anchored to the frame 2412 or another suitable and generally static structure at a second end portion. The plurality of first actuation elements 2422a and the plurality of second actuation elements 2422b can be positioned radially around the flow control element 2420 (e.g., in a "spoke-like" configuration, with the orifice forming the central hub and the actuation elements extending outward therefrom as spokes).

The first actuation elements 2422a and the second actuation elements 2422b can be composed of a shape memory material, such as a shape memory alloy (e.g., nitinol). Accordingly, the first actuation elements 2422a and the second actuation elements 2422b can be transitionable between a first material state (e.g., a martensitic state, a R-phase, etc.) and a second material state (e.g., a R-phase, an austenitic state, etc.). In the first state, the first actuation elements 2422a and the second actuation elements 2422b may be relatively deformable (e.g., plastic, malleable, compressible, expandable, etc.). In the second state, the first actuation elements 2422a and the second actuation elements 2422b may have a preference toward a specific manufactured geometry (e.g., shape, length, and/or or dimension). The first actuation elements 2422a and the second actuation elements 2422b can be transitioned between the first state and the second state by applying energy (e.g., heat) to the actuation elements to heat the actuation elements above a transition temperature. In some embodiments, the transition temperature for both the first actuation elements 2422a and the second actuation elements 2422b is above an average body temperature. Accordingly, both the first actuation elements 2422a and the second actuation elements 2422b are typically in the deformable first state when the device 2400 is implanted in the body until they are heated (e.g., actuated).

If the actuation elements (e.g., the first actuation elements 2422a) are deformed relative to their manufactured geometry while in the first state, heating the actuation elements (e.g., the first actuation elements 2422a) above their transition temperature causes the actuation elements to transition to the second state and therefore transition from the deformed shape towards a manufactured shape. As described in detail below, heat can be applied to the actuation elements via RF heating, resistive heating, or the like. In some embodiments, the first actuation elements 2422a can be selectively heated independently of the second actuation elements 2422b, and the second actuation elements 2422b can be selectively heated independently of the first actuation elements 2422a. In some embodiments, portions of the actuation elements (e.g., the first nitinol portion $2422a_1$ or the second nitinol portion $2422a_2$ (FIG. 3A)) can be heated independently of the other portion of the same actuation element. As described in detail below, selectively heating first actuation elements 2422a (or a portion of the first actuation elements 2422a) reduces the diameter of the lumen 2401 and selectively heating the second actuation elements 2422b (or a portion of the second actuation elements 2422b) increases the diameter of the lumen 2401.

Figure 25A:
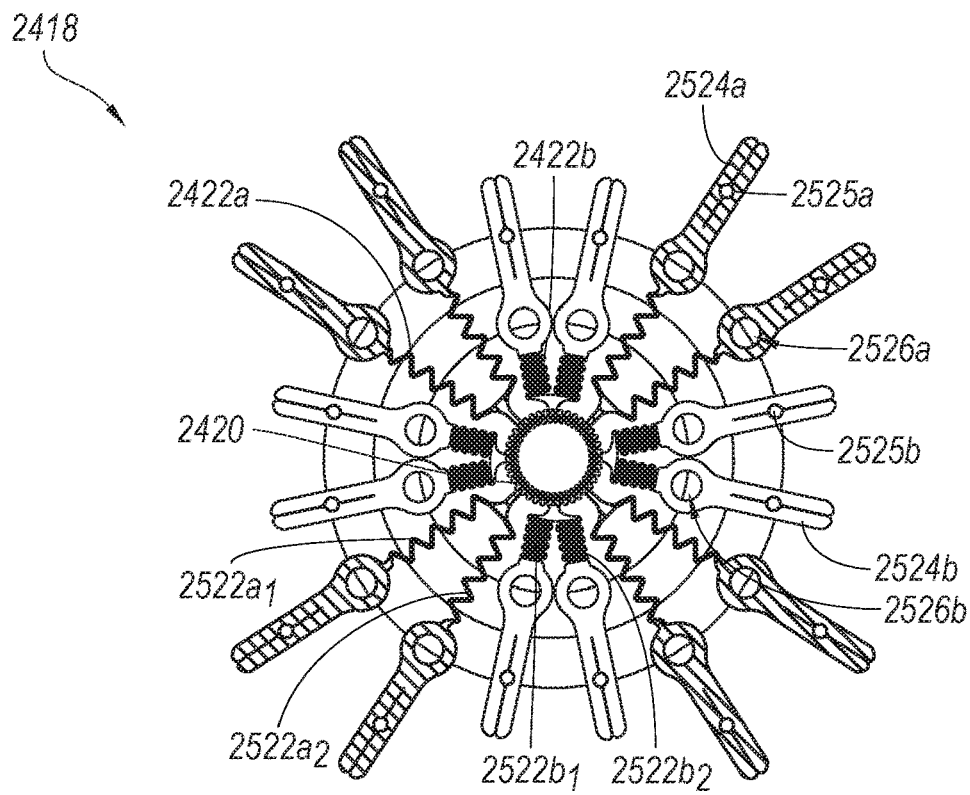
FIGS. 25A-25D illustrate additional features of the radially arranged actuation elements of the adjustable interatrial shunting system of FIG. 24.

FIGS. 25A-25D illustrate, among other things, how the first actuation elements 2422a and the second actuation elements 2422b can change a diameter of the orifice 2405. A number of features of the device 2400 are not illustrated in FIGS. 25A-25D for purposes of clarity. Referring first to FIG. 25A, for example, the first actuation elements 2422a and the second actuation elements 2422b are shown in a state before being secured to the shunting element 2410 and/or frame 2412 (FIG. 24). In particular, the first actuation elements 2422a and the second actuation elements 2422b are in their manufactured shapes. As will be apparent to one skilled in the art from the disclosure herein, the first actuation elements 2422a and the second actuation elements 2422b generally have different manufactured shapes such that the flow control element 2420 can be driven through a plurality of configurations by actuating the actuation elements 2422a/2422b. For example, in the illustrated configuration, the first actuation elements 2422a generally have a greater length than the second actuation elements 2422b when in their manufactured shape.

Figure 25B:
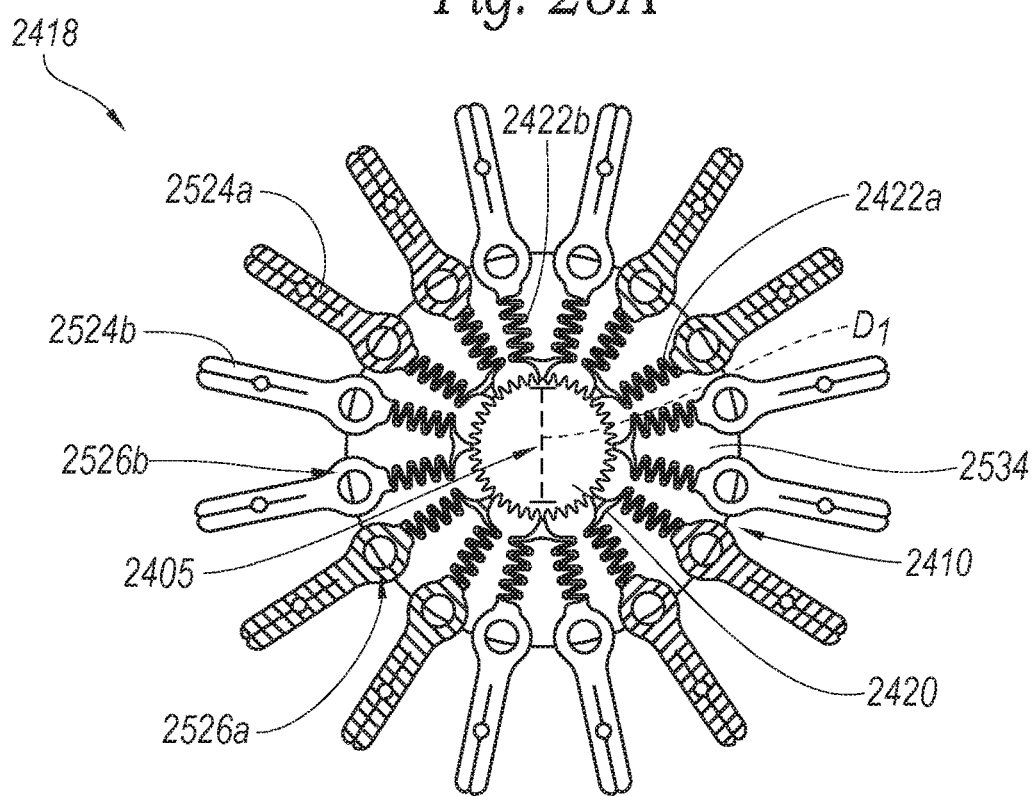

Each first actuation element 2422a can further comprise (or be coupled to) a first clip element 2524a having a first fixation element 2526a. The first fixation element 2526a can secure the corresponding first actuation element 2422a to the frame 2412 or another suitable component of the device 2400 (FIG. 25B). For example, the first fixation element 2526a can comprise an aperture to facilitate suturing of the first clip element 2524a to the frame 2412. The first clip element 2524a can further include a first hole 2525a. Together, the first clip element 2524a and the first hole 2525a can form an electrical connection point for receiving electricity and directing it through the corresponding first actuation element 2422a, thereby resistively heating the first actuation element 2422a. In the illustrated embodiment, each of the first actuation elements 2422a can from a general "U" or "V" shape such that the valley of the "U" or "V" is coupled to the flow control element 2420. For example, each of the first actuation elements 2422a can have a first nitinol portion $2522a_1$ coupled to a second nitinol portion $2522a_2$. The first nitinol portion $2522a_1$ and the second nitinol portion $2522a_2$ can be electrically coupled such that a current delivered to the first nitinol portion $2522a_1$ also flows through the second nitinol portion $2522a_2$, and vice versa. Accordingly, the first nitinol portion $2522a_1$ and the second nitinol portion $2522a_2$ can form an electrical circuit for resistively heating the first actuation elements 2422a. The first nitinol portion $2522a_1$ and the second nitinol portion $2522a_2$ can be composed of a unitary (e.g., single) structure, or can comprise distinct elements coupled together.

Likewise, each second actuation element 2422b can further comprise (or be coupled to) a second clip element 2524b having a second fixation element 2526b. The second fixation element 2526b can secure the corresponding second actuation element 2422b to the frame 2412 or another suitable component of the device 2400 (FIG. 24). For example, the second fixation element 2526b can comprise an aperture to facilitate suturing of the second clip element 2524b to the frame 2412. The second clip element 2524b can further include a second hole 2525b. Together, the second clip element 2524b and the second hole 2525b can form an electrical connection point for receiving electrical energy and directing it through the corresponding second actuation element 2422b, thereby resistively heating the second actuation element 2422b. In the illustrated embodiment, each of the second actuation elements 2422b can form a general "U" or "V" shape such that the valley of the "U" or "V" is coupled to the flow control element 2420. For example, each of the second actuation elements 2422b can have a first nitinol portion $2522b_1$ coupled to a second nitinol portion $2522b_2$. The first nitinol portion $2522b_1$ and the second nitinol portion $2522b_2$ can be electrically coupled such that a current delivered to the first nitinol portion $2522b_1$ also flows through the second nitinol portion $2522b_2$, and vice versa. Accordingly, the first nitinol portion $2522b_1$ and the second nitinol portion $2522b_2$ can form an electrical circuit for resistively heating the second actuation elements 2422b. The first nitinol portion $2522b_1$ and the second nitinol portion $2522b_2$ can be composed of a unitary (e.g., single) structure, or can comprise distinct elements coupled together.

FIG. 25B is a schematic illustration of aspects of the device 2400 after the first actuation elements 2422a and the second actuation elements 2422b have been fixed to the shunting element 2410 (FIG. 2) via the corresponding first fixation elements 2526a and the second fixation elements 2526b. In particular, FIG. 25B illustrates the device 2400 in a first configuration (e.g., a composite configuration) in which both the first actuation elements 2422a and the second actuation elements 2422b are at least partially deformed relative to their manufactured geometric configurations. To fix the first actuation elements 2422a to the shunting element 2410 (FIG. 2), the first actuation elements 2422a are compressed (e.g., shortened) relative to their manufactured geometry (FIG. 25A). To fix the second actuation elements 2422b to the shunting element 2410 (FIG. 2), the second actuation elements 2422b are stretched (e.g., lengthened) relative to their manufactured geometry (FIG. 25B). Both the first actuation elements 2422a and the second actuation elements 2422b retain the deformed positions shown in FIG. 25B because they are unheated (e.g., at room temperature or body temperature) and therefore in the relatively malleable material state (e.g., martensitic state). In the first configuration shown in FIG. 25B, the orifice 2405 defined by the second membrane portion 2434 and/or the flow control element 2420 has a first diameter $D_1$.

Figure 25C:
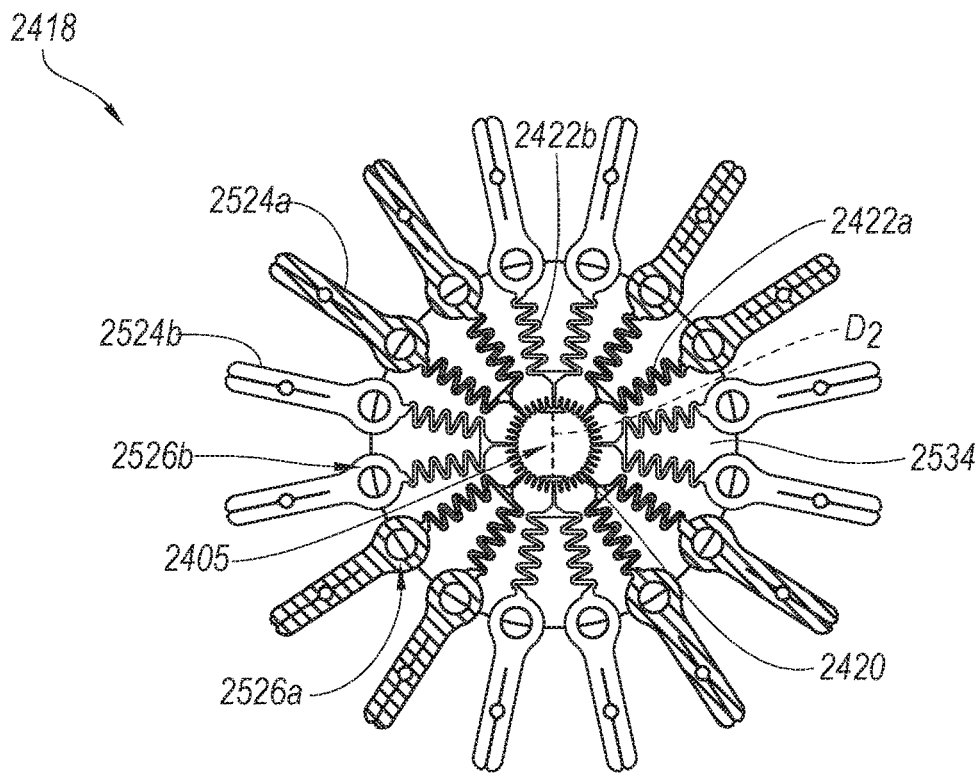

FIG. 25C illustrates the device 2400 in a second configuration different than the first (e.g., composite) configuration. In particular, in the second configuration the device 2400 has been actuated relative to the first configuration shown in FIG. 25B to transition the first actuation elements 2422a from a first (e.g., martensitic) material state to a second (e.g., austenitic) material state. Because the first actuation elements 2422a were deformed (e.g., compressed) relative to their manufactured geometry while in the first (e.g., composite) configuration, heating the first actuation elements 2422a above the transition temperature causes the first actuation elements 2422a to expand in length as they move toward their manufactured geometry (FIG. 25A). As described above, the first actuation elements 2422a are secured to the frame 2412 or another generally static structure on the shunting element 2410 via the first fixation elements 2526a. Accordingly, as the first actuation elements 2422a increase in length toward their manufactured geometry, they compress the flow control element 2420 radially inward. This deforms (e.g. stretches, relaxes, etc.) the second membrane such that it moves radially inward and the orifice 2405 assumes a second diameter $D_2$ that is less than the first diameter $D_1$. Because the flow control element 2420 is also coupled to the second actuation elements 2422b, the expansion of the first actuation elements 2422a (and corresponding contraction of the flow control element 2420) also causes the second actuation elements 2422b, which are not heated above their transition temperature and therefore still in a deformable (e.g., martensitic) state, to also expand (e.g., increase in length). For example, the second actuation elements 2422b are expanded even further from their manufactured geometry (FIG. 25A) than they were in the first (e.g., composite) configuration (FIG. 25B). When implanted in a human heart, decreasing the diameter of the orifice 2405 is expected to reduce the flow volume of blood from the LA to the RA.

Figure 25D:
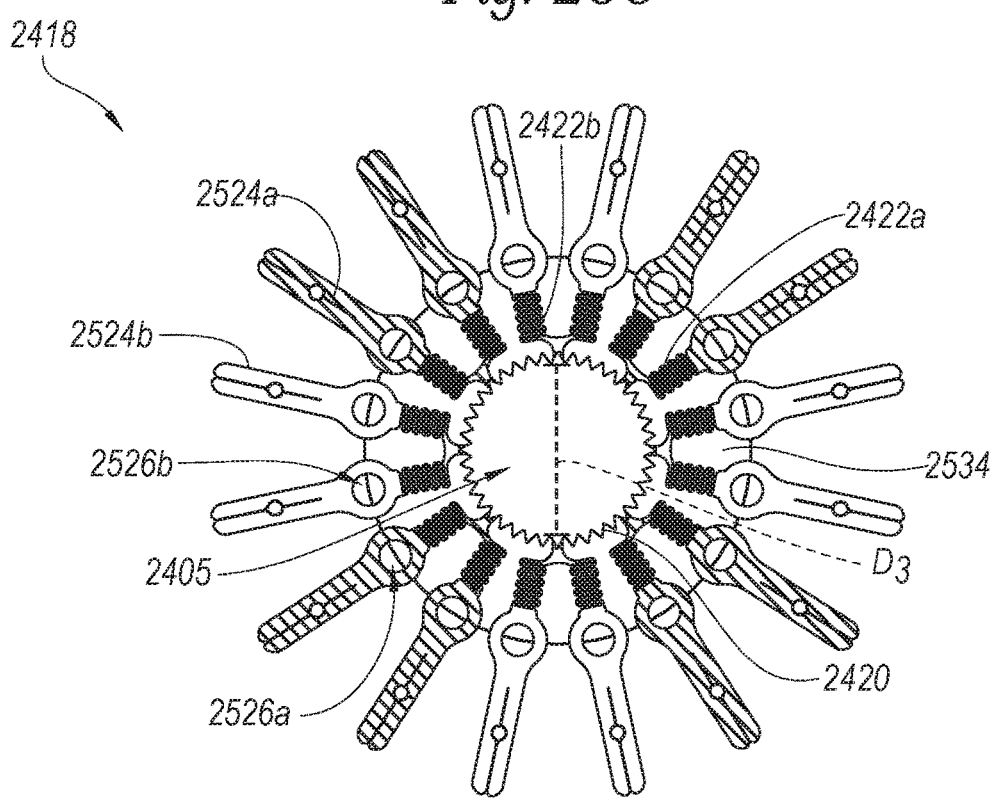

FIG. 25D illustrates the device 2400 in a third configuration different than the first or second configuration. In particular, in the third configuration, the device 2400 has been actuated relative to the first configuration shown in FIG. 25B to transition the second actuation elements 2422b from a first (e.g., martensitic) material state to a second (e.g., austenitic) material state. Because the second actuation elements 2422b were expanded relative to their manufactured geometry (e.g., when placed into either of the first configuration or the second configuration), heating the second actuation elements 2422b above the transition temperature causes the second actuation elements 2422b to contract in length as they move toward their manufactured geometry (FIG. 25A). As described above, the second actuation elements 2422b are secured to the frame 2412 or another generally static structure on the shunting element 2410 via the second fixation elements 2526b. Accordingly, as the second actuation elements 2422b decrease in length toward their manufactured geometry, they expand the flow control element 2420 radially outward. Because the flow control element 2420 is coupled to the second membrane portion 2434, the second membrane portion 2434 is deformed (e.g. compressed, relaxed, etc.) such that it moves radially outward and the orifice 2405 assumes a third diameter $D_3$ that is greater than the first diameter $D_1$ and the second diameter $D_2$. Because the flow control element 2420 is also coupled to the first actuation elements 2422a, contraction of the second actuation elements 2422b (and the corresponding expansion of the flow control element 2420) causes the first actuation elements 2422a, which are not heated above their transition temperature and therefore still in a deformable (e.g., martensitic) state, to also contract (e.g., decrease in length). For example, the first actuation elements 2422a are compressed even further from their manufactured geometry (FIG. 25A) than they were in the first (e.g., composite) configuration (FIG. 25B). When implanted in a human heart, increasing the diameter of the orifice 2405 is expected to increase the flow volume of blood from the LA to the RA.

The device 2400 can be repeatedly transitioned between the second configuration and the third configuration. For example, the device 2400 can be returned to the second configuration from the third configuration by heating the first actuation elements 2422a above their transition temperature once the second actuation elements 2422b have returned to a deformable first state (e.g., by allowing the second actuation elements 2422b to cool below the transition temperature after being heated, etc.). Heating the first actuation elements 2422a above their transition temperature causes the first actuation elements to move towards their manufactured geometry, which in turn pushes the flow control element 2420 radially inward and transitions the device 2400 to the second configuration (FIG. 25C).

In some embodiments, device 2400 can also be transitioned to or from intermediate configurations between the second and third configurations. In some embodiments, for example, the device 2400 can initially transition from a first composite configuration into the second configuration, the third configuration, or another configuration (e.g., the device may be transitioned to the third configuration or another configuration before being actuated to the second configuration). In some embodiments, the configuration of device 2400 can also be altered without inducing a change in material state of either the first actuation elements 2422a or the second actuation elements 2422b. This may be accomplished, for example, via direct mechanical methods that apply external forces to a component or portion of the device (e.g., via a balloon expansion of flow control element 2420, similar to previously described with respect to FIGS. 23A-23C).

Accordingly, the device 2400 can be selectively transitioned between a variety of configurations by selectively actuating some or all of either the first actuation elements 2422a or the second actuation elements 2422b. After actuation, the device 2400 can be configured to substantially retain the given configuration until further actuation of the opposing actuation elements. In some embodiments, the device 2400 can be transitioned to intermediate configurations between the second configuration and the third configuration (e.g., the first configuration) by heating some, but not all, of either the first actuation elements 2422a or the second actuation elements 2422b.

As provided above, heat can be applied to the actuation elements via RF heating, resistive heating, or the like. In some embodiments, the first actuation elements 2422a can be selectively heated independently of the second actuation elements 2422b, and the second actuation elements 2422b can be selectively heated independently of the first actuation elements 2422a. For example, in some embodiments, the first actuation elements 2422a are on a first electrical circuit for selectively and resistively heating the first actuation elements 2422a and the second actuation elements 2422b are on a second electrical circuit for selectively and resistively heating the second actuation elements 2422b. As described in detail above, selectively heating the first actuation elements 2422a reduces the diameter of the orifice 2405 and selectively heating the second actuation elements 2422b increases the diameter of the orifice 2405. In some embodiments, each individual first actuation element 2422a is on its own selectively and independently activatable electric circuit, and each individual second actuation element 2422b is on its own selectively and independently activatable electric circuit. Without being bound by theory, this permits individual actuation elements to be selectively actuated, thereby increasing the granularity of potential adjustments to the diameter of the orifice 2405.

In some embodiments, actuation elements may be configured differently than as described above. For example, in some embodiments both the first actuation elements 2422a and second actuation elements 2422b are compressed (or alternatively, expanded) from their manufactured geometry when placed into an initial composite configuration. For example, each set of actuation elements may be compressed (or alternatively, expanded) a different amount. Variation embodiments may include more than two sets of actuation elements that are manufactured to have two or more manufactured geometries.

Figure 26:
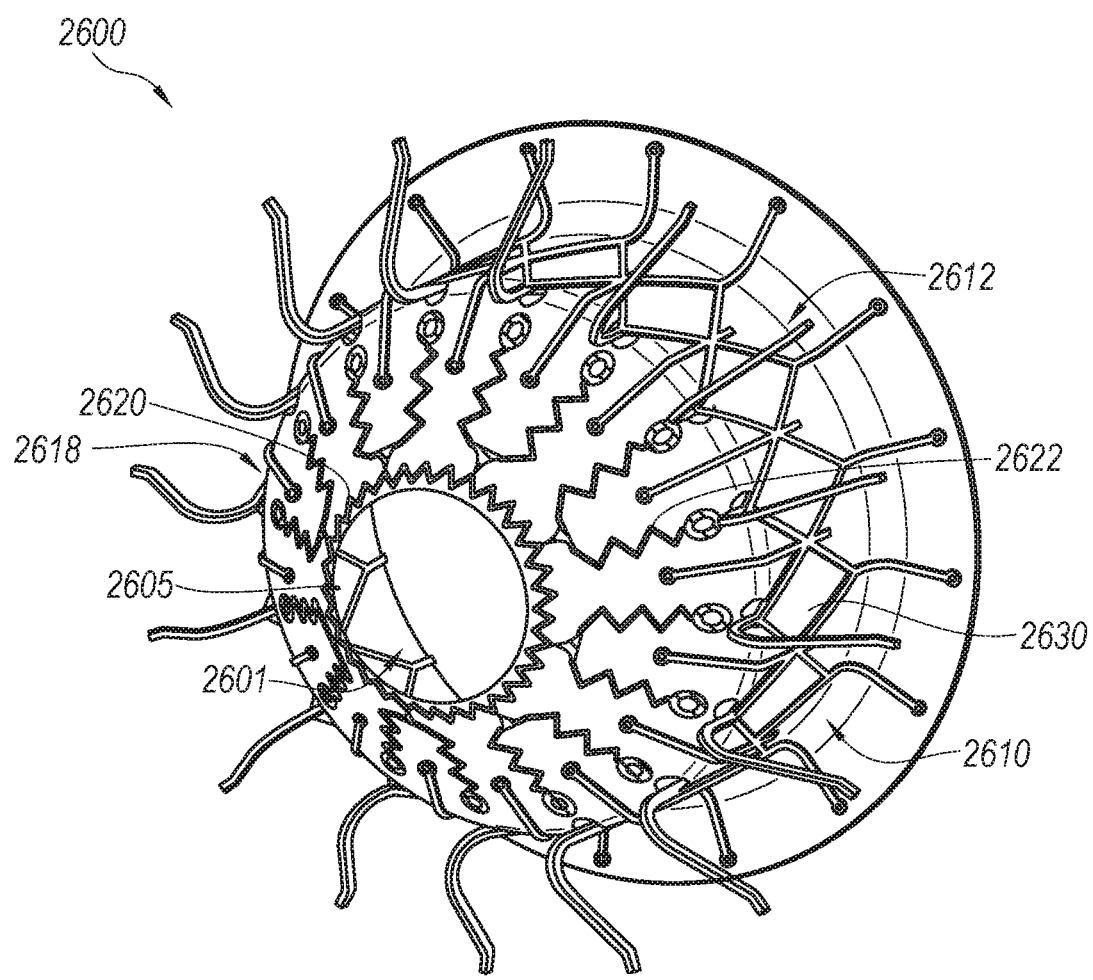
FIG. 26 is a partially isometric view of another adjustable interatrial shunting system having radially arranged actuation elements and configured in accordance with select embodiments of the present technology.

FIG. 26 illustrates an adjustable interatrial device 2600 ("device 2600") configured in accordance with select embodiments of the present technology. The device 2600 can include certain features generally similar to the features described above with respect to device 2400. For example, the device 2600 includes a shunting element 2610 comprising a frame 2612 and a membrane 2630 disposed around and/or coupled to the frame 2612. The shunting element 2610 defines a lumen 2601 extending therethrough for fluidly connecting the LA and the RA. The membrane 2630 extends radially inward at a first (e.g., RA) end portion of the shunting element 2610 to define an orifice 2605. As described below, a shape and/or size (e.g., diameter) of the orifice 2605 can be selectively adjusted via an actuation assembly 2618 to control the flow of blood through the lumen 2601. The actuation assembly 2618 can include actuation elements 2622 and a flow control element 2620.

However, in contrast with the device 2400 described previously, the device 2600 incorporates an actuatable flow control element 2620 disposed around the orifice 2605 (e.g., the flow control element 2620 is an annular actuation element). For example, the flow control element 2620 can be composed of a shape memory material, such as a shape memory alloy (e.g., nitinol). Accordingly, the flow control element 2620 can be transitionable between a first material state (e.g., a martensitic state, a R-phase, etc.) and a second material state (e.g., a R-phase, an austenitic state, etc.). In the first state, the flow control element 2620 may be deformable (e.g., plastic, malleable, compressible, expandable, etc.). In the second state, the flow control element 2620 may have a preference toward a specific manufactured geometry (e.g., shape, diameter, and/or dimension). The flow control element 2620 can be transitioned between the first state and the second state by applying energy to heat the flow control element 2620 above a transition temperature. Heating the flow control element 2620 above its transition temperature to transform the material to the second state causes the flow control element 2620 to move towards its manufactured geometry. If the flow control element 2620 is deformed relative to its manufactured geometry while in the first state, these deformations may be partially or completely recovered when material transitions into the second state. In some embodiments, the transition temperature for the flow control element 2620 is above an average body temperature. In some embodiments, the flow control element 2620 can be heated via RF energy, resistive heating, and the like. The flow control element 2620 can be coupled to the membrane 2630 such that dimensional adjustments to the flow control element 2620 impart a corresponding dimensional change to the orifice 2605.

The device 2600 further includes a plurality of actuation elements 2622 disposed radially around the flow control element 2620. The plurality of actuation elements 2622 can be generally similar to the plurality of first actuation elements 2422a described above with respect to FIGS. 24-25D. However, because the flow control element 2620 is actuatable, the device 2600 does not necessarily need a plurality of second actuation elements positioned radially around the flow control element 2620 (e.g., in contrast with the second actuation elements 2422b in device 2400). Instead, as described below, the flow control element 2620 replaces the function of the second actuation elements. The actuation elements 2622 can be heated independently of the flow control element 2620. For example, in some embodiments, the actuation elements 2622 can be on a different electrical circuit than the flow control element 2620.

The device 2600 can be transitioned between a variety of configurations by selectively heating either the flow control element 2620 or the actuation elements 2622 (or, alternatively, by directly applying mechanical forces to flow control element 2620 while it is a relatively deformable (e.g., martensitic) material state). The illustrated configuration, for example, may be a composite configuration in which both the flow control element 2620 and the actuation elements 2622 are deformed relative to their manufactured geometries. For example, the actuation elements 2622 may be compressed (e.g., shortened) relative to their manufactured geometry, and the flow control element 2620 may be compressed (e.g., having a smaller diameter) relative to its manufactured geometry. Accordingly, to increase the diameter of the orifice, the flow control element 2620 can be heated above its transition temperature (while the actuation elements remain below the transition temperature) to transition from a first state (e.g., a martensitic state) to a second state (e.g., austenitic state), inducing a change in configuration towards its manufactured geometry due to the shape memory effect. To decrease the diameter of the orifice, the actuation elements 2622 can be heated above the transition temperature (while the flow control element 2620 remains below its transition temperature) to transition from a first state (e.g., martensitic state) to a second state (e.g., austenitic state), inducing a change in configuration towards their manufactured geometry due to the shape memory effect. In other embodiments, the actuation elements 2622 may be expanded (e.g., lengthened) relative to their manufactured geometry, and the flow control element 2620 may be expanded (e.g., having a larger diameter) relative to its manufactured geometry when the device 2600 is in the composite configuration. In such embodiments, the actuation elements 2622 are selectively heated to increase the diameter of the orifice 2605, and the flow control element 2620 is selectively heated to decrease the diameter of the orifice 2605. In some embodiments, stabilization features (not shown) may be included proximate to actuation elements 2622 to restrict the movement of the actuation elements in a desired way (e.g., restrict the movement to be solely or primarily the plane of elements' long axis). Such features may facilitate the transfer of forces and/or movements between various aspects of device 2600, for example between actuation elements 2622, flow control element 2620, and membrane 2630. In embodiments, any number of flow control elements and sets of actuation elements may be used in combination with one another.

Figure 27:
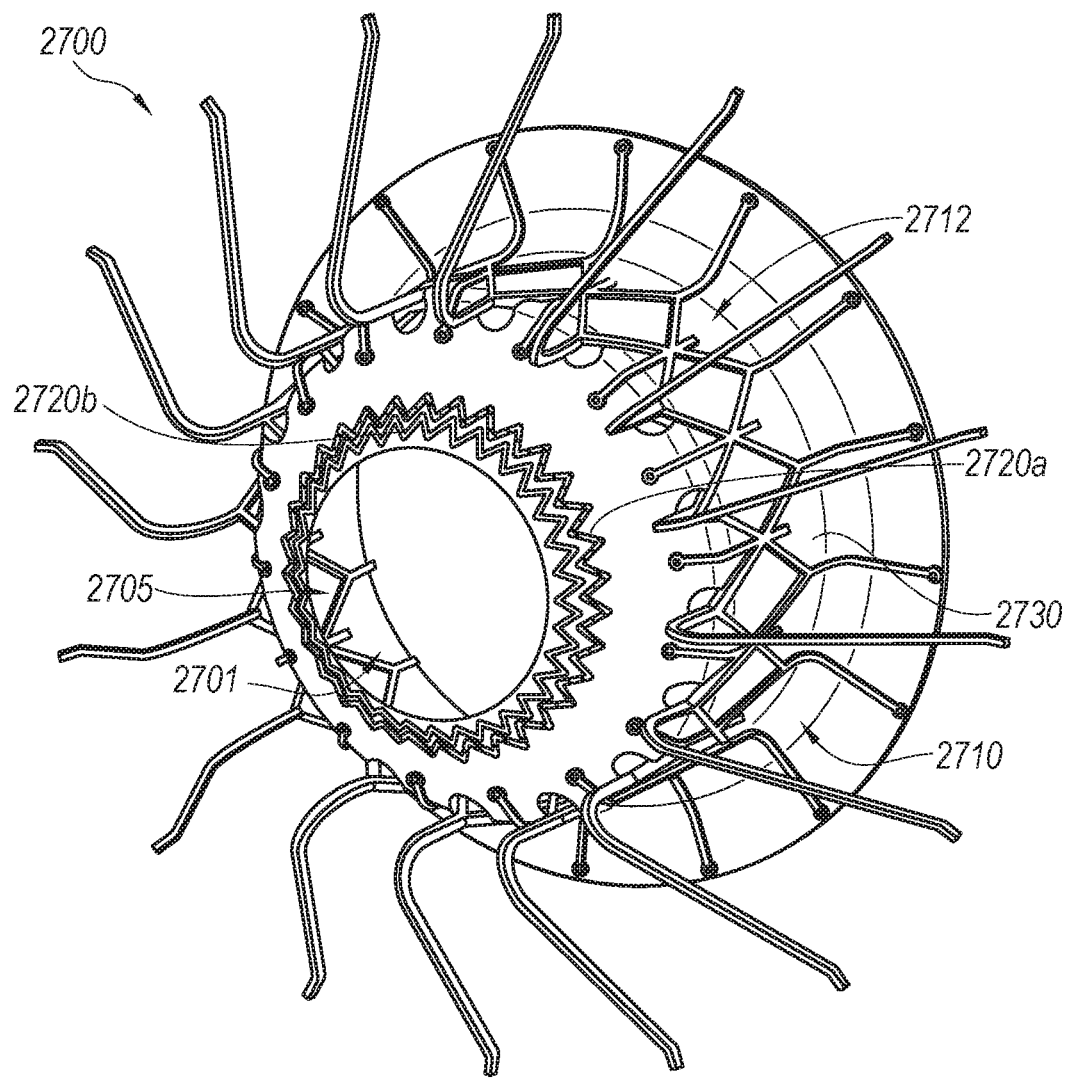
FIG. 27 is a partially isometric view of another adjustable interatrial shunting system having radially arranged actuation elements and configured in accordance with select embodiments of the present technology.

FIG. 27 illustrates an adjustable interatrial device 2700 ("device 2700") configured in accordance with select embodiments of the present technology. The device 2700 can include certain features generally similar to the features described above with respect to devices 2400 and 2600. For example, the device 2700 includes a shunting element 2710 comprising a frame 2712 and a membrane 2730 disposed around and/or coupled to the frame 2712. The shunting element 2710 defines a lumen 2701 extending therethrough for fluidly connecting the LA and the RA. The membrane 2730 extends radially inward at a first (e.g., RA) end portion of the shunting element 2710 to define an orifice 2705. As described below, a shape and/or size (e.g., diameter) of the orifice 2705 can be selectively adjusted via an actuation assembly 2718 to control the flow of blood through the lumen 2701.

The actuation assembly 2718 includes two independently actuatable flow control elements. In particular, the actuation assembly 2718 includes a first actuatable flow control element 2720a and a second actuatable flow control element 2720b. Accordingly, in some embodiments, the device 2700 does not include other actuation elements that are distinct from the flow control elements 2720a, 2720b (e.g., such as actuation elements 2422a, 2422b, described with respect to FIGS. 24-25D). Rather, the flow control elements 2720a, 2720b are themselves actuation elements (flow control elements 2720a,b can therefore also be referred to as first and second actuation elements. The first flow control element 2720a is disposed around an outer circumference of the second flow control element 2720b. Both the first flow control element 2720a and the second flow control element 2720b are coupled to the membrane 2730 such that adjustments to the first flow control element 2720a or the second flow control element 2720b imparts a corresponding dimensional change to the orifice 2705.

The first flow control element 2720a and the second flow control element 2720b can be composed of a shape memory material, such as a shape memory alloy (e.g., nitinol). Accordingly, the first flow control element 2720a and the second flow control element 2720b can be transitionable between a first state (e.g., a martensitic state, a R-phase, etc.) and a second state (e.g., a R-phase, an austenitic state, etc.). In a first state, the first flow control element 2720a and the second flow control element 2720b may be deformable (e.g., malleable, compressible, expandable, etc.). In a second state, the first flow control element 2720a and the second flow control element 2720b may have a preference toward a specific manufactured geometry (e.g., shape, length, and/or or dimension). The first flow control element 2720a and the second flow control element 2720b can be transitioned between a first state and a second state by applying energy to the actuation elements to heat the flow control elements above a transition temperature. In some embodiments, the transition temperature for both the first flow control element 2720a and the second flow control element 2720b is above an average body temperature. Accordingly, both the first flow control element 2720a and the second flow control element 2720b are typically in the deformable first state when the device 2700 is implanted in the body except for when they are heated (e.g., actuated).

Heating the flow control elements (e.g., the first flow control element 2720a) above their transition temperature causes the flow control elements to transform to the second state and therefore transition towards their manufactured geometries. If the flow control elements (e.g., the first flow control element 2720a) are deformed while in the first state, these deformations may be partially or completely recovered when material transitions into the second state. Heat can be applied to the flow control elements via RF heating, resistive heating, or the like. In some embodiments, the first flow control element 2720a can be selectively heated independently of the second flow control element 2720b, and the second flow control element 2720b can be selectively heated independently of the first flow control element 2720a. As described in detail below, selectively heating the first flow control element 2720a reduces the diameter of the orifice 2705 and selectively heating the second flow control element 2720b increases the diameter of the orifice 2705. Although two flow control elements are shown in FIG. 27, in embodiments any number of flow control elements may be integrated into device 2700. One advantage to using a greater number of elements may be a greater degree of precision and/or granularity regarding size and/or shape changes that can be induced in orifice 2705.

The device 2700 can be transitioned between a variety of configurations by selectively heating either the first flow control element 2720a or the second flow control element 2720b. The illustrated configuration may be a composite configuration in which both the first flow control element 2720a and the second flow control element 2720b are deformed relative to their manufactured geometries. For example, the first flow control element 2720a may be expanded (e.g., having a greater diameter) relative to its manufactured geometry, and the second flow control element 2720b may be compressed (e.g., having a smaller diameter) relative to its manufactured geometry. Accordingly, to increase the size (e.g., diameter) of the orifice 2705, the second flow control element 2720b can be heated above its transition temperature (while the first flow control element remains below the transition temperature) to transition from a first relatively malleable state (e.g., martensitic state) to a second state (e.g., austenitic state) and move towards its manufactured geometry. To decrease the size (e.g., diameter) of the orifice 2705, the first flow control element 2720a can be heated above the transition temperature (while the second flow control element 2720b remains below its transition temperature) to transition from a first relatively malleable state (e.g., martensitic state) to a second state (e.g., austenitic state) and move towards its manufactured geometry.

Figure 28A:
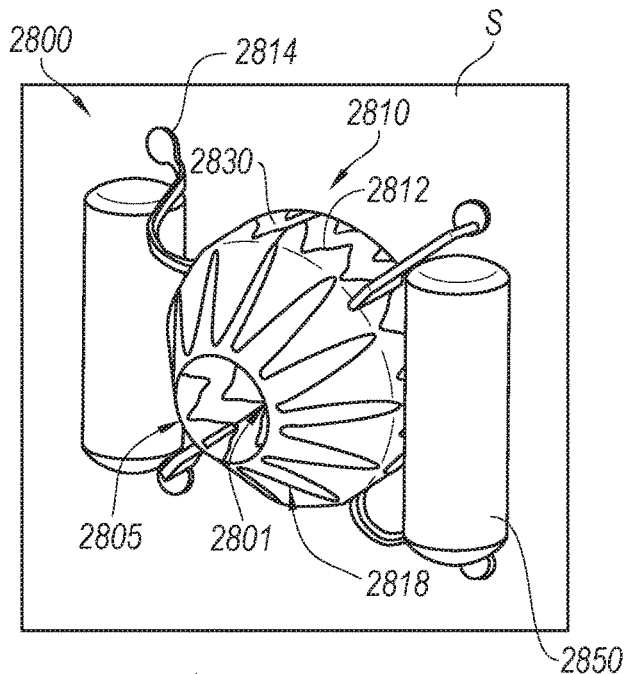
FIGS. 28A-28D are partially isometric views of an adjustable interatrial shunting system having stent-like actuation elements and configured in accordance with select embodiments of the present technology.
Figure 28B:
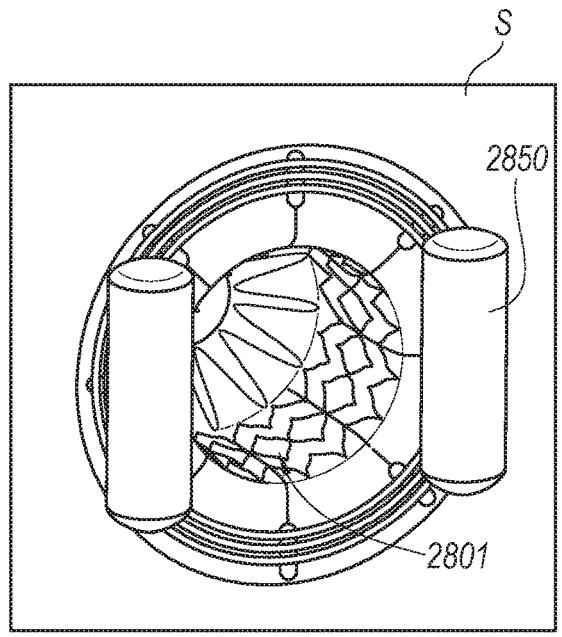
Figure 28C:
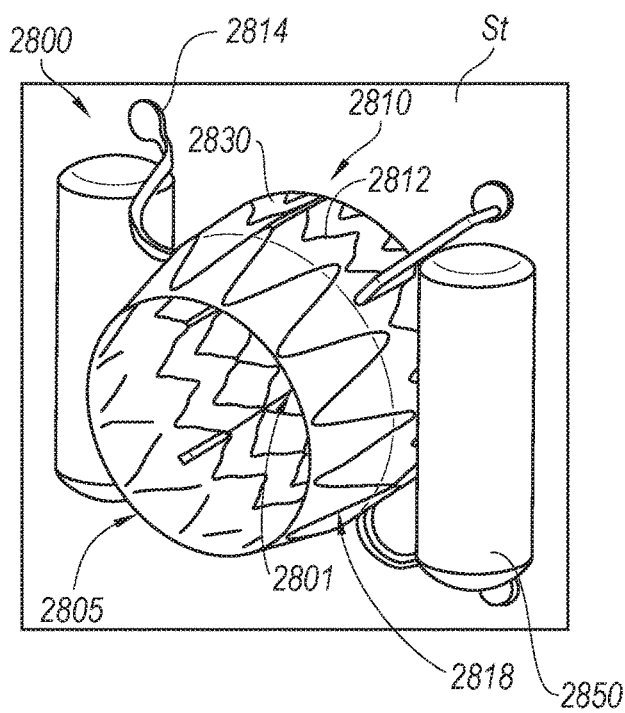
Figure 28D:
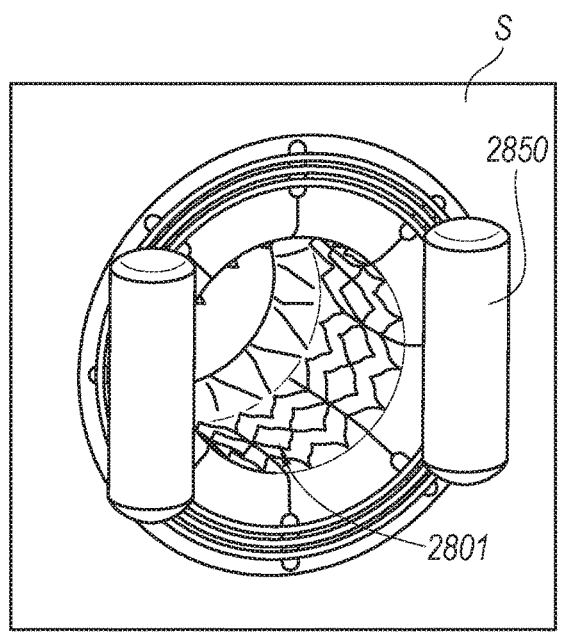
Figure 28E:
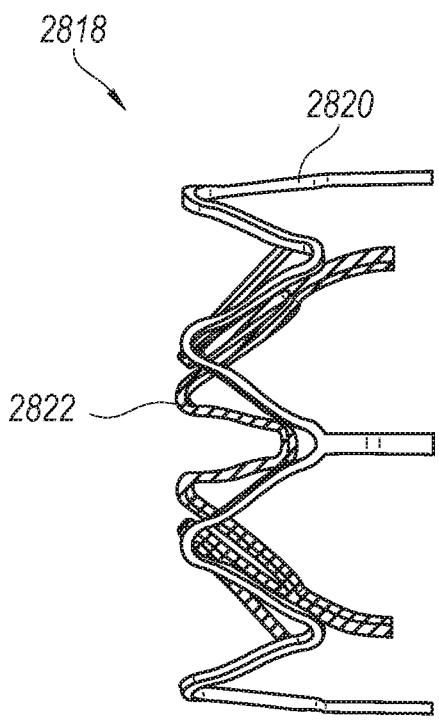
FIGS. 28E-28H are partially schematic views of the stent-like actuation elements of the adjustable interatrial shunting system of FIGS. 28A-28D.
Figure 28F:
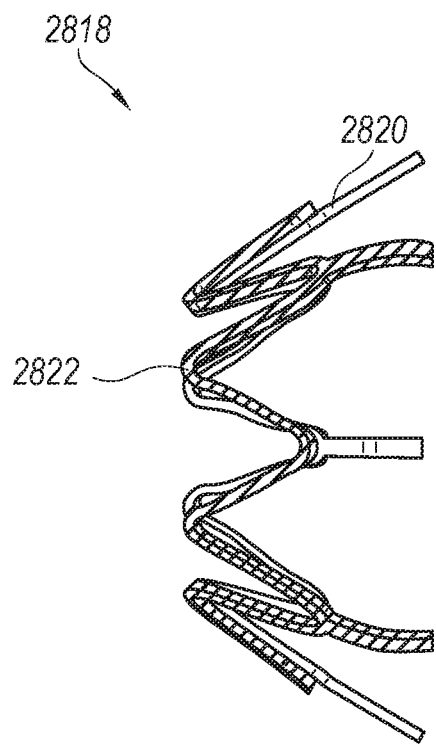
Figure 28G:
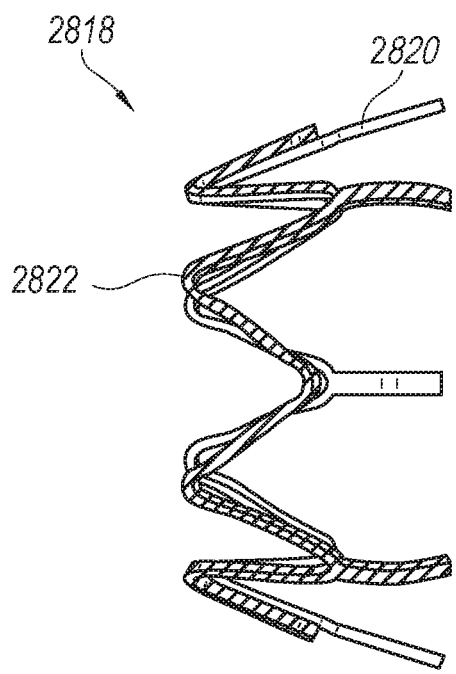
Figure 28H:
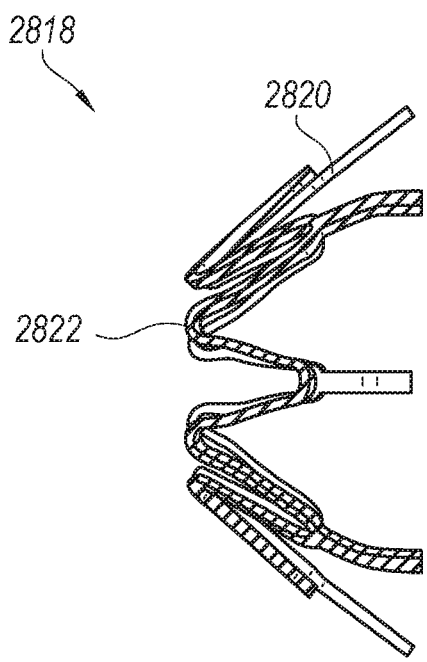

FIGS. 28A-28D illustrate an adjustable interatrial system 2800 ("system 2800") configured in accordance with select embodiments of the present technology. More specifically, FIG. 28A is a partially isometric view of the system 2800 in a first configuration from an RA side of a septal wall S, FIG. 28B is a partially isometric view of the system 2800 in the first configuration and from a LA side of the septal wall S, FIG. 28C is a partially isometric view of the system 2800 in a second configuration from the RA side of the septal wall S, and FIG. 28D is a partially isometric view of the system 2800 in the second configuration and from the LA side of the septal wall S. The system 2800 can include certain features generally similar to the features described above with respect to devices 2400, 2600, and 2700. For example, the system 2800 includes a shunting element 2810 comprising a frame 2812 and a membrane 2830 disposed around and/or coupled to the frame 2812. The shunting element 2810 can further comprise one or more anchors 2814 for securing the shunting element 2810 in place. The shunting element 2810 defines a lumen 2801 extending therethrough for fluidly connecting the LA and the RA. The membrane 2830 extends radially inward at a first (e.g., RA) end portion of the shunting element 2810 to define an orifice 2805. As described below, a shape and/or size (e.g., diameter) of the orifice 2805 can be selectively adjusted via an actuation assembly 2818 to control the flow of blood through the lumen 2801.

FIGS. 28E-28H illustrate addition details of the actuation assembly 2818. The actuation assembly 2818 can include a first stent-like actuation element 2820 and a second stent-like actuation element 2822. The first and second actuation elements 2820, 2822 can be tapered or otherwise angled radially inwards, extending from the frame 2812 towards the orifice 2805. Some aspects of the first and second actuation elements 2820, 2822 can be generally similar to the nested stent-like actuation elements previously described with respect to FIGS. 3A-4C. For example, FIG. 29E illustrates the first and second actuation elements 2820, 2822 in their manufactured shapes (e.g., before deformation and coupling). FIG. 29F illustrates a composite configuration in which the first actuation element 2820 is nested within the second actuation element 2822, and both the first and second actuation elements 2820, 2822 are deformed relative to their manufactured geometries. FIG. 29G illustrates a second configuration after the first actuation element 2822 has been heated above its transition temperature, thereby transitioning toward its manufactured geometry and increasing a composite diameter of the nested actuation elements (and thus increasing a diameter of the orifice 2805, as shown in FIG. 28C). FIG. 29H illustrates a third configuration after the second actuation element 2822 has been heated above its transition temperature, thereby transitioning toward its manufactured geometry and decreasing a composite diameter of the nested actuation elements (and thus decreasing a diameter of the orifice 2805, as shown in FIG. 28A).

Returning to FIGS. 28A-28D, and unlike the nested actuation elements described with respect to FIGS. 3A-4C, the first and second actuation elements 2820, 2822 are positioned within or coupled to a distal portion of the membrane 2830 residing within the RA, rather than a central portion of the membrane 2830 situated across the septal wall. Positioning the nested actuation in the distal portion of the membrane 2830 enables the geometry of the orifice 2805 to be adjusted while maintaining a geometry of a central portion of the lumen 2801 (e.g., as defined by the central portion of the membrane 2830). Accordingly, rather than adjusting the geometry of a substantial portion of the lumen 2801, the actuation assembly 2818 enables a user to selectively adjust a diameter of a portion of lumen 2801 (e.g., at and adjacent the orifice 2805). The system 2800 can also include one or more energy storage components 2850 (e.g., battery, supercapacitor, etc.) for storing energy that can be used to resistively heat the first and/or second actuation elements 2820, 2822.

Figure 29A:
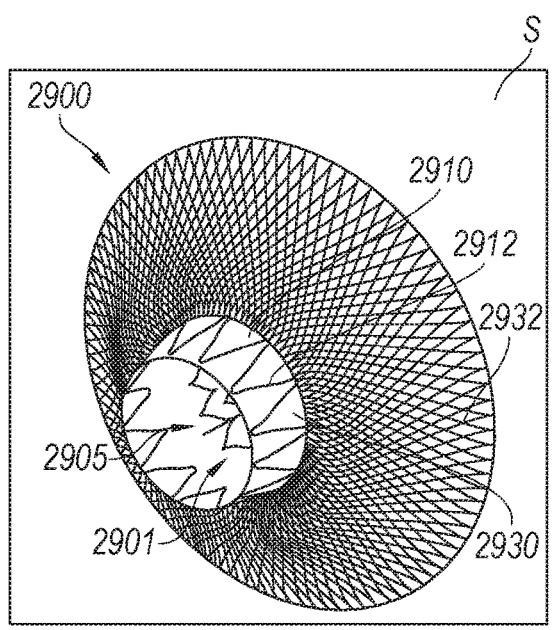
FIGS. 29A-29D illustrate an adjustable interatrial system configured in accordance with further embodiments of the present technology.
Figure 29B:
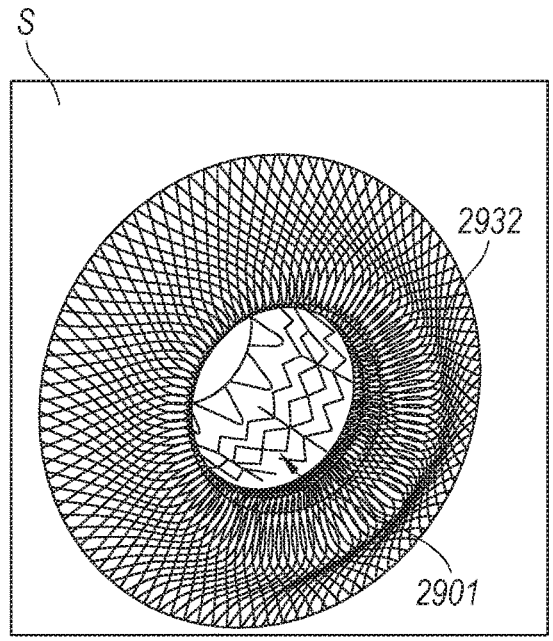
Figure 29C:
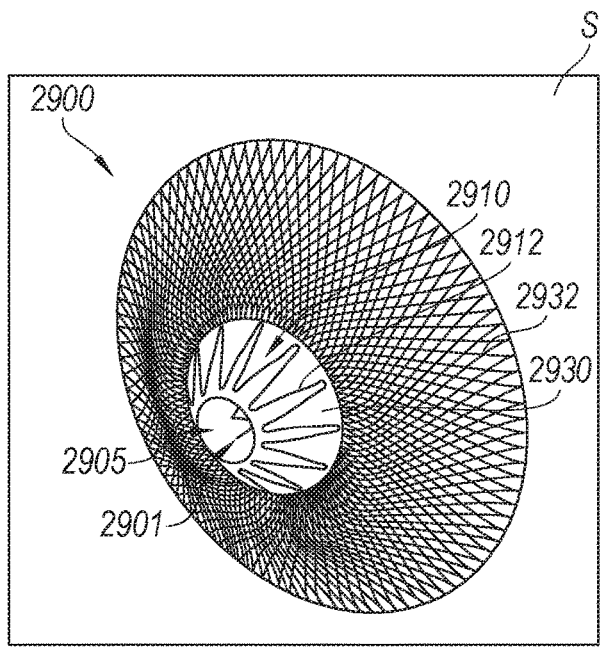
Figure 29D:
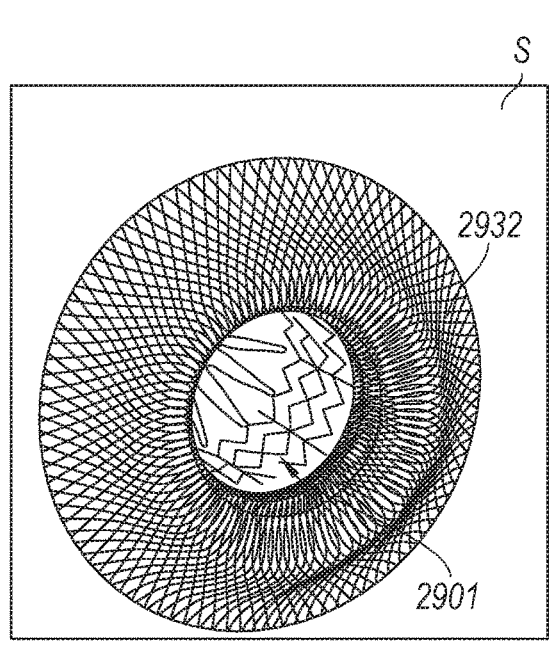

FIGS. 29A-29D illustrate an adjustable interatrial system 2900 ("system 2900") configured in accordance with further embodiments of the present technology. More specifically, FIG. 29A is a partially isometric view of the system 2900 in a first configuration from an RA side of a septal wall S, FIG. 29B is a partially isometric view of the system 2900 in the first configuration and from a LA side of the septal wall S, FIG. 29C is a partially isometric view of the system 2900 in a second configuration from the RA side of the septal wall S, and FIG. 29D is a partially isometric view of the system 2900 in the second configuration and from the LA side of the septal wall S. The system 2900 can include certain features generally similar to the features described above with respect to the system 2800. For example, the system 2900 includes a shunting element 2910 comprising a frame 2912 and a first membrane 2930 disposed around and/or coupled to the frame 2912. The shunting element 2910 defines a lumen 2901 extending therethrough for fluidly connecting the LA and the RA. The first membrane 2930 extends radially inward at a first (e.g., RA) end portion of the shunting element 2910 to at least partially define an orifice 2905. As described previously, a shape and/or size (e.g., diameter) of the orifice 2905 can be selectively adjusted via an actuation assembly to control the flow of blood through the lumen 2901.

In this embodiment, the system 2900 can further comprise a second membrane 2932 engaged with the frame 2912 and first membrane 2930 and extending at least partially over components of the system 2900 that are spaced apart from the shunting element 2910 (e.g., anchor(s), energy storage component(s), etc.). The second membrane 2932 may be composed of, for example, a braided mesh or other suitable material. During operation of the system 2900, the second membrane 2932 is configured to at least partially isolate the energy storage component(s) from blood within the RA and LA. This arrangement is expected to further inhibit thrombus formation after implantation of the system 2900 within the patient. The second membrane 2932 is an optional component that may have a different configuration/arrangement than the embodiment shown in FIGS. 29A-29D. Further, in some embodiments the second membrane 2932 may be omitted.

Figure 30A:
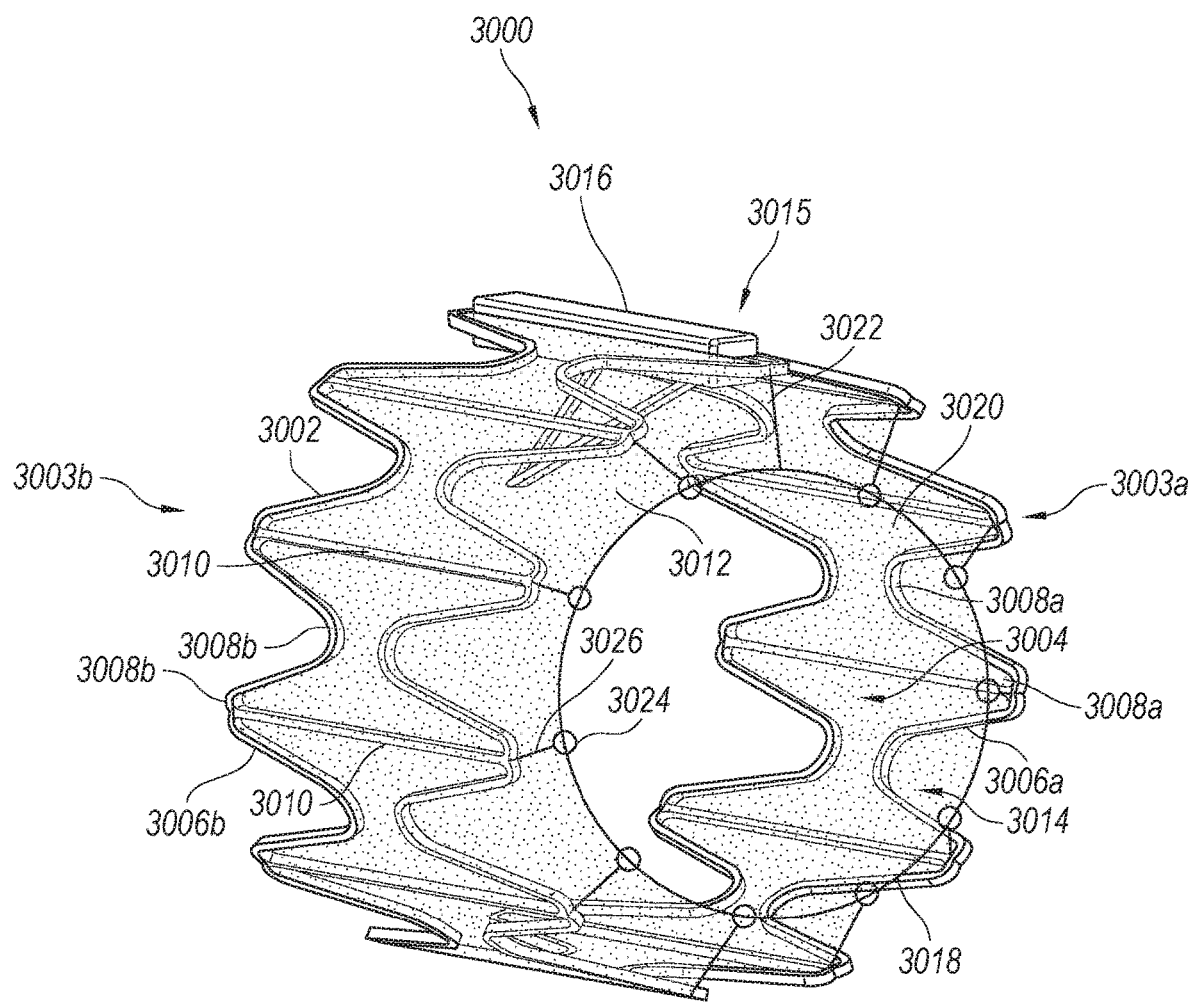
FIGS. 30A-30E illustrate an adjustable interatrial shunting system having a linear actuation mechanism and configured in accordance with select embodiments of the present technology.
Figure 30B:
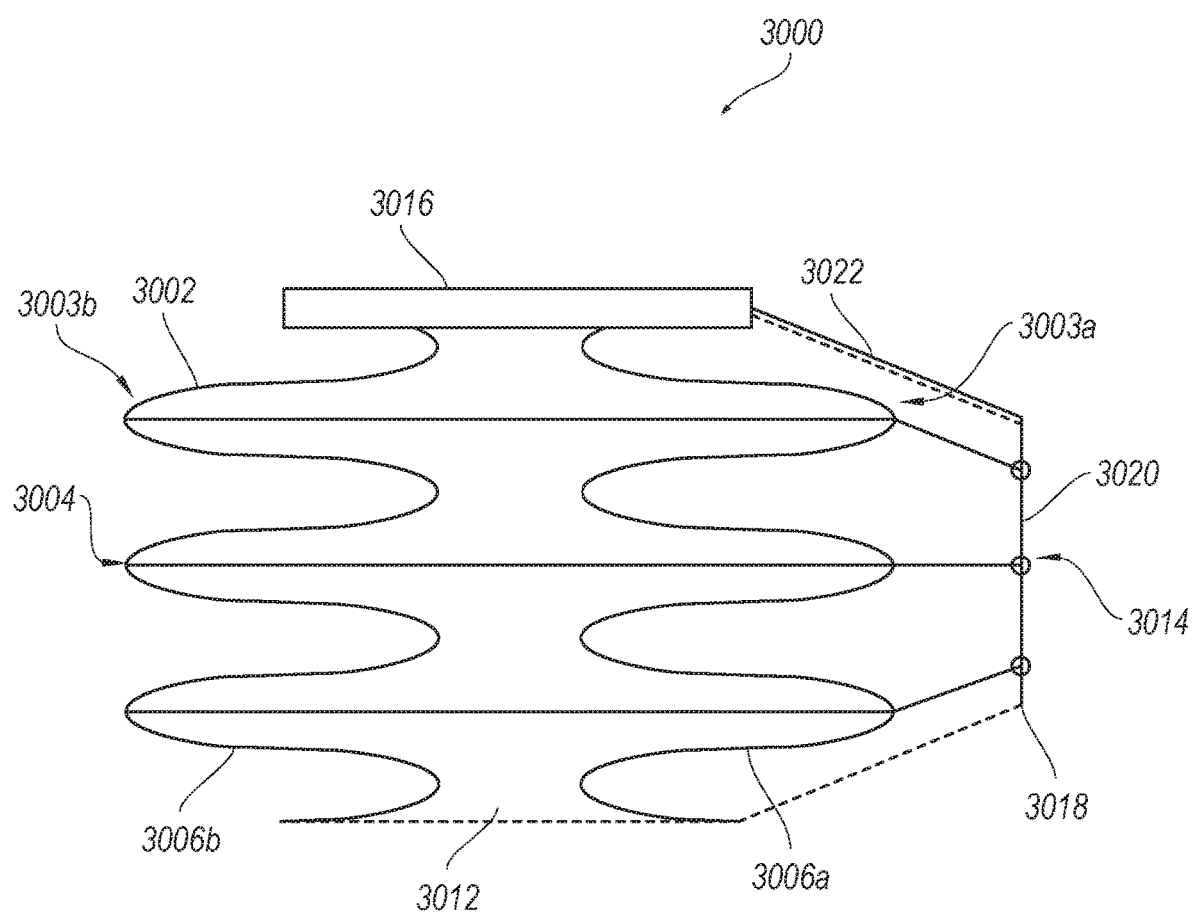
Figure 30C:
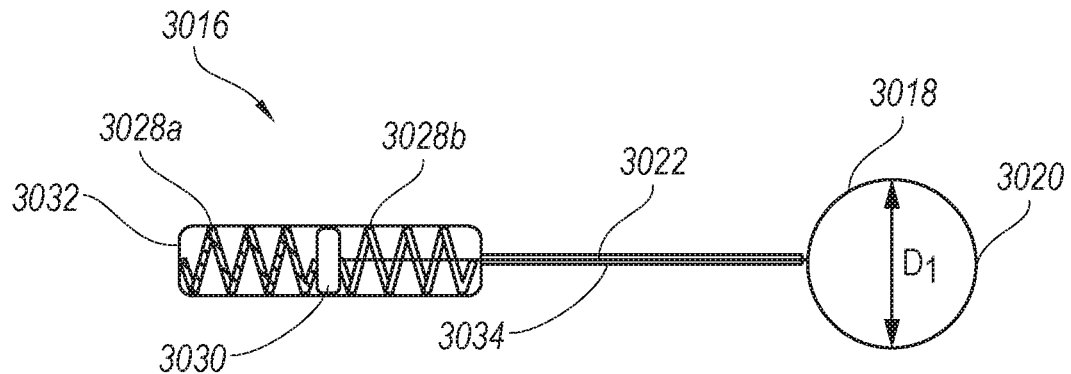
Figure 30D:
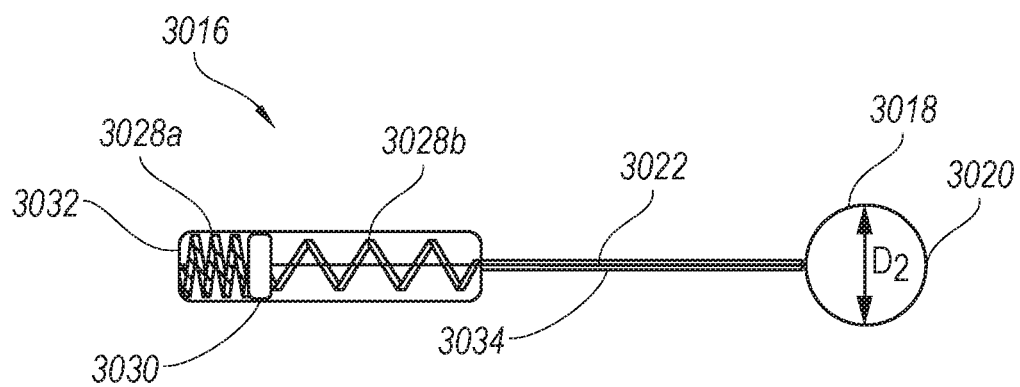
Figure 30E:
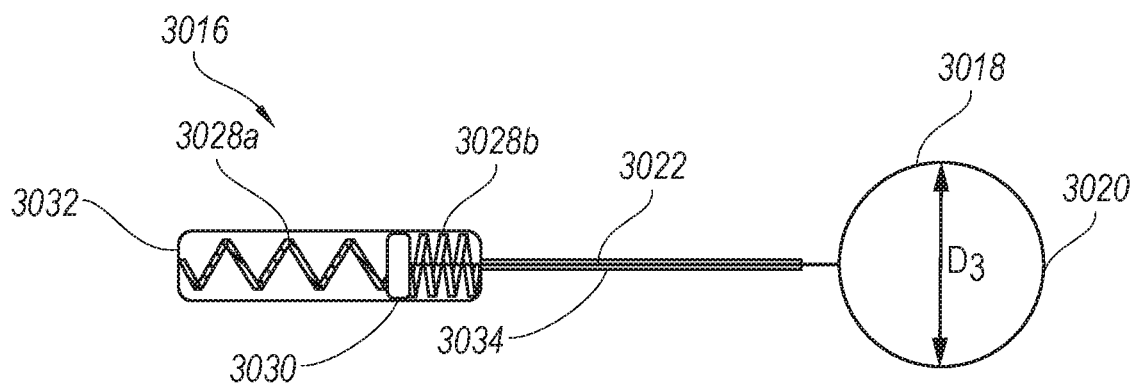

FIGS. 30A-30E illustrate an interatrial shunting system 3000 ("system 3000") configured in accordance with select embodiments of the present technology. More specifically, FIG. 30A is a perspective view of the system 3000, FIG. 30B is a side view of the system 3000, and FIGS. 30C-30E are schematic illustrations of an actuation assembly 3015 of the system 3000 during various stages of operation. Referring first to FIGS. 30A and 30B together, the system 3000 includes a shunting element 3002 defining a lumen 3004 therethrough. The shunting element 3002 can include a first end portion 3003a configured to be positioned in or near the RA (not shown) and a second end portion 3003b configured to be positioned in or near the LA (not shown). Accordingly, when implanted in the septal wall (not shown) of a patient, the system 3000 fluidly connects the LA and the RA via the lumen 3004. In some embodiments, the system 3000 serves as a sub-system that interfaces with additional structures (not shown), for example, anchoring and/or frame components, to form an interatrial shunting system configured in accordance with an embodiment of the present technology.

The shunting element 3002 can be a frame including a first annular element 3006a at the first end portion 3003a and a second annular element 3006b at the second end portion 3003b. The first and second annular elements 3006a-b can each extend circumferentially around the lumen 3004 to form a stent-like frame structure. In the illustrated embodiment, the first and second annular elements 3006a-b each have a serpentine shape with a plurality of respective apices 3008a-b. The apices 3008a-b can be curved or rounded. In other embodiments, the apices 3008a-b can be pointed or sharp such that the first and second annular elements 3006a-b have a zig-zag shape. Optionally, the first and second annular elements 3006a-b can have different and/or irregular patterns of apices 3008a-b, or can be entirely devoid of apices 3008a-b. The first and second annular elements 3006a-b can be coupled to each other by a plurality of struts 3010 extending longitudinally along the shunting element 3002. The struts 3010 can be positioned between the respective apices 3008a-b of the first and second annular elements 3006a-b.

The system 3000 further includes a membrane 3012 operably coupled (e.g., affixed, attached, or otherwise connected) to the shunting element 3002. In some embodiments, the membrane 3012 is flexible and can be made of a material that is impermeable to or otherwise resists blood flow therethrough. In some embodiments, for example, membrane 3012 can be made of a thin, elastic material such as a polymer. For example, the membrane 3012 can be made of PTFE, ePTFE, silicone, nylon, PET, polyether block amide (pebax), polyurethane, blends or combinations of these materials, or other suitable materials.

The membrane 3012 can cover at least a portion of the shunting element 3002, such as the exterior surface of the shunting element 3002 between the first end portion 3003a and the second end portion 3003b. The membrane 3012 can extend circumferentially around the shunting element 3002 to at least partially surround and enclose the lumen 3004. For example, in the illustrated embodiment, the membrane 3012 extends between the first and second annular elements 3006a-b and over the struts 3010. The membrane 3012 can couple the first and second annular elements 3006a-b to each other, in combination with or as an alternative to the struts 3010. The membrane 3012 can extend past the first end portion 3003a and/or the first annular element 3006a (e.g., as best seen in FIG. 30B) so that a portion of the membrane 3012 is positioned over and partially covers the lumen 3004. In some embodiments, the membrane 3012 does not extend past the second end portion 3003b and/or the second annular element 3006b.

The membrane 3012 includes an aperture 3014 formed therein. When the membrane 3012 is coupled to the shunting element 3002, the aperture 3014 can be at least generally aligned with or otherwise overlap the lumen 3004 to permit blood flow therethrough. In some embodiments, the aperture 3014 is positioned at or near the first end portion 3003a of the shunting element 3002. In other embodiments, the aperture 3014 can be positioned at or near the second end portion 3003b. Additionally, although FIG. 30A illustrates the aperture 3014 as having an elliptical shape, in other embodiments the aperture 3014 can have a different shape, such as a circular, square, rectangular, polygonal, or curvilinear shape.

The geometry (e.g., size and/or shape) of the aperture 3014 can be varied by deforming (e.g., stretching and/or compressing) or otherwise moving the portions of the membrane 3012 surrounding the aperture 3014. The change in geometry of the aperture 3014 can affect the amount of blood flow through the lumen 3004. In some embodiments, depending on the size of the aperture 3014 relative to the size of the lumen 3004, blood flow through the lumen 3004 can be partially or completely obstructed by the membrane 3012. Accordingly, an increase in the size (e.g., a diameter, an area) of the aperture 3014 can increase the amount of blood flow through the lumen 3004, while a decrease in the size of the aperture 3014 can decrease the amount of blood flow.

The system 3000 can include an actuation assembly 3015 operably coupled to the aperture 3014 to selectively adjust the size thereof. The actuation assembly 3015 can include an actuation mechanism 2016 and a string element 3018 (e.g., a cord, thread, fiber, wire, tether, ligature, or other flexible elongated element). The actuation mechanism 3016 is coupled to the string element 3018 around the aperture 3014 for controlling the size thereof. For example, the string element 3018 can include a loop portion 3020 surrounding the aperture 3014 and a connecting portion 3022 coupling the loop portion 3020 to the actuation mechanism 3016. In some embodiments, the loop portion 3020 and the connecting portion 3022 are different portions of one contiguous elongated element (e.g., arranged similarly to a lasso or snare) that attain their relative shapes (e.g., an elliptical, loop-like shape) as a consequence of how they are connected to the system 3000. In other embodiment, the loop portion 3020 and the connecting portion 3022 can be separate elements that are directly or indirectly coupled to each other.

One or more portions of the string element 3018 (e.g., the loop portion 3020) can be coupled to the portion of the membrane 3012 near the aperture 3014. In the illustrated embodiment, the string element 3018 (e.g., loop portion 3020) passes through a plurality of openings or holes 3024 (e.g., eyelets) located near the peripheral portion of the aperture 3014. The openings 3024 can be coupled to the shunting element 3002 (e.g., to the first end portion 3003a and/or first annular element 3006a) via a plurality of flexible ribs 3026 (e.g., sutures, strings, threads, metallic structures, polymeric structures, etc.). In other embodiments, the openings 3024 are formed in or coupled directly to the membrane 3012 such that the ribs 3026 are omitted.

In some embodiments, the string element 3018 has a lasso- or noose-like configuration in which the loop portion 3020 can be tightened to a smaller size or loosened to a larger size by making an adjustment to (e.g., translating, rotating, applying or releasing tension, etc.) on the connecting portion 3022. In some embodiments, a motion caused by the adjustment of connecting portion 3022 creates an induced motion in loop portion 3020 (e.g., a motion that results in the loop portion 3020 shifting to a larger or a smaller size). Due to the coupling between the string element 3018 and the membrane 3012, the size of the aperture 3014 (e.g., a diameter, an area) can change along with the size of the loop portion 3020 such that the size of the aperture 3014 increases as the size of the loop portion 3020 increases, and decreases as the size of the loop portion 3020 decreases. For example, as the size of the loop portion 3020 decreases, the portions of the membrane 3012 surrounding the aperture 3014 can be cinched, stretched, or otherwise drawn together by the loop portion 3020 so that the size of the aperture 3014 decreases. Conversely, as the size of the loop portion 3020 increases, the portions of the membrane 3012 surrounding the aperture can be released, loosened, stretched, or otherwise allowed to move apart so that the size of the aperture 3014 increases. Accordingly, the actuation mechanism 3016 can adjust the size of the loop portion 3020, and thus the size of the aperture 3014, by controlling the amount of force (e.g., tension) applied to the loop portion 3020 via the connecting portion 3022. For example, in some embodiments, the actuation mechanism 3016 increases the size of the loop portion 3020 and aperture 3014 by increasing the amount of force applied to the connecting portion 3022, and decreases the size of the loop portion 3020 and aperture 3014 by decreasing the amount of applied force.

In other embodiments, the system 3000 can implement different mechanisms for mechanically and/or operably coupling the actuation mechanism 3016, the loop portion 3020, and the connecting portion 3022. For example, there can be an inverse relationship between these components, e.g., the actuation mechanism 3016 can increase the size of the loop portion 3020 and aperture 3014 by increasing the amount of force applied to the connecting portion 3022, and can decrease the size of the loop portion 3020 and aperture 3014 by decreasing the amount of applied force. In some embodiments, changes in the size of the loop portion 3020 and aperture 3014 are created via the actuation mechanism 3016 translating, rotating, or otherwise manipulating the connecting portion 3022 in a way that does not substantially increase or decrease the amount of force applied to the connecting portion 3022. In other embodiments, the adjustment to the connecting portion 3022 made by the actuation mechanism 3016 can result in an alteration of the shape of (rather than the size of) loop portion 3020 and aperture 3014.

In some embodiments, the connecting portion 3022 can be surrounded by a relatively stiff conduit 3034 (e.g., a plastic or metallic hypotube, shown in FIGS. 30C-30E) that can facilitate the transfer of forces from the actuation mechanism 3016, as further described below. The conduit 3034 can be flexible or hinged to such that it can move with one or more degrees of freedom with respect to the actuation mechanism 3016 and/or the aperture 3014.

The actuation mechanism 3016 can be configured in a number of different ways. In some embodiments, for example, the actuation mechanism 3016 includes one or more motors, such as electromagnetic motors, implanted battery and mechanical motors, MEMS motors, micro brushless DC motors, piezoelectric based motors, solenoids, and other motors. In other embodiments, the actuation mechanism 3016 includes one or more shape memory elements. For example, referring to FIGS. 30C-30E together, in some embodiments, the actuation mechanism 3016 includes a first shape memory actuation element 3028a, a second shape memory actuation element 3028b, and a shuttle element 3030. The shuttle element 3030 can be positioned between and coupled to the first and second shape memory actuation elements 3028a-b. The shuttle element 3030 can be also coupled to the string element 3018 (e.g., coupled to connecting portion 3022). Optionally, the first shape memory actuation element 3028a, second shape memory actuation element 3028b, and shuttle element 3030 can be located within a housing 3032. The shuttle element 3030 can move within the housing 3032 to adjust the force on and/or the position of the connecting portion 3022 and vary the size of the loop portion 3020, as described in greater detail below.

In some embodiments, the connecting portion 3022 can be received within the conduit 3034 (e.g., a flexible tube). The conduit 3034 can serve as a guide for the connecting portion 3022. In some embodiments, the conduit 3034 also provides mechanical stabilization that impacts how the loop portion 3020 and aperture 3014 move in response to manipulation of the connecting portion 3022. The conduit 3034 can be coupled to the housing 3032 or to another component of the system 3000 (e.g., in embodiments wherein the housing 3032 is omitted).

The movement of the shuttle element 3030 can be actuated by the first and second shape memory actuation elements 3028a-b. For example, the first and second shape memory actuation elements 3028a-b can each be configured to change in shape in response to a stimulus such as heat or mechanical loading. In some embodiments, the first and second shape memory actuation elements 3028a-b are each manufactured or otherwise configured to approach (e.g., change in shape, deform, transform, etc.) a relatively lengthened configuration upon application of heat. In other embodiments, the first and second shape memory actuation elements 3028a-b are each manufactured or otherwise configured to approach a relatively shortened configuration upon application of heat. Optionally, one shape memory actuation element can approach a relatively lengthened configuration when heated, while the other shape memory actuation element can approach a relatively shortened configuration when heated. In some embodiments, at least one shape memory actuation element is manufactured so that, at a first temperature (e.g., body temperature), it is relatively more thermoelastically deformable in response to a fixed force or stress than it would be at a second temperature. The second temperature can be a higher temperature (e.g., a temperature resulting from the application of heat to an element) than the first temperature.

The shape change (e.g., due to deformation by externally-applied forces, due to heating that results in a deformation related to the shape memory effect, etc.) of the first and/or second shape memory actuation elements 3028a-b can actuate movement of the shuttle element 3030 relative to the housing 3032. In some embodiments, the first and second shape memory actuation elements 3028a-b, when at an unheated temperature (e.g., at or close to body temperature), are relatively more thermoelastically deformable as described above. In such embodiments, actuation (e.g., expansion/lengthening) of one shape memory actuation element via heating can move shuttle element 3030 in such a way that deforms/compresses the other shape memory actuation element.

Referring initially to FIG. 30C, in a first stage of operation, the first and second shape memory actuation elements 3028a-b can reside in a neutral configuration, with both elements deformed from their original manufactured geometric configurations. As a result, the shuttle element 3030 can be positioned at or near the center of the housing 3032 and the loop portion 3020 can have a diameter $D_1$. The size of the aperture (not shown) can be similar to the size of the loop portion 3020 (e.g., the aperture has a diameter equal or similar to $D_1$). The aperture size can permit a first amount of blood flow through the lumen of the shunting element (not shown).

Referring next to FIG. 30D, in a different stage of operation, the first shape memory actuation element 3028a has changed in shape to a relatively shortened configuration and the second shape memory actuation element 3028b has changed in shape to a relatively lengthened configuration. For example, the second shape memory actuation element 3028b can be heated to induce a change in shape to a lengthened configuration (e.g., towards its original manufactured geometric configuration) relative to its shape in the neutral position shown in FIG. 30C. This shape change can apply a force to the shuttle element 3030 that moves it along a first direction (e.g., away from the loop portion 3020). As a result, the shuttle element 3030 can apply an increased amount of tension to the connecting portion 3022 to retract it at least partially into the housing 3032. The tension on the connecting portion 3022 can cause the loop portion 3020 to tighten and/or decrease in a size to a smaller diameter $D_2$ (e.g., by forcing a larger portion of the string element 3018 into the conduit 3034). The decrease in size of the loop portion 3020 can cause the aperture size to also decrease (e.g., to a diameter equal or similar to $D_2$). The decreased aperture size can permit a decreased amount of blood flow or no blood flow through the lumen. In some embodiments, the force applied by the shape change of the second shape memory actuation element 3028b can also cause the first shape memory actuation element 3028a (which is unheated and accordingly can be relatively more thermoelastically deformable than when at an elevated temperature) to change in shape to a relatively shortened configuration.

Referring to FIG. 30E, in a further stage of operation, the first shape memory actuation element 3028a has changed in shape to a relatively lengthened configuration and the second shape memory actuation element 3028b has changed in shape to a relatively shortened configuration. For example, the first shape memory actuation element 3028a can be heated to induce a change in shape to a lengthened configuration (e.g., towards its original manufactured geometric configuration) relative to its shape in the neutral position shown in FIG. 30C and relative to its compressed shape shown in FIG. 30D. This shape change can apply a force to the shuttle element 3030 that moves it along a second, opposite direction (e.g., towards the loop portion 3020). As a result, the shuttle element 3030 can apply a decreased amount of tension on the connecting portion 3022 to release it at least partially from the housing 3032. The decreased tension on the connecting portion 3022 can cause the loop portion 3020 to loosen and/or increase in a size to a larger diameter $D_3$ (e.g., by allowing a larger portion of string element 3018 to reside outside the conduit 3034). The increase in size of the loop portion 3020 can cause the aperture size to also increase (e.g., to a diameter equal or similar to $D_3$). The increased aperture size can permit an increased amount of blood flow through the lumen. In some embodiments, the force applied by the shape change of the first shape memory actuation element 3028a can also cause the second shape memory actuation element 3028b (which is unheated and accordingly can be relatively more thermoelastically deformable than when at an elevated temperature) to change in shape to a relatively shortened configuration.

It will be appreciated that the system 3000 can be configured in a number of different ways. In some embodiments, for example, the system 3000 can include multiple membrane structures and/or materials. For example, a first membrane can interface with a first portion of the system 3000 (e.g., between first and second annular elements 3006a-b) and a second membrane can interface with a second portion of the system 3000 (e.g., between first annular element 3006a and a string element 3018). In such embodiments, the first and second membranes can be made of different materials having different material properties (e.g., flexibility, elasticity, permeability, tear strength, etc.). This approach is expected to be advantageous in embodiments where different material properties are optimal or otherwise beneficial for different regions of the system 3000. For example, flexibility may be an important characteristic in one region of the system 3000, while in a second region, lack of permeability may be more important than flexibility. The system 3000 can include any suitable number of membrane structure and/or materials. Optionally, some portions of the system 3000 can include multiple (e.g., overlapping) membranes made of the same material or different materials.

The actuation mechanism 3016 can be configured in a number of different ways. For example, in some embodiments the first and/or second shape memory actuation elements 3028a-b can be manufactured or otherwise configured to approach a relatively shortened configuration rather than a relatively lengthened configuration when heated. As a result, heat can be applied to the first shape memory actuation element 3028a to retract more of the string element 3018 into the housing 3032, and heat can be applied to the second shape memory actuation element 3028b to release more of the string element 3018 from the housing 3032. Additionally, although FIGS. 30C-30E illustrate the first and second shape memory actuation elements 3028a-b as having a folded or zig-zag shape, in other embodiments the first and second shape memory actuation elements 3028a-b can have a different shape, such as a serpentine, curved, bent, or coiled shape.

In some embodiments, the first and second shape memory actuation elements 3028a-b are positioned on the same side of the shuttle element 3030. In such embodiments, one shape memory actuation element can be manufactured such that when it is heated it moves towards a relatively lengthened/expanded configuration, and the second shape memory actuation element can be manufactured such that when it is heated it moves towards a relatively shortened/contracted configuration. In other embodiments, any number of shape memory actuation elements that have been manufactured to have similar or dissimilar original geometric configurations may be utilized.

In some embodiments, the string element 3018 itself acts as an actuation mechanism. In such embodiments, any additional actuation mechanism (e.g., actuation mechanism 3016) can be omitted. For example, an embodiment may consist of a string element 3018 that is composed entirely of a loop portion 3020 (e.g., there is no connecting portion 3022) that interfaces with openings or holes 3024 (e.g., eyelets). The loop portion 3020 may also interface directly or indirectly with membrane 3012 so as to form aperture 3014. The string element 3018 can include a shape memory material (e.g., a nitinol wire or strut). In a mode of operation, the size and/or shape of the loop portion 3020 can be altered to vary the shape of the aperture 3014. For example, a shape memory material comprising the loop portion 3020 can be manufactured to have a relatively small geometry (e.g., a small diameter). Prior to or following implantation, a force can be applied (e.g., a radial outward force provided by an expanding balloon) to the loop portion 3020 to deform it into a configuration with a relatively larger geometry. Subsequently, heat can be applied to the shape memory loop portion 3020 to induce a shape change towards its relatively smaller manufactured geometry. A series of similar operations can be performed over a period of time to allow a care provider to change an aperture size multiple times within a range of possible sizes. In other embodiments, the shape memory material comprising the loop portion 3020 can be manufactured to have a relatively large geometry. Prior to or following implantation, a force can be applied (e.g., a compressive force from a snare tool) to the loop portion 3020 to deform it into a configuration with a relatively smaller geometry. Subsequently, heat can be applied to the shape memory loop portion to induce a shape change towards its relatively larger manufactured geometry.

In some embodiments, the string element 3018 includes two or more shape memory elements that have been coupled together mechanically (e.g., with welds, sutures, glue/adhesives, rivets/crimps, etc.) in a way such that the two or more elements are electrically and/or thermally insulated from one another. In such embodiments, for example, a first shape memory element may be manufactured to have a relatively larger geometry, and a second shape memory element may be manufactured to have a relatively smaller geometry. As these elements are mechanically coupled, a heat-driven actuation of one element towards its original geometric configuration may drive a similar motion in the non-heated element, since the non-heated element will remain in a relatively more thermoelastically deformable material phase. As such, the size of the loop portion 3020, and thereby the size of aperture 3014, may be adjusted to be both larger and smaller using energy applied to different portions of the string element 3018. In such embodiments, the size of the loop portion 3020 can also be altered by applying an external force (e.g., via an expandable balloon).

In embodiments of the present technology that utilize heat or another form of energy applied to a shape memory element or another component of the system, the energy/heat can be applied both invasively (e.g., via a catheter delivering laser, radiofrequency, or another form of energy, via an internal stored energy source such as a supercapacitor, etc.), non-invasively (e.g., using radiofrequency energy delivered by a transmitter outside of the body, by focused ultrasound, etc.), or through a combination of these methods.

Figure 31A:
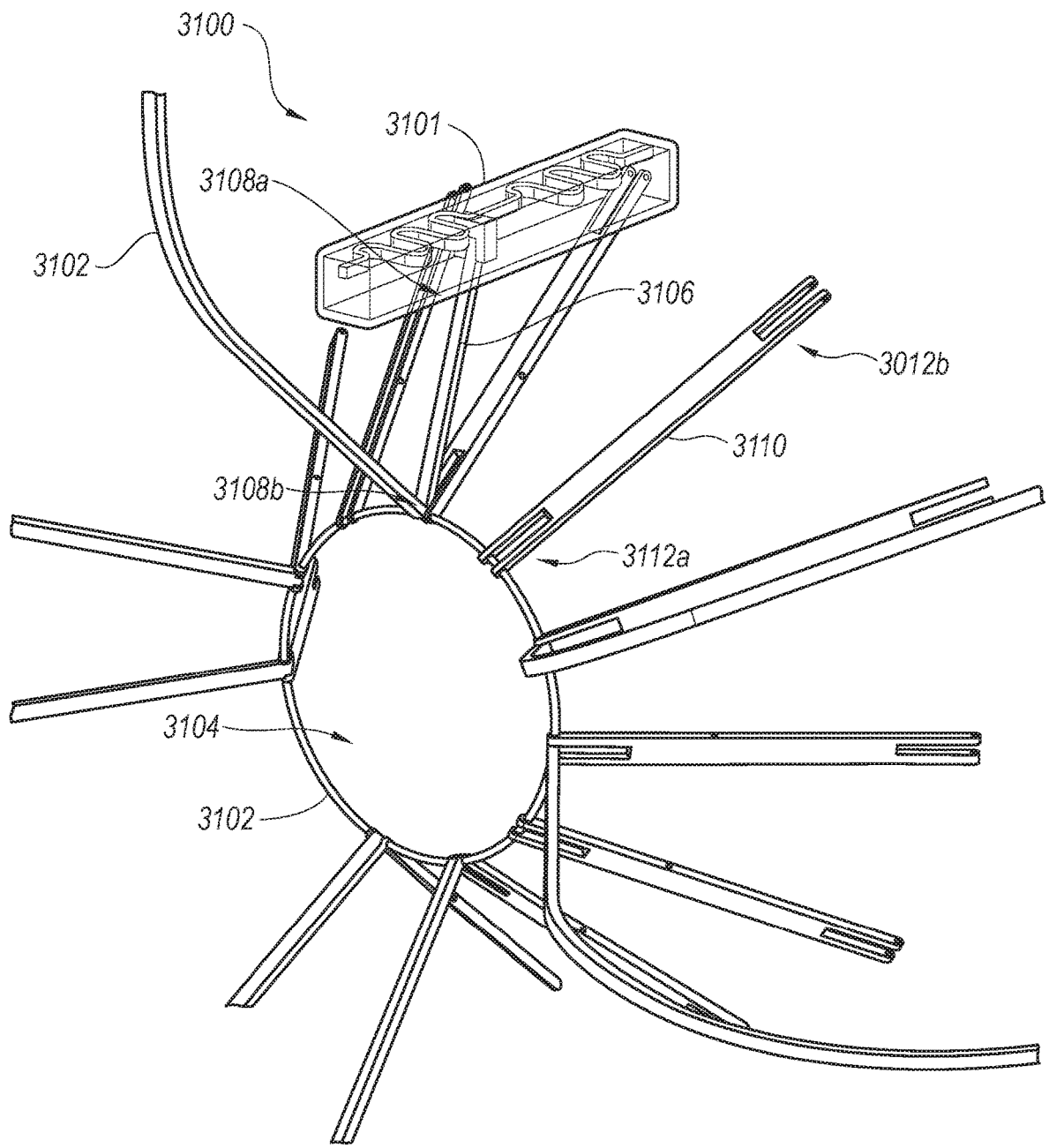
FIGS. 31A and 31B illustrate another adjustable interatrial shunting system having a linear actuation mechanism and configured in accordance with select embodiments of the present technology.
Figure 31B:
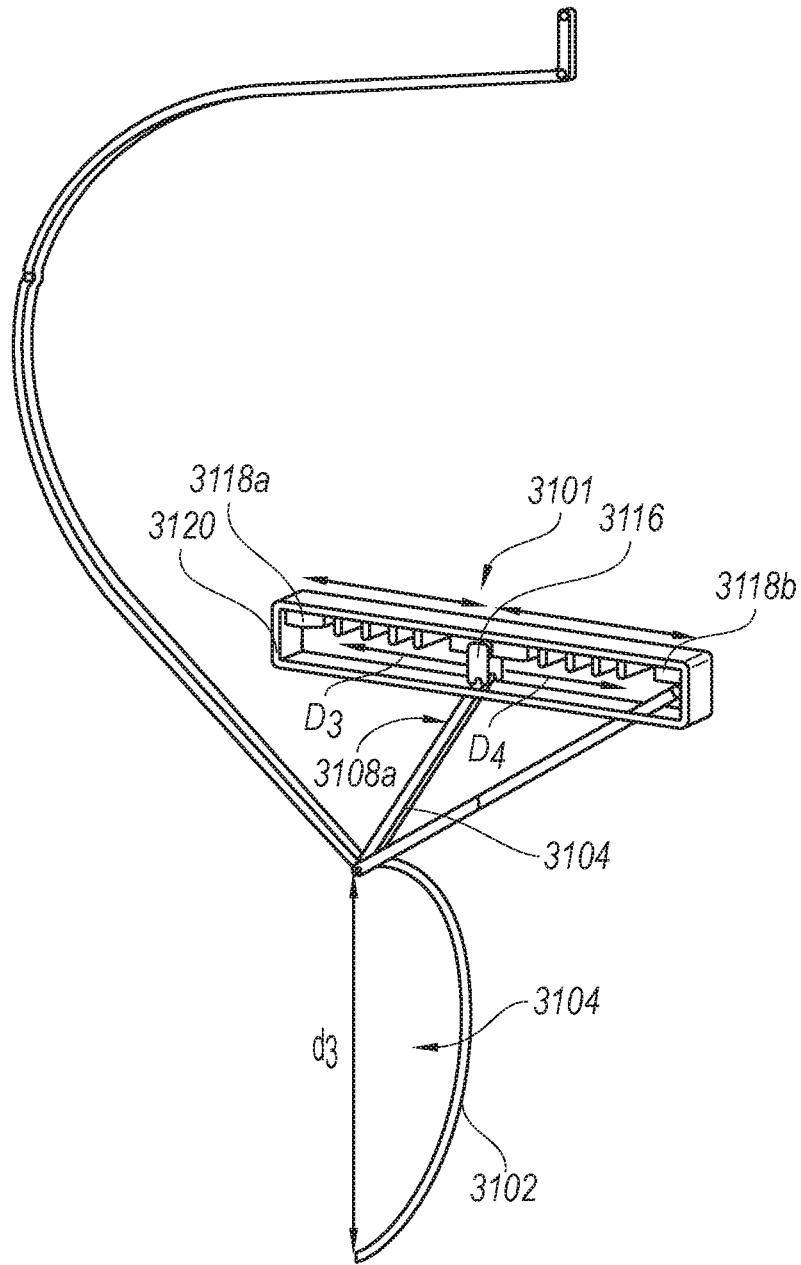

FIGS. 31A and 31B illustrate a portion of an interatrial shunting system 3100 configured in accordance with another embodiment of the present technology. More specifically, FIG. 31A is a closeup perspective view of the portion of the system 3100 and FIG. 31B is a closeup perspective view of an actuation mechanism 3101 and cross-section of adjustable structure 3102 of the system 3100. The components of the system 3100 can be implemented in or combined with any of the other embodiments disclosed herein, e.g., the system 200 described with respect to FIGS. 30A-30E.

Referring first to FIG. 31A, the system 3100 includes an actuation mechanism 3101 coupled to an adjustable structure 3102. The adjustable structure 3102 can be operably coupled to a membrane (e.g., membrane 3012 of FIGS. 30A-30B—omitted for purposes of clarity) and an aperture 3104. The aperture 3104 can at least partially overlap a lumen of a shunting element (not shown) to impact fluid flow therethrough, as previously described with respect to aperture 3014 of FIGS. 30A-30E. In the illustrated embodiment, the adjustable structure 3102 is a band, ring or other annular structure that forms the perimeter of the aperture 3104. The adjustable structure 3102 can be coupled to the portions of the membrane surrounding the aperture 3104 using fasteners, adhesives, sutures, or any other suitable technique known to those of skill in the art.

The adjustable structure 3102 can be made of a flexible and/or relatively malleable material (e.g., a metal or a polymer) configured to deflect and/or deform (e.g., elastically and/or plastically deform) when force is applied thereto. In one particular example, the adjustable structure 3102 can be an annealed stainless-steel wire. As another particular example, the adjustable structure 3102 can be a polyurethane string or suture. As a result, when force is applied to the adjustable structure 3102 (e.g., by actuation mechanism 3101), the adjustable structure 3102 can change in geometry (e.g., size and/or shape) to produce a corresponding change in geometry of the aperture 3104. For example, as the size (e.g., diameter) of the adjustable structure 3102 decreases, the portions of the membrane surrounding the aperture 3104 can be cinched, stretched, loosened, or otherwise drawn together by the adjustable structure 3102 so that the size of the aperture 3104 decreases. Conversely, as the size of the adjustable structure 3102 increases, the portions of the membrane surrounding the aperture 3104 can be released, loosened, stretched, or otherwise allowed to move apart so that the size of the aperture 3104 increases. In some embodiments, the adjustable structure 3102 is transformable between a plurality of different configurations having different geometries, such as an expanded configuration having a relatively large size (e.g., as measured by diameter, cross-sectional area) and/or a compressed configuration having a relatively small size. When the adjustable structure 3102 is in the expanded configuration, the aperture 3104 can provide relatively lower resistance to fluid flow therethrough, thus permitting a greater amount of fluid flow. When the adjustable structure 3102 is in the compressed configuration, the aperture 3104 can provide relatively increased resistance to fluid flow therethrough, thus partially or completely inhibiting the volume of fluid flow.

Optionally, the adjustable structure 3102 can be made of a shape memory material such as nitinol. In such embodiments, for example, changes to the size and/or geometry of the adjustable structure 3102 (and therefore the aperture 3104) can be induced both by applying external stresses to the adjustable structure 3102 and/or by inducing internal stresses in the adjustable structure 3102 via the application of energy (e.g., heating the adjustable structure 3102 beyond a transition temperature that results in at least a temporary alteration of the material state).

The actuation mechanism 3101 can be configured to selectively change the geometry of the adjustable structure 3102 in order to modulate the size of the aperture 3104 and, accordingly, the relative volume of fluid flow therethrough. In some embodiments, the actuation mechanism 3101 is coupled to the adjustable structure 3102 via a lever element 3106. The lever element 3106 can be any elongated structure (e.g., a strut, bar, rod, tube, etc.) configured to transmit a force and/or motion applied by the actuation mechanism 3101 to the adjustable structure 3102. The lever element 3106 can be made of a superelastic material (e.g., nitinol) or another suitable material (e.g., stainless steel, cobalt chromium, a polymer, etc.). Optionally, the lever element 3106 can be made of a non-shape memory material. In other embodiments the lever element 3106 can be made of a shape memory material, but the shape memory properties of the material are not used during operation of the lever element 3106 (e.g., the lever element 3106 is not heated during operation).

In some embodiments, the lever element 3106 includes a first end portion 3108*a* coupled to the actuation mechanism 3101 and a second end portion 3108*b* coupled to the adjustable structure 3102. The first end portion 3108*a* can be pivotally coupled to the actuation mechanism 3101 so that the lever element 3106 can pivot or otherwise rotate relative to the actuation mechanism 3101. The second end portion 3108*b* can be pivotally coupled to the adjustable structure 3102 so that the lever element 3106 can pivot or otherwise rotate relative to the adjustable structure 3102. The pivotal coupling(s) can be implemented in various ways known to those of skill in the art. For example, the first and/or second end portions 3108*a-b* can be pivotally coupled using a hinge or other rotational fastener. As another example, the first and/or second end portions 3108*a-b* can be configured to bend, e.g., by reducing the thickness and/or stiffness of these portions compared to other portions of the lever element 3106.

In some embodiments, the actuation mechanism 3101 is configured to alter the geometry of the adjustable structure 3102 by pivoting the lever element 3106 (e.g., relative to the adjustable structure 3102 and/or the actuation mechanism 3101). For example, pivoting of the lever element 3106 in a first direction $D_1$ can apply an outwardly-directed and/or tensile force against the adjustable structure 3102 to increase the size thereof. Pivoting of the lever element 3106 in a second, opposite direction $D_2$ can apply an inwardly-directed and/or compressive force against the adjustable structure 3102 to decrease the size thereof. In other embodiments pivoting of the lever element 3106 in one direction (e.g., $D_1$ or $D_2$) can release a force that was applied to the adjustable structure 3102 via pivoting of the lever element 3106 in the opposite direction. Additional features of the actuation mechanism 3101 are described in detail below.

The adjustable structure 3102 can be coupled to one or more struts 3110 that connect the adjustable structure 3102 to the shunting element (not shown). The struts 3110 can each be made of a superelastic material (e.g., nitinol) or another suitable material (e.g., stainless steel, cobalt chromium, a polymer, etc.). Each strut can include a first end portion 3112*a* coupled to the adjustable structure 3102 and second end portion 3112*b* coupled to the shunting element or to another portion of the system 200. The struts 3110 can be arranged radially around the perimeter (e.g., circumference) of the adjustable structure 3102 in a spoke-like configuration. The struts 3110 can be configured to restrict the extent to which the adjustable structure 3102 can move relative to the shunting element (e.g., along the longitudinal axis of the shunting element). As a result, when the lever element 3106 applies or releases force to the adjustable structure 3102, the adjustable structure 3102 can expand or contract radially in a plane (e.g., a plane including the aperture 3104 or parallel thereto), rather than moving longitudinally (e.g., along the longitudinal axis of the shunting element). In some embodiments, the first and second end portions 3112*a-b* of each strut 3110 are pivotally coupled to the adjustable structure 3102 and the shunting element, respectively, such that each strut 3110 pivots (e.g., relative to the adjustable structure 3102 and/or shunting element) as the adjustable structure 3102 changes in geometry. The pivotal couplings of the struts 3110 can be implemented as hinges, bendable regions, or any other suitable structure known to those of skill in the art. Although FIG. 31A illustrates ten struts 3110, in other embodiments the system 3100 can include a different number of struts (e.g., one, two, three, four, five, six, seven, eight, nine, eleven, fifteen, or twenty struts).

In some embodiments, the adjustable structure 3102 can be coupled to one or more structural members 3114. The structural members 3114 can be arranged radially around the adjustable structure 3102 in a spoke-like configuration. In the illustrated embodiment, for example, each structural member 3114 is attached to the adjustable structure 3102 at or near a corresponding strut 3110. In other embodiments, some or all of the structural members 3114 can be spaced apart from the struts 3110. The structural members 3114 can be attached to, contact, or otherwise engage the membrane (not shown) to define the shape thereof. In the illustrated embodiment, for example, each structural member 3114 has a curved or bent shape and extends over the struts 3110. As a result, when the membrane is attached to the structural members 3114, the struts 3110 are positioned within the interior space enclosed by the membrane. In some embodiments, the structural members 3114 also extend over the actuation mechanism 3101 and lever element 3106 so that these components are also enclosed within the membrane. Although FIG. 31A illustrates seven structural members 3114, in other embodiments the system 3100 can include a different number of structural members (e.g., one, two, three, four, five, six, eight, nine, ten, 15, or 20 structural members).

Referring to FIG. 31B, in some embodiments, the actuation mechanism 3101 is a linear actuation mechanism including at least one linear actuator (e.g., a shuttle, slider, or other moveable component) configured to move linearly (e.g., translate) to actuate the adjustable structure 3102. Translational movement of the linear actuator in a first direction can cause at least a portion of the adjustable structure to move (e.g., expand or contract) in a second, different direction (e.g., a direction oblique to the first direction, such as a radial direction). In the illustrated embodiment, for example, the actuation mechanism 3101 includes a shuttle element 3116 coupled (e.g., pivotally coupled) to the lever element 3106 (e.g., to the first end portion 3108a) so that movement of the shuttle element 3116 causes pivoting of the lever element 3106. Translational movement of the shuttle element 3116 in a first direction (e.g., direction $D_3$) can pivot the lever element 3106 (e.g., forward to be relatively more perpendicular to the aperture 3104) to decrease the size (e.g., diameter $d_3$) of the adjustable structure 3102, while translation of the shuttle element 3116 in a second, opposite direction (e.g., direction $D_4$) can pivot the lever element (e.g., backward to be relatively more parallel to the aperture 3104) to increase the size of the adjustable structure 3102. As a result, the lever element 3106 can convert linear motion of shuttle element 3116 into radial motion of at least a portion of the adjustable structure 3102 that alters the size of the aperture 3104. As described in greater detail below, the lever element 3106 can amplify the motion of the shuttle element 3116 such that the magnitude of the size change of the aperture 3104 is larger than the magnitude of the movement distance of the shuttle element 3116.

The actuation mechanism 3101 can include one or more shape memory actuation elements configured to drive the movement of the shuttle element 3116. In the illustrated embodiment, for example, the actuation mechanism 3101 includes a first shape memory actuation element 3118a and a second shape memory actuation element 3118b coupled to the shuttle element 3116. The shuttle element 3116 can be positioned between and coupled to the first and second shape memory actuation elements 3118a-b. In other embodiments one side of the shuttle element 3116 can be mechanically coupled to more than one shape memory actuation element (e.g., both the first and second shape memory actuation elements 3118a-b). Optionally, the first shape memory actuation element 3118a, the second shape memory actuation element 3118b, and the shuttle element 3116 can be located within a housing 320. In such embodiments, the shuttle element 3116 can move (e.g., translate) within the housing 320 to pivot the lever element 3106. In other embodiments the housing 320 can be omitted.

The movement of the shuttle element 3116 can be actuated by the first and second shape memory elements 3118a-b. For example, the first and second shape memory elements 3118a-b can each be configured to change in shape in response to a stimulus, such as heat or mechanical loading. In some embodiments, the first and second shape memory elements 3118a-b are each manufactured or otherwise configured to approach (e.g., change in shape, deform, transform, etc.) a relatively lengthened configuration upon application of heat of sufficient heat to induce at least a temporary change in material state. In other embodiments, the first and second shape memory elements 3118a-b are each manufactured or otherwise configured to approach a relatively shortened configuration upon application of heat. Optionally, one shape memory element can approach a relatively lengthened configuration when sufficiently heated, while the other shape memory element can approach a relatively shortened configuration when sufficiently heated. In some embodiments, at least one shape memory element is manufactured so that, at a first temperature (e.g., body temperature), it is relatively more thermoelastically deformable in response to a fixed force or stress than it would be at a second temperature. The second temperature can be a higher temperature (e.g., a temperature resulting from the application of heat to an element) than the first temperature.

The shape change (e.g., due to deformation by externally-applied forces, due to heating that results in a deformation related to the shape memory effect, etc.) of the first and/or second shape memory elements 3118a-b can actuate movement of the shuttle element 3116 relative to the housing 320. In some embodiments, the first and second shape memory elements 3118a-b, when at an unheated temperature (e.g., at or close to body temperature), are relatively more thermoelastically deformable as described above. In such embodiments, actuation (e.g., expansion/lengthening) of one shape memory element via heating can move shuttle element 3116 in such a way that deforms (e.g., compresses or expands) the other shape memory element.

In a first stage of operation, the first and second shape memory elements 3118a-b can reside in a neutral configuration (e.g., as shown in FIG. 31B), with one or both elements deformed from their original manufactured geometric configurations. As a result, the shuttle element 3116 can be positioned at or near the center of the housing 320, and the adjustable structure 3102 and aperture 3104 can have a first size permitting a first amount of blood flow through the lumen of the shunting element (not shown).

In a different stage of operation, the first shape memory actuation element 3118a can change in shape to a relatively shortened configuration and the second shape memory actuation element 3118b can changed in shape to a relatively lengthened configuration. For example, the second shape memory actuation element 3118b can be heated to induce a change in shape to a lengthened configuration (e.g., toward its original manufactured geometric configuration) relative to its shape in the neutral position shown in FIG. 31B. This shape change can apply a force to the shuttle element 3116 that moves it along a first direction (e.g., direction $D_3$). As a result, the shuttle element 3116 can pivot the lever element 3106 to alter the size and/or geometry of the adjustable structure 3102 and aperture 3104 (e.g., to a decreased aperture size that permits a decreased amount of blood flow or no blood flow through the lumen). In some embodiments, the force applied by the shape change of the second shape memory actuation element 3118b can also cause the first shape memory actuation element 3118a (which is unheated and accordingly can be relatively more thermoelastically deformable than when at an elevated temperature) to change in shape to a relatively shortened configuration.

In a further stage of operation, the first shape memory actuation element 3118a can change in shape to a relatively lengthened configuration and the second shape memory actuation element 3118b can change in shape to a relatively shortened configuration. For example, the first shape memory actuation element 3118a can be heated to induce a change in shape to a lengthened configuration (e.g., toward its original manufactured geometric configuration) relative to its shape in the neutral position shown in FIG. 31B. This shape change can apply a force to the shuttle element 3116 that moves it along a second, opposite direction (e.g., direction $D_4$). As a result, the shuttle element 3116 can pivot the lever element 3106 to alter the size and/or geometry of the adjustable structure 3102 and aperture 3104 (e.g., to an increased aperture size that permits an increased amount of blood flow through the lumen). In some embodiments, the force applied by the shape change of the first shape memory actuation element 3118a can also cause the second shape memory actuation element 3118b (which is unheated and accordingly can be relatively more thermoelastically deformable than when at an elevated temperature) to change in shape to a relatively shortened configuration.

The actuation mechanism 3101 can be configured in a number of different ways. For example, in some embodiments the first and/or second shape memory actuation elements 3118*a-b* can be manufactured or otherwise configured to approach a relatively shortened configuration rather than a relatively lengthened configuration when sufficiently heated. Additionally, although FIGS. 31A and 31B illustrate the first and second shape memory actuation elements 3118*a-b* as having a serpentine or zig-zag shape, in other embodiments the first and second shape memory actuation elements 3118*a-b* can have a different shape, such as a folded, curved, bent, or coiled shape.

In some embodiments, the first and second shape memory actuation elements 3118*a-b* are positioned on the same side of the shuttle element 3116. In such embodiments, one shape memory actuation element can be manufactured such that when it is heated it moves towards a relatively lengthened/expanded configuration, and the second shape memory actuation element can be manufactured such that when it is heated it moves towards a relatively shortened/contracted configuration. In other embodiments, any number of shape memory actuation elements that have been manufactured to have similar or dissimilar original geometric configurations may be utilized.

In embodiments of the present technology that utilize heat or another form of energy applied to a shape memory actuation element or another component of the system, the energy/heat can be applied both invasively (e.g., via a catheter delivering laser, radiofrequency, or another form of energy, via an internal stored energy source such as a supercapacitor, etc.), non-invasively (e.g., using radiofrequency energy delivered by a transmitter outside of the body, by focused ultrasound, etc.), or through a combination of these methods.

Although FIGS. 31A-31B illustrate a single actuation mechanism 3101, in other embodiments the system 3100 can include a different number of actuation mechanisms (e.g., two, three, four, five, or more actuation mechanisms). The actuation mechanisms can be arranged radially around the adjustable structure 3102. Each actuation mechanism can be coupled to the adjustable structure 3102 via a respective lever element. The actuation mechanisms can operate simultaneously or sequentially to adjust the geometry of the adjustable structure 3102 and aperture 3104. This approach may be beneficial in embodiments in which a greater amount of force is used to alter the geometry of the adjustable structure 3102 and aperture 3104.

Figure 32:
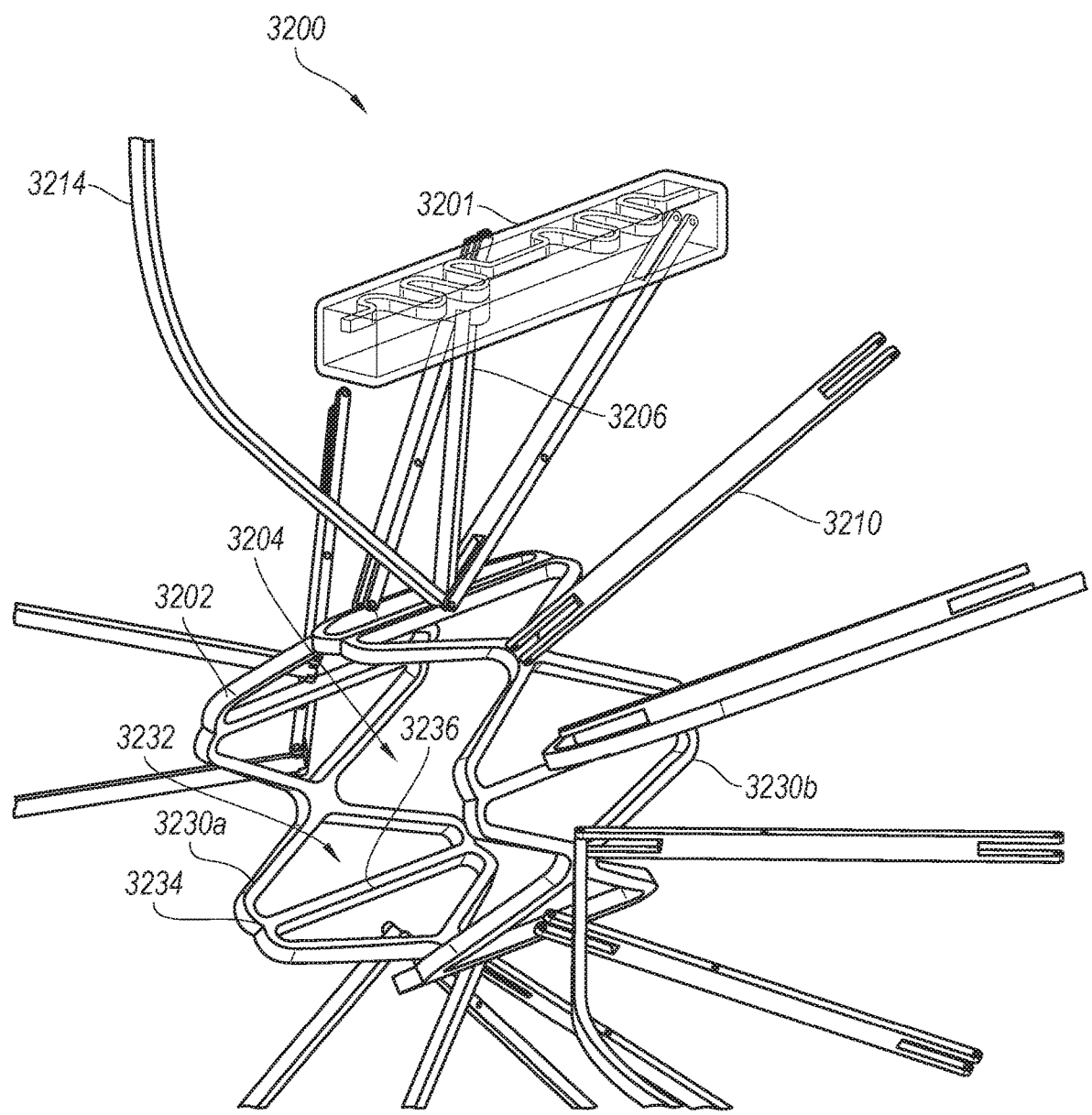
FIG. 32 illustrates yet another adjustable interatrial shunting system having a linear actuation mechanism and configured in accordance with select embodiments of the present technology.

FIG. 32 is a closeup perspective view of a portion of an interatrial shunting system 3200 configured in accordance with a further embodiment of the present technology. The system 3200 can be generally similar to the system 3100 described with respect to FIGS. 31A-31B, such that like reference numbers (e.g., actuation mechanism 3201 versus actuation mechanism 3101) indicate similar or identical components. Accordingly, the following discussion of system 3200 will be limited to those features that differ from system 3100 of FIGS. 31A-31B. Additionally, the components of the system 3200 can be implemented in or combined with any of the other embodiments disclosed herein.

The system 3200 includes an actuation mechanism 3201 coupled to an adjustable structure 3202. In some embodiments, the adjustable structure 3202 can be operably coupled to a membrane (not shown) and an aperture 3204. The aperture 3204 can at least partially overlap a lumen of a shunting element (not shown) to control fluid flow therethrough, as previously described. Optionally, the adjustable structure 3202 can itself serve as a shunting element defining a lumen for blood flow. In the illustrated embodiment, the adjustable structure 3202 is a stent (e.g., a laser-cut metal stent) positioned at the perimeter of the aperture 3204. The stent can be configured to transform between multiple different geometries (e.g., an expanded configuration, a compressed configuration, and configurations therebetween) when force is applied thereto by the actuation mechanism 3201 and lever element 3206. As shown in FIG. 4, for example, the stent can include a first annular structure 3230*a* and a second annular structure 3230*b* connected to each other to form a plurality of cells 3232. The first and second annular structures 3230*a-b* can each have a curved and/or serpentine shape having a plurality of apices or bend regions 3234. The first and second annular structures 3230*a-b* can be connected to each other at the apices 3234, e.g., directly and/or via connectors 3236. When the adjustable structure 3202 is in an expanded configuration, the first and second annular structures 3230*a-b* can deflect, deform, and/or otherwise move apart from each other so that the size of the cells 3232 increases. Conversely, when the adjustable structure 3202 is in a compressed configuration, the first and second annular structures 3230*a-b* can deflect, deform, and/or otherwise move closer together so that the size of the cells 3232 decreases. The size of the aperture 3204 can increase or decrease correspondingly to modulate the amount of fluid flow therethrough, as previously described.

Figure 33:
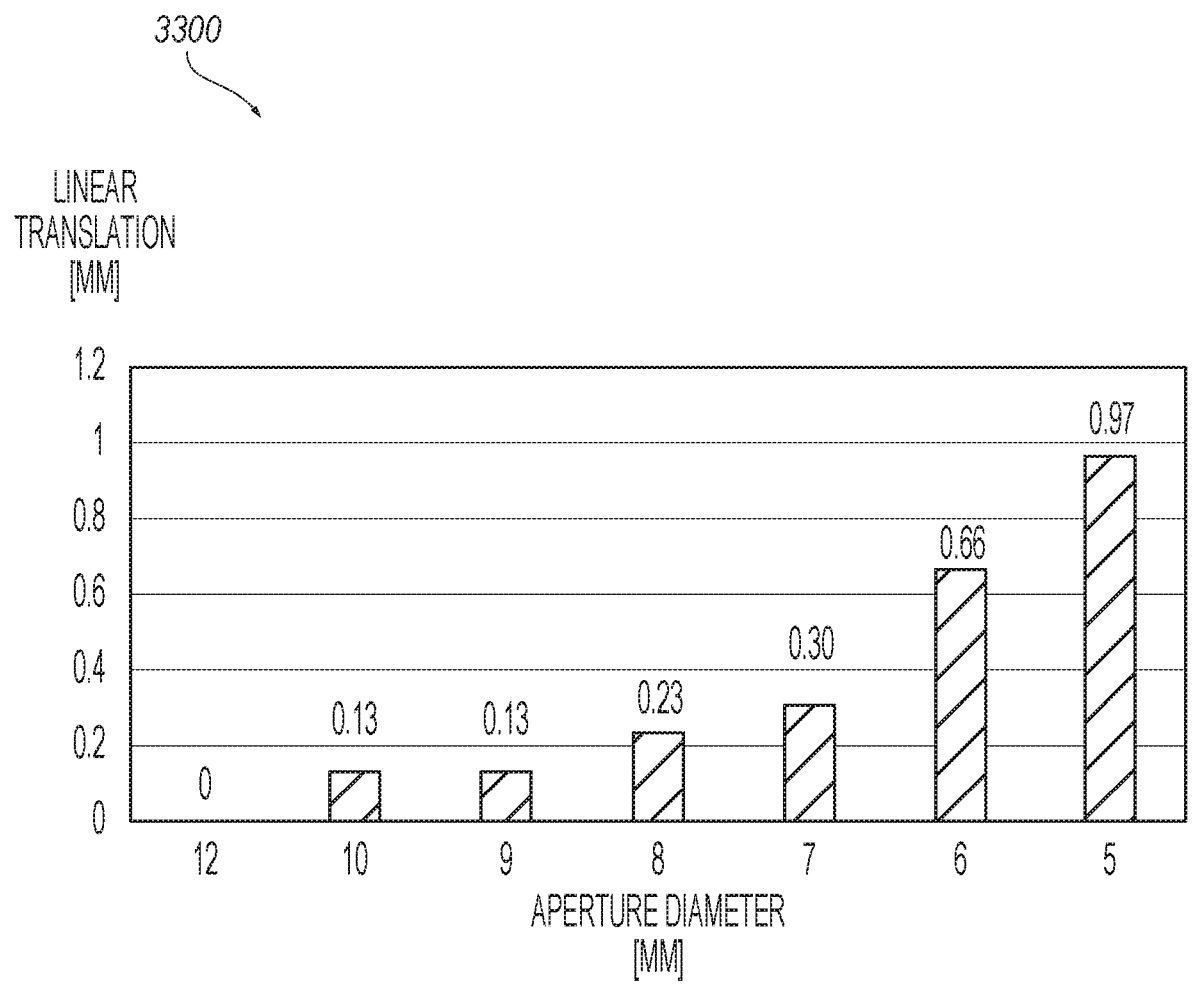
FIG. 33 is a graph illustrating the relationship between aperture diameter and translation of a linear actuation mechanism in an interatrial shunting system configured in accordance with an embodiment of the present technology.

FIG. 33 is a graph 3300 illustrating an example relationship between aperture diameter and movement of a linear actuation mechanism in an interatrial shunting system configured in accordance with embodiments of the present technology. The actuation mechanisms described herein (e.g., with respect to FIGS. 30A-32) can be configured such that relatively small translational and/or linear movements of a shuttle element or other linear actuator produce relatively large changes in aperture geometry (e.g., size). In the illustrated embodiment, for example, a change in aperture diameter from 10 mm to 9 mm can be produced by a linear translation of the shuttle element over a distance of 0.13 mm; a change in aperture diameter from 9 mm to 8 mm can be produced by a translation distance of 0.23 mm; and so on. The change in the aperture size can be greater than the translation distance of the shuttle element. For example, the ratio of the change in aperture diameter to the translation distance of the shuttle element can be at least 1:1, 2:1, 3:1, 4:1, 5:1, 10:1, 15:1, or 20:1. In some embodiments, the ratio varies over the size range of the aperture (e.g., the ratio decreases as the aperture size decreases as shown in FIG. 33). In other embodiments the ratio can be generally constant over the size range of the aperture. Optionally, the shuttle element can be coupled to an adjustable structure defining the aperture via a lever element, and the angle of the lever element relative to the shuttle element (e.g., as measured from the axis of movement of the shuttle element) can determine the extent to which incremental movements of the shuttle element affect the size of the aperture. For example, the angle of the lever element relative to the shuttle element can be equal or approximately equal to 10°, 20°, 30°, 40°, 50°, 60°, 70°, 80°, or 90°.

E. Anchors

FIGS. 34A-34D show various embodiments of anchoring scaffolds 3420 configured in accordance with select embodiments of the present technology. As one skilled in the art will appreciate, the various shunting systems described herein can incorporate various anchoring scaffolds, such as anchoring scaffolds 3420, although other suitable anchoring mechanisms are possible. As illustrated, the anchoring scaffolds 3420 generally include right atrium elements 3422 and left atrium elements 3434. The right atrium elements 3422 and the left atrium elements 3434 engage the septal wall to secure the interatrial shunt device in position. In some embodiments, the anchoring scaffolds 3420 are configured to minimize the squeezing force on the septal wall. In some embodiments, the right atrium elements 3422 are symmetrical with the left atrium elements 3434. In other embodiments, the right atrium elements 3422 are not symmetrical with the left atrium elements. The anchoring scaffolds 3420 can be partially or completely covered by a biocompatible and/or anti-thrombogenic material (e.g., ePTFE).

The anchoring scaffolds 3420 can also define chambers. As illustrated in FIG. 34A, the right atrium elements 3422a can extend into the right atrium such that they define a chamber 3426a. The chamber 3426a can be partially or completely enclosed by the right atrium elements 3422a and the septal wall. In some embodiments, the chamber 3426a can house electronic components of the interatrial shunt devices, including motors, batteries, capacitors, electronics board and the like. Housing the electronic components within the chamber 3426a can mitigate thrombosis risks and protect the electronic components from excess exposure.

The anchoring scaffolds 3420 can be composed of a superelastic material such as nitinol or another suitable material (e.g., an alloy derivative of nitinol, cobalt chromium, stainless steel, etc.). In embodiments in which the anchoring scaffolds 3420 are composed of nitinol, the nitinol has a transition temperature less than body temperature such that the nitinol is in an austenitic material state when implanted, and thus the anchoring scaffolds 3420 are resistant to geometric changes, even if heated.

F. Shunting Assemblies Having Superelastic and Shape Memory Properties

As previously described, in many embodiments described herein the interatrial shunting systems include a nitinol-based actuation element manufactured so as to intentionally utilize the shape-memory properties of the material in vivo rather than the superelastic properties. For example, in some embodiments at least some components utilized will have an austenite finish temperature above body temperature (e.g., above 37 degrees C.). Consequently, the microstructure of these components exists largely in the thermally-induced martensitic material state and/or the R-phase material state throughout assembly, catheterization, deployment, and at least some periods of post-implantation in vivo operation. When deployed from the catheter during a percutaneous delivery to the target organ (e.g., the septal wall of a heart), these components will not generally exhibit self-expanding attributes like traditional superelastic nitinol components. Instead, they may behave similar to a balloon-expandable device (e.g., a cobalt chromium stent) whereby the shape memory component may recover some small amount of elastic recoil when deployed, but the vast majority of the shape change is achieved by applying a force to the component (e.g., a balloon expansion force). However, unlike traditional balloon-expandable devices which achieve this macroscopic shape change via a microstructural non-reversible plastic deformation, the shape memory components achieve their macroscopic shape change via a microstructural reversible thermoelastic deformation. As disclosed above, further deformation of these shape memory elements may be achieved by subsequently applying energy (e.g., heat) to the elements to partially or fully recover the thermoelastic deformation. In some embodiments, an interatrial shunting device may include both nitinol components manufactured to exhibit largely superelastic properties (e.g., anchor elements of the device) and nitinol components manufactured to exhibit largely shape memory properties (e.g., all or portions of actuation elements) at temperature ranges encountered during delivery/deployment and/or post-implantation use.

Figure 35B:
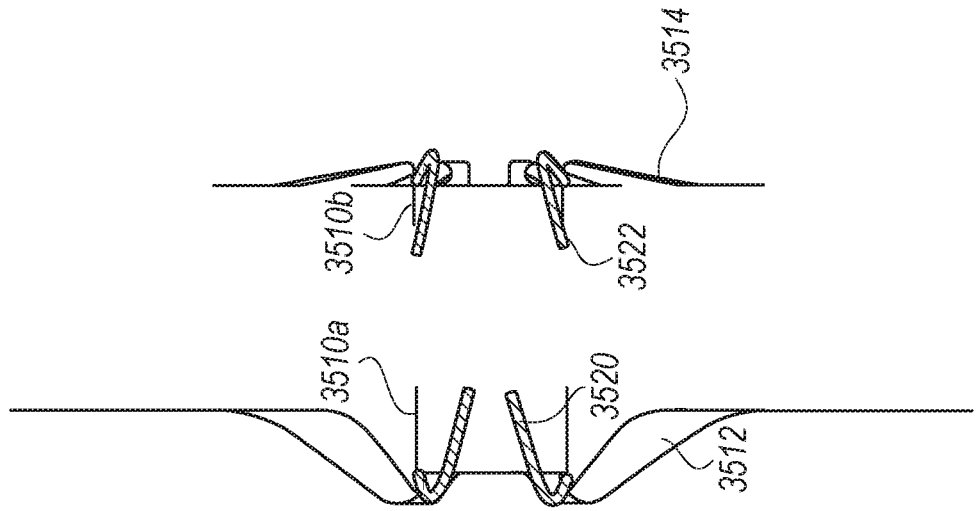
FIGS. 35A and 35B are schematic illustrations of an adjustable interatrial shunting system having both superelastic and shape memory properties and configured in accordance with select embodiments of the present technology.
Figure 35A:
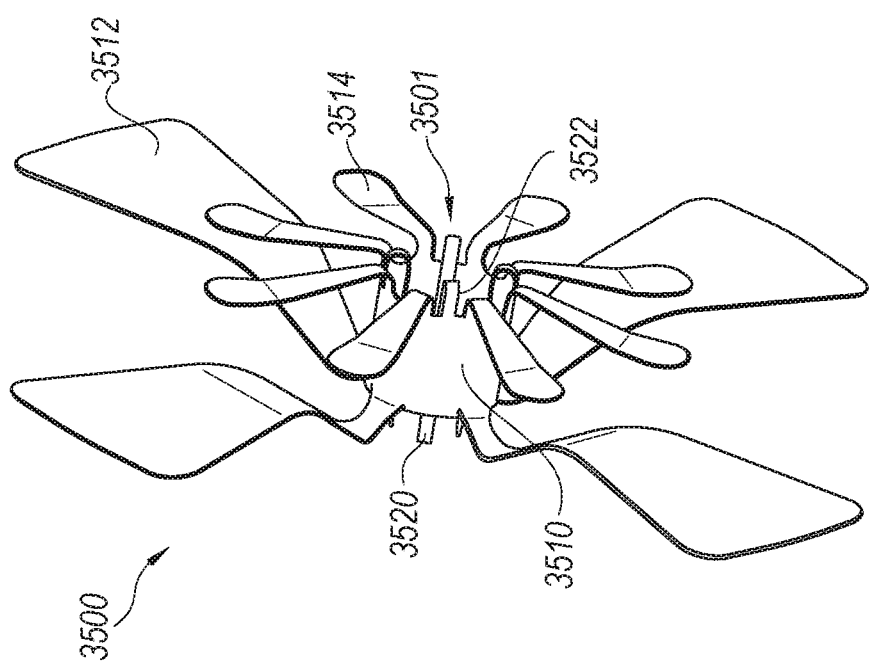

For example, FIGS. 35A and 35B illustrate an interatrial shunting system/device 3500 configured in accordance with select embodiments of the present technology. The interatrial shunting system 3500 includes portions that have been manufactured to exhibit largely superelastic material properties and portions that have been manufactured to exhibit largely shape memory material properties. Referring to FIG. 35A, the interatrial shunting system 3500 includes a body element or frame 3510. The body element 3510 can have a generally cylindrical shape, although other shapes and configurations are within the scope of the present technology. The body element 3510 is configured to extend generally between the LA and RA of a heart when implanted in the patient, and can include a lumen 3501 extending therethrough for shunting blood from the LA to the RA.

The interatrial shunting system 3500 can further include a first plurality of anchors 3512 extending from a first side (e.g., the right atrial side) of the body element 3510 and a second plurality of anchors 3514 extending from an opposing side (e.g., the left atrial side) of the body element 3510. When implanted in the heart, the first plurality of anchors 3512 can engage the septal wall from the right atrial side of the heart and the second plurality of anchors 3514 can engage the septal wall from the left atrial side of the heart. The anchors 3512/3514 can have any suitable shape configured to secure the system 3500 to the septal wall, including, for example a flower petal configuration, a flange configuration, or the like. As illustrated, the first plurality of anchors 3512 can have a different (e.g., larger) size than the second plurality of anchors 3514, although in other configurations the first plurality of anchors 3512 are smaller than or have the same size as the second plurality of anchors 3514.

Referring to FIG. 35B, which is a cross-sectional view of the system 3500, the body element 3510 can comprise a first body element 3510a (e.g., a right atrial body element) and a second body element 3510b (e.g., a left atrial body element). The first body element 3510a includes the first plurality of anchors 3512 and is generally positionable at least partially in and/or adjacent the RA when the system 3500 is implanted. The second body element 3510b includes the second plurality of anchors 3514 and is generally positionable at least partially in and/or adjacent the LA when the system 3500 is implanted. The first body element 3510a and the second body element 3510b can be joined together to form the body element 3510 illustrated in FIG. 35A. The first body element 3510a and the second body element 3510b can be joined via suturing, riveting, gluing, welding, or other suitable techniques. In some embodiments, the first body element 3510a and the second body element 3510b are a single unitary component, rather than two modular components secured together. In some embodiments, the first body element 3510a and the second body element 3510b are electrically and/or thermally isolated.

The body element 3510, the first plurality of anchors 3512, and the second plurality of anchors 3514 may be composed of a material (e.g., nitinol) and that has been manufactured such that it exhibits superelastic material properties at and above body temperature. For example, during manufacturing the body element 3510, the first plurality of anchors 3512, and the second plurality of anchors 3514 can be shape set using processes (e.g., high temperatures) that produce a material state transition temperature (e.g., an austenite start temperature, an austenite finish temperature) in these sections of the device that is below body temperature (e.g. below 37 degrees C.). As such, the body element 3510, the first plurality of anchors 3512, and the second plurality of anchors 3514 exhibit superelastic material properties upon implantation into the body. For example, the foregoing sections of the device may be in an austenitic material state while at or above body temperature. Because they are already in an austenitic material state at or above body temperature, applying additional energy (e.g., heat) to the body element 3510, the first plurality of anchors 3512, and the second plurality of anchors 3514 after the system 3500 is implanted in the heart will not change the shape or other dimension of these sections of the device. As a result, the body element 3510, the first plurality of anchors 3512, and the second plurality of anchors 3514 are configured to retain a relatively stable geometry in the heart (e.g., an outer diameter of the body element 3510 does not change, even in response to heat).

Referring to both FIGS. 35A and 35B, the system 3500 can include a first actuation element 3520 and a second actuation element 3522. The first actuation element 3520 and the second actuation element 3522 can be positioned within the body element 3510 and can at least partially define an actuation assembly configured to selectively adjust a dimension of the lumen 3501. In some embodiments, the first actuation element 3520 and the second actuation element 3522 can be comprised of a material (e.g., nitinol) that has been manufactured to exhibit shape memory material properties at temperatures close to body temperature. In the illustrated embodiment, the first actuation elements 3520 and the second actuation elements 3522 are interlocked actuation elements and can function in a manner similar to the embodiments shown in FIGS. 5A-7. However, the system 3500 can alternatively (or additionally) include an actuation assembly that comprises nested stents in a manner similar to the embodiment shown in FIGS. 3-4, elongated or serially arranged actuation elements (e.g., rings) in a manner similar to the embodiment shown in FIGS. 8-12, or other suitable arrangements. The first actuation elements 3520 and the second actuation elements 3522 can have a transition temperature (e.g., an austenite start temperature, an austenite final temperature, etc.) that is above body temperature (e.g., 37 degrees Celsius). Accordingly, when the system 3500 is implanted in the heart, the first actuation elements 3520 and the second actuation elements 3522 are in a relatively malleable or deformable state (e.g., a martensitic material state and/or a R-phase material state).

A dimension of the lumen 3501 can be adjusted by selectively heating either the first actuation elements 3520 or the second actuation elements 3522, as described in detail previously. For example, heating (e.g., resistively heating) the first actuation elements 3520 above their transition temperature decreases a diameter or other dimension of the lumen 3501, and heating the second actuation elements 3522 above their transition temperature increases a diameter or other dimension of the lumen 3501. However, because the body element 3510 and the anchors 3512, 3514 are partially or entirely in an austenitic material state at body temperature, incidental (or purposeful, as described below) heating of the body element 3510 and/or the anchors 3512, 3514 during actuation of the first actuation elements 3520 and/or the second actuation elements 3522 does not induce a geometry or other dimensional change in the body element 3510 or anchors 3512, 3514. Accordingly, the body element 3510 will maintain a relatively constant outer diameter even during actuation of the first actuation elements 3520 and/or the second actuation elements 3522, and the anchors 3512, 3514 will remain in a desired orientation.

In some embodiments, the first actuation elements 3520 are electrically coupled to and/or integral with the first body element 3510*a* and/or the first anchors 3520. Because the first body element 3510*a* and the first anchors 3520 are manufactured such that they are partially or entirely in an austenitic material state at and above body temperature, energy (e.g., an electric current which induces resistive heating) can be applied to any of the foregoing components to help heat, and thereby induce a shape change in, the first actuation elements 3520. For example, heat applied to the first body element 3510*a* may be passively and/or actively transferred to, and drive actuation of, the first actuation element 3520. Likewise, the second actuation elements 3522 can be electrically coupled to and/or integral with the second body element 3510*b* and/or the second anchors 3522. Because the second body element 3510*b* and the second anchors 3522 are also manufactured such that they are partially or entirely in an austenitic material state at and above body temperature, energy can be applied to any of the foregoing components to heat, and thereby induce a shape change in, the second actuation elements 3522. For example, heat applied to the second body element 3510*b* may be passively and/or actively transferred to, and drive actuation of, the second actuation element 3522. Accordingly, rather than solely applying heat to the actuation elements themselves, heat can be applied to portions of the desired system that surround and/or are in thermal communication with the actuation elements.

G. Operation of Adjustable Interatrial Shunting Systems

Without wishing to be bound by theory, the adjustability of the shunting systems provided herein are expected to advantageously address a number of challenges associated with heart failure treatment. First, heart failure is a heterogenous disease and many patients have various co-morbidities, and the resulting disease presentation can be diverse. Accordingly, a "one size fits all" approach to heart failure treatment will not provide the same therapeutic benefit to each patient. Second, heart failure is a chronic and progress disease. Use of a non-adjustable (i.e., static) device does not permit treatment to be adapted to changes in disease progression. The adjustable shunting systems described herein, however, are expected to advantageously provide increased flexibility to better tailor treatment to a particular patient and/or to various disease stages.

For example, the shunting systems described can enable a clinician to periodically (e.g., monthly, bi-monthly, annually, as needed, etc.) adjust the diameter of a lumen to improve patient treatment. For example, during a patient visit, the clinician can assess a number of patient parameters and determine whether adjusting the geometry and/or size of the lumen, and thus altering blood flow between the LA and the RA, would provide better treatment and/or enhance the patient's quality of life. Patient parameters can include, for example, physiological parameters (e.g., left atrial blood pressure, right atrial blood pressure, the difference between left atrial blood pressure and right atrial blood pressure, flow velocity, heart rate, cardiac output, myocardial strain, etc.), subjective parameters (e.g., whether the patient is fatigued, how the patient feels during exercise, etc.), and other parameters known in the art for assessing whether a treatment is working. If the clinician decides to adjust the diameter of the lumen, the clinician can adjust the device lumen using the techniques described herein.

In some embodiments, the systems described herein can include or be operably coupled to one or more sensors. The sensor(s) can measure one or more physiological parameters related to the system or the environment proximate to the sensor(s), such as left atrial pressure, right atrial pressure, and/or a pressure differential between the LA and RA. The system can adjust the size or geometry of the lumen and/or lumen orifice based on the physiological parameter(s). For example, the sensor(s) can be operably coupled to the actuation assembly such that the actuation assembly adjusts the lumen and/or lumen orifice in response to the sensor data.

Some embodiments of the present technology adjust the relative size and/or shape of the lumen and/or lumen aperture consistently (e.g., continuously, hourly, daily, etc.). Consistent adjustments might be made, for example, to adjust the flow of blood based on a blood pressure level, respiratory rate, heart rate, and/or another parameter of the patient, which changes frequently over the course of a day. For example, the systems described herein can have a baseline state in which the lumen or lumen orifice is substantially closed and does not allow substantial blood flow between the LA and RA, and an active state in which the lumen and lumen orifice are open and allows blood to flow between the LA and RA. The system can transition between the baseline state and the active state whenever one or more patient status parameters change due to exercise, stress, or other factors. In other embodiments, consistent adjustments can be made based on, or in response to, physiological parameters that are detected using sensors, including, for example, sensed left atrial pressure and/or right atrial pressure. If the left atrial pressure increases, the systems can automatically increase a diameter of the lumen and/or lumen orifice to decrease flow resistance between the LA and the RA and allow increased blood flow. In another example, the systems can be configured to adjust based on, or in response to, an input parameter from another device such as a pulmonary arterial pressure sensor, insertable cardiac monitor, pacemaker, defibrillator, cardioverter, wearable, external ECG or PPG, and the like.

Some embodiments of the present technology adjust the relative size and/or shape of the lumen and/or lumen orifice only after a threshold has been reached (e.g., a sufficient period of time has elapsed). This may be done, for example, to avoid unnecessary back and forth adjustments and/or avoid changes based on clinically insignificant changes. In some embodiments, adjustments may occur occasionally as a patient's condition changes. For example, the lumen and/or lumen orifice may gradually open if a patient experiences a sustained rise in left atrial pressure (e.g., rate of change is above a predetermined threshold, and/or the left atrial pressure remains higher than a predetermined threshold for longer than a predetermined amount of time), pulmonary artery pressure, weight, or another physiologically relevant parameters. Additionally or alternatively, adjustments can occur if pressure exceeds a threshold or increases by a threshold amount over a period of time (e.g., several days or more). The diameter of the lumen and/or lumen orifice can then be increased to increase blood flow between the LA and RA and to avoid decompensation.

In some embodiments, the adjustable interatrial shunting systems described herein can include additional or alternative features, such as those described in PCT Patent Application No. PCT/US20/38549, titled ADJUSTABLE INTERATRIAL SHUNTS AND ASSOCIATED SYSTEMS AND METHODS, filed Jun. 18, 2020, the disclosure of which is incorporated by reference herein in its entirety.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the LA and RA, the LV and the right ventricle (RV), or the LA and the coronary sinus, it should be appreciated that similar embodiments could be utilized for shunts between other chambers of heart or for shunts in other regions of the body.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An adjustable shunt assembly, comprising:
   a self-expanding frame configured to anchor across a tissue wall dividing a first body region and a second body region of a patient;
   a lumen extending through at least a portion of the frame and configured to extend between the first body region of a patient and the second body region of the patient to create an artificial flow path therebetween, wherein the lumen includes an orifice configured to be in fluid communication with the first body region and/or the second body region; and
   at least one shape memory actuation element having a first end portion and a second end portion, wherein
      the first end portion is coupled to the frame and the second end portion is oriented away from the frame and at least partially defines the lumen orifice,
      the at least one shape memory actuation element is transitionable from a first material state to a second material state when heated above a transition temperature that is a temperature greater than body temperature, and
      transitioning the at least one shape memory actuation element from the first material state to the second material state adjusts a geometry of the lumen orifice at least partially defined by the second end portion.

2. The adjustable shunt assembly of claim 1 wherein the at least one shape memory actuation element is a first actuation element, the adjustable shunt further comprising a second shape memory actuation element configured to adjust the geometry of the lumen orifice, wherein the second shape memory actuation element is transitionable from the first material state to the second material state when heated above the transition temperature.

3. The adjustable shunt assembly of claim 2 wherein the first shape memory actuation element is configured to increase a cross-sectional area of the lumen orifice when heated above its transition temperature, and wherein the second shape memory actuation element is configured to decrease a cross-sectional area of the lumen orifice when heated above its transition temperature.

4. The adjustable shunt assembly of claim 2 wherein the first shape memory actuation element has a first manufactured geometry and the second shape memory actuation element has a second manufactured geometry different than the first manufactured geometry, and wherein the first shape memory actuation element is coupled to the second shape memory actuation element such that at body temperature the first shape memory actuation element is deformed relative to the first manufactured geometry and the second shape memory actuation element is deformed relative to the second manufactured geometry.

5. The adjustable shunt assembly of claim 4 wherein the first shape memory actuation element is configured to move toward the first manufactured geometry when heated above the transition temperature, and wherein the second shape memory actuation element is configured to move toward the second manufactured geometry when heated above the transition temperature.

6. The adjustable shunt assembly of claim 2 wherein the first shape memory actuation element is thermally insulated from the second shape memory actuation element.

7. The adjustable shunt assembly of claim 2 wherein the first shape memory actuation element and the second shape memory actuation element are configured to be thermally insulated from tissue and blood adjacent the first shape memory actuation element and the second shape memory actuation element when the adjustable shunt assembly is implanted in the patient.

8. The adjustable shunt assembly of claim 7 wherein the first shape memory actuation element is electrically isolated from the second shape memory actuation element.

9. The adjustable shunt assembly of claim 8 wherein the first shape memory actuation element and the second shape memory actuation element are configured to be electrically isolated from tissue and blood adjacent the first and second shape memory actuation elements when the adjustable shunt assembly is implanted in the patient.

10. The adjustable shunt assembly of claim 1, further comprising a membrane, wherein the membrane at least partially defines the lumen.

11. The adjustable shunt assembly of claim 10 wherein the at least one shape memory actuation element is coupled to the membrane and has a stent-like structure.

12. The adjustable shunt assembly of claim 10 wherein the membrane includes a first membrane portion coupled to the frame and a second membrane portion coupled to the shape memory actuator and configured to extend into the first body region or the second body region.

13. The adjustable shunt assembly of claim 12 wherein the at least one shape memory actuation element is disposed within the second membrane portion.

14. The adjustable shunt assembly of claim 1 wherein the at least one shape memory actuation element is disposed radially around the orifice.

15. The adjustable shunt assembly of claim 1 wherein the at least one shape memory actuation element is composed of a shape memory alloy, and wherein the first material state is a martensitic or R-phase material state, and wherein the second material state is an R-phase or austenitic material state.

16. The adjustable shunt assembly of claim 1 wherein the frame is composed of superelastic Nitinol.

17. The adjustable shunt assembly of claim 1 wherein the transition temperature is a temperature greater than 40 degrees Celsius.

18. The adjustable shunt assembly of claim 1 wherein the first body region is a left atrium of a heart and the second body region is a right atrium of the heart.

19. An adjustable shunt assembly, comprising:
   a self-expanding frame configured to anchor across a tissue wall dividing a first body region and a second body region of a patient;
   a membrane coupled to the frame, wherein the membrane at least partially defines a lumen configured to extend between the first body region and the second body region to create an artificial flow path therebetween; and at least one shape memory actuation element having a frustoconical shape with a first end portion coupled to the frame and a second end portion spaced apart from the frame, wherein the at least one shape memory actuation element is transitionable from a first material state to a second material state when heated above a transition temperature that is a temperature greater than body temperature, and wherein transitioning the at least one shape memory actuation element from the first material state to the second material state modifies the geometry of the lumen.

20. The adjustable shunt assembly of claim 19 wherein the at least one shape memory actuation element is a first actuation element, the adjustable shunt further comprising a second shape memory actuation element configured to adjust the geometry of the lumen, and wherein the second shape memory actuation element is transitionable from the first material state to the second material state when heated above the transition temperature greater than body temperature.

21. The adjustable shunt assembly of claim 20 wherein the first shape memory actuation element is configured to increase a cross-sectional area of the lumen when heated above its transition temperature, and wherein the second shape memory actuation element is configured to decrease a cross-sectional area of the lumen when heated above its transition temperature.

22. The adjustable shunt assembly of claim 20 wherein the first shape memory actuation element is configured to increase the cross-sectional area along a length of the lumen, and wherein the second shape memory actuation element is configured to decrease a cross-sectional area of the lumen along a length of the lumen.

23. The adjustable shunt assembly of claim 20 wherein the first shape memory actuation element has a first manufactured geometry and the second shape memory actuation element has a second manufactured geometry different than the first manufactured geometry, and wherein the first shape memory actuation element is coupled to the second shape memory actuation element such that at body temperature the first shape memory actuation element is deformed relative to the first manufactured geometry and the second shape memory actuation element is deformed relative to the second manufactured geometry.

24. The adjustable shunt assembly of claim 20 wherein the first shape memory actuation element is configured to move toward the first manufactured geometry when heated above the transition temperature, and wherein the second shape memory actuation element is configured to move toward the second manufactured geometry when heated above the transition temperature.

25. The adjustable shunt assembly of claim 20 wherein the first shape memory element is concentrically nested within the second shape memory element.

26. The adjustable shunt assembly of claim 20 wherein:
the second shape memory element has a third end portion and a fourth end portion generally opposite the third end portion,
wherein the first end portion of the first shape memory element is coupled to the third end portion of the second shape memory element and the second end portion of the first shape memory element is coupled to the fourth end portion of the second shape memory element.

27. The adjustable shunt assembly of claim 20 wherein the first shape memory actuation element is thermally insulated from the second shape memory actuation element.

28. The adjustable shunt assembly of claim 20 wherein the first shape memory actuation element and the second shape memory actuation element are configured to be thermally insulated from tissue adjacent the first shape memory actuation element and the second shape memory actuation element when the adjustable shunt assembly is implanted in the patient.

29. The adjustable shunt assembly of claim 20 wherein the first shape memory actuation element is electrically isolated from the second shape memory actuation element.

30. The adjustable shunt assembly of claim 19 wherein the at least one shape memory actuation element is coupled to the membrane and has a stent-like structure.

31. The adjustable shunt assembly of claim 19 wherein the at least one shape memory actuation element is composed of a shape memory alloy, and wherein the first material state is a martensitic or R-phase material state, and wherein the second material state is an R-phase or austenitic material state.

32. The adjustable shunt assembly of claim 19 wherein the frame is composed of superelastic Nitinol.

33. The adjustable shunt assembly of claim 19 wherein the transition temperature is a temperature greater than 40 degrees Celsius.

34. The adjustable shunt assembly of claim 19 wherein the first body region is a left atrium of a heart and the second body region is a right atrium of the heart.

35. The adjustable shunt assembly of claim 1 wherein the actuation element is composed a shape memory alloy.

36. The adjustable shunt assembly of claim 1 wherein at least a portion of the frame is configured to receive heat in the form of energy, and wherein the received heat at least partially drives actuation of the actuation element between the first material state and the second material state.

37. The adjustable shunt assembly of claim 1 wherein the first material state is a martensitic or R-phase material state.

38. The adjustable shunt assembly of claim 1 where the second material state is an R-phase or an austenitic material state.

39. The adjustable shunt assembly of claim 1 wherein the frame is configured to retain a generally stable geometry upon application of heat.

40. The adjustable shunt assembly of claim 1 wherein transitioning the at least one shape memory actuation element from the first material state to the second material state adjusts a cross-sectional area of the orifice.

41. The adjustable shunt assembly of claim 1 wherein the shape memory actuation element has a frustoconical shape.

42. The adjustable shunt assembly of claim 1 wherein the shape memory actuation element and the frame are configured such that transitioning the at least one shape memory element from the first material state to the second material state adjusts a geometry of the second end portion of the shape memory while maintaining a geometry of the first end portion of the shape memory actuator.

43. An adjustable shunt assembly, comprising:
a superelastic frame sized and shaped to anchor across a tissue wall dividing a first body region and a second body region;
a shape memory actuation element having a first end portion coupled to the frame and a second end portion spaced apart from the frame, wherein the shape memory actuation element has a transition temperature greater than body temperature; and
a lumen extending through the frame and the shape memory actuation element, wherein the second end portion of the shape memory actuation element at least partially defines an opening to the lumen,
wherein the shape memory actuation element is configured to adjust a size and/or shape of the opening in response to being heated above its transition temperature.

44. The adjustable shunt assembly of claim 43 wherein the shape memory actuation element has a frustoconical profile.

45. The adjustable shunt assembly of claim 43, further comprising a membrane, wherein the membrane is coupled to the shape memory actuation element and forms at least a portion of the lumen.

46. The adjustable shunt assembly of claim 43 wherein the frame is composed of superelastic Nitinol and the shape memory actuation element is composed of shape memory Nitinol.

* * * * *